United States Patent
Pradhan et al.

(10) Patent No.: US 11,229,686 B2
(45) Date of Patent: Jan. 25, 2022

(54) REDUCED FREQUENCY DOSAGE REGIMENS FOR TISSUE NON-SPECIFIC ALKALINE PHOSPHATASE (TNSALP)-ENZYME REPLACEMENT THERAPY OF HYPOPHOSPHATASIA

(71) Applicant: Alexion Pharmaceuticals, Inc., Boston, MA (US)

(72) Inventors: Rajendra Pradhan, Middletown, CT (US); Xiang Gao, Guilford, CT (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 15/760,656

(22) PCT Filed: Sep. 27, 2016

(86) PCT No.: PCT/US2016/054013
§ 371 (c)(1),
(2) Date: Mar. 16, 2018

(87) PCT Pub. No.: WO2017/058822
PCT Pub. Date: Apr. 6, 2017

(65) Prior Publication Data
US 2019/0298810 A1 Oct. 3, 2019

Related U.S. Application Data

(60) Provisional application No. 62/234,025, filed on Sep. 28, 2015, provisional application No. 62/238,015, filed on Oct. 6, 2015.

(51) Int. Cl.
| | |
|---|---|
| *A61P 19/08* | (2006.01) |
| *A61K 38/46* | (2006.01) |
| *A61K 9/00* | (2006.01) |
| *A61P 3/00* | (2006.01) |
| *A61K 38/00* | (2006.01) |

(52) U.S. Cl.
CPC .......... *A61K 38/465* (2013.01); *A61K 9/0019* (2013.01); *A61P 3/00* (2018.01); *A61P 19/08* (2018.01); *C12Y 301/03001* (2013.01); *A61K 38/00* (2013.01)

(58) Field of Classification Search
CPC ............................................. C12Y 301/03001
USPC .......................................................... 435/21
See application file for complete search history.

(56) References Cited

U.S. PATENT DOCUMENTS

| | | | |
|---|---|---|---|
| 5,336,759 A | 8/1994 | Matsuo et al. | |
| 5,338,830 A | 8/1994 | Matsuo et al. | |
| 5,340,920 A | 8/1994 | Matsuo et al. | |
| 5,352,770 A | 10/1994 | Matsuo | |
| 5,428,130 A | 6/1995 | Capon et al. | |
| 5,434,133 A | 7/1995 | Tanaka et al. | |
| 5,583,108 A | 12/1996 | Wei et al. | |
| 5,665,704 A | 9/1997 | Lowe et al. | |
| 5,714,147 A | 2/1998 | Capon et al. | |
| 5,767,239 A | 6/1998 | Immer et al. | |
| 5,846,932 A | 12/1998 | Lowe et al. | |
| 5,948,761 A | 9/1999 | Seilhamer et al. | |
| 5,973,134 A | 10/1999 | Matsuo et al. | |
| 6,020,168 A | 2/2000 | Matsuo et al. | |
| 6,028,055 A | 2/2000 | Lowe et al. | |
| 6,034,231 A | 3/2000 | Tanaka et al. | |
| 6,290,952 B1 | 9/2001 | Poelstra et al. | |
| 6,406,697 B1 | 6/2002 | Capon et al. | |
| 6,407,211 B1 | 6/2002 | Burnett, Jr. et al. | |
| 6,420,384 B2 | 7/2002 | Weigele et al. | |
| 6,436,386 B1 | 8/2002 | Roberts et al. | |
| 6,455,495 B1 | 9/2002 | Orgel et al. | |
| 6,458,579 B2 | 10/2002 | Hopwood et al. | |
| 6,525,022 B1 | 2/2003 | Lowe et al. | |
| 6,541,610 B1 | 4/2003 | Smith | |
| 6,743,425 B2 | 6/2004 | Nakao | |
| 6,790,649 B1 | 9/2004 | Crine et al. | |
| 6,818,619 B2 | 11/2004 | Burnett, Jr. et al. | |
| 6,830,885 B1 | 12/2004 | Lanctot et al. | |
| 6,849,714 B1 | 2/2005 | Bridon et al. | |
| 6,887,470 B1 | 5/2005 | Bridon et al. | |
| 6,905,689 B2 | 6/2005 | Schneidinger et al. | |
| 6,946,484 B2 | 9/2005 | Adams et al. | |

(Continued)

FOREIGN PATENT DOCUMENTS

| | | |
|---|---|---|
| EP | 0478797 B1 | 4/1995 |
| EP | 0769554 A2 | 4/1997 |

(Continued)

OTHER PUBLICATIONS

Whyte et al, Enzyme-replacement therapy in life-threatening hypophosphatasia. n engl j med 366;10 Mar. 8, 2012 904-913.*

(Continued)

*Primary Examiner* — Sheridan Swope
(74) *Attorney, Agent, or Firm* — Clark & Elbing LLP

(57) ABSTRACT

A method of treating a human having a condition or disease related to a bone defect characterized by at least one of: increased level of an alkaline phosphatase ligand, particularly PPi, PLP, or PEA; and decreased alkaline phosphatase activity, compared to a human without said condition or disease, comprising administering to the human a therapeutically effective amount of a polypeptide comprising the amino acid sequence of SEQ ID NO: 1, wherein the polypeptide is administered through at least one subcutaneous injection to the human in a frequency of fewer than three times each week.

16 Claims, 26 Drawing Sheets

Specification includes a Sequence Listing.

(56) References Cited

U.S. PATENT DOCUMENTS

| | | |
|---|---|---|
| 7,026,293 B2 | 4/2006 | Kitakaze |
| 7,033,997 B2 | 4/2006 | Forssmann et al. |
| 7,070,974 B1 | 7/2006 | Desgroseillers et al. |
| 7,105,539 B2 | 9/2006 | Gravel et al. |
| 7,179,903 B2 | 2/2007 | McArthur et al. |
| 7,256,253 B2 | 8/2007 | Bridon et al. |
| 7,271,149 B2 | 9/2007 | Glaesner et al. |
| 7,276,481 B2 | 10/2007 | Golembo et al. |
| 7,341,838 B2 | 3/2008 | Buechler et al. |
| 7,365,091 B2 | 4/2008 | Gravel et al. |
| 7,384,917 B2 | 6/2008 | Burnett, Jr. et al. |
| 7,399,466 B2 | 7/2008 | Boileau |
| 7,414,107 B2 | 8/2008 | Larsen |
| 7,425,531 B2 | 9/2008 | Lanctot et al. |
| 7,427,498 B2 | 9/2008 | Crine et al. |
| 7,470,668 B2 | 12/2008 | Lanctot et al. |
| 7,488,713 B2 | 2/2009 | Vesely |
| 7,527,939 B2 | 5/2009 | Davey et al. |
| 7,563,769 B2 | 7/2009 | Bogin et al. |
| 7,625,564 B2 | 12/2009 | Wang et al. |
| 7,642,243 B2 | 1/2010 | Nakao et al. |
| 7,648,962 B2 | 1/2010 | James et al. |
| 7,662,773 B2 | 2/2010 | James et al. |
| 7,678,391 B2 | 3/2010 | Graham et al. |
| 7,732,406 B2 | 6/2010 | Mitrovic et al. |
| 7,736,653 B2 | 6/2010 | Kim et al. |
| 7,754,852 B2 | 7/2010 | Burnett, Jr. et al. |
| 7,763,712 B2 | 7/2010 | Crine et al. |
| 7,803,769 B2 | 9/2010 | Sullivan et al. |
| 7,803,901 B2 | 9/2010 | Burnett, Jr. et al. |
| 7,825,092 B2 | 11/2010 | Vesely |
| 7,846,900 B2 | 12/2010 | Vesely |
| 7,858,560 B2 | 12/2010 | Koster et al. |
| 7,919,591 B2 | 4/2011 | Sheffer et al. |
| 7,943,126 B2 | 5/2011 | Tomatsu et al. |
| 7,960,529 B2 | 6/2011 | Crine et al. |
| 8,058,242 B2 | 11/2011 | Alewood et al. |
| 8,691,208 B2 | 4/2014 | Tomatsu et al. |
| 9,266,939 B2 | 2/2016 | Crine et al. |
| 9,988,620 B2 | 6/2018 | Crine et al. |
| 10,000,532 B2 | 6/2018 | Crine et al. |
| 10,603,361 B2 | 3/2020 | Odrljin |
| 2002/0183276 A1 | 12/2002 | Millan et al. |
| 2003/0158132 A1 | 8/2003 | Kovesdi |
| 2004/0023916 A1 | 2/2004 | Millan et al. |
| 2004/0077537 A1 | 4/2004 | Schreiner |
| 2004/0234518 A1 | 11/2004 | Crine et al. |
| 2005/0113286 A1 | 5/2005 | Schreiner et al. |
| 2005/0142217 A1 | 6/2005 | Adams et al. |
| 2005/0202442 A1 | 9/2005 | Morris et al. |
| 2005/0244904 A1 | 11/2005 | Ng |
| 2005/0276796 A1 | 12/2005 | Tomatsu et al. |
| 2006/0014687 A1 | 1/2006 | Crine et al. |
| 2006/0019890 A1 | 1/2006 | Kapoun et al. |
| 2006/0074009 A1 | 4/2006 | James et al. |
| 2006/0110359 A1 | 5/2006 | Sanchez-Ramos et al. |
| 2006/0172929 A1 | 8/2006 | Rappold-Hoerbrand et al. |
| 2006/0228710 A1 | 10/2006 | Morris et al. |
| 2007/0041972 A1 | 2/2007 | Rother et al. |
| 2007/0042957 A1 | 2/2007 | Burnett et al. |
| 2007/0081984 A1 | 4/2007 | Tomatsu et al. |
| 2007/0081986 A1 | 4/2007 | Tomatsu et al. |
| 2007/0197434 A1 | 8/2007 | Nakao et al. |
| 2007/0281887 A1 | 12/2007 | Pan |
| 2007/0292966 A1 | 12/2007 | Prickett et al. |
| 2007/0293418 A1 | 12/2007 | Larsen |
| 2008/0032933 A1 | 2/2008 | Burnett et al. |
| 2008/0081768 A1 | 4/2008 | Watt et al. |
| 2008/0085862 A1 | 4/2008 | Kim et al. |
| 2008/0113411 A1 | 5/2008 | Sheffer et al. |
| 2008/0113412 A1 | 5/2008 | Sheffer et al. |
| 2008/0125574 A1 | 5/2008 | Sheffer et al. |
| 2008/0153747 A1 | 6/2008 | Alewood et al. |
| 2008/0161243 A1 | 7/2008 | Rosen et al. |
| 2008/0181903 A1 | 7/2008 | Bhaskar et al. |
| 2008/0182299 A1 | 7/2008 | Colocaru et al. |
| 2008/0194481 A1 | 8/2008 | Rosen et al. |
| 2008/0194682 A1 | 8/2008 | Golembo et al. |
| 2008/0227713 A1 | 9/2008 | Rotter |
| 2008/0293632 A1 | 11/2008 | Rappold-Hoerbrand et al. |
| 2008/0312142 A1 | 12/2008 | Nakao et al. |
| 2009/0011997 A1 | 1/2009 | Peri et al. |
| 2009/0023652 A1 | 1/2009 | Bell et al. |
| 2009/0053192 A1 | 2/2009 | Millan et al. |
| 2009/0069243 A1 | 3/2009 | Burnett, Jr. et al. |
| 2009/0092582 A1 | 4/2009 | Bogin et al. |
| 2009/0142347 A1 | 6/2009 | Millan |
| 2009/0170756 A1 | 7/2009 | Burnett, Jr. et al. |
| 2009/0221803 A1 | 9/2009 | Dall'Acqua et al. |
| 2009/0238814 A1 | 9/2009 | Tomatsu et al. |
| 2009/0240031 A1 | 9/2009 | Immer et al. |
| 2009/0247462 A1 | 10/2009 | Bogin et al. |
| 2009/0252729 A1 | 10/2009 | Farrington et al. |
| 2009/0258018 A1 | 10/2009 | Medich et al. |
| 2009/0275506 A1 | 11/2009 | Bakis et al. |
| 2009/0325195 A1 | 12/2009 | Davey et al. |
| 2010/0008979 A1 | 1/2010 | Tomatsu et al. |
| 2010/0055150 A1 | 3/2010 | Golembo et al. |
| 2010/0093678 A1 | 4/2010 | Della-Fera et al. |
| 2010/0160212 A1 | 6/2010 | Sheffer et al. |
| 2010/0168443 A1 | 7/2010 | Geysen |
| 2010/0184680 A1 | 7/2010 | Bevec |
| 2010/0197574 A1 | 8/2010 | Chen et al. |
| 2010/0204094 A1 | 8/2010 | Simari et al. |
| 2010/0204109 A1 | 8/2010 | Bevec |
| 2010/0204446 A1 | 8/2010 | Forssmann |
| 2010/0209958 A1 | 8/2010 | Nakao et al. |
| 2010/0216714 A1 | 8/2010 | James et al. |
| 2010/0221234 A1 | 9/2010 | Crine et al. |
| 2010/0240125 A1 | 9/2010 | Crine et al. |
| 2010/0249017 A1 | 9/2010 | Bevec et al. |
| 2010/0260706 A1 | 10/2010 | Bogin et al. |
| 2010/0261248 A1 | 10/2010 | Kim et al. |
| 2010/0297021 A1 | 11/2010 | Wendt et al. |
| 2010/0297119 A1 | 11/2010 | Crine et al. |
| 2010/0305031 A1 | 12/2010 | Wakabayashi et al. |
| 2010/0305051 A1 | 12/2010 | Burnett, Jr. et al. |
| 2010/0310561 A1 | 12/2010 | Canada et al. |
| 2010/0311660 A1 | 12/2010 | Simari et al. |
| 2010/0317600 A1 | 12/2010 | Immer et al. |
| 2010/0331256 A1 | 12/2010 | Wendt et al. |
| 2011/0152194 A1 | 6/2011 | Burnett, Jr. et al. |
| 2011/0250187 A1 | 10/2011 | Tomatsu et al. |
| 2011/0269684 A1 | 11/2011 | Burnett, Jr. et al. |
| 2011/0300143 A1 | 12/2011 | Sly et al. |
| 2012/0088771 A1 | 4/2012 | Millan |
| 2012/0164142 A1 | 6/2012 | Crine et al. |
| 2013/0108635 A1 | 5/2013 | Crine et al. |
| 2013/0323244 A1* | 12/2013 | Crine ............... A61K 38/465 424/134.1 |
| 2014/0193388 A1 | 7/2014 | Velders et al. |
| 2014/0194484 A1 | 7/2014 | Coats et al. |
| 2015/0353633 A1 | 12/2015 | Kakkis et al. |
| 2016/0052968 A1 | 2/2016 | Crine et al. |
| 2016/0097100 A1 | 4/2016 | Trent et al. |
| 2017/0175094 A1 | 6/2017 | Hatch |
| 2017/0360899 A1 | 12/2017 | Marozsan et al. |
| 2018/0230445 A1 | 8/2018 | Jaluria et al. |

FOREIGN PATENT DOCUMENTS

| | | |
|---|---|---|
| EP | 0771875 B1 | 5/1997 |
| EP | 0466174 B1 | 6/1997 |
| EP | 0475394 B1 | 6/1997 |
| EP | 0466175 B1 | 1/1998 |
| EP | 0477971 B1 | 1/1998 |
| EP | 0475290 B1 | 12/1998 |
| EP | 0475291 B1 | 12/1998 |
| EP | 0497368 B1 | 6/2002 |
| EP | 1492567 | 9/2003 |
| EP | 1502604 A1 | 2/2005 |
| EP | 1623994 A2 | 2/2006 |
| EP | 1759001 B1 | 3/2007 |
| EP | 1759710 A1 | 3/2007 |

(56) References Cited

FOREIGN PATENT DOCUMENTS

| | | |
|---|---|---|
| EP | 2158319 | 3/2010 |
| EP | 2158319 B1 | 12/2011 |
| JP | H0870875 A | 3/1996 |
| JP | 2000-327583 A | 11/2000 |
| JP | 2002-541776 A | 12/2002 |
| JP | 2007-511209 A | 5/2007 |
| JP | 2010-501026 A | 1/2010 |
| JP | 2010-526543 A | 8/2010 |
| JP | 2010-530222 A | 9/2010 |
| JP | 2011-504506 A | 2/2011 |
| JP | 2015-502336 A | 1/2015 |
| WO | WO-92/20371 A1 | 11/1992 |
| WO | WO-94/20534 A1 | 9/1994 |
| WO | WO-95/05456 A1 | 2/1995 |
| WO | WO-95/13296 A1 | 5/1995 |
| WO | WO-95/33769 A1 | 12/1995 |
| WO | WO-98/17690 A1 | 4/1998 |
| WO | WO-98/35703 A2 | 8/1998 |
| WO | WO-99/46283 A1 | 9/1999 |
| WO | WO-00/18954 A2 | 4/2000 |
| WO | WO-00/50580 A2 | 8/2000 |
| WO | WO-00/53755 A2 | 9/2000 |
| WO | WO-00/64486 A2 | 11/2000 |
| WO | WO-00/69900 A2 | 11/2000 |
| WO | WO-01/36620 A2 | 5/2001 |
| WO | WO-01/44284 A2 | 6/2001 |
| WO | WO-01/80890 A2 | 11/2001 |
| WO | WO-02/15918 A2 | 2/2002 |
| WO | WO-02/47871 A1 | 6/2002 |
| WO | WO-02/067639 A1 | 8/2002 |
| WO | WO-02/068579 A2 | 9/2002 |
| WO | WO-02/074234 A2 | 9/2002 |
| WO | WO-03/074082 A1 | 9/2003 |
| WO | WO-03/079979 A2 | 10/2003 |
| WO | WO-03/092581 A2 | 11/2003 |
| WO | WO-03/094835 A2 | 11/2003 |
| WO | WO-2004/011498 A2 | 2/2004 |
| WO | WO-2004/022579 A2 | 3/2004 |
| WO | WO-2004/046194 A2 | 6/2004 |
| WO | WO-2004/047871 A2 | 6/2004 |
| WO | WO-2004/062555 A2 | 7/2004 |
| WO | WO-2004/074320 A2 | 9/2004 |
| WO | WO-2004/094460 A2 | 11/2004 |
| WO | WO-2005/000095 A2 | 1/2005 |
| WO | WO-2005/007809 A2 | 1/2005 |
| WO | WO-2005/042034 A1 | 5/2005 |
| WO | WO-2005/047337 A1 | 5/2005 |
| WO | WO-2005/070446 A1 | 8/2005 |
| WO | WO-2005/072055 A2 | 8/2005 |
| WO | WO-2005/094890 A1 | 10/2005 |
| WO | WO-2005/098490 A1 | 10/2005 |
| WO | WO-2005/103263 A1 | 11/2005 |
| WO | WO-2005/105156 A1 | 11/2005 |
| WO | WO-2005/110435 A1 | 11/2005 |
| WO | WO-2006/005140 A2 | 1/2006 |
| WO | WO-2006/026663 A1 | 3/2006 |
| WO | WO-2006/039480 A2 | 4/2006 |
| WO | WO-2006/060641 A2 | 6/2006 |
| WO | WO-2006/110743 A1 | 10/2006 |
| WO | WO-2006/116260 A2 | 11/2006 |
| WO | WO-2007/041645 A2 | 4/2007 |
| WO | WO-2007/071295 A1 | 6/2007 |
| WO | WO-2007/097923 A2 | 8/2007 |
| WO | WO-2007/130113 A2 | 11/2007 |
| WO | WO-2008/021872 A1 | 2/2008 |
| WO | WO-2008/030558 A2 | 3/2008 |
| WO | WO-2008/031045 A2 | 3/2008 |
| WO | WO-2008/053362 A2 | 5/2008 |
| WO | WO-2008/058016 A2 | 5/2008 |
| WO | WO-2008/079995 A2 | 7/2008 |
| WO | WO-2008/088422 A2 | 7/2008 |
| WO | WO-2008/109903 A1 | 9/2008 |
| WO | WO-2008/136611 A1 | 11/2008 |
| WO | WO-2008/138131 A1 | 11/2008 |
| WO | WO-2008/154226 A1 | 12/2008 |
| WO | WO-2009/006520 A1 | 1/2009 |
| WO | WO-2009/006732 A9 | 1/2009 |
| WO | WO-2009/015011 A1 | 1/2009 |
| WO | WO-2009/023270 A2 | 2/2009 |
| WO | WO-2009/033680 A2 | 3/2009 |
| WO | WO-2009/033724 A1 | 3/2009 |
| WO | WO-2009/033796 A1 | 3/2009 |
| WO | WO-2009/033807 A2 | 3/2009 |
| WO | WO-2009/034134 A2 | 3/2009 |
| WO | WO-2009/036448 A2 | 3/2009 |
| WO | WO-2009/040030 A1 | 4/2009 |
| WO | WO-2009/040031 A2 | 4/2009 |
| WO | WO-2009/040083 A2 | 4/2009 |
| WO | WO-2009/046861 A1 | 4/2009 |
| WO | WO-2009/058322 A1 | 5/2009 |
| WO | WO-2009/067639 A2 | 5/2009 |
| WO | WO-2009/086126 A2 | 7/2009 |
| WO | WO-2009/090553 A2 | 7/2009 |
| WO | WO-2009/142307 A1 | 11/2009 |
| WO | WO-2009/149161 A9 | 12/2009 |
| WO | WO-2009/156481 A1 | 12/2009 |
| WO | WO-2009/158035 A2 | 12/2009 |
| WO | WO-2010/002583 A2 | 1/2010 |
| WO | WO-2010/011096 A2 | 1/2010 |
| WO | WO-2010/048308 A2 | 4/2010 |
| WO | WO-2010/078325 A2 | 7/2010 |
| WO | WO-2010/082804 A2 | 7/2010 |
| WO | WO-2010/117760 A2 | 10/2010 |
| WO | WO-2010/129655 A2 | 11/2010 |
| WO | WO-2010/135541 A2 | 11/2010 |
| WO | WO-2011/134084 A1 | 11/2011 |
| WO | WO-2012/088608 A1 | 7/2012 |
| WO | WO-2012/099851 A2 | 7/2012 |
| WO | WO-2013/058833 A1 | 4/2013 |
| WO | WO-2013/059491 A1 | 4/2013 |
| WO | WO-2013/071262 A1 | 5/2013 |
| WO | WO-2015/112015 A1 | 7/2015 |
| WO | WO-2016/007873 A1 | 1/2016 |
| WO | WO-2016/090251 A1 | 6/2016 |
| WO | WO-2016/123342 A2 | 8/2016 |
| WO | WO-2016/153191 A1 | 9/2016 |
| WO | WO-2017/031114 A1 | 2/2017 |
| WO | WO-2017/058822 A1 | 4/2017 |
| WO | WO-2017/074466 A1 | 5/2017 |
| WO | WO-2017/155569 A1 | 9/2017 |
| WO | WO-2017/171871 A1 | 10/2017 |
| WO | WO-2017/173395 A1 | 10/2017 |
| WO | WO-2017/173413 A1 | 10/2017 |
| WO | WO-2017/214130 A1 | 12/2017 |
| WO | WO-2018/004517 A1 | 1/2018 |
| WO | WO-2018/035420 A1 | 2/2018 |
| WO | WO-2018/164995 A1 | 9/2018 |

OTHER PUBLICATIONS

Dutta et al, Men and mice: Relating their ages. LifeSci . May 1, 2016;152:244-8. doi: 10.1016/j.lfs.2015.10.025. Epub Oct. 24, 2015.*

International Search Report and Written Opinion for International Patent Application No. PCT/US2016/054013, dated Dec. 13, 2016 (19 pages).

Whyte et al., "Alkaline phosphatase: placental and tissue-nonspecific isoenzymes hydrolyze phosphoethanolamine, inorganic pyrophosphate, and pyridoxal 5'-phosphate. Substrate accumulation in carriers of hypophosphatasia corrects during pregnancy," J Clin Invest. 95(4):1440-5 (1995).

Ali et al., "Isolation and characterization of calcifying matrix vesicles from epiphyseal cartilage," Proc Natl Acad Sci USA. 67(3):1513-1520 (1970).

Anderson et al., "Pyrophosphate stimulation of calcium uptake into cultured embryonic bones. Fine structure of matrix vesicles and their role in calcification," Dev Biol. 34:211-227 (1973).

Anderson et al., "Sustained osteomalacia of long bones despite major improvement in other hypophosphatasia-related mineral deficits in tissue nonspecific alkaline phosphatase/nucleotide pyrophosphatase phosphodiesterase 1 double-deficient mice," Am J Pathol. 166(6):1711-1720 (2005).

(56) References Cited

OTHER PUBLICATIONS

Anderson et al., "The role of matrix vesicles in growth plate development and biomineralization," Front Biosci. 10:822-837 (2005).
Beertsen et al., "Root development in mice lacking functional tissue non-specific alkaline phosphatase gene: Inhibition of acellular cementum formation," J Dent Res. 78(6):1221-1229 (1999) (10 pages).
Bennett et al., "Extracellular domain-IgG fusion proteins for three human natriuretic peptide receptors," J Biol Chem. 266(34):23060-23067 (1991).
Bernard, "Ultrastructural localization of alkaline phosphatase in initial intramembranous osteogenesis," Clin Orthop Relat Res. 135:218-225 (1978).
Bonilla, "Pharmacokinetics of immunoglobulin administered via intravenous or subcutaneous routes," Immunol Allergy Clin N Am. 28:803-819 (2008).
Byers et al., "Effect of enzyme replacement therapy on bone formation in a feline model of mucopolysaccharidosis type VI," Bone. 21(5):425-431 (1997).
Cameron et al., "Minireview: Natriuretic peptides during development of the fetal heart and circulation," Endocrinology. 144(6):2191-2194 (2003).
Clemens et al., "Pharmacokinetics and biological actions of subcutaneously administered human brain natriuretic peptide," J Pharmacol Exp Ther. 287(1):67-71 (1998).
Declaration of Dr. Philippe Crine for EP 08757088.3, executed Jan. 14, 2011 (6 pages).
Engel et al., "Characterization of the hormone binding site of natriuretic peptide receptor-C," FEBS Lett. 360:169-172 (1995).
Extended European Search Report for European Application No. 08757088.3, dated Jun. 21, 2010 (6 pages).
Farley et al., "Effects of tunicamycin, mannosamine, and other inhibitors of glycoprotein processing on skeletal alkaline phosphatase in human osteoblast-like cells," Calcif Tissue Int. 76:63-74 (2005).
Fedde et al., "Alkaline phosphatase knock-out mice recapitulate the metabolic and skeletal defects of infantile hypophosphatasia," available in PMC Mar. 7, 2011, published in final edited form as: J Bone Miner Res. 14(12):2015-2026 (1999) (19 pages).
Garg, "Investigation of the role of FcRn in the absorption, distribution, and elimination of monoclonal antibodies," Dissertation: State University of New York at Buffalo, 2007 (Abstract only) (2 pages).
Greenberg et al., "A homoallelic Gly$^{317}$ to Asp mutation in ALPL causes the perinatal (lethal) form of hypophosphatasia in Canadian mennonites," Genomics. 17:215-217 (1993).
Harmey et al., "Concerted regulation of inorganic pyrophosphate and osteopontin by Akp2, Enppl, and Ank," Am J Pathol. 164(4):1199-1209 (2004).
Harmey et al., "Elevated skeletal osteopontin levels contribute to the hypophosphatasia phenotype in Akp$^{-/-}$mice," J Bone Miner Res. 21(9):1377-1386 (2006).
Hawrylak et al., "The solubilization of tetrameric alkaline phosphatase from human liver and its conversion into various forms by phosphatidylinositol phospholipase C or proteolysis," J Biol Chem. 263(28):14368-14373 (1988).
Henthorn et al., "Different missense mutations at the tissue-nonspecific alkaline phosphatase gene locus in autosomal recessively inherited forms of mild and severe hypophosphatasia," Proc Natl Acad Sci USA. 89:9924-9928 (1992).
Hessle et al., "Tissue-nonspecific alkaline phosphatase and plasma cell membrane glucoprotein-1 are central antagonistic regulators of bone mineralization," Proc Natl Acad Sci USA. 99(14): 9445-9449 (2002).
Jansonius, "Structure, evolution and action of vitamin B$_6$-dependent enzymes," Curr Opin Struct Biol. 8:759-769 (1998).
Jin et al., "Novel analog of atrial natriuretic peptide selective for receptor-A produces increased diuresis and natriuresis in rats," J Clin Invest. 98(4):969-976 (1996).
Johnson et al., "Matrix vesicle plasma cell membrane glycoprotein-1 regulates mineralization by murine osteoblastic MC3T3 cells," J Bone Miner Res. 14(6):883-892 (1999).
Kochendoerfer, "Protein & peptide drug delivery—third international conference: Minimally invasive delivery methods," Sep. 22-23, Philadelphia, PA. IDrugs. 6(11):1043-1045 (2003).
Kostenuik et al., "Infrequent delivery of a long-acting PTH-Fc fusion protein has potent anabolic effects on cortical and cancellous bone," J Bone Miner Res. 22(10):1534-1547 (2007).
Mahmood et al., "Selection of the first-time dose in humans: comparison of different approaches based on interspecies scaling of clearance," J Clin Pharmacol. 43:692-697 (2003).
Millan, "Mammalian Alkaline Phosphatases," Wiley-WCH Verlag GmbH & Co., Weinheim, Germany, 1-322 (2006).
Morris et al., "Immunolocalization of alkaline phosphatase in osteoblasts and matrix vesicles of human fetal bone," Bone Miner. 19:287-298 (1992).
Nasu et al., "Aberrant interchain disulfide bridge of tissue-nonspecific alkaline phosphatase with an Arg433 to Cys substitution associated with severe hypophosphatasia," FEBS Journal. 273:5612-5624 (2006).
NCBI Protein Database Accession No. AAF64516. Retrieved on Apr. 16, 2013 (2 pages).
NCBI Protein Database Accession No. AAC33858. Retrieved on Apr. 16, 2013 (1 page).
NCBI Protein Database Accession No. AAH21289. Retrieved on Apr. 16, 2013 (2 pages).
NCBI Protein Database Accession No. AAH66116. Retrieved on Apr. 16, 2013 (2 pages).
NCBI Protein Database Accession No. AAH90861. Retrieved on Apr. 16, 2013 (2 pages).
NCBI Protein Database Accession No. AAI10910. Retrieved on Apr. 16, 2013 (2 pages).
NCBI Protein Database Accession No. AAI26166. Retrieved on Apr. 16, 2013 (2 pages).
NCBI Protein Database Accession No. AAI18209. Retrieved on Apr. 17, 2013 (2 pages).
NCBI Protein Database Accession No. AAN64273. Retrieved on Apr. 16, 2013 (1 page).
NCBI Protein Database Accession No. NP_000469. Retrieved on Apr. 16, 2013 (3 pages).
NCBI Protein Database Accession No. NP_001623. Retrieved on Apr. 16, 2013 (3 pages).
NCBI Protein Database Accession No. NP_001036028. Retrieved on Apr. 16, 2013 (2 pages).
NCBI Protein Database Accession No. NP_001253798.1, downloaded on Apr. 17, 2013. (2 pages).
NCBI Protein Database Accession No. NP_112603. Retrieved on Apr. 16, 2013 (3 pages).
NCBI Protein Database Accession No. P05186. Retrieved on Apr. 16, 2013 (19 pages).
NCBI Protein Database Accession No. P05187. Retrieved on Apr. 16, 2013 (10 pages).
NCBI Protein Database Accession No. P08289. Retrieved on Apr. 16, 2013 (5 pages).
NCBI Protein Database Accession No. P09487. Retrieved on Apr. 16, 2013 (4 pages).
NCBI Protein Database Accession No. P09242. Retrieved on Apr. 16, 2013 (6 pages).
NCBI Protein Database Accession No. P09923. Retrieved on Apr. 16, 2013 (6 pages).
NCBI Protein Database Accession No. P10696. Retrieved on Apr. 16, 2013 (7 pages).
NCBI Protein Database Accession No. Q29486. Retrieved on Apr. 16, 2013 (3 pages).
NCBI Protein Database Accession No. Q9N0V0. Retrieved on Apr. 16, 2013 (1 page).
Nosjean et al., "Human tissue non-specific alkaline phosphatases: sugar-moiety-induced enzymic and antigenic modulations and genetic aspects," Biochem J. 321:297-303 (1997).
Ramachandran et al., "Treatment of an anabolic bone deficiency in neurofibromatosis with bone morphogenetic proteins and its potential application for congenital pseudarthrosis of the tibia," J Bone Joint Surg Br. 91-B (Suppl. 1), Abstract 137 (2009).
Srinivas et al., "Assessment of dose proportionality, absolute bioavailability, and immunogenicity response of CTLA4Ig (BMS-188667),

(56) References Cited

OTHER PUBLICATIONS a novel immunosuppressive agent, following subcutaneous and intravenous administration to rats," Pharmaceutical Res. 14(7):911-916 (1997).
Tye et al., "Delineation of the hydroxyapatite-nucleating domains of bone sialoprotein," J Biol Chem. 278(10):7949-7955 (2003).
Urlaub et al., "Deletion of the diploid dihydrofolate reductase locus from cultured mammalian cells," Cell. 33:405-412 (1983).
Wang et al., "A mouse model for achondroplasia produced by targeting fibroblast growth factor receptor 3," Proc Natl Acad Sci USA. 96:4455-4460 (1999).
Wang et al., "Structure-based chemical modification strategy for enzyme replacement treatment of phenylketonuria," Mol Genet Metab. 86:134-140 (2005).
Weiss et al., "A missense mutation in the human liver/bone/kidney alkaline phosphatase gene causing a lethal form of hypophosphatasia," Proc Natl Acad Sci USA. 85:7666-7669 (1988).
Whyte et al., "Enzyme-replacement therapy in life-threatening hypophosphatasia," N Engl J Med. 366(10):904-13 (2012).
Whyte et al., "Markedly increased circulating pyridoxal-5'-phosphate levels in hypophosphatasia," J Clin Invest. 76:752-756 (1985).
Wroblewski et al., "Pharmacokinetics, metabolic stability, and subcutaneous bioavailability of a genetically engineered analog of DcR3, flint [DcR3(R218Q)], in cynomolgus monkeys and mice," Drug Metab Dispos. 31(4):502-507 (2003).
Yamamoto et al., "Long term phenotypic correction of severe infantile hypophosphatasia in a mouse model by neonatal injection of lentiviral vector," Mol Ther. 17:S67-S68, Abstract 171 (2009).
Zierhut et al., "Population PK-PD model for Fc-osteoprotegerin in healthy postmenopausal women," J Pharmacokinet Pharmacodyn. 35:379-399 (2008).
Zurutuza et al., "Correlations of genotype and phenotype in hypophosphatasia," Hum Mol Genet. 8(6):1039-1046 (1999).
International Preliminary Report on Patentability for International Patent Application No. PCT/CA2011/050258, dated Nov. 15, 2012 (9 pages).
International Search Report and Written Opinion for International Patent Application No. PCT/US2012/039004, dated Nov. 2, 2012 (22 pages).
Invitation to Pay Additional Fees for International Patent Application No. PCT/US2012/039004, dated Aug. 29, 2012 (2 pages).
Oikawa et al., "Enzyme replacement therapy on hypophosphatasia mouse model," J Inherit Metab Dis. 9 pages (2013).
Whyte et al., "Infantile hypophosphatasia: normalization of circulating bone alkaline phosphatase activity followed by skeletal remineralization. Evidence for an intact structural gene for tissue nonspecific alkaline phosphatase," J Pediatr. 108(1):82-8 (1986).
Achord et al., "Human beta-glucuronidase: in vivo clearance and in vitro uptake by a glycoprotein recognition system on reticuloendothelial cells," Cell 15(1):269-278 (1978).
Anderson et al., "Matrix vesicles in osteomalacic hypophosphatasia bone contain apatite-like mineral crystals," Am J Pathol. 151(6):1555-61 (1997).
Barton et al., "Replacement therapy for inherited enzyme deficiency-macrophage-targeted glucocerebrosidase for Gaucher's disease," N Engl J Med. 324(21):1464-70 (1991) (abstract only).
Bernardi, "Chromatography of proteins on hydroxyapatite," Methods Enzymol. 27:471-9 (1973).
Boskey et al., "Matrix vesicles promote mineralization in a gelatin gel," Calcif Tissue Int 60(3):309-15 (1997).
Ciancaglini et al., "Contribution of matrix vesicles and alkaline phosphatase to ectopic bone formation," Braz. J Med Biol Res. 39(5):603-10 (2006).
Crawley et al., "Enzyme replacement therapy in a feline model of Maroteaux-Lamy Syndrome," J Clin Invest. 97(8):1864-73 (1996).
Di Mauro et al., "Kinetic characterization of hypophosphatasia mutations with physiological substrates," J Bone Miner Res. 17(8):1383-91 (2002).

Dumont et al., "Monomeric Fc fusions: impact on pharmacokinetic and biological activity of protein therapeutics," BioDrugs. 20(3):151-60 (2006).
Eng et al., "Safety and efficacy of recombinant human alpha-galactosidase A-replacement therapy in Fabry's disease," N Engl J Med. 345(1):9-16 (2001).
Gilbert et al., "Chimeric peptides of statherin and osteopontin that bind hydroxyapatite and mediate cell adhesion," J Biol Chem. 275(21):16213-8 (2000).
Guo et al., "Protein tolerance to random amino acid change," Proc Natl Acad Sci USA. 101(25):9205-9210 (2004).
Henthorn et al., "Missense mutations of the tissue-nonspecific alkaline phosphatase gene in hypophosphatasia," Clin Chem. 38(12):2501-5 (1992).
Hosain et al., "Targeted delivery of antineoplastic agent to bone: biodistribution studies of technetium-99m-labeled gem-bisphosphonate conjugate of methotrexate," J Nucl Med. 37(1):105-7 (1996).
Kakkis et al., "Enzyme-replacement therapy in mucopolysaccharidosis I," N Engl J Med. 344(3):182-8 (2001).
Kaufmann et al., "Influence of low temperature on productivity, proteome and protein phosphorylation of CHO cells," Biotechnol Bioeng. 63(5):573-82 (1999).
Millán et al., "Enzyme replacement therapy for murine hypophosphatasia," J Bone Miner Res. 23(6): 777-87 (2008).
Murray, "Lectin-specific targeting of lysosomal enzymes to reticuloendothelial cells," Methods Enzymol. 149:25-42 (1987).
Oda et al., "A general method for rapid purification of soluble versions of glycosylphosphatidylinositol-anchored proteins expressed in insect cells: an application for human tissue-nonspecific alkaline phosphatase," J Biochem. 126(4):694-9 (1999).
Pedersen et al., "Removal of N-terminal polyhistidine tags from recombinant proteins using engineered aminopeptidases," Protein Expr Purif. 15(3):389-400 (1999).
Salih et al., "Identification of the phosphorylated sites of metabolically 32P-labeled osteopontin from cultured chicken osteoblasts," J Biol Chem. 272(21):13966-73 (1997).
Sands et al., "Enzyme replacement therapy for murine mucopolysaccharidosis type VII," J Clin Invest. 93(6):2324-31 (1994).
Sekido et al., "Novel drug delivery system to bone using acidic oligopeptide: pharmacokinetic characteristics and pharmacological potential," J Drug Target. 9(2):111-21 (2001).
Sturtz et al., "A study of the delivery-targeting concept applied to antineoplasic drugs active on human osteosarcoma. I. Synthesis and biological activity in nude mice carrying human osteosarcoma xenografts of gem-bisphosphonic methotrexate analogues," Eur J Med Chemistry. 27:825-33 (1992).
Tomatsu, Declaration Under 37 C.F.R. § 1.132 for U.S. Appl. No. 11/484,870, dated Jun. 1, 2009 (3 pages).
Uludag et al., "Bone affinity of a bisphosphonate-conjugated protein in vivo," Biotechnol Prog. 16(6):1115-8 (2000).
Waymire et al., "Mice lacking tissue non-specific alkaline phosphatase die from seizures due to defective metabolism of vitamin B-6," Nat Genet. 11(1):45-51 (1995).
Weinberg, "An overview of infliximab, etanercept, efalizumab, and alefacept as biologic therapy for psoriasis," Clin Ther. 25(10):2487-505 (2003).
Weiss et al., "Isolation and characterization of a cDNA encoding a human liver/bone/kidney-type alkaline phosphatase," Proc Natl Acad Sci USA. 83(19):7182-6 (1986).
Weiss et al., "Structure of the human liver/bone/kidney alkaline phosphatase gene," J Biol Chem. 263(24):12002-10 (1988).
Weninger et al., "Biochemical and morphological effects of human hepatic alkaline phosphatase in a neonate with hypophosphatasia," Acta Paediatr Scand. Suppl. 360:154-160 (1989).
Whyte et al., "Infantile hypophosphatasia: enzyme replacement therapy by intravenous infusion of alkaline phosphatase-rich plasma from patients with Paget bone disease," J Pediatr. 101(3):379-86 (1982).
Whyte et al., "Enzyme replacement therapy for infantile hypophosphatasia attempted by intravenous infusions of alkaline phosphatase-rich Paget plasma: results in three additional patients," J Pediatr. 105(6):926-33 (1984).

(56) References Cited

OTHER PUBLICATIONS

Whyte et al., "Hypophosphatasia," in The Metabolic and Molecular Bases of Inherited Disease (8th ed.), pp. 5313-5329, 2001 (McGraw-Hill Book Company) (epub pp. 1-41).
Whyte et al., "Heritable Forms of Rickets and Osteomalacia," in Connective Tissues and Its Heritable Disorders, pp. 765-787, 2002 (eds. R.M. Royce and B. Steinmann, Wiley-Liss, Inc. Hoboken).
Whyte et al., "Marrow cell transplantation for infantile hypophosphatasia," J Bone Miner Res. 18(4):624-36 (2003).
Yamamoto et al., "Prolonged survival and phenotypic correction of Akp2(-/-) hypophosphatasia mice by lentiviral gene therapy," J Bone Miner Res. 26(1):135-42 (2011).
Communication from Examining Division for European Application No. EP 05 73 9065.0, dated Jun. 18, 2009 (6 pages).
Communication from Examining Division for European Application No. EP 05 73 9065.0, dated Jun. 11, 2010 (5 pages).
Office Action for U.S. Appl. No. 12/793,517, dated Aug. 16, 2010 (9 pages).
Office Action for U.S. Appl. No. 13/071,445, dated Feb. 6, 2012 (12 pages).
Supplementary European Search Report for European Application No. EP 05 73 9065 (date of completion of search Nov. 7, 2008, dated Dec. 2, 2008) (3 pages).
Choe et al., "Substrate profiling of cysteine proteases using a combinatorial peptide library identifies functionally unique specificities," J Biol Chem. 281(18):12824-12832 (2006).
Official Action for Japanese Application No. 2013-544989, dated Oct. 27, 2015 (3 pages).
Harris, "The human alkaline phosphatases: what we know and what we don't know," Clin Chim Acta. 186:133-50 (1989).
De la Croix Ndong et al., "Asfotase-alpha improves bone growth, mineralization and strength in mouse models of neurofibromatosis type-1," Nat Med. 20(8):904-10 (2014) (10 pages).
International Search Report and Written Opinion for International Patent Application No. PCT/US2016/047166, dated Nov. 7, 2016 (15 pages).
Ratner, "Alexion pays big for Synageva's rare disease drug candidate," Nat Biotechnol. 33(7):679 (2015).
Addison et al., "Pyrophosphate inhibits mineralization of osteoblast cultures by binding to mineral, up-regulating osteopontin, and inhibiting alkaline phosphatase activity," J Biol Chem. 282(21):15872-15883 (2007).
Advisory Action for U.S. Appl. No. 11/484,870, dated Dec. 20, 2007 (4 pages).
Altarescu et al., "The efficacy of enzyme replacement therapy in patients with chronic neuronopathic Gaucher's disease," J Pediatr. 138(4):539-547 (2001).
Anderson et al., "Impaired calcification around matrix vesicles of growth plate and bone in alkaline phosphatase-deficient mice," *Am J Pathol.* 164:841-847 (2004).
Barranger et al., "Lessons learned from the development of enzyme therapy for Gaucher disease," J Inherit Metab Dis. 24(Supp 2):89-96 (2001).
Bobé et al., "Fas-mediated liver damage in MRL hemopoietic chimeras undergoing lpr-mediated graft-versus-host disease," J Immunol. 159:4197-4204 (1997).
Boskey, "Amorphous calcium phosphate: The contention of bone," J Dent Res. 76:1433-1436 (1997).
Campbell et al., "Insulin-like growth factor (IGF)-binding protein-5-(201-218) region regulates hydroxyapatite and IGF-I binding," Am J Physiol. 273:E1005-1013 (1997).
Cleland et al., "Emerging protein delivery methods," Curr Opin Biotechnol. 12:212-219 (2001).
Communication from Examining Division for European Application No. EP 08 757 088.3, dated Apr. 20, 2011 (4 pages).
Data Sheet for pFUSE-SEAP-hFC "Plasmid designed for the expression of a SEAP-Fc Fusion protein," Invivogen, San Diego, CA (4 pages) (1989).
Extended European Search Report for European Application No. 11774253.6, dated Oct. 14, 2013 (8 pages).
Extended European Search Report for European Application No. EP 11 00 0196.3, dated Jun. 22, 2011 (6 pages).
Extended European Search Report for European Application No. EP 11 00 4496.3, dated Aug. 26, 2011 (7 pages).
Fujisaki et al., "Osteotropic Drug Delivery System (ODDS) based on bisphosphonic prodrug. IV effects of osteotropic estradiol on bone mineral density and uterine weight in ovariectomized rats," J Drug Target. 5(2):129-138 (1997) (11 pages).
Fujisawa et al., "Acidic amino acid-rich sequences as binding sites of osteonectin to hydroxyapatite crystals," Biochim Biophys Acta. 1292:53-60 (1996).
Furbish et al., "Uptake and distribution of placental glucocerebrosidase in rat hepatic cells and effects of sequential deglycosylation," Biochim Biophys Acta. 673:425-434 (1981).
Halling Linder et al., "Glycosylation differences contribute to distinct catalytic properties among bone alkaline phosphotase isoforms," available in PMC Nov. 1, 2010, published in final edited form as: Bone. 45(5):987-993 (2009) (17 pages).
Hardy et al., "Dissection of a carboxy-terminal region of the yeast regulatory protein RAP1 with effects on both transcriptional activation and silencing," Mol Cell Biol. 12(3):1209-1217 (1992).
Hult et al., "Engineered enzymes for improved organic synthesis," Curr Opin Biotechnol. 14:395-400 (2003).
Hunter et al., "Modulation of crystal formation by bone phosphoproteins: structural specificity of the osteopontin-mediated inhibition of hydroxyapatite formation," Biochem J. 300:723-728 (1994).
Ikezawa, "Glycosylphosphatidylinositol (GPI)-anchored proteins," *Biol Pharm Bull.* 25(4):409-417 (2002).
International Search Report and Written Opinion for International Patent Application No. PCT/CA2005/000615, dated Aug. 18, 2005 (14 pages).
International Search Report and Written Opinion for International Patent Application No. PCT/CA2008/000923, dated Sep. 12, 2008 (11 pages).
International Search Report and Written Opinion for International Patent Application No. PCT/CA2011/050258, dated Jul. 29, 2011 (14 pages).
Kasugai et al., "Selective drug delivery system to bone: small peptide $(Asp)_6$ conjugation," J Bone Miner Res. 15(5):936-943 (2000).
Leone et al., "Allosteric modulation of pyrophosphatase activity of rat osseous plate alkaline phosphatase by magnesium ions," Int J Biochem Cell Biol. 30:89-97 (1998).
Meyer, "Can biological calcification occur in the presence of pyrophosphate?" Arch Biochem Biophys. 231:1-8 (1984).
Michigami et al., "Common mutations F310L and T1559del in the tissue-nonspecific alkaline phosphatase gene are related to distinct phenotypes in Japanese patients with hypophosphatasia," Eur J Pediatr. 164:277-282 (2005).
Moss et al., "Association of inorganic-pyrophosphatase activity with human alkaline-phosphatase preparations," Biochem J. 102:53-57 (1967).
Murshed et al., "Unique coexpression in osteoblasts of broadly expressed genes accounts for the spatial restriction of ECM mineralization to bone," Genes Dev. 19:1093-1104 (2005).
Narisawa et al., "Abnormal vitamin B6 metabolism in alkaline phosphatase knock-out mice causes multiple abnormalities, but not the impaired bone mineralization," J Pathol. 193:125-133 (2001).
Narisawa et al., "Inactivation of two mouse alkaline phosphatase genes and establishment of a model of infantile hypophosphatasia," Dev Dyn. 208:432-446 (1997).
NCBI Protein Database Accession No. NP_001622. Retrieved on Apr. 16, 2013 (3 pages).
NCBI Protein Database Accession No. NP_031457. Retrieved on Apr. 16, 2013 (3 pages).
NCBI Protein Database Accession No. NP_037191. Retrieved on Apr. 16, 2013 (3 pages).
NCBI Protein Database Accession No. NP_776412. Retrieved on Apr. 17, 2013 (2 pages).
NCBI Protein Database Accession No. NP_789828. Retrieved on Apr. 16, 2013 (3 pages).
NCBI Protein Database Accession No. P01857. Retrieved on Apr. 18, 2013 (7 pages).

(56) References Cited

OTHER PUBLICATIONS

NCBI Protein Database Accession No. Q6PYX1. Retrieved on Oct. 15, 2013 (2 pages).
Ngo et al., Computational complexity, protein structure prediction, and the levinthal paradox. *The Protein Folding Problem and Tertiary Structure Prediction.* Merz et al. (ed.), 433, 492-495 (1994).
Nishioka et al., "Enhancement of drug delivery to bone: characterization of human tissue-nonspecific alkaline phosphatase tagged with an acidic oligopeptide," Mol Genet Metab. 88:244-255 (2006).
Office Action for U.S. Appl. No. 11/111,664, dated Dec. 4, 2008 (7 pages).
Office Action for U.S. Appl. No. 11/111,664, dated May 14, 2008 (8 pages).
Office Action for U.S. Appl. No. 11/111,664, dated Oct. 4, 2007 (11 pages).
Office Action for U.S. Appl. No. 11/484,870, dated Aug. 11, 2009 (15 pages).
Office Action for U.S. Appl. No. 11/484,870, dated Feb. 2, 2009 (16 pages).
Office Action for U.S. Appl. No. 11/484,870, dated Jan. 25, 2007 (15 pages).
Office Action for U.S. Appl. No. 11/484,870, dated Jul. 5, 2007 (13 pages).
Office Action for U.S. Appl. No. 11/484,870, dated Jun. 25, 2008 (16 pages).
Office Action for U.S. Appl. No. 11/484,870, dated Oct. 1, 2007 (12 pages).
Office Action for U.S. Appl. No. 12/405,920, dated Aug. 9, 2010 (7 pages).
Office Action for U.S. Appl. No. 12/405,920, dated Dec. 17, 2009 (14 pages).
Office Action for U.S. Appl. No. 13/071,445, dated May 25, 2012 (14 pages).
Official Notification and Search Report for Eurasian Patent Application No. 201291138, dated May 17, 2013 (3 pages).
Patti et al., "Critical residues in the ligand-binding site of the *Staphylococcus aureus* collagen-binding adhesin (MSCRAMM)," J Biol Chem. 270(20):12005-12011 (1995).
Reply to Final Office Action for U.S. Appl. No. 13/071,445, dated Oct. 25, 2012 (14 pages).
Reply to Office Action for U.S. Appl. No. 11/111,664, dated Sep. 10, 2008 (32 pages).
Restriction Requirement for U.S. Appl. No. 12/599,679, dated Jun. 12, 2012 (5 pages).
Rezende et al., "Inorganic pyrophosphate-phosphohydrolytic activity associated with rat osseous plate alkaline phosphatase," Cell Mol Biol. 44(2):293-302 (1998).
Rowe et al., "MEPE, a new gene expressed in bone marrow and tumors causing osteomalacia," Genomics. 67:54-68 (2000).
Russell et al., "Inorganic pyrophosphate in plasma in normal persons and in patients with hypophosphatasia, osteogenesis imperfecta, and other disorders of bone," J Clin Invest. 50:961-969 (1971).
Sharom et al., "Glycosylphosphatidylinositol-anchored proteins: structure, function, and cleavage by phosphatidylinositol-specific phospholipase C," Biochem Cell Biol. 80:535-549 (2002).
Shull et al., "Enzyme replacement in a canine model of Hurler syndrome," Proc Natl Acad Sci USA. 91:12937-12941 (1994).
Spears et al., "Deoxyuridylate effects on thymidylate synthase-5-fluorodeoxyuridylate-folate ternary complex formation," Biochem Pharmacol. 38(18):2985-2993 (1989).
Stahl et al., "Evidence for receptor-mediated binding of glycoproteins, glycoconjugates, and lysosomal glycosidases by alveolar macrophages," Proc Natl Acad Sci USA. 75(3):1399-1403 (1978).
Extended European Search Report for European Application No. EP 08757088, date of completion Jun. 7, 2010 (6 pages).
Symersky et al., "Structure of the collagen-binding domain from a *Staphylococcus aureus* adhesin," Nat Struct Biol. 4(10):833-838 (1997).
Tomatsu, Declaration Under 37 C.F.R. § 1.132 for U.S. Appl. No. 11/484,870, dated Nov. 27, 2007 (2 pages).
Whyte, "Hypophosphatasia and the role of alkaline phosphatase in skeletal mineralization," Endocr Rev. 15(4):439-461 (1994).
Whyte, "Hypophosphatasia: Nature's window on alkaline phosphatase function in man," *Principles of Bone Biology*, 2nd ed., Bilezikian, Raisz, and Rodan. 2:1229-1248 (2002).
Yadav et al., "Dose response of bone-targeted enzyme replacement for murine hypophosphatasia," available in PMC Aug. 1, 2012, published in final edited form as: Bone. 49(2):250-6 (2011) (20 pages).
Yokogawa et al., "Selective delivery of estradiol to bone by aspartic acid oligopeptide and its effects on ovariectomized mice," Endocrinology. 142(3):1228-1233 (2001).
Young et al., "Structure, expression, and regulation of the major noncollagenous matrix proteins of bone," Clin Orthop Relat Res. 281:275-294 (1992).
Orimo, "The mechanism of mineralization and the role of alkaline phosphatase in health and disease," J Nippon Med Sch. 77(1):4-12 (2010).
Attwood, "The Babel of Bioinformatics," Genomics. 290(5491):471-3 (2000).
Skolnick et al., "From genes to protein structure and function: novel applications of computational approaches in the genomic era," Trends Biotechnol. 18(1):34-9 (2000).
Bocciardi et al., "Overexpression of the C-type natriuretic peptide (CNP) is associated with overgrowth and bone anomalies in an individual with balanced t(2;7) translocation," Hum Mutat. 28(7):724-731 (2007).
Brenner et al., "Diverse biological actions of atrial natriuretic peptide," Physiol Rev. 70(3):665-699 (1990).
Chen et al., "Gly369Cys mutation in mouse FGFR3 causes achondroplasia by affecting both chondrogenesis and osteogenesis," J Clin Invest. 104(11):1517-1525 (1999).
Chusho et al., "Dwarfism and early death in mice lacking C-type natriuretic peptide," Proc Natl Acad Sci USA. 98(7):4016-4021 (2001).
Daggubati et al., "Adrenomedullin, endothelin, neuropeptide Y, atrial, brain, and C-natriuretic prohormone peptides compared as early heart failure indicators," Cardiovasc Res. 36:246-255 (1997).
De Plater et al., "The natriuretic peptide (OVCNP-39) from platypus (*Ornithorhynchus anatinus*) venom relaxes the isolated rat uterus and promotes oedema and mast cell histamine release," Toxicon. 36(3):847-857 (1998).
Furuya et al., "Structural requirements of C-type natriuretic peptide for elevation of cyclic GMP in cultured vascular smooth muscle cells," Biochem Biophys Res Commun. 183(3):964-969 (1992).
Hagiwara et al., "Autocrine regulation of rat chondrocyte proliferation by natriuretic peptide C and its receptor, natriuretic peptide receptor-B," J Biol Chem. 269(14):10729-10733 (1994).
Hagiwara et al., "cGMP produced in response to ANP and CNP regulates proliferation and differentiation of osteoblastic cells," Am J Physiol. 270:C1311-C1318 (1996).
Horton et al., "Achondroplasia," Lancet. 370:162-172, 2007.
Inoue et al., "Four functionally distinct C-type natriuretic peptides found in fish reveal evolutionary history of the natriuretic peptide system," Proc Natl Acad Sci USA. 100(17):10079-10084 (2003).
International Search Report and Written Opinion for International Patent Application No. PCT/CA2011/050807, dated Apr. 13, 2012 (18 pages).
International Search Report for International Patent Application No. PCT/US2012/060869, dated Mar. 25, 2013 (5 pages).
Invitation to Pay Additional Fees for International Patent Application No. PCT/CA2011/050807, dated Feb. 13, 2012 (2 pages).
Kalra et al., "The role of C-type natriuretic peptide in cardiovascular medicine," Eur Heart J. 22:997-1007 (2001).
Lo et al., "High level expression and secretion of Fc-X fusion proteins in mammalian cells," Protein Eng. 11(6):495-500 (1998).
Mericq et al., "Regulation of fetal rat bone growth by C-type natriuretic peptide and cGMP," Pediatr Res. 47(2):189-193 (2000) (9 pages).
Miyazawa et al., "Cyclic GMP-dependent protein kinase II plays a critical role in C-type natriuretic peptide-mediated endochondral ossification," Endocrinology. 143(9):3604-3610 (2002).

(56) References Cited

OTHER PUBLICATIONS

Nakao et al., "The pharmacokinetics of alpha-human atrial natriuretic polypeptide in healthy subjects," Eur J Clin Pharmacol. 31:101-103 (1986).
NCBI Protein Database Accession No. XP_001109717. Retrieved on Apr. 17, 2013 (1 page).
Pfeifer et al., "Intestinal secretory defects and dwarfism in mice lacking cGMP-dependent protein kinase II," Science. 274:2082-2086 (1996).
Potter et al., "Natriuretic peptides, their receptors, and cyclic guanosine monophosphate-dependent signaling functions," Endocr Rev. 27(1):47-72 (2006).
Shukla et al., "RNA interference and inhibition of MEK-ERK signaling prevent abnormal skeletal phenotypes in a mouse model of craniosynostosis," Nat Genet. 39(9):1145-1150 (2007).
Suda et al., "C-type natriuretic peptide as an autocrine/paracrine regulator of osteoblast: evidence for possible presence of bone natriuretic peptide system," Biochem Biophys Res Commun. 223:1-6 (1996).
Takano et al., "Molecular evolution of shark C-type natriuretic peptides," Zoolog Sci. 11:451-454 (1994).
Tamura et al., "Critical roles of the guanylyl cyclase B receptor in endochondral ossification and development of female reproductive organs," Proc Natl Acad Sci USA. 101(49):17300-17305 (2004).
Teixeira et al., "Nitric oxide, C-type natriuretic peptide and cGMP as regulators of endochondral ossification," Dev Biol. 319:171-178 (2008).
Tsuji et al., "A loss-of-function mutation in natriuretic peptide receptor 2 (Npr2) gene is responsible for disproportionate dwarfism in cn/cn mouse," J Biol Chem. 280(14):14288-14292 (2005).
Wang et al., "Mice lacking Nf1 in osteochondroprogenitor cells display skeletal dysplasia similar to patients with neurofibromatosis type 1," Hum Mol Genet. 20(20):3910-3924 (2011).
Williams et al., "Solute transport in growth plate cartilage: In vitro and in vivo," Biophys J. 93(3):1039-1050 (2007).
Yasoda et al., "Natriuretic peptide regulation of endochondral ossification. Evidence for possible roles of the C-type natriuretic peptide/guanylyl cyclase-B pathway," J Biol Chem. 273(19):11695-11700 (1998).
Yasoda et al., "Systemic administration of C-type natriuretic peptide as a novel therapeutic strategy for skeletal dysplasias," Endocrinology. 150(7):3138-3144 (2009).
Yoder et al., "Reduced ability of C-type natriuretic peptide (CNP) to activate natriuretic peptide receptor B (NPR-B) causes dwarfism in lbab-/-mice," Peptides. 29(9):1575-1581 (2008).
Farnum et al., "In vivo delivery of fluoresceinated dextrans to the murine growth plate: imaging of three vascular routes by multiphoton microscopy," available in PMC Oct. 28, 2008, published in final edited form as: Anat Rec A Discov Mol Cell Evol Biol. 288(1):91-103 (2006) (22 pages).
Husain et al., "Fc site-specific labeling of immunoglobulins with calf intestinal alkaline phosphatase," Bioconjug Chem. 5(5):482-90 (1994).
Mayer, "Microbiology and immunology on-line: Immunoglobulins: structure and function" <http://pathmicro.med.sc.edu/mayer/IgStruct2000.htm>, University of South Carolina School of Medicine, 12 pages (2009).
Yasoda et al., "Overexpression of CNP in chondrocytes rescues achondroplasia through a MAPK-dependent pathway," Nat Med. 10(1):80-86 (2004).
EBI Blast for Accession No. ATD17216. Entered Oct. 16, 2008 (1 page).
Supplementary European Search Report for European Patent Application No. 11853820.6, dated Mar. 25, 2014 (3 pages).
International Preliminary Report on Patentability for International Patent Application No. PCT/US2012/060869, dated Apr. 22, 2014 (7 pages).
International Preliminary Report on Patentability for International Patent Application No. PCT/US2012/039004, dated Apr. 22, 2014 (8 pages).
Siris et al., "Paget's disease of bone," Trends Endocrinol Metab. 2(6):207-12 (1991).
European Search Report for European Patent Application No. 12842640.0, dated Mar. 13, 2015 (7 pages).
Lee et al., "Disturbed osteoblastic differentiation of fibrous hamartoma cell from congenital pseudarthrosis of the tibia associated with neurofibromatosis type I," Clin Orthop Surg. 3(3):230-7 (2011).
Schindeler et al., "Modeling bone morphogenetic protein and bisphosphonate combination therapy in wild-type and Nf1 haploinsufficient mice," J Orthop Res. 26(1):65-74 (2008).
Nahabet et al., "Postnatal Pancraniosynostosis in a Patient With Infantile Hypophosphatasia," Cleft Palate Craniofac J. 53(6):741-4 (2016).
International Search Report and Written Opinion for International Patent Application No. PCT/US2015/058498, dated Jan. 22, 2016 (12 pages).
Kosnik-Infinger et al., "Enzyme replacement therapy for congenital hypophosphatasia allows for surgical treatment of related complex craniosynostosis: a case series," Neurosurg Focus. 38(5):E10 (2015) (8 pages).
Mornet et al., "Identification of fifteen novel mutations in the tissue-nonspecific alkaline phosphatase (TNSALP) gene in European patients with severe hypophosphatasia," Eur J Hum Genet. 6(4):308-14 (1998).
Alexion Pharma International, "Strensiq Product Monograph," <http://alexionpharma.ca/documents/Strensiq-PM-asfotase-alfa-14Aug2015.aspx>, Prepared Aug. 14, 2015 (32 pages).
Madson et al., "Asfotase alfa: sustained efficacy and tolerability in children with hypophosphatasia treated for 5 years," ESPE Abstracts. 84:FC2.4 (2015) (2 pages).
International Search Report and Written Opinion for International Patent Application No. PCT/US2016/025721, dated Aug. 17, 2016 (18 pages).
Invitation to Pay Additional Fees for International Patent Application No. PCT/US2016/015366, dated Jun. 1, 2016 (7 pages).
Phillips et al., "A modified performance-oriented mobility assessment tool for assessing clinically relevant gait impairments and change in children with hypophosphatasia: development and validation," Bone Abstracts. 4 P136 (2015).
Highlights of Prescribing Information for Strensiq™, Alexion Pharmaceuticals, Inc., available <http://www.alexion.com/Documents/strensiq_pi-10-2015.aspx>, 2015 (19 pages).
Phillips et al., "Gait assessment in children with childhood hypophosphatasia: impairments in muscle strength and physical function," The Endocrine Society's 97th Annual Meeting & Expo, Mar. 5-8, 2015, San Diego, California (2 pages).
"View of NCT02235493 on Nov. 19, 2015," ClinicalTrials.gov archive, Nov. 19, 2015 (4 pages).
Hofmann et al., "Improvement in bone manifestations and respiratory status in infants and young children with HPP treated with asfotase alfa: an update on the ENB-010-10 trial," 7th International Conference on Children's Bone Health, Jun. 27-30, Austria, Salzburg. Bone Abstracts. 4: OC18 (2015) (3 pages).
Epps, "Application No. 125513Orig1s000 Medical Review(s)," Center for Drug Evaluation and Research, <http://www.accessdata.fda.gov/drugsatfda_docs/nda/2015/125513Orig1s000MedR.pdf>, Oct. 20, 2015 (254 pages).
International Search Report and Written Opinion for International Patent Application No. PCT/US2016/039595, dated Feb. 21, 2017 (16 pages).
Liu et al., "Tissue-nonspecific alkaline phosphatase deficiency causes abnormal craniofacial bone development in the Alpl(-/-) mouse model of infantile hypophosphatasia," available in PMC Oct. 1, 2015, published in final edited form as: Bone. 67:81-94 (2014) (30 pages).
Appeal Brief as Filed in U.S. Appl. No. 12/638,527, dated Oct. 9, 2015 (101 pages).
Reply Brief as Filed in U.S. Appl. No. 12/638,527, dated Apr. 22, 2016 (4 pages).
Examiner's Answer to Appeal Brief for U.S. Appl. No. 12/638,527, dated Feb. 23, 2016 (9 pages).
Phillips et al., "Significantly improved muscle strength, running speed, and agility in children with hypophosphatasia treated with

(56) References Cited

OTHER PUBLICATIONS asfotase alfa," Endocrine Society's 97th Annual Meeting and Expo, Mar. 5-8, San Diego, CA. Abstract OR29-4 (2015) (2 pages).

Millán et al., "Alkaline phosphatase and hypophosphatasia," Calcif Tissue Int. 98(4):398-416 (2016).

Kishnani et al., "Biochemical and physical function outcomes in adolescents and adults with hypophosphatasia treated with asfotase alfa for up to 4 years: interim results from a phase II study," Endocrine Society's 98th Annual Meeting and Expo, Apr. 1-4, Boston, MA. Abstract OR26-3 (2016) (2 pages).

International Search Report and Written Opinion for International Patent Application No. PCT/US2017/025590, dated Jun. 29, 2017 (18 pages).

Iqbal et al., "Recurrent Metatarsal Fractures in Postmenopausal Woman With Low Serum Alkaline Phosphatase: A Rare Diagnosis Not to Miss," J Investig Med High Impact Case Rep. 5(3):1-3 (2017).

Ahn et al., "Idiopathic calcium pyrophosphate dihydrate (CPPD) crystal deposition disease in a young male patient: a case report," J Korean Med Sci. 18(6):917-20 (2003).

Cahill et al., "Infantile hypophosphatasia: transplantation therapy trial using bone fragments and cultured osteoblasts,"J. Clin Endocrinol Metab. 92(8): 2923-30 (2007).

Glass et al., "The infant skull: a vault of information," Radiographics. 24(2):507-22 (2004).

Herasse et al., "Molecular study of three cases of odontohypophosphatasia resulting from heterozygosity for mutations in the tissue non-specific alkaline phosphatase gene," J Med Genet. 40(8):605-9 (2003).

Ishida et al., "Tissue-nonspecific alkaline phosphatase with an Asp(289)—>Val mutation fails to reach the cell surface and undergoes proteasome-mediated degradation," J Biochem. 134(1):63-70 (2003).

Mornet, "Hypophosphatasia," Orphanet J Rare Dis. 2:(40) (2007) (8 pages).

Spentchian et al., "Severe hypophosphatasia: characterization of fifteen novel mutations in the ALPL gene," Hum Mutat. 22(1) (2003) (5 pages).

Takinami et al., "The mutant (F310L and V365I) tissue-nonspecific alkaline phosphatase gene from hypophosphatasia," J Med Dent Sci. 51(1):67-74 (2004).

Sawai et al., "Severe perinatal hypophosphatasia due to homozygous deletion of T at nucleotide 1559 in the tissue nonspecific alkaline phosphatase gene,". Prenat Diagn. 23(9):743-6 (2003).

Wickramasinghe et al., "A case of hypophosphatasia," Ceylon Med J. 48(3):94-5 (2003).

Yamamoto et al., "A successful treatment with pyridoxal phosphate for West syndrome in hypophosphatasia," Pediatr Neurol. 30(3):216-8 (2004).

International Preliminary Report on Patentability for International Patent Application No. PCT/US2016/015366, dated Aug. 10, 2017 (10 pages).

International Search Report and Written Opinion for International Patent Application No. PCT/US2017/047527, dated Nov. 6, 2017 (10 pages).

Millán et al., "Hypophosphatasia—pathophysiology and treatment," available in PMC Sep. 22, 2014, published in final edited form as: Actual Osteol. 8(3):164-182 (2012) (21 pages).

Padidela et al., "P1-118: Management of Tracheobronchomalacia During Asfotase Alfa Treatment in Infants with Perinatal-Onset Hypophosphatasia: A Case Series," European Society for Paediatric Endocrinology (ESPE), Paris, France, Sep. 10-12, 2016 (1 page).

Mornet et al., "Structural evidence for a functional role of human tissue nonspecific alkaline phosphatase in bone mineralization," J Biol Chem. 276(33):31171-8 (2001).

Bhattacharyya et al., "Hypophosphatasia and the risk of atypical femur fractures: a case-control study," BMC Muscoloskelet Disord. 17:332 (2016) (4 pages).

Bishop, "Asfotase alfa for hypophosphatasia," Horizon Scanning Centre. National Institute for Health Research, http://www.hsric.nihr.ac.uk/topics/asfotase-alfa-for-hypophosphatasia/download, retrieved Oct. 20, 2013 (9 pages).

Bishop et al., "Transformative therapy in hypophosphatasia," Arch Dis Child. 101(6):514-5 (2016).

Bishop, "Clinical management of hypophosphatasia," Clin Cases Miner Bone Metab. 12(2):170-3 (2015).

Durussel et al., "Bone mineralization-dependent craniosynostosis and craniofacial shape abnormalities in the mouse model of infantile hypophosphatasia," Dev Dyn. 245(2):175-82 (2016).

Braunstein, "Multiple fractures, pain, and severe disability in a patient with adult-onset hypophosphatasia," Bone Rep. 4:1-4 (2015).

Bloch-Zupan, "Hypophosphatasia: diagnosis and clinical signs—a dental surgeon perspective," Int J Paediatr Dent. 26(6):426-438 (2016).

Kishnani et al., "Monitoring guidance for patients with hypophosphatasia treated with asfotase alfa," Mol Genet Metab. 122(1-2):4-17 (2017).

Güzel et al., "Pyridoxine-responsive seizures in infantile hypophosphatasia and a novel homozygous mutation in ALPL gene," J Clin Res Pediatr Endocrinol. 8(3):360-4 (2016).

Gasque et al., "Improvement of the skeletal and dental hypophosphatasia phenotype in Alpl-/-mice by administration of soluble (non-targeted) chimeric alkaline phosphatase," Available in PMC Mar. 1, 2016, published in final edited form as: Bone. 72:137-147 (2015) (25 pages).

Fodor et al., "Differencial diagnosis of the low alkaline phosphatase activities," Orv Hetil. 158(26):1003-1007 (2017) (Article in Hungarian) (English Abstract included).

McKiernan et al., "Clinical and radiographic findings in adults with persistent hypophosphatasemia," J Bone Miner Res. 29(7):1651-60 (2014).

Martos-Moreno et al., "Hypophosphatasia: clinical manifestations, diagnostic recommendations and therapeutic options," An Pediatr (Barc). S1695-4033(17)30223-0 (2017) (11 pages) (Article in Spanish) (English Abstract included).

Kulikova et al., "Hypophosphatasia: the clinical description of 3 cases of the disease with the molecular-genetic verification of the diagnosis," Problems of Endocrinology. 61(3):37-42 (2015) (Article in Russian) (English Abstract included).

Orimo, "Pathophysiology of hypophosphatasia and the potential role of asfotase alfa," Ther Clin Risk Manag. 12:777-86 (2016).

Morrow, "Expensive new biologic helps children fight hypophosphatasia," Manag Care. 24(12) (2015) (7 pages).

Mornet et al., "Hypophosphatasia," GeneReviews. https://www.ncbi.nlm.nih.gov/books/NBK1150/, retrieved Dec. 6, 2017, initially published Nov. 20, 2007, last updated Feb. 4, 2016 (25 pages).

Mori et al., "Case series: odontohypophosphatasia or missed diagnosis of childhood/adult-onset hypophosphatasia?—Call for a long-term follow-up of premature loss of primary teeth," Bone Rep. 5:228-232 (2016).

Remde et al., "Successful asfotase alfa treatment in an adult dialysis patient with childhood-onset hypophosphatasia," J Endoc Soc. 1(9):1188-93 (2017).

Panesar, "Hypophosphatasia: a rare disorder," US Pharm. 42(5) (2017) (8 pages).

Padidela et al., "Enzyme-replacement therapy in life-threatening perinatal hypophosphatasia in a premature infant," Endocrine Abstracts. 33:P9 (2013) (1 page).

Sotillo et al., "Signs and symptoms of hypophosphatasia," Dimensions of Dental Hygiene. 15(4):44-47 (2017) (6 pages).

Simm et al., "Successful use of enzyme replacement therapy in infantile hypophosphatasia," J Paediatr Child Health. 53(9):925-926 (2017).

Sheikh et al., "A newborn with no bones: neonatal hypophosphatasia with respiratory distress," J Pediatr. 188:306 (2017).

Saglam et al., "Clinical and genetic findings of Turkish hypophosphatasia cases," J Clin Res Pediatr Endocrinol. 9(3):229-236 (2017).

Whyte et al., "Asfotase alfa treatment improves survival for perinatal and infantile hypophosphatasia," J Clin Endocrinol Metab. 101(1):334-42 (2016) (17 pages).

(56) References Cited

OTHER PUBLICATIONS

Wang et al., "Current concepts in odontohypophosphatasia form of hypophosphatasia and report of two cases," BMC Oral Health. 16(1):70 (2016) (8 pages).
Taketani et al., "Ex vivo expanded allogeneic mesenchymal stem cells with bone marrow transplantation improved osteogenesis in infants with severe hypophosphatasia," Cell Transplant. 24(10):1931-43 (2015).
Belachew et al., "Infantile hypophosphatasia secondary to a novel compound heterozygous mutation presenting with pyridoxine-responsive seizures," JIMD Rep. 11:17-24 (2013).
Whyte et al., "Asfotase alfa therapy for children with hypophosphatasia," JCI Insight. 1(9):e85971 (2016) (11 pages).
Whyte, "Hypophosphatasia: enzyme replacement therapy brings new opportunities and new challenges," J Bone Miner Res. 32(4):667-675 (2017).
Alexion Third Quarter 2017 Earnings Call, "http://files.shareholder.com/downloads/ALXN/5636824573x0x961197/3B361D6E-80E2-463E-B0E5-3EAD7FC5B9D0/Alexion_Q3_2017_Earnings_Slides.pdf" (43 pages).
Urlaub et al., "Isolation of Chinese hamster cell mutants deficient in dihydrofolate reductase activity," Proc Natl Acad Sci U S A. 77(7):4216-20 (1980).
Graham et al., "Characteristics of a human cell line transformed by DNA from human adenovirus type 5," J Gen Virol. 36(1):59-72 (1977).
Mather, "Establishment and characterization of two distinct mouse testicular epithelial cell lines," Biol Reprod. 23(1):243-52 (1980).
Le Du et al., "Crystal structure of alkaline phosphatase from human placenta at 1.8 A resolution. Implication for a substrate specificity," J Biol Chem. 276(12):9158-65 (2001) (9 pages).
Stec et al., "A revised mechanism for the alkaline phosphatase reaction involving three metal ions," J Mol Biol. 299(5):1303-11 (2000).
Alexion, "Highlights of Prescribing Information" for Strensiq®, 2018 (8 pages).
European Collection of Authenticated Cell Cultures (ECACC) Accession No. 85110503. Retrieved May 2, 2018 (3 pages).
UniProtKB Accession No. P05186. Retrieved May 2, 2018 (19 pages).
UniProtKB Accession No. P01857. Retrieved May 2, 2018 (13 pages).
Belkhouribchia et al., "Case Report: Osteomalacia with low alkaline phosphatase: a not so rare condition with important consequences," BMJ Case Rep. doi: 10.1136/bcr-2015-212827 (2016) (4 pages).
Berkseth et al., "Clinical spectrum of hypophosphatasia diagnosed in adults," Bone. 54(1):21-7 (2013).
Bianchi, "Hypophosphatasia: an overview of the disease and its treatment," Osteoporos Int. 26(12):2743-57; DOI 10.1007/s00198-015-3272-1 (2015) (15 pages).
Bobryshev et al., "Role of bone-type tissue-nonspecific alkaline phosphatase and PHOSPO1 in vascular calcification," Curr Pharm Des. 20(37):5821-8 (2014).
Bowden et al., "Asfotase alfa treatment for 1 year in a 16 year-old male with severe childhood hypophosphatasia," Osteoporos Int. 29(2):511-5; DOI: 10.1007/s00198-017-4267-x (2018) (5 pages).
Briot et al., "Adult hypophosphatasia," Curr Opin Rheumatol. 28(4):448-51 (2016).
Buchet et al., "Multisystemic functions of alkaline phosphatases," Methods Mol Biol. 1053:27-51 (2013).
Deeb et al., "Could alerting physicians for low alkaline phosphatase levels be helpful in early diagnosis of hypophosphatasia?," J Clin Res Pediatr Endocrinol. 10(1):19-24 (2018).
Hofmann et al., "Recombinant enzyme replacement therapy in hypophosphatasia," Subcell Biochem. 76:323-41 (2015).
Hofmann et al., "Asfotase alfa: enzyme replacement for the treatment of bone disease in hypophosphatasia," Drugs Today (Barc). 52(5):271-85 (2016).

Kitaoka et al., "Safety and efficacy of treatment with asfotase alfa in patients with hypophosphatasia: results from a Japanese clinical trial," Clin Endocrinol (Oxf). 87(1):10-19 (epub pp. 1-10) (2017).
Linglart et al., "Hypophosphatasia," Curr Osteoporos Rep. 14(3):95-105; DOI 10.1007/s11914-016-0309-0 (2016) (11 pages).
Mornet, "Hypophosphatasia," Metabolism. 82:142-155; DOI: 10.1016/j.metabol.2017.08.013 (2018) (30 pages).
Mornet, "Molecular genetics of hypophosphatasia and phenotype-genotype correlations," Subcell Biochem. 76:25-43 (2015).
Okazaki et al., "Lethal hypophosphatasia successfully treated with enzyme replacement from day 1 after birth," Eur J Pediatr. 175(3):433-7; DOI 10.1007/s00431-015-2641-2 (2016) (5 pages).
Park et al., "First Korean case of infantile hypophosphatasia with novel mutation in ALPL and literature review," Ann Clin Lab Sci. 46(3):302-7 (2016).
Phillips et al., "Physical therapy management of infants and children with hypophosphatasia," Mol Genet Metab. 119(1-2):14-9 (2016).
Rockman-Greenberg, "Hypophosphatasia," Pediatr Endocrinol Rev. 10 Suppl 2:380-8 (2013) (Abstract only).
Rodriguez et al., "Respiratory mechanics in an infant with perinatal lethal hypophosphatasia treated with human recombinant enzyme replacement therapy," Pediatr Pulmonol. 47(9):917-22 (2012).
Saraff et al., "A diagnostic algorithm for children with low alkaline phosphatase activities: lessons learned from laboratory screening for hypophosphatasia," J Pediatr. 172:181-6 (2016) (7 pages).
Sather, "008-case study: 3 year old female with hypophosphatasia, treated with asfotase alfa replacement," Journal of Pediatric Nursing. 34:104 (2017).
Schmidt et al., "Hypophosphatasia: What is currently available for treatment?" Internist (Berl). 57(12):1145-1154 (2016) (Article in German) (English abstract).
Schmidt et al., "Clinical, radiographic and biochemical characteristics of adult hypophosphatasia," Osteoporos Int. 28(9):2653-2662 (2017).
Scott, "Asfotase alfa in perinatal/infantile-onset and juvenile-onset hypophosphatasia: a guide to its use in the USA," BioDrugs. 30(1):41-8 (2016).
Scott, "Asfotase alfa: a review in paediatric-onset hypophosphatasia," Drugs. 76(2):255-62 (2016).
Shapiro et al., "Hypophosphatasia in adults: clinical assessment and treatment considerations," J Bone Miner Res. 32(10):1977-1980 (2017).
Siller et al., "Alkaline phosphatase: discovery and naming of our favorite enzyme," J Bone Miner Res. 33(2):362-4 (2018).
Takahashi et al., "Parental serum alkaline phosphatase activity as an auxiliary tool for prenatal diagnosis of hypophosphatasia," Prenat Diagn. 37(5):491-6 (2017).
Tenorio et al., "Molecular and clinical analysis of ALPL in a cohort of patients with suspicion of hypophosphatasia," Am J Med Genet A. 173(3):601-10 (2017).
Tsiantouli et al., "Hypophosphatasia," Rev Med Suisse. 13(559):855-8 (2017) (Article in French) (English Abstract Included).
Weber et al., "Burden of disease in adult patients with hypophosphatasia: Results from two patient-reported surveys," Metabolism. 65(10):1522-30 (2016).
Whyte, "Hypophosphatasia—aetiology, nosology, pathogenesis, diagnosis and treatment," Nat Rev Endocrinol. 12(4):233-46 (2016).
Whyte, "Hypophosphatasia: an overview for 2017," Bone. 102:15-25 (2017).
Whyte et al., "Hypophosphatasia: natural history study of 101 affected children investigated at one research center," Bone. 93:125-138 (2016).
Whyte et al., "Hypophosphatasia: validation and expansion of the clinical nosology for children from 25 years experience with 173 pediatric patients," Bone. 75:229-39 (2015).
Seefried et al., "Pharmacodynamic results from a phase 2a, randomized, multicenter, open-label, dose-ranging study of asfotase alfa in adults with pediatric hypophosphatasia," 100th Annual Meeting and Expo of the Endocrine Society, Mar. 17-20, 2018, Chicago, IL. (1 page).

(56) References Cited

OTHER PUBLICATIONS

International Search Report and Written Opinion for International Patent Application No. PCT/US2018/020859, dated Jun. 19, 2018 (14 pages).

López-Delgado et al., "Abnormal bone turnover in individuals with low serum alkaline phosphatase," Osteoporosis Int. 29(9):2147-2150; doi: 10.1007/s00198-018-4571-0 (Supplementary information included) (2018) (6 pages).

Matsumoto et al., "Rescue of severe infantile hypophosphatasia mice by AAV-mediated sustained expression of soluble alkaline phosphatase," Hum Gene Ther. 22(11):1355-64 (2011).

Hofmann et al., "Clinical aspects of hypophosphatasia: an update," Clinic Rev Bone Miner Metab. 11(2):60-70 (2013).

Taketani et al., "Clinical and genetic aspects of hypophosphatasia in Japanese patients," Arch Dis Child. 99(3):211-5 (2014) (6 pages).

Whyte, "Physiological role of alkaline phosphatase explored in hypophosphatasia," Ann N Y Acad Sci. 1192:190-200 (2010).

Hofmann et al., "Compound heterozygosity of two functional null mutations in the ALPL gene associated with deleterious neurological outcome in an infant with hypophosphatasia," Bone. 55:150-7 (2013).

De Roo et al., "Infantile hypophosphatasia without bone deformities presenting with severe pyridoxine-resistant seizures," Molecular Genetics and Metabolism 111(3):404-7 (2014).

International Search Report and Written Opinion for International Patent Application No. PCT/US2015/064003, dated Mar. 31, 2016 (13 pages).

Lazdunski et al., "Structure-function relationships for some metalloalkaline phosphatases of E. coli," Eur J Biochem. 8(4):510-7 (1969).

Bobyr et al., "High-resolution analysis of Zn(2+) coordination in the alkaline phosphatase superfamily by EXAFS and x-ray crystallography," J Mol Biol. 415(1):102-17 (2012).

International Search Report and Written Opinion for International Patent Application No. PCT/US2017/036133, dated Aug. 24, 2017 (10 pages).

International Search Report and Written Opinion for International Patent Application No. PCT/US2018/025206, dated Jul. 3, 2018 (25 pages).

Kishnani et al., "OR26-3 Biochemical and Physical Function Outcomes in Adolescents and Adults with Hypophosphatasia Treated with Asfotase Alfa for up to 4 Years: Interim Results from a Phase II Study," ENDO 2016, Boston, MA, Apr. 3, 2016 (22 pages).

International Search Report and Written Opinion for International Patent Application No. PCT/US2017/025618, dated Jul. 11, 2017 (22 pages).

Li et al., "Standard reference for the six-minute-walk test in healthy children aged 7 to 16 years," Am J Respir Crit Care Med. 176(2):174-80 (2007).

Park et al., "Ex vivo assessment of contractility, fatigability and alternans in isolated skeletal muscles," J Vis Exp. 69:e4198 (2012) (8 pages).

Phillips et al., "FRI-224: Improved activities of daily living and physical function, with decreased pain, in children with hypophosphatasia treated for three years with asfotase alfa: results from the childhood health assessment questionnaire and the pediatric outcomes data collection instrument," The Endocrine Society's 97th Annual Meeting & Expo, San Diego, California, Mar. 5-8, 2015 (1 page).

Whyte et al., "Hypophosphatasia: Enzyme replacement therapy (asfotase alfa) decreases TNSALP substrate accumulation and improves functional outcomes in affected adolescents and adults," Bull Group Int Rech Sci Stomatol Odontol. 51(1):35 (2012).

Sugano et al., "Successful gene therapy in utero for lethal murine hypophosphatasia," Hum Gene Ther. 23(4):399-406 (2012).

International Search Report and Written Opinion for International Patent Application No. PCT/US2015/039973, dated Oct. 5, 2015 (12 pages).

Johnson et al., "Motor proficiency in children with neurofibromatosis type 1," Pediatr Phys Ther. 22(4):344-8 (2010).

Gates et al., "Effects of age, sex, and comorbidities on the pediatric outcomes data collection instrument (PODCI) in the general population," J Pediatr Orthop. 35(2):203-9 (2015).

International Search Report and Written Opinion for International Patent Application No. PCT/US2016/049983, dated Nov. 29, 2016 (12 pages).

International Search Report and Written Opinion for International Patent Application No. PCT/US2016/015366, dated Aug. 9, 2016 (14 pages).

Extended European Search Report for European Application No. 18173111.8, dated Aug. 21, 2018 (9 pages).

"Highly Specialised Technology Evaluation: Asfotase alfa for treating paediatric-onset hypophosphatasia [ID 758]," Oct. 21, 2015, <https://www.nice.org.uk/guidance/hst6/documents/committee-papers-8>, (99 pages).

Tomazos et al., "Determination of the Minimal Clinically Important Difference in the Six-Minute Walk Test for Patients with Hypophosphatasia," European Society for Paediatric Endocrinology, 55th Annual ESPE, Paris, France, Sep. 10-12, 2016, <http://abstracts.eurospe.org/hrp/0086/hrp0086FC2.5.htm>, (4 pages).

International Search Report and Written Opinion for International Application No. PCT/US18/26868, dated Sep. 7, 2018 (30 pages).

Agochukwu et al., "Hearing loss in syndromic craniosynostoses: Introduction and consideration of mechanisms," available in PMC Aug. 13, 2014, published in final edited form as: Am J Audiol. 23(2):135-41 (2014) (13 pages).

Anderson, "Mechanism of Mineral Formation in Bone," *Pathology Reviews.* Emanuel Rubin and Ivan Damjanov (eds.), 13-23 (1990).

Balasubramaniam et al., "Perinatal hypophosphatasia presenting as neonatal epileptic encephalopathy with abnormal neurotransmitter metabolism secondary to reduced co-factor pyridoxal-5'-phosphate availability," J Inherit Metab Dis. 33(Suppl 3):S25-33 (2010).

Barcia et al., "Infantile hypophosphatasia: treatment options to control hypercalcemia, hypercalciuria, and chronic bone demineralization," J Pediatr. 130(5):825-8 (1997).

Barvencik et al., "Skeletal mineralization defects in adult hypophosphatasia—a clinical and histological analysis," Osteoporosis Int. 22(10):2667-75 (2011).

Baumgartner-Sigl et al., "Pyridoxine-responsive seizures as the first symptom of infantile hypophosphatasia caused by two novel missense mutations (c.677T>C, p.M226T; c.1112C>T, p.T371I) of the tissue-nonspecific alkaline phosphatase gene," Bone. 40(6):1655-61 (2007).

Beck et al., "Whole-body MRI in the childhood form of hypophosphatasia," Rheumatol Int. 31(10):1315-20 (2011).

Beederman et al., "Molecular basis of cranial suture biology and disease: osteoblastic and osteoclastic perspectives," Genes Dis. 1(1):120-5 (2014).

Boulet et al., "A population-based study of craniosynostosis in metropolitan Atlanta, 1989-2003," Am J Med Genet A. 146A(8):984-91 (2008).

Chan et al., "Endoscope-assisted versus open repair of craniosynostosis: a comparison of perioperative cost and risk," J Craniofac Surg. 24(1):170-4 (2013).

Choi et al., "Craniosynostosis in growing children: pathophysiological changes and neurosurgical problems," J Korean Neurosurg Soc. 59(3):197-203 (2016).

Chong et al., "Minimally invasive suturectomy and postoperative helmet therapy: advantages and limitations," J Korean Neurosurg Soc. 59(3):227-32 (2016).

Clarke, "Normal bone anatomy and physiology," Clin J Am Soc Nephrol. 3(Suppl 3):S131-9 (2008).

Colantonio et al., "Closing the gaps in pediatric laboratory reference intervals: a CALIPER database of 40 biochemical markers in a healthy and multiethnic population of children," Clin Chem. 58(5):854-68 (2012).

Collmann et al., "Neurosurgical aspects of childhood hypophosphatasia," Childs Nerv Syst. 25(2):217-23 (2009).

Communication pursuant to Rule 164(2)(b) and Article 94(3) EPC for European Application No. 16707571.2, dated Feb. 26, 2019 (12 pages).

(56) References Cited

OTHER PUBLICATIONS

Czerwinski et al., "Major morbidity and mortality rates in craniofacial surgery: an analysis of 8101 major procedures," Plast Reconstr Surg. 126(1):181-6 (2010).
Del Angel et al., "Birth prevalence estimation of severe Hypophosphatasia in European populations using large-scale protein-coding genetic variation databases," American Society of Human Genetics 66th Annual Meeting, Oct. 18-22, Vancouver, Canada. Poster abstract 1670T (2016) (2 pages).
Di Rocco et al., "Craniosynostosis and hypophosphatasia," Arch Pediatr. 24(5S2):5S89-5S92 (2017).
Eade et al., "Pyrophosphate arthropathy in hypophosphatasia," Ann Rheum Dis. 40(2):164-70 (1981).
Esparza et al., "Complications in the surgical treatment of craniosynostosis and craniofacial syndromes: apropos of 306 transcranial procedures," Childs Nerv Syst. 24(12):1421-30 (2008).
Esparza et al., "Surgical treatment of isolated and syndromic craniosynostosis. Results and complications in 283 consecutive cases," Neurocirugía. 19(6):509-29 (2008).
Fong et al., "Hypocalcemia: Updates in diagnosis and management for primary care," Can Fam Physician. 58(2):158-62 (2012).
Fraser, "Hypophosphatasia," Am J Med. 22(5):730-46 (1957).
Garber et al., "Comparing outcomes and cost of 3 surgical treatments for sagittal synostosis: a retrospective study including procedure-related cost analysis," Neurosurgery. 81(4):680-7 (2017).
Ginelliová et al., "Sudden death associated with syndromic craniosynostosis," Forensic Sci Med Pathol. 12(4):506-9 (2016).
Greenwood et al., "Familial incidence and associated symptoms in a population of individuals with nonsyndromic craniosynostosis," Genet Med. 16(4):302-10 (2014).
Guañabens et al., "Calcific periarthritis as the only clinical manifestation of hypophosphatasia in middle-aged sisters," J Bone Miner Res. 29(4):929-34 (2014).
Herring, "Mechanical influences on suture development and patency," Front Oral Biol. 12:41-56 (2008).
Hollis et al., "Current concepts in hypophosphatasia: case report and literature review," Int J Paediatr Dent. 23(3):153-9 (2013).
Hwang et al., "Update of diagnostic evaluation of craniosynostosis with a focus on pediatric systematic evaluation and genetic studies," J Korean Neurosurg Soc. 59(3):214-218 (2016).
Johnson et al., "Craniosynostosis," Eur J Hum Genet. 19(4):369-376 (2011).
Kabbani et al., "Craniosynostosis," Am Fam Physician. 69(12):2863-2870 (2004).
Kajdic et al., "Craniosynostosis—Recognition, clinical characteristics, and treatment," Bosn J Basic Med Sci. 18(2):110-116 (2018).
Katsianou et al., "Signaling mechanisms implicated in cranial sutures pathophysiology: Craniosynostosis," BBA Clin. 6:165-176 (2016).
Khanna et al., "Pictorial essay: the many faces of craniosynostosis," Indian J Radiol J. 21(1):49-56 (2011).
Kim et al., "Craniosynostosis: Updates in radiologic diagnosis," J Korean Neurosurg Soc. 59(3):219-226 (2016).
Kozlowski et al., "Hypophosphatasia. Review of 24 Cases," Pediatr Radiol. 5(2):103-117 (1976) (15 pages).
Krakow et al., "Clinical and radiographic delineation of bent bone dysplasia-FGFR2 type or bent bone dysplasia with distinctive clavicles and angel-shaped phalanges," Am J Med Genet A. 170(10):2652-2661 (2016).
Makras et al., "Medical treatment of Hypercalcaemia," Hormones. 8(2):83-95 (2009).
Mathijssen, "Guideline for care of patients with the diagnoses of craniosynostosis: working group on craniosynostosis," J Craniofac Surg. 26(6):1735-1807 (2015).
Merrill et al., "Bent bone dysplasia-FGFR2 type, a distinct skeletal disorder, has deficient canonical FGF signaling," Am J Hum Genet. 90(3):550-557 (2012).
Miller et al., "Ultrasound diagnosis of craniosynostosis," Cleft Palate Craniofac J. 39(1):73-80 (2002).

Millichap, "Cognitive Development of Children with Craniosynostosis," Pediatr Neurol Briefs. 29(6):47 (2015).
Millán, "The role of phosphatases in the initiation of skeletal mineralization," Calcif Tissue Int. 93(4):299-306 (2013).
Mohn et al., "Hypophosphatasia in a child with widened anterior fontanelle: lessons learned from late diagnosis and incorrect treatment," Acta Paediatr. 100(7):e43-6 (2011).
Mornet et al., "A molecular-based estimation of the prevalence of hypophosphatasia in the European population," Ann Hum Genet. 75(3):439-445 (2011).
Mornet, "Hypophosphatasia," Best Pract Res Clin Rheumatol. 22(1):113-127 (2008).
Nakamura-Utsunomiya et al., "Clinical characteristics of perinatal lethal hypophosphatasia: a report of 6 cases," Clin Pediatr Endocrinol. 19(1):7-13 (2010).
Oginni et al., "Radiological and biochemical resolution of nutritional rickets with calcium," Arch Dis Child. 88(9):812-817 (2003).
Opperman, "Cranial sutures as intramembranous bone growth sites," Dev Dyn. 219(4):472-485 (2000).
Reginato et al., "Musculoskeletal manifestations of osteomalacia and rickets," Best Pract Res Clin Rheumatol. 17(6):1063-1080 (2003).
Rockman-Greenberg et al., "Hypophosphatasia: Enzyme Replacement with ENB-0040, a Bone-Targeted Human Recombinant Tissue Nonspecific Alkaline Phosphatase (TNSALP) Fusion Protein," American College of Medical Genetics, 16th Annual Clinical Genetics Meeting, Mar. 25-29, Tampa, Florida (2009) (1 page).
Rodgers et al., "Spring-assisted cranioplasty for the correction of non-syndromic scaphocephaly: a quantitative analysis of 100 consecutive cases," Plast Reconstr Surg. 140(1):125-134 (2017).
Rottgers et al., "Outcomes of endoscopic suturectomy with post-operative helmet therapy in bilateral coronal craniosynostosis," J Neurosurg Pediatr. 18(3):281-286 (2016).
Rozovsky et al., "Cranial ultrasound as a first-line imaging examination for craniosynostosis," Pediatrics. 137(2):e20152230 (2016) (9 pages).
Sabbagh et al., "Hypophosphatemia leads to rickets by impairing caspase-mediated apoptosis of hypertrophic chondrocytes," Proc Natl Acad Sci U S A. 102(27):9637-9642 (2005).
Sakamoto et al., "Physiological changes and clinical implications of syndromic craniosynostosis," J Korean Neurosurg Soc. 59(3):204-213 (2016).
Salva et al., "Signaling networks in joint development," Dev Dyn. 246(4):262-274 (2017).
Seshia et al., "Myopathy with hypophosphatasia," Arch Dis Child. 65(1):130-131 (1990).
Shah et al., "Sudden infant death in a patient with FGFR3 P250R mutation," Am J Med Genet A. 140A(24):2794-2796 (2006).
Sharma et al., "Bilateral femoral neck fractures in a young patient suffering from hypophosphatasia, due to a first time epileptic seizure," J Orthop Case Rep. 5(3):66-68 (2015).
Sharma, "Craniosynostosis," Indian J Plast Surg. 46(1):18-27 (2013).
Silver et al., "Pulmonary hypoplasia in neonatal hypophosphatasia," Pediatr Pathol. 8(5):483-493 (1988) (12 pages).
Simmons, "Best Practices In: Recognizing and Diagnosing Hypophosphatasia," Clinical Endocrinology News. <https://www.mdedge.com/sites/default/files/issues/articles/Alexion_10_11_Final_Web.pdf>, published Sep. 30, 2013, retrieved on Mar. 27, 2019 (8 pages).
Stoll et al., "Severe hypophosphatasia due to mutations in the tissue-nonspecific alkaline phosphatase (TNSALP) gene," Genet Couns. 13(3):289-295 (2002).
Thacher et al., "Radiographic scoring method for the assessment of the severity of nutritional rickets," J Trop Pediatr. 46(3):132-139 (2000).
Thurner et al., "Osteopontin deficiency increases bone fragility but preserves bone mass," Bone. 46(6):1564-1573 (2010).
Tokumaru et al., "Skull base and calvarial deformities: association with intracranial changes in craniofacial syndromes," Am J Neuroradiol. 17(4):619-630 (1996).
Watanabe et al., "Prevalence of c.1559delT in ALPL, a common mutation resulting in the perinatal (lethal) form of hypophosphatasia

(56) References Cited

OTHER PUBLICATIONS in Japanese and effects of the mutation on heterozygous carriers," J Hum Genet. 56(2):166-168 (2011).
Weber et al., "Burden of disease in children with hypophosphatasia: results from patient-reported surveys," 7th International Conference on Children's Bone Health, Jun. 27-30, Salzburg, Austria. *Bone Abstracts*. 4: P119 (2015) (3 pages).
Whyte et al., "A retrospective, multi-national, non-interventional, natural history study of the childhood form of hypophosphatasia," ENDO 2015: The Endocrine Society Annual Meeting, Mar. 5-8, San Diego, California. Abstract LB-OR01-4 (2015) (2 pages).
Whyte et al., "Adult hypophosphatasia treated with teriparatide," J Clin Endocrinol Metab. 92(4):1203-1208 (2007).
Whyte et al., "Adult hypophosphatasia with chondrocalcinosis and arthropathy: variable penetrance of hypophosphatasemia in a large Oklahoma kindred," Am J Med. 72(4):631-641 (1982).
Whyte et al., "Asfotase alfa: Sustained Efficacy and Tolerability in Infants and Young Children with Life-Threatening Hypophosphatasia," 2014 Pediatric Academic Societies and Asian Society for Pediatric Research Joint Meeting, May 3-6, Vancouver, BC, Canada. Poster 69 (2014) (1 page).
Whyte et al., "Hypophosphatasia: A Retrospective Natural History Study of the Severe Perinatal and Infantile Forms," 2014 European Calcified Tissue Society Congress, May 17-20, Prague, Czech Republic. Poster P364 (2014) (1 page).
Whyte et al., "Rickets and osteomalacia," Medicine. 37(9):483-488 (2009).
Whyte, Chapter 22: Hypophosphatasia, *Genetics of Bone Biology and Skeletal Disease*. Rajesh V. Thakker, Michael P. Whyte, John A. Eisman and Takashi Igarashi (eds.), 337-360 (2013).
Whyte, Chapter 73: Hypophosphatasia: Nature's Window on Alkaline Phosphatase Function in Humans, *Principles of Bone Biology*, vol. 1, Third Edition. John P. Bilezikian, Lawrence G. Raisz and T. John Martin (eds.), 1573-1598 (2008).
Zaleckas et al., "Diagnosis and treatment of craniosynostosis: Vilnius team experience," Acta Med Litu. 22(2):111-121 (2015).
Abrams, "Calcium and Vitamin D Requirements of Enterally Fed Preterm Infants," Pediatrics. 131(5): e1676-e1683 (2013).
Carden et al., "Tracheomalacia and tracheobronchomalacia in children and adults: an in-depth review," Chest. 127(3):984-1005 (2005).
Hancarova et al., "Hypophosphatasia due to uniparental disomy," Bone. 81:765-766 (2015).
Leung et al., "Outcome of perinatal hypophosphatasia in Manitoba Mennonites: a retrospective cohort analysis," JIMD Rep. 11:73-78 (2013).
Mornet, "The tissue nonspecific alkaline phosphatase gene mutations database," <www.sesep.uvsq.fr/03_hypo_mutations.php>, last updated Nov. 28, 2019 (14 pages).
Morrison et al., "Mitigation of tracheobronchomalacia with 3D-printed personalized medical devices in pediatric patients," available in PMC Apr. 29, 2016, published in final edited form as: Sci Transl Med. 7(285):285ra264 (2015) (23 pages).
Murgu et al., "Tracheobronchomalacia and excessive dynamic airway collapse," Respirology. 11(4):388-406 (2006).
Taketani et al., Chapter 9: Hypophosphatasia. *Human Pathobiochemistry*. T. Oohashi et al. (eds.), 91-100 (2019).
Wang et al., "The effects of tissue-non-specific alkaline phosphatase gene therapy on craniosynostosis and craniofacial morphology in the FGFR2C342Y/+ mouse model of Crouzon craniosynostosis," Orthod Craniofac Res. 18 Suppl 1:196-206 (2015).
Whyte et al., "Asfotase alfa for infants and young children with hypophosphatasia: 7 year outcomes of a single-arm, open-label, phase 2 extension trial," Lancet Diabetes Endocrinol. 7(2):93-105 (2019) (52 pages).
Whyte et al., "Hypophosphatasia (HPP) in children: enzyme replacement therapy (EzRT) using bone-targeted, tissue-nonspecific alkaline phosphatase (TNSALP)," Ann Neurol. 68(Suppl 14):S70 Abstract WIP-28 (2010) (1 page).
Whyte et al., "Natural history of perinatal and infantile hypophosphatasia: a retrospective study," J Pediatr. 209:116-124.e4 (2019) (13 pages).
Little et al., "Lineage tracking of myogenic progenitors in surgical models of tibial bone repair," Bone. 48(2):S82 (2011).
Kim et al., "Comparison of phenylketonuria (PKU) patients' height, weight and body mass index (BMI) to the general population," Molecular Genetics and Metabolism. 105(3):328-329 (2012).
Whyte et al. "Treatment of children with hypophosphatasia (HPP) with ENB-0040: radiographic and DXA outcomes after 6 months of therapy," Horm. Res. Paediatr. 76: 26 (2011).
Sequencia—"Bone targeted alkaline phosphatase, kits and methods of use thereof," UniParc, (Nov. 2, 2010), Database No. HI520929 (1 page).
Seefried et al., "Long-term Effectiveness of Asfotase Alfa Treatment in Adults with Pediatric-onset Hypophosphatasia in Routine Clinical Practice" 2020 American Society for Bone and Mineral Research Virtual Conference, Sep. 11-15 (2020).
Seefried et al., "Real-world Clinical Profiles of Adults with Hypophosphatasia (HPP) from the Global HPP Registry," The American Society for Bone and Mineral Research 2020 Annual Meeting, Sep. 11-15, virtually (2020).
Seefried et al., "Bone Turnover and Mineral Metabolism in Adult Patients with Pediatric-Onset Hypophosphatasia Treated With Asfotase Alfa," The American Society for Bone and Mineral Research 2020 Annual Meeting, Sep. 11-15, virtually (2020).
Seefried et al., "Long-term Effectiveness of Asfotase Alfa Treatment in Adults with Pediatric-onset Hypophosphatasia in Routine Clinical Practice" 22nd European Congress of Endocrinology, Sep. 5-9, virtual (2020).
Seefried et al., "Long-term Effectiveness of Asfotase Alfa Treatment in Adults with Pediatric-onset Hypophosphatasia in Routine Clinical Practice" 2020 World Congress of Osteoporosis, Osteoarthritis, and Muscoskeletal Diseases, Aug. 20-23, Barcelona, Spain (2020).
Anonymous: "Scale-up of CHO fed-batch cultures in HyClone (TM) ActiPro (TM) medium supplemented with Cell Boost (TM) 7a and 7b," Oct. 11, 2016, pp. 1-4, XP055461185.
Fu-Hang et al., "Preliminary study on the effect of $Zn^{2+}$ on the activities of peptidase and alkaline phosphatase," Marine Sciences. 27(3):64-65 (2003).
Office Action for Chinese Patent Application No. 201680048588.5, dated Jan. 18, 2021 (13 pages).
Zhang et al., "Engineering *E. coli* Alkaline Phosphatase Yields Changes of Catalytic Activity, Thermal Stability and Phosphate Inhibition," Biocatal Biotransfor. 20(6):381-389 (2002).
Nangia et al., "Disorders of Calcium Metabolism in Newborns," Journal of Neonatology. 17(2):43-49 (2003).
Kochanowski et al., "Medium and feed optimization for fed-batch production of a monoclonal antibody in CHO cells," BMC Proc. 5(Suppl 8):P75 (2011) (3 pages).
"Xcellerex™ XDR cell culture bioreactor systems," GE Healthcare Life Sciences, retrieved from <https://www.cytivallifesciences.co.jp/catalog/pdf/29092925AA.pdf>, published Feb. 2014 (4 pages).
Yagasaki et al., "Animal Cell Technology: Basic & Applied Aspects," Proceedings of the Fifteenth Annual Meeting of the Japanese Association for Animal Cell Technology (JAACT), vol. 13, Fuchu, Nov. 11-15, 2002 (461 pages).
Kozlenkov et al., "Residues determining the binding specificity of uncompetitive inhibitors to tissue-nonspecific alkaline phosphatase," J Bone Miner Res. 19(11):1862-72 (2004).
NCBI Protein Database Accession No. NM_000478, retrieved on Feb. 23, 2021 (7 pages).
Pradhan et al., "Exposure-Response Modeling and Simulation to Support Evaluation of Efficacious and Safe Exposure and Dose Range for Asfotase alfa in Pateints with Hypophosphatasia," ASBMR 2015 Annual Meeting Abstracts. J Bone and Med Res. SU0380:S316 (2015) (1 page).
Abbruzzese, L., "The Tinetti Performance-Oriented Mobility Assessment Tool," Am J Nursing. 98(12):16J-16L (1998) (3 pages).
International Search Report and Written Opinion for International Patent Application No. PCT/US20/64140, dated Apr. 23, 2021 (70 pages).

(56) References Cited

OTHER PUBLICATIONS

Kishnani et al., "Five-year efficacy and safety of asfotase alfa therapy for adults and adolescents with hypophosphatasia," Bone. 121:149-162 (2019).
Alexion Pharmaceuticals, "Safety Study of Human Recombinant Tissue Non-Specific Alkaline Phosphatase Fusion Protein Asfotase Alfa in Adults With Hypophosphatasia (HPP)," ClinicalTrials.gov. NCT00739505 (2008).
Alexion Pharmaceuticals, "Safety and Efficacy Study of Asfotase Alfa in Adolescents and Adults With Hypophosphatasia (HPP)," ClinicalTrials.gov. NCT01163149 (2010).
Alexion Pharmaceuticals, "Strensiq (asfotase alfa) for injection," <World wide web at globalgenes.org/2015/11/05/alexion-announces-fda-approval-for--strensiq/?gclid=CjwKCAjwwqaGBhBKEiwAMk-FtFQOKvuVN-WmNcDVyu9Q9X3f6QB-V0Two0x216TR2H4_Qc6jSlhvxoCiLMQAvD_BwE>, dated Nov. 5, 2015 (1 page).
European Medicines Agency, "Strensiq: Asfotase Alfa," <www.ema.europa.eu/en/medicines/human/EPAR/strensiq>, dated Mar. 25, 2021 (8 pages).
Hoffmann et al. "Efficacy and safety of asfotase alfa in infants and young children with hypophosphatasia: a phase 2 open-label study." The Journal of Clinical Endocrinology & Metabolism. 104(7): pp. 2735-2747, 2019 (14 pages).

\* cited by examiner

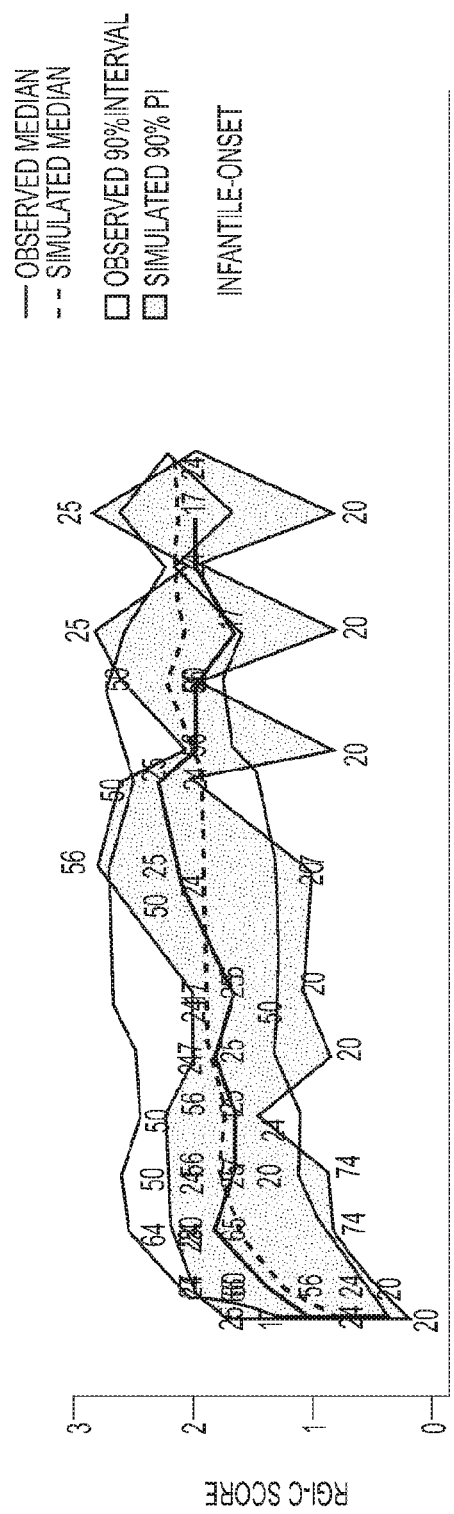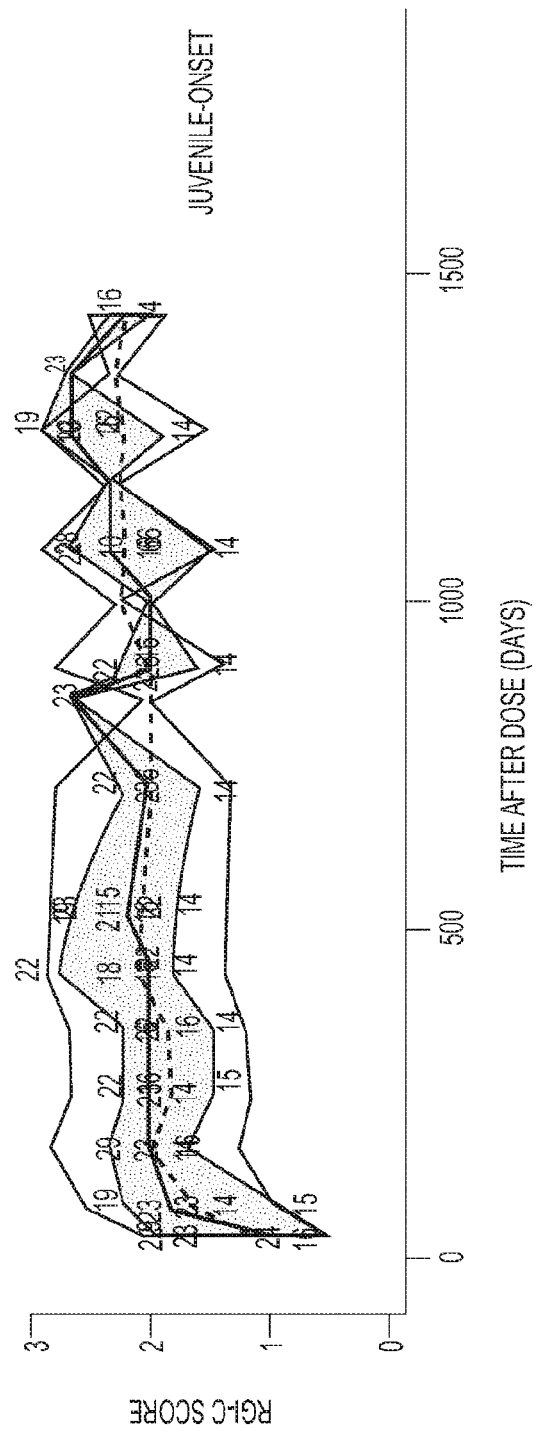
FIG. 8A

SEQUENCE LISTING

<160> NUMBER OF SEQ ID NOS: 1

<210> SEQ ID NO 1
<211> LENGTH: 726
<212> TYPE: PRT
<213> ORGANISM: Artificial Sequence
<220> FEATURE:
<223> OTHER INFORMATION: Synthetic Construct

<400> SEQUENCE: 1

```
Leu Val Pro Glu Lys Glu Lys Asp Pro Lys Tyr Trp Arg Asp Gln Ala
1               5                   10                  15

Gln Glu Thr Leu Lys Tyr Ala Leu Glu Leu Gln Lys Leu Asn Thr Asn
            20                  25                  30

Val Ala Lys Asn Val Ile Met Phe Leu Gly Asp Gly Met Gly Val Ser
        35                  40                  45

Thr Val Thr Ala Ala Arg Ile Leu Lys Gly Gln Leu His His Asn Pro
    50                  55                  60

Gly Glu Glu Thr Arg Leu Glu Met Asp Lys Phe Pro Phe Val Ala Leu
65                  70                  75                  80

Ser Lys Thr Tyr Asn Thr Asn Ala Gln Val Pro Asp Ser Ala Gly Thr
                85                  90                  95

Ala Thr Ala Tyr Leu Cys Gly Val Lys Ala Asn Glu Gly Thr Val Gly
            100                 105                 110

Val Ser Ala Ala Thr Glu Arg Ser Arg Cys Asn Thr Thr Gln Gly Asn
        115                 120                 125

Glu Val Thr Ser Ile Leu Arg Trp Ala Lys Asp Ala Gly Lys Ser Val
    130                 135                 140

Gly Ile Val Thr Thr Arg Val Asn His Ala Thr Pro Ser Ala Ala
145                 150                 155                 160

Tyr Ala His Ser Ala Asp Arg Asp Trp Tyr Ser Asp Asn Glu Met Pro
                165                 170                 175

Pro Glu Ala Leu Ser Gln Gly Cys Lys Asp Ile Ala Tyr Gln Leu Met
            180                 185                 190

His Asn Ile Arg Asp Ile Asp Val Ile Met Gly Gly Gly Arg Lys Tyr
        195                 200                 205

Met Tyr Pro Lys Asn Lys Thr Asp Val Glu Tyr Glu Ser Asp Glu Lys
    210                 215                 220

Ala Arg Gly Thr Arg Leu Asp Gly Leu Asp Leu Val Asp Thr Trp Lys
225                 230                 235                 240

Ser Phe Lys Pro Arg Tyr Lys His Ser His Phe Ile Trp Asn Arg Thr
                245                 250                 255

Glu Leu Leu Thr Leu Asp Pro His Asn Val Asp Tyr Leu Leu Gly Leu
            260                 265                 270

Phe Glu Pro Gly Asp Met Gln Tyr Glu Leu Asn Arg Asn Asn Val Thr
        275                 280                 285

Asp Pro Ser Leu Ser Glu Met Val Val Ala Ile Gln Ile Leu Arg
    290                 295                 300

Lys Asn Pro Lys Gly Phe Phe Leu Leu Val Glu Gly Gly Arg Ile Asp
305                 310                 315                 320

His Gly His His Glu Gly Lys Ala Lys Gln Ala Leu His Glu Ala Val
                325                 330                 335

Glu Met Asp Arg Ala Ile Gly Gln Ala Gly Ser Leu Thr Ser Ser Glu
            340                 345                 350

Asp Thr Leu Thr Val Val Thr Ala Asp His Ser His Val Phe Thr Phe
```

```
            355                 360                 365
Gly Gly Tyr Thr Pro Arg Gly Asn Ser Ile Phe Gly Leu Ala Pro Met
        370                 375                 380

Leu Ser Asp Thr Asp Lys Lys Pro Phe Thr Ala Ile Leu Tyr Gly Asn
385                 390                 395                 400

Gly Pro Gly Tyr Lys Val Val Gly Gly Glu Arg Glu Asn Val Ser Met
            405                 410                 415

Val Asp Tyr Ala His Asn Asn Tyr Gln Ala Gln Ser Ala Val Pro Leu
        420                 425                 430

Arg His Glu Thr His Gly Gly Glu Asp Val Ala Val Phe Ser Lys Gly
    435                 440                 445

Pro Met Ala His Leu Leu His Gly Val His Glu Gln Asn Tyr Val Pro
        450                 455                 460

His Val Met Ala Tyr Ala Ala Cys Ile Gly Ala Asn Leu Gly His Cys
465                 470                 475                 480

Ala Pro Ala Ser Ser Leu Lys Asp Lys Thr His Thr Cys Pro Pro Cys
            485                 490                 495

Pro Ala Pro Glu Leu Leu Gly Gly Pro Ser Val Phe Leu Phe Pro Pro
        500                 505                 510

Lys Pro Lys Asp Thr Leu Met Ile Ser Arg Thr Pro Glu Val Thr Cys
    515                 520                 525

Val Val Val Asp Val Ser His Glu Asp Pro Glu Val Lys Phe Asn Trp
        530                 535                 540

Tyr Val Asp Gly Val Glu Val His Asn Ala Lys Thr Lys Pro Arg Glu
545                 550                 555                 560

Glu Gln Tyr Asn Ser Thr Tyr Arg Val Val Ser Val Leu Thr Val Leu
            565                 570                 575

His Gln Asp Trp Leu Asn Gly Lys Glu Tyr Lys Cys Lys Val Ser Asn
        580                 585                 590

Lys Ala Leu Pro Ala Pro Ile Glu Lys Thr Ile Ser Lys Ala Lys Gly
    595                 600                 605

Gln Pro Arg Glu Pro Gln Val Tyr Thr Leu Pro Pro Ser Arg Glu Glu
        610                 615                 620

Met Thr Lys Asn Gln Val Ser Leu Thr Cys Leu Val Lys Gly Phe Tyr
625                 630                 635                 640

Pro Ser Asp Ile Ala Val Glu Trp Glu Ser Asn Gly Gln Pro Glu Asn
            645                 650                 655

Asn Tyr Lys Thr Thr Pro Pro Val Leu Asp Ser Asp Gly Ser Phe Phe
        660                 665                 670

Leu Tyr Ser Lys Leu Thr Val Asp Lys Ser Arg Trp Gln Gln Gly Asn
    675                 680                 685

Val Phe Ser Cys Ser Val Met His Glu Ala Leu His Asn His Tyr Thr
        690                 695                 700

Gln Lys Ser Leu Ser Leu Ser Pro Gly Lys Asp Ile Asp Asp Asp Asp
705                 710                 715                 720

Asp Asp Asp Asp Asp Asp
            725
```

REDUCED FREQUENCY DOSAGE REGIMENS FOR TISSUE NON-SPECIFIC ALKALINE PHOSPHATASE (TNSALP)-ENZYME REPLACEMENT THERAPY OF HYPOPHOSPHATASIA

BACKGROUND

Hypophosphatasia (HPP) is a life-threatening, genetic, and ultra-rare metabolic disorder that results in a failure to produce functional tissue nonspecific alkaline phosphatase (TNSALP, or TNALP; both terms are used interchangeably in the present disclosure). Untreated HPP leads to the accumulation of unmineralized bone matrix (e.g. rickets, osteomalacia), characterized by hypo-mineralization of bones and teeth. When growing bone does not mineralize properly, impairment of growth results in disfigurement of joints and bones, which in turn impacts motor performance and respiratory function, and may ultimately lead to death in severe cases. Four different forms of HPP were initially described, i.e., perinatal, infantile, juvenile, and adult HPP. More recently, six clinical forms have been further delineated, based upon age at symptom onset, including perinatal, benign prenatal, infantile, juvenile, adult, and odonto-HPP.

Asfotase alfa is a soluble fusion glycoprotein comprised of the catalytic domain of human TNSALP, a human immunoglobulin G1 Fc domain and a deca-aspartate peptide (i.e., $D_{10}$) used as a bone-targeting domain. Asfotase alfa is an approved, first-in-class targeted enzyme replacement therapy designed to address defective endogenous TNSALP levels (Whyte et al., 2012 *N Engl J Med.* 366:904-13; STRENSIQ®, Alexion Pharmaceuticals, Inc.)

BRIEF SUMMARY

Disclosed herein are novel dosage amounts and schedules based on clinical trial data from HPP patients treated with asfotase alfa. New dosing regimens to increase patient compliance and to decrease patient burden from multiple injection sites have been validated as described herein.

In one aspect, the present disclosure provides a method of treating a human having a condition or disease related to a bone defect characterized by at least one of:

(i) increased level of an alkaline phosphatase ligand, particularly PPi, PLP, or PEA; and (ii) decreased alkaline phosphatase activity, compared to a human without said condition or disease, comprising administering to the human a therapeutically effective amount of a polypeptide comprising the amino acid sequence of SEQ ID NO:1, wherein the polypeptide is administered through at least one subcutaneous injection to the human in a frequency of fewer than three times each week.

In a second aspect, the present disclosure provides a method of treating a human having a condition or disease related to a bone defect characterized by at least one of:

increased level of an alkaline phosphatase ligand, particularly PPi, PLP, or PEA; and decreased alkaline phosphatase activity, compared to a human without said condition or disease, including administering to the human a therapeutically effective amount of a polypeptide including the amino acid sequence of SEQ ID NO:1, in which the polypeptide is administered through at least one subcutaneous injection to the human less frequently than once every eight days.

In some embodiments, the human has a lack of or an insufficient amount of functional alkaline phosphatase. In some embodiments, the human has a lack of or an insufficient amount of tissue-non-specific alkaline phosphatase (TNALP, or TNSALP).

In some embodiments, the bone defect disclosed herein is a failure to mineralize bone matrix. In some embodiments, the condition or disease related to a bone defect is hypophosphatasia (HPP).

In some embodiments, the polypeptide disclosed herein catalyzes the cleavage of at least one of inorganic pyrophosphate (PPi), pyridoxal 5'-phosphate (PLP), and phosphoethanolamine (PEA).

In some embodiments, the polypeptide disclosed herein is administered through at least one subcutaneous injection to the human in a frequency of more than once every twenty-four days.

In some embodiments, the polypeptide disclosed herein is administered once each week, twice each month, once every three weeks, once every 22 days, once every 23 days, or once every 24 days.

In some embodiments, the polypeptide disclosed herein is administered through at least one subcutaneous injection to the human in a dosage and frequency selected from the group consisting of about 6 mg/kg once each week, about 18 mg/kg twice each month, about 50 mg/kg once every three weeks, about 52 mg/kg once every 22 days, about 55 mg/kg once every 23 days, and about 57 mg/kg once every 24 days.

In some embodiments, the method disclosed herein comprises administering the polypeptide in at least one dosage to the human through an intravenous or subcutaneous route prior to the at least one subcutaneous administration. In some embodiments, such method comprises administering the polypeptide in at least one dosage to the human through an intravenous or subcutaneous route at least one day, three days, or one week prior to the at least one subcutaneous administration.

In some embodiments, administering the polypeptide disclosed herein reduces the levels of at least one of pyridoxal-5'-phosphate (PLP), inorganic pyrophosphate (PPi), and phosphoethanolamine (PEA) in the human.

In some embodiments, the method disclosed herein comprises improving in the human at least one of the Radiographic Global Impression of Change (RGI-C) score, the Rickets Severity Scale (RSS) score, and osteoid thickness.

In some embodiments, the method disclosed herein comprises improving in the human at least one of the functional efficacy endpoints selected from the group consisting of the Bruininks-Oseretsky Test of Motor Proficiency, Second Edition (BOT-2), the percent predicted distance walked on a 6-minute walk test (6MWT), and the modified performance-oriented mobility assessment-gait (MPOMA-G).

In some embodiments, administering the polypeptide disclosed herein results in a therapeutic effect comparable to administering the polypeptide at the same time-averaged dosage but in a higher frequency.

In some embodiments, the comparable therapeutic effect comprises at least one endpoint measurement selected from the group consisting of the levels of pyridoxal-5'-phosphate (PLP), the levels of inorganic pyrophosphate (PPi), the levels of phosphoethanolamine (PEA), the RGI-C score, the RSS score, the osteoid thickness, the BOT-2 score, the 6MWT score, and the MPOMA-G score.

In some embodiments, the human has juvenile-onset or adult-onset HPP. The human can be an adult or adolescent.

In some embodiments, the human does not have or exhibit symptoms of craniosynostosis or the human has not been diagnosed with craniosynostosis. In particular, the human does not have or exhibit symptoms of craniosynostosis prior to administration of a polypeptide comprising the amino acid sequence of SEQ ID NO: 1.

BRIEF DESCRIPTION OF THE DRAWINGS

In the appended drawings:

FIG. 8A-8B depicts the model performance for PD endpoints (RGI-C and 6MWT), showing the agreement between the observed (shaded) and model-predicted (open) for these PD endpoints.

DETAILED DESCRIPTION

Definitions

Figure 1:
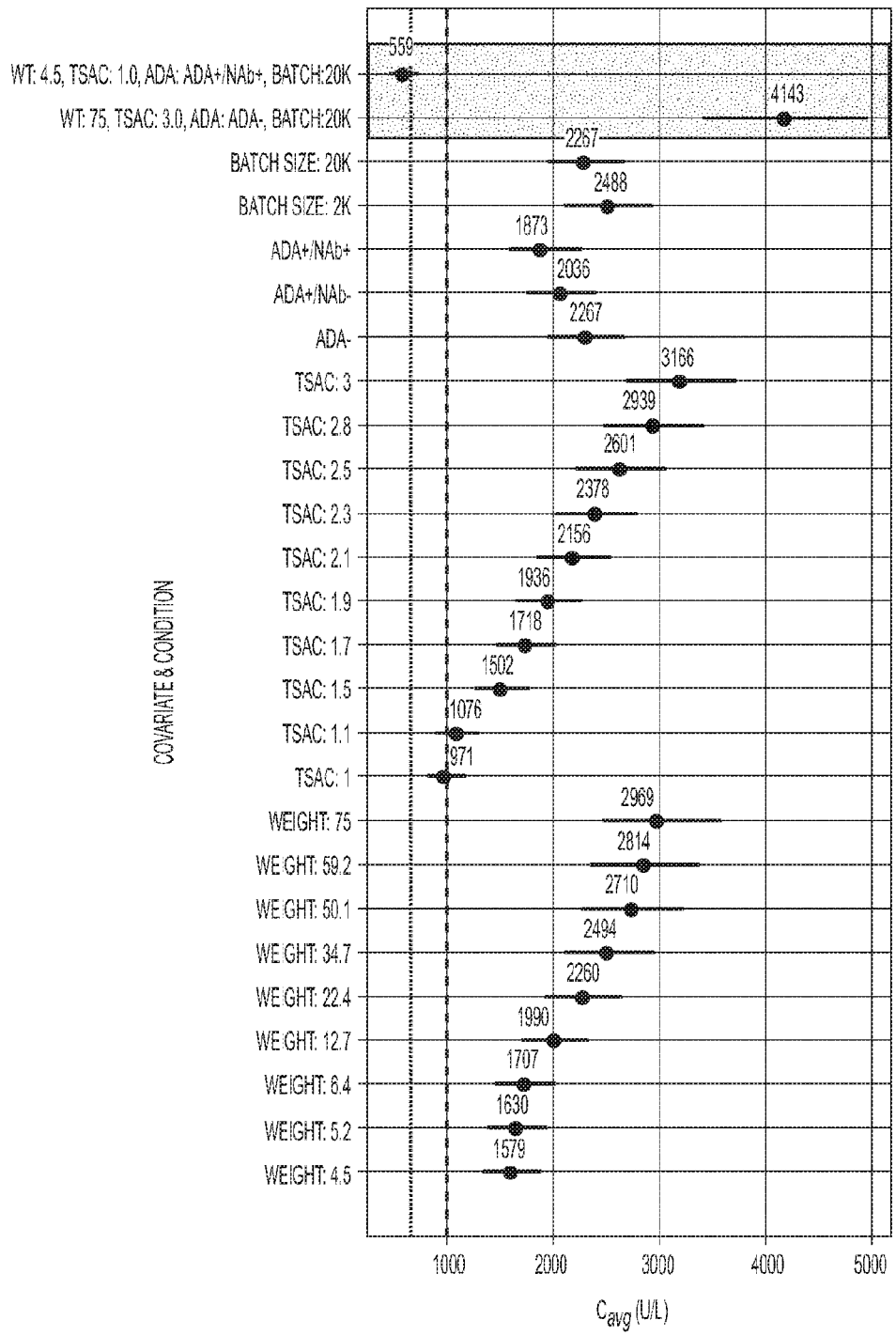
FIG. 1 depicts covariates vs. simulated average concentration at steady-state ($C_{avg,ss}$) relationship. Simulated $C_{avg,ss}$ values are based on a regimen of 2 mg/kg given three times per week. Dose activity is assumed to be 990 U/mg. Covariates were fixed at the following values, except when the subject of perturbation: TSAC was set at 2.2; weight, 22.7 kg; anti-drug and neutralizing antibodies, negative; and batch size, 20,000 L. The dashed lines depict efficacious exposure levels from nonclinical efficacy studies that defined the targeted exposure for clinical effect.

"About", "Approximately": As used herein, the terms "about" and "approximately", as applied to one or more particular cell culture conditions, refer to a range of values that are similar to the stated reference value for that culture condition or conditions. In certain embodiments, the term "about" refers to a range of values that fall within 25, 20, 19, 18, 17, 16, 15, 14, 13, 12, 11, 10, 9, 8, 7, 6, 5, 4, 3, 2, 1 percent or less of the stated reference value for that culture condition or conditions. For example, the term "about" can refer to ±10% of the stated value.

"Amino acid": The term "amino acid," as used herein, refers to any of the twenty naturally occurring amino acids that are normally used in the formation of polypeptides, or analogs or derivatives of those amino acids. Amino acids of the present disclosure can be provided in medium to cell cultures. The amino acids provided in the medium may be provided as salts or in hydrate form.

"Culture" and "cell culture": These terms, as used herein, refer to a cell population that is suspended in a medium (see definition of "medium" below) under conditions suitable for survival and/or growth of the cell population. As will be clear to those of ordinary skill in the art, these terms as used herein may refer to the combination comprising the cell population and the medium in which the population is suspended.

"Fragment": The term "fragment," as used herein, refers to a polypeptide and is defined as any discrete portion of a given polypeptide that is unique to or characteristic of that polypeptide. The term as used herein also refers to any discrete portion of a given polypeptide that retains at least a fraction of the activity of the full-length polypeptide. In some embodiments the fraction of activity retained is at least 10% of the activity of the full-length polypeptide. In various embodiments the fraction of activity retained is at least 20%, 30%, 40%, 50%, 60%, 70%, 80% or 90% of the activity of the full-length polypeptide. In other embodiments the fraction of activity retained is at least 95%, 96%, 97%, 98% or 99% of the activity of the full-length polypeptide. In one embodiment, the fraction of activity retained is 100% of the activity of the full-length polypeptide. The term as used herein also refers to any portion of a given polypeptide that includes at least an established sequence element found in the full-length polypeptide. In some embodiments, the sequence element spans at least 4-5 amino acids of the full-length polypeptide. In some embodiments, the sequence element spans at least about 10, 15, 20, 25, 30, 35, 40, 45, 50 or more amino acids of the full-length polypeptide.

"Polypeptide": The term "polypeptide," as used herein, refers a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond.

"Protein": The term "protein," as used herein, refers to one or more polypeptides that function as a discrete unit. If a single polypeptide is the discrete functioning unit and does not require permanent physical association with other polypeptides in order to form the discrete functioning unit, the terms "polypeptide" and "protein" as used herein are used interchangeably.

"Recombinantly-expressed polypeptide" and "recombinant polypeptide": These terms, as used herein, refer to a polypeptide expressed from a host cell that has been genetically engineered to express that polypeptide. The recombinantly-expressed polypeptide can be identical or similar to a polypeptide that is normally expressed in the mammalian host cell. The recombinantly-expressed polypeptide can also be foreign to the host cell, i.e., heterologous to peptides normally expressed in the host cell. Alternatively, the recombinantly-expressed polypeptide can be chimeric in that portions of the polypeptide contain amino acid sequences that are identical or similar to polypeptides normally expressed in the mammalian host cell, while other portions are foreign to the host cell.

"TNALP" or "TNSALP": These terms, as used herein, refer interchangeably to tissue non-specific alkaline phosphatase protein.

The present disclosure provides methods of treating a human patient having a lack of or an insufficient amount of tissue-non-specific alkaline phosphatase (TNALP) with a specific dosing regimen as described herein. The term "lack (of)" refers to the state of such human having TNALP levels not sufficient for routine detection.

Proteins

The present disclosure provides administering alkaline phosphatase proteins to a subject having decreased and/or malfunctioned endogenous alkaline phosphatase, or having overexpressed (e.g., above normal level) alkaline phosphatase substrates. In some embodiments, the alkaline phosphatase protein in this disclosure is a recombinant protein. In some embodiments, the alkaline phosphatase protein is a fusion protein. In some embodiments, the alkaline phosphatase protein in this disclosure specifically targets a cell type, tissue (e.g., connective, muscle, nervous, or epithelial tissues), or organ (e.g., liver, heart, kidney, muscles, bones, cartilage, ligaments, tendons, etc.). For example, such alkaline phosphatase protein may comprise a full-length alkaline phosphatase (ALP) or fragment of at least one alkaline phosphatase (ALP). In some embodiments, the alkaline phosphatase protein comprises a soluble ALP (sALP) linked to a bone-targeting moiety (e.g., a negatively-charged peptide as described below). In some embodiments, the alkaline phosphatase protein comprises a soluble ALP (sALP) linked to an immunoglobulin moiety (full-length or fragment). For example, such immunoglobulin moiety may comprise a fragment crystallizable region (Fc). In some embodiments, the alkaline phosphatase protein comprises a soluble ALP (sALP) linked to both a bone-targeting moiety and an immunoglobulin moiety (full-length or fragment). In some embodiments, the alkaline phosphatase protein comprises any one of the structures selected from the group consisting of: sALP-X, X-sALP, sALP-Y, Y-sALP, sALP-X-Y, sALP-Y-X, X-sALP-Y, X-Y-sALP, Y-sALP-X, and Y-X-sALP, wherein X comprises a bone-targeting moiety, as described herein, and Y comprises an immunoglobulin moiety, as described herein. In one embodiment, the alkaline phosphatase protein comprises the structure of W-sALP-X-Fc-Y-$D_n/E_n$-Z, wherein W is absent or is an amino acid sequence of at least one amino acid; X is absent or is an amino acid sequence of at least one amino acid; Y is absent or is an amino acid sequence of at least one amino acid; Z is absent or is an amino acid sequence of at least one amino acid; Fc is a fragment crystallizable region; $D_n/E_n$ is a polyaspartate, polyglutamate, or combination thereof wherein n=8-20; and sALP is a soluble alkaline phosphatase (ALP). In some embodiments, $D_n/E_n$ is a polyaspartate sequence. For example, $D_n$ may be a polyaspartate sequence wherein n is any number between 8 and 20 (both included) (e.g., n may be 8, 9, 10, 11, 12, 13, 14, 15, 16, 17, 18, 19, and 20). In one embodiment, $D_n$ is $D_{10}$ or $D_{16}$. In some embodiments, $D_n/E_n$ is a polyglutamate sequence. For example, $E_n$ may be a polyglutamate sequence wherein n is any number between 8 and 20 (both included) (e.g., n may be 8, 9, 10, 11, 12, 13, 14, 15, 16, 17, 18, 19, and 20). In one embodiment, $E_n$ is $E_{10}$ or $E_{16}$. In one embodiment, the alkaline phosphatase protein comprises the structure of TNALP-Fc-$D_{10}$ (SEQ ID NO: 1, as listed below). Underlined asparagine (N) residues correspond to potential glycosylation sites (i.e., N 123, 213, 254, 286, 413 & 564). Bold underlined amino acid residues ($L_{486}$-$K_{487}$ & $D_{715}$-$I_{716}$) correspond to linkers between sALP and Fc, and Fc and $D_{10}$ domains, respectively.

(SEQ ID NO: 1)

```
          10         20         30         40         50         60
    LVPEKEKDPK YWRDQAQETL KYALELQKLN TNVAKNVIMF LGDGMGVSTV TAARILKGQL 70         80         90        100        110        120
    HHNPGEETRL EMDKFPFVAL SKTYNTNAQV PDSAGTATAY LCGVKANEGT VGVSAATERS 130        140        150        160        170        180
    RCNTTQGNEV TSILRWAKDA GKSVGIVTTT RVNHATPSAA YAHSADRDWY SDNEMPPEAL 190        200        210        220        230        240
    SQGCKDIAYQ LMHNIRDIDV IMGGGRKYMY PKNKTDVEYE SDEKARGTRL DGLDLVDTWK 250        260        270        280        290        300
    SFKPRYKHSH FIWNRTELLT LDPHNVDYLL GLFEPGDMQY ELNRNNVTDP SLSEMVVVAI 310        320        330        340        350        360
    QILRKNPKGF FLLVEGGRID HGHHEGKAKQ ALHEAVEMDR AIGQAGSLTS SEDTLTVVTA 370        380        390        400        410        420
    DHSHVFTFGG YTPRGNSIFG LAPMLSDTDK KPFTAILYGN GPGYKVVGGE RENVSMVDYA 430        440        450        460        470        480
    HNNYQAQSAV PLRHETHGGE DVAVFSKGPM AHLLHGVHEQ NYVPHVMAYA ACIGANLGHC 490        500        510        520        530        540
    APASSLKDKT HTCPPCPAPE LLGGPSVFLF PPKPKDTLMI SRTPEVTCVV VDVSHEDPEV 550        560        570        580        590        600
    KFNWYVDGVE VHNAKTKPRE EQYNSTYRVV SVLTVLHQDW LNGKEYKCKV SNKALPAPIE 610        620        630        640        650        660
    KTISKAKGQP REPQVYTLPP SREEMTKNQV SLTCLVKGFY PSDIAVEWES NGQPENNYKT 670        680        690        700        710        720
    TPPVLDSDGS FFLYSKLTVD KSRWQQGNVF SCSVMHEALH NHYTQKSLSL SPGKDIDDDD

DDDDDD
```

Asfotase alfa is a soluble Fc fusion protein consisting of two TNALP-Fc-$D_{10}$ polypeptides each with 726 amino acids as shown in SEQ ID NO:1. Each polypeptide or monomer is composed of five portions. The first portion (sALP) containing amino acids L1-S485 is the soluble part of the human tissue non-specific alkaline phosphatase enzyme, which contains the catalytic function. The second portion contains amino acids L486-K487 as a linker. The third portion (Fc) containing amino acids D488-K714 is the Fc part of the human Immunoglobulin gamma 1 (IgG1) containing hinge, $CH_2$ and $CH_3$ domains. The fourth portion contains D715-1716 as a linker. The fifth portion contains amino acids D717-D726 ($D_{10}$), which is a bone targeting moiety that allows asfotase alfa to bind to the mineral phase of bone. In addition, each polypeptide chain contains six potential glycosylation sites and eleven cysteine (Cys) residues. Cys102 exists as free cysteine. Each polypeptide chain contains four intra-chain disulfide bonds between Cys122 and Cys184, Cys472 and Cys480, Cys528 and Cys588, and Cys634 and Cys692. The two polypeptide chains are connected by two inter-chain disulfide bonds between Cys493 on both chains and between Cys496 on both chains. In addition to these covalent structural features, mammalian alkaline phosphatases are thought to have four metal-binding sites on each polypeptide chain, including two sites for zinc, one site for magnesium and one site for calcium.

Alkaline Phosphatases (ALPs)

There are four known isozymes of ALP, namely tissue non-specific alkaline phosphatase (TNALP) further described below, placental alkaline phosphatase (PALP) (as described e.g., in GenBank Accession Nos. NP_112603 and NP_001623), germ cell alkaline phosphatase (GCALP) (as described, e.g., in GenBank Accession No. P10696) and intestinal alkaline phosphatase (IAP) (as described, e.g., in GenBank Accession No. NP_001622). These enzymes possess very similar three-dimensional structures. Each of their catalytic sites contains four metal-binding domains, for metal ions that are necessary for enzymatic activity, including two Zn and one Mg. These enzymes catalyze the hydrolysis of monoesters of phosphoric acid and also catalyze a transphosphorylation reaction in the presence of high concentrations of phosphate acceptors. Three known natural substrates for ALP (e.g., TNALP) include phosphoethanolamine (PEA), inorganic pyrophosphate (PPi) and pyridoxal 5'-phosphate (PLP) (Whyte et al., 1995 *J Clin Invest* 95:1440-1445). An alignment between these isozymes is shown in FIG. 30 of International Publication No. WO 2008/138131, the entire teaching of which is incorporated by reference herein in its entirety.

The alkaline phosphatase protein in this disclosure may comprise a dimer or multimers of any ALP protein, alone or in combination. Chimeric ALP proteins or fusion proteins may also be produced, such as the chimeric ALP protein that is described in Kiffer-Moreira et al. 2014 *PLoS One* 9:e89374, the entire teachings of which are incorporated by reference herein in its entirety.

TNALP

As indicated above, TNALP is a membrane-bound protein anchored through a glycolipid to its C-terminus (for human TNALP, see UniProtKB/Swiss-Prot Accession No. P05186). This glycolipid anchor (GPI) is added post translationally after removal of a hydrophobic C-terminal end which serves both as a temporary membrane anchor and as a signal for the addition of the GPI. Hence, in one embodiment a soluble human TNALP comprises a TNALP wherein the first amino acid of the hydrophobic C-terminal sequence, namely alanine, is replaced by a stop codon. The soluble TNALP (herein called sTNALP) so formed contains all amino acids of the native anchored form of TNALP that are necessary for the formation of the catalytic site but lacks the GPI membrane anchor. Known TNALPs include, e.g., human TNALP [GenBank Accession Nos. NP-000469, AAI10910, AAH90861, AAH66116, AAH21289, and AAI26166]; rhesus TNALP [GenBank Accession No. XP-001109717]; rat TNALP [GenBank Accession No. NP_037191]; dog TNALP [GenBank Accession No. AAF64516]; pig TNALP [GenBank Accession No. AAN64273], mouse TNALP [GenBank Accession No. NP_031457], bovine TNALP [GenBank Accession Nos. NP_789828, NP_776412, AAM 8209, and AAC33858], and cat TNALP [GenBank Accession No. NP_001036028].

As used herein, the terminology "extracellular domain" is meant to refer to any functional extracellular portion of the native protein (e.g., without the peptide signal). It has been shown that recombinant sTNALP retaining original amino acids 1 to 501 (18 to 501 when secreted) (see Oda et al., 1999 *J. Biochem* 126:694-699), amino acids 1 to 504 (18 to 504 when secreted) and amino acids 1 to 505 (18-505 when secreted), are enzymatically active. Examples presented herein also show that a recombinant sTNALP comprising amino acids 1 to 502 (18 to 502 when secreted) of the original TNALP is enzymatically active. This indicates that amino acid residues can be removed from the C-terminal end of the native protein without affecting its enzymatic activity. Furthermore, the soluble human TNALP may comprise one or more amino acid substitutions, wherein such substitution(s) does not reduce or at least does not completely inhibit the enzymatic activity of the sTNALP. For example, certain mutations that are known to cause hypophosphatasia (HPP) are listed in International Publication No. WO 2008/138131 and should be avoided to maintain a functional sTNALP.

Negatively-Charged Peptide

The alkaline phosphatase protein of the present disclosure may comprise a target moiety which may specifically target the alkaline phosphatase protein to a pre-determined cell type, tissue, or organ. In some embodiments, such pre-determined cell type, tissue, or organ is bone tissues. Such bone-targeting moiety may include any known polypeptide, polynucleotide, or small molecule compounds known in the art. For example, negatively-charged peptides may be used as a bone-targeting moiety. In some embodiments, such negatively-charged peptides may be a poly-aspartate, poly-glutamate, or combination thereof (e.g., a polypeptide comprising at least one aspartate and at least one glutamate, such as a negatively-charged peptide comprising a combination of aspartate and glutamate residues). In some embodiments, such negatively-charged peptides may be D6, D7, D8, D9, D10, D11, D12, D13, D14, D15, D16, D17, D18, D19, D20, or a polyaspartate having more than 20 aspartates. In some embodiments, such negatively-charged peptides may be E6, E7, E8, E9, E10, E11, E12, E13, E14, E15, E16, E17, E18, E19, E20, or a polyglutamate having more than 20 glutamates. In one embodiment, such negatively-charged peptides may comprise at least one selected from the group consisting of $D_{10}$ to $D_{16}$ or $E_{10}$ to $E_{16}$.

Spacer

In some embodiments, the alkaline phosphatase protein of the present disclosure comprises a spacer sequence between the ALP portion and the targeting moiety portion. In one embodiment, such alkaline phosphatase protein comprises a spacer sequence between the ALP (e.g., TNALP) portion and the negatively-charged peptide targeting moiety. Such spacer may be any polypeptide, polynucleotide, or small molecule compound. In some embodiments, such spacer may comprise fragment crystallizable region (Fc) fragments. Useful Fc fragments include Fc fragments of IgG that comprise the hinge, and the $CH_2$ and $CH_3$ domains. Such IgG may be any of IgG-1, IgG-2, IgG-3, IgG-3 and IgG-4, or any combination thereof.

Without being limited to this theory, it is believed that the Fc fragment used in bone-targeted sALP fusion proteins (e.g., asfotase alfa) acts as a spacer, which allows the protein to be more efficiently folded given that the expression of sTNALP-Fc-$D_{10}$ was higher than that of sTNALP-$D_{10}$ (see Example 2 below). One possible explanation is that the introduction of the Fc fragment alleviates the repulsive forces caused by the presence of the highly negatively-charged $D_{10}$ sequence added at the C-terminus of the sALP sequence exemplified herein. In some embodiments, the alkaline phosphatase protein described herein comprises a structure selected from the group consisting of: sALP-Fc-$D_{10}$, sALP-$D_{10}$-Fc, $Dz_{10}$-sALP-Fc, $D_{10}$-Fc-sALP, Fc-sALP-$D_{10}$, and Fc-$D_{10}$-sALP. In other embodiments, the $D_{10}$ in the above structures is substituted by other negatively-charged polypeptides (e.g., $D_8$, $D_{16}$, $E_{10}$, $E_8$, $E_{16}$, etc.).

Useful spacers for the present disclosure include, e.g., polypeptides comprising a Fc, and hydrophilic and flexible polypeptides able to alleviate the repulsive forces caused by the presence of the highly negatively-charged bone-targeting sequence (e.g., $D_{10}$) added at the C-terminus of the sALP sequence.

Dimers/Tetramers

In specific embodiments, the bone-targeted sALP fusion proteins of the present disclosure are associated so as to form dimers or tetramers.

In the dimeric configuration, the steric hindrance imposed by the formation of the interchain disulfide bonds is presumably preventing the association of sALP domains to associate into the dimeric minimal catalytically-active protein that is present in normal cells.

Without being limited to this particular theory, it is believed that in its tetrameric structure, the association of the fusion proteins involves one sALP domain from one dimer linking to another sALP domain from a different dimer.

The bone-targeted sALP may further optionally comprise one or more additional amino acids 1) downstream from the negatively-charged peptide (e.g., the bone tag); and/or 2) between the negatively-charged peptide (e.g., the bone tag) and the Fc fragment; and/or 3) between the spacer (e.g., an Fc fragment) and the sALP fragment. This could occur, for example, when the cloning strategy used to produce the bone-targeting conjugate introduces exogenous amino acids in these locations. However, the exogenous amino acids should be selected so as not to provide an additional GPI anchoring signal. The likelihood of a designed sequence being cleaved by the transamidase of the host cell can be predicted as described by Ikezawa, 2002 Glycosylphosphatidylinositol (GPI)-anchored proteins. *Biol Pharm Bull.* 25:409-17.

The present disclosure also encompasses a fusion protein that is post-translationally modified, such as by glycosylation including those expressly mentioned herein, acetylation, amidation, blockage, formylation, gamma-carboxyglutamic acid hydroxylation, methylation, phosphorylation, pyrrolidone carboxylic acid, and sulfation.

Asfotase Alfa

The alkaline phosphatase protein described herein includes, e.g., bone-targeted sALP fusion proteins, such as asfotase alfa (i.e., TNALP-Fc-$D_{10}$; SEQ ID NO:1; STRENSIQ®, Alexion Pharmaceuticals, Inc.). Specifically, asfotase alfa is a complex soluble glycoprotein with a polypeptide length of 726 amino acids. Asfotase alfa is an Fc-fusion protein composed of 3 domains. From the N-terminus to the C terminus, asfotase alfa comprises: (1) the soluble catalytic domain of human tissue non-specific alkaline phosphatase (TNSALP) (UniProtKB/Swiss-Prot Accession No. P05186), (2) the human immunoglobulin G1 Fc domain (UniProtKB/Swiss-Prot Accession No. P01857) and (3) a deca-aspartate peptide ($D_{10}$) used as a bone-targeting domain (Nishioka et al. 2006 *Mol Genet Metab* 88:244-255). The protein associates into a homo-dimer from two primary protein sequences. This fusion protein contains 6 confirmed complex N-glycosylation sites. Five of these N-glycosylation sites are located on the sALP domain and one on the Fc domain. Another important post-translational modification present on asfotase alfa is the presence of disulfide bridges stabilizing the enzyme and the Fc-domain structure. A total of 4 intra-molecular disulfide bridges are present per monomer and 2 inter-molecular disulfide bridges are present in the dimer. One cysteine of the alkaline phosphatase domain is free.

Asfotase alfa is an approved enzyme-replacement therapy for the treatment of hypophosphatasia (HPP). In patients with HPP, loss-of-function mutation(s) in the gene encoding TNSALP causes a deficiency in TNSALP enzymatic activity, which leads to elevated circulating levels of substrates, such as inorganic pyrophosphate (PPi) and pyridoxal-5'-phosphate (PLP). Administration of asfotase alfa to patients with HPP cleaves PPi, releasing inorganic phosphate for combination with calcium, thereby promoting hydroxyapatite crystal formation and bone mineralization, and restoring a normal skeletal phenotype. For more details on asfotase alfa and its uses in treatment, see PCT Publication Nos. WO 2005/103263 and WO 2008/138131, the teachings of which are incorporated herein by reference in their entirety. In another embodiment, asfotase alfa may be used as an enzyme-replacement therapy for the treatment of Neurofibromatosis type I (NF1). For more details on asfotase alfa and its uses (together with the uses of other alkaline phosphatases) in treatment of NF1, see PCT Publication No. WO 2013/058833, the teaching of which is incorporated herein by reference in its entirety.

All references cited herein are incorporated by reference in their entirety.

Although the foregoing disclosure has been described in some detail by way of illustration and example for purposes of clarity of understanding, it is apparent to those skilled in the art that certain minor changes and modifications will be practiced. Therefore, the description and examples should not be construed as limiting the scope of the invention which is appropriately defined by the claims.

EXAMPLES

Example 1 Population Pharmacokinetic and Pharmacodynamic Modeling and Simulation of Asfotase Alfa in Patients with Hypophosphatasia Multiple clinical trials were carried out on asfotase alfa treatment of patients with hypophosphatasia (HPP). Data from the ongoing clinical trials up to a date certain were collected and analyzed. The aim was to establish a basis for asfotase alfa dose and regimen selection for HPP treatment, given an understanding of the underlying pharmacokinetic (PK) and exposure-response relationships for biomarkers, efficacy, and safety endpoints.

Clinical trial #1 design: This was a Phase 1, multi-center, multi-national, open-label, dose escalating study of asfotase alfa. Six (6) adult patients with HPP received a single intravenous (IV) infusion of 3 mg/kg followed by 3 subcutaneous (SC) injections (Cohort 1 [n=3] received 1 mg/kg/week; Cohort 2 [n=3] received 2 mg/kg/week) at weekly intervals for three weeks.

Clinical trial #2 design: This was a Phase 2, multi-center, multi-national, open-label, single group assignment study of asfotase alfa. Infants and children no more than 36 months of age with Infantile-onset HPP received a single IV infusion of 2 mg/kg. After one week, patients received SC injections of 1 mg/kg 3 times per week. After one month, dose adjustments could be made up to 2 mg/kg 3 times per week. After three months, dose adjustments could be made up to 3 mg/kg 3 times per week.

Clinical trial #3 design: This was a multi-center, multi-national, open-label, single group assignment extension study of Clinical trial #2. Infants and young children received SC injections of asfotase alfa 3 times per week at the final dose received in Clinical trial #2 for up to 60 months of treatment. Dose adjustments were allowed with a maximum dose of 40 mg per injection.

Clinical trial #4 design: This was a multi-center, multi-national, open-label, dose comparison, parallel assignment, historical control study. Children and early adolescents received SC injections of asfotase alfa at 2 mg/kg or 3 mg/kg three times per week (a total of 6 mg/kg/week or 9 mg/kg/week) for 24 weeks.

Clinical trial #5 design: This was a multi-center, multi-national, open-label, dose comparison, parallel assignment extension study of Clinical trial #4. Children and early adolescents received SC injections of asfotase alfa at 1 mg/kg 6 times per week or at 2 mg/kg 3 times per week (a total of 6 mg/kg/week) for 42 months or until regulatory approval of the drug.

Clinical trial #6 design: This is a randomized, open-label, multi-center, multi-national, dose ranging, and concurrent control study in adolescent and adult patients with HPP. Patients were enrolled and randomized to one of the following three cohorts for the first 24 weeks: 1) Daily SC injections of 0.3 mg/kg asfotase alfa (a total of 2.1 mg/kg/week), 2) Daily SC injections of 0.5 mg/kg asfotase alfa (a total of 3.5 mg/kg/week), or 3) No treatment. All patients were eligible to continue in the extension phase where they were treated with daily SC injections of 0.5 mg/kg/day asfotase alfa (a total of 3.5 mg/kg/week) for 24 weeks then received 1 mg/kg/day 6 days per week for approximately 48 weeks or until regulatory approval of the drug.

Clinical trial #7 design: This is an open-label, multi-center, multi-national study of asfotase alfa in infants and children no more than 5 years of age with Infantile-onset HPP. Patients received a SC injection of either 1 mg/kg asfotase alfa 6 days per week or 2 mg/kg asfotase alfa 3 days per week, with a maximum dose of 40 mg per injection. The total duration of treatment was 24 months.

Methods

Data representing the complete clinical course for all individuals, with respect to the repeated measures pharmacokinetic (PK) and pharmacodynamic (PD) endpoints, were assembled for analyses. In addition to PK and PD endpoints, the entire dosing history (amount and frequency), including lot sialic acid content (TSAC) and lot potency was represented, along with covariate factors such as age, weight, clinical laboratory values, neutralizing antibody status, and disease phenotype. The rationale for endpoint selection is listed in Table 1.

TABLE 1

Endpoint Selection Rationale

| Response Endpoint | Pharmacologic Rationale | Dose Selection Rationale | Phenotypes Characterized |
|---|---|---|---|
| Biomarkers Plasma PPi and PLP | Provides Evidence of Mechanism (engages target) | Select dose associated with near maximal reduction Infantile/perinatal | Infantile/ perinatal and Juvenile |
| Radiographic endpoints RGI-C, RSS, and osteoid thickness | Provides Evidence of Pharmacology (modifies disease) | Select dose that shows near maximal change from baseline | Infantile/ perinatal and Juvenile |
| Functional endpoints 6MWT and BOT2 | Provides Evidence of Clinical Benefit (results in clinically meaningful benefit) | Select dose that shows near maximal change from baseline indicating improvement in ambulation | Juvenile* |

*Proof of clinical benefit for the infantile/perinatal phenotype patient population is improved overall survival.

Population PK and pharmacokinetic-pharmacodynamic (PK-PD) analyses for repeated-measures endpoints were conducted via nonlinear mixed effects modeling. Population PK data were described with a linear two-compartment model, and population PD data (for all efficacy endpoints) were described with indirect PD response models using time-continuous patient-specific predicted serum asfotase alfa activity. A full covariate model was constructed given prespecified covariates and some exploratory variables with care to avoid correlation or collinearity in predictors. The resulting models were evaluated for goodness of fit and qualified. Model-based simulations were conducted to explore the dose-exposure-response relationships for all endpoints. Comparisons of dosing regimens and time-course of treatment effects were also conducted via simulation, in the context of PK and PD endpoints.

Relationships between quartiles of average concentration since first dose ($C_{avg,study}$), calculated as $AUC_{cumulative}$/time after first dose ("TAFD"), and the incidence rate of adverse events (AEs) was examined for ectopic calcification, injection/infusion associated reactions, and injection site reactions.

X-Ray

X-ray evaluations were reported using two assessments, RGI-C and RSS. The RGI-C scale scores are described as follows:
  very much better (i.e., complete or near complete healing of HPP-associated rickets; +3)
  much better (i.e., substantial healing of HPP associated rickets; +2)
  minimally better (i.e., minimal healing of HPP associated rickets; +1)
  unchanged (0)
  minimally worse (i.e., minimal worsening of HPP-associated rickets; −1)
  much worse (i.e., moderate worsening of HPP-associated rickets; −2)
  very much worse (i.e., severe worsening of HPP-associated rickets; −3)

Three pediatric radiologists not affiliated with the conduct of the studies participated in a training session conducted by a pediatric radiologist with expertise in skeletal dysplasias. The training was followed by a test to confirm the ability of the radiologists to identify HPP-associated skeletal abnormalities. After completion of training, the radiologists were asked to assign a single RGI-C score for each patient to reflect perceived change in the appearance of radiographic images of the chest and upper and lower extremities from baseline to a post-baseline timepoint. The average of the three RGI-C scores was used in this PK-PD analysis.

Radiographic changes were also evaluated using a RSS developed to assess the severity of nutritional rickets based on the degree of metaphyseal fraying and cupping and the proportion of growth plate affected. The maximum total score on the RSS is 10 points, with a maximum score of 4 points for the wrists and 6 points for the knees (higher scores are associated with more severe rickets). Individual radiographs of the wrists and knees were presented to the developer of this instrument in random order for scoring. The rater was blinded to patient identifiers and the timepoint in which X-rays were taken.

6MWT

The 6MWT was administered in specific studies at select times to evaluate walking ability. Patients were instructed to walk the length of a premeasured hallway for 6 minutes. The primary measure was the distance walked (in meters). This distance was then transformed to a percent predicted of a reference population. Percent predicted 6MWT values were calculated based on reference age groups as follows: Ages 13-19 years reference, Ages 20-39 years reference, and Ages 40-65 reference.

BOT-2 (Strength and Agility Composite Standard Scores)

The BOT-2 test was administered in specific studies as a measure of gross motor function. The BOT-2 assesses motor proficiency in normally developing individuals as well as in those with moderate motor deficits, from 4 to 21 years of age, inclusive. Two gross motor subtests (running speed/agility and strength) were administered and used to calculate a strength and agility composite score (standard score and percentile rank). BOT-2 strength and agility composite standard scores were calculated according to Bruininks and Bruininks (Bruininks-Oseretsky Test of Motor Proficiency, Second Edition (BOT-2) (2005). URL http://www.pearson-assessments.com/HAIWEB/Cultures/en-us/Productdetail.htm?Pid=PAa58000). Briefly, Running Speed and Agility and Strength standardized subscores (called scale-scores) were standardized to scores of a reference age-matched group. For BOT-2, standard scores range from 20 to 80 and have a mean of 50 and a standard deviation of 10.

Pharmacokinetics (PK)

The pharmacokinetic (PK) properties of intravenous (IV) and subcutaneous (SC) asfotase alfa have been studied in pediatric and adult patients with HPP. The absolute bioavailability of SC asfotase alfa ranged from 46% to 98%. Mean clearance in L/day (CL) and volume of distribution (V) values ranged from 7.90 to 11.4 mL/min (11.4 to 16.4 L/day) and 39.7 to 71.0 L, respectively. Median times of maximum concentration in the dosing interval (Tmax) values were 24 to 48 hours after SC injection. The maximum concentration in the dosing interval (mass units/volume) ($C_{max}$) (U/L) and the $AUC_{0-168}$ (U*h/L) of asfotase alfa increased in a dose-proportional manner from 1 mg/kg to 2 mg/kg following SC injection. After SC dosing, asfotase alfa exhibits flip-flop kinetics, where the effective half-life ($t_{1/2}$) is rate-limited by the relatively slower absorption kinetics. The elimination $t_{1/2}$ after IV dosing was 59 to 73 hours and was independent of dose, while the effective $t_{1/2}$ after SC dosing was 112 to 135 hours and was also independent of dose.

For multiple multicenter studies disclosed herein on the safety and efficacy of asfotase alfa, the analysis was performed to update the model-based description of the HPP population PK and exposure-response relationships of asfotase alfa using completed safety-efficacy studies as well as data from ongoing studies with a defined "data cut", and expands the dataset used and reported for prior analyses.

Pharmacodynamics (PD)

A number of pharmacodynamic (PD) endpoints related to mechanism of action, imaging-based and functional efficacy and safety/tolerability were collected in the asfotase alfa development program for understanding the exposure-response for various effects of asfotase alfa. Two biomarkers to be examined are substrates of TNSALP: PLP and PPi. Elevated levels of TNSALP substrates are characteristic of HPP. Likewise, reductions in these substrates are indicative of pharmacologic response. Evidence from radiographs of the wrists and knees was described using Radiographic Global Impression of Change (RGI-C) and Rickets Severity Scale (RSS), both of which are expected to improve with asfotase alfa therapy. These two particular endpoints are also useful in that natural history data are available, and will allow the quantitative assessment of disease progression in the absence of treatment. Osteoid thickness (OT) is a histomorphometric measurement of bone disease, which should also reflect efficacy-related pharmacologic response. From a functional point of view, useful endpoints for exposure-response purposes include the Bruininks-Oserestsky Test of Motor Proficiency, Second Edition (BOT-2, the strength and agility composite standardized score) and Six-Minute Walk Test (6MWT). Key safety endpoints for assessment of exposure-response include: EctopicCalcification (EC), Injection/Infusion Associated Reactions (IAR), and Injection Site Reactions (ISR).

Data Assembly

Data for the population PK-PD analyses were assembled and formatted according to the general provisions disclosed herein. Population PK and exposure-response data sets were developed from the pooled data across studies. The dosing, covariate, labs, pharmacodynamic (PD), and PK data were formatted for NMTRAN and saved as ASCII text, using version 3.0.2 or above of R, (see the website for "the R project for statistical computing" at www.r-project.org), a data analysis language suitable for use in regulated environments (www.r-project.org/doc/R-FDA.pdf). All data manipulation programs and data files were documented and archived in order to maintain an audit trail. A quality control check of the data assembly process was also conducted.

Endpoint observations that are below the analytical assay quantification limit or any values that were otherwise missing were excluded from the estimation analysis, but those time points may be included for prediction purposes. Individual, clinical and demographic covariate factors may also be included. If greater than 10% of any covariate value was missing, that covariate was not included in the analysis. Otherwise, missing covariates was imputed using a single imputation method, based on the remaining available data (typically with the median of remaining values). Endpoint observations with missing observation or dosing times were imputed per protocol design if applicable, or were otherwise excluded from the analyses.

Data Analyses

To address the overall goals of these analyses, population PK and exposure-response assessments were conducted. The lack of traditional clinical pharmacology and dose-ranging study designs in the asfotase alfa development program necessitated pooled data and model-based approaches to support inferences about exposure, dose, and regimen. Note that exposure-response models for repeated measures data (where available) provide the additional advantage of exploring within-individual changes in exposure and response, whereas non-repeated measures endpoints must rely on PK variability to elucidate the typical population exposure-response relationships.

Individual, clinical, and demographic factors included in the population PK dataset were sex, height, weight, age, age of disease symptom onset, phenotype, concomitant medications, tanner stage, and race. Time-varying factors such as immunogenicity status, body weight, and age required special attention in the data assembly. Enrollment of infants and children in these studies necessitated relatively intensive imputations of age and body weight. Age calculated in years was explicitly calculated at dosing and observation records using the patient's birthdate. If the specific day was missing from the patient's birthdate, the first day of the month in which the patient was born was assumed. Weight was interpolated at all dosing and observation records assuming a linear interpolation between recorded body weight records.

Phenotype was assigned using the age of first signs and symptoms as follows: <6 months=Perinatal/Infantile; ≥6 months and ≤18 years=Juvenile; and ≥18 years=Adult. If age of first signs and symptoms was missing then phenotype was also missing, and characterized as Unknown.

Complete dosing histories had to be reconstructed during data assembly. Incomplete dosing information in several patients required imputation of dosing records between explicit records. Doses were imputed by carrying forward recorded dose amounts (mg/kg) and regimens (times/week) until the next recorded dose. This continued until the last recorded dose. Additionally, drug lot information was not recorded with all dosing records. Since drug lot information such as sialic acid content and asfotase alfa specific activity varied across lots and this information was used in PK model development, lot shipment dates were assumed to be the start dates for administration of a given lot to a given patient if lot was not otherwise specified. In this manner, lot numbers, sialic acid content, and asfotase alfa specific activity were defined for all administered doses. In some cases, lot assignments were unknown and values for asfotase alfa activity and sialic acid content were imputed given the averages of these characteristics across all lots.

Several patients were enrolled in more than one study, requiring some modifications to the dataset. In most of these cases, patients were enrolled from an initial study into an extension study (e.g., study #2 and extension study #3 and study #4 and extension study #5). Some duplicate dosing records were noted at the intersection of these studies and in such cases only a single record was retained. Also, four patients in study #6 were previously enrolled in study #1. Time after first dose (days) for these patients enrolled in more than one study were calculated from the time of administration of the first dose in the original study.

Generally, a record was discarded as a duplicate wherever the subject, time, and quantity of interest were identical to a prior record. Near exceptions were resolved in collaboration with the sponsor.

All serum asfotase alfa activities and plasma PLP and PPi concentrations reported as below the limit of quantification (BLQ) were set to an NONMEM data item EVID value of 0 and identified in the dataset with a flag (BLQ=1). If the percentage of BLQ data was small (<15%), these values were excluded from the analysis.

Plasma PLP data were analyzed using two bioanalytical assays. In some cases, samples were analyzed using both assays, allowing for the development of an algorithm to convert ARUP values to Biotrial values. This algorithm was applied to any ARUP assay values without corresponding Biotrial assay values and these values were flagged in the dataset in the column fit.

For model-based analysis of PD endpoints, maximum a-posteriori (MAP) Bayes estimates of individual random effects for CL, central volume of distribution ($V_2$), peripheral volume of distribution ($V_3$), intercompartmental clearance (Q), absolute bioavailability (F), absorption rate constant ($k_a$), and absorption lag time (ALAG) were estimated from the final PK model then merged by subject ID with the original PK-PD dataset for sequential PK-PD analysis. For patients with PD observations but no PK observations, individual PK random effect estimates defaulted to the typical population values.

Derivation of Estimated Glomerular Filtration Rate

For patients aged 18 and older, renal function was represented by eGFR, calculated using a standard MDRD formula as shown in Eq. 1.

$$eGFR_{MDRD} = 175 \times SCR^{-1.154} \times AGE^{-0.203} \times 0.742_{female} \times 1.212_{Afr.\ Amer.} \quad (1)$$

For patients younger than 18 years, eGFR was calculated using the Schwartz formula as shown in Eq. 2.

$$eGFR_{Schwartz} = HEIGHT \times k/SCR \quad (2)$$

where k=0.45 for children up to 1 year of age, 0.55 for children from 1-13 years of age and adolescent females (13-18 years), and 0.7 in adolescent males (13-18 years).

The units for eGFR are mL/min/1.73 $m^2$. Use of these formulae resulted in some non-physiologic estimates of glomerular filtration rate. Any calculated value greater than 150 mL/min/1.73 $m^2$ was replaced with 150 mL/min/1.73 $m^2$ for modeling purposes. The value 150 approximately represents the mean plus one standard deviation of eGFR values derived using the NHANES database and the MDRD formula (Levey et al. 2009 *Ann Intern Med* 150:604-12).

Computational Environment and Version Control

In general, population analyses for repeated-measures endpoints were conducted via nonlinear mixed effects modeling with a qualified installation of the NONMEM software, Version 7.2 or higher (ICON Development Solutions, Hanover, Md.) and Intel Fortran Compiler, version 12.0.4 on a Linux computing grid. NMQual 8.2.7 or higher were used to track all code patches/options and install the NONMEM software. The first-order conditional estimation with η-ε interaction (FOCEI) was employed for all model runs. Assessment of model adequacy and decisions about increasing model complexity were driven by the data and guided by goodness-of-fit criteria, including (1) visual inspection of diagnostic scatter plots (observed vs. predicted concentration, residual/weighted residual vs. predicted concentration or time and histograms of individual random effects, for example), (2) successful convergence of the minimization routine with at least 3 significant digits in parameter estimates, (3) plausibility of parameter estimates, (4) precision of parameter estimates, (5) correlation between model parameter estimation errors <0.95, and (6) the Akaike information criterion (AIC), given the minimum objective function value and number of estimated parameters. All parameter estimates were reported with a measure of estimation uncertainty, such as the standard error of the estimates (obtained from the NONMEM $COVARIANCE step). Descriptive statistics, and naive pooled modeling approaches may be applied to nonrepeated measures data, using R. All codes were maintained using the version control system Subversion (subversion.tigris.org/). Specific analysis methods are described below, by endpoint.

Population PK Modeling and Simulation

Initial modeling of the IV and SC PK data was conducted using a two-compartment disposition model with first-order absorption, parameterized in terms of CL, central volume of distribution model with first-order absorption, parameterized in terms of CL, central volume of distribution ($V_2$), peripheral volume of distribution ($V_3$), intercompartmental clearance (Q), absorption rate constant ($k_a$), and absolute bioavailability (F), with interindividual random effect parameters supportable by the data. The parameters CL, $V_2$, $V_3$, and Q were described initially using allometric relationships to patient body weight. Model-based inferences regarding the effect of the following covariates on asfotase alfa CL are prespecified: presence of anti-drug antibodies, presence of neutralizing antibodies, and lot sialic acid content. The effect of batch size (2,000 L or 20,000 L) on F and $k_a$ were also characterized. Asfotase alfa lot specific activity was accounted for in the dose amount administered. Additionally, the effect of estimated glomerular filtration rate (eGFR) was evaluated in a post hoc context. This is due to the correlation between body weight and eGFR measures. Exploratory covariates, including serum alanine transaminase in U/L (ALT) and serum aspartate transaminase in U/L (AST), may be investigated post hoc for effects on CL.

An investigation of covariate-parameter relationships was also undertaken as part of the population PK and PK-PD analyses. Covariate model building for population PK and PK-PD models have typically been conducted as an exploratory stepwise regression exercise characterized by varying degrees of prior scientific thought about inclusion of potential predictor variables. Stepwise forward or backward comparisons, based on the likelihood ratio test and a prespecified alpha level, are made across multiple models, each expressing different covariate parameter relationships (see Jonsson and Karlsson, 1998 *Pharmaceutical Research* 15:1463-1468 and Mandema et al., 1992 *Journal of Pharmacokinetics and Biopharmaceutics* 20:511-528). According to the likelihood ratio test, the difference in 2*log-likelihood from nested models is assumed to be asymptotically 2 distributed with degrees of freedom (df) equal to the difference in number of model parameters (Beal et al., 1989-2006 *NONMEM Users Guide: Part I-VII* (Icon Development Solutions, Ellicott City, Md., USA). It has been shown, however, that actual significance levels obtained from nonlinear mixed effects modeling are sensitive to likelihood approximations in the estimation routine and can be quite different from the nominal significance levels under the assumed 2 distribution, even when the model is known (Gobburu and Lawrence 2002 *Pharmaceutical Research* 19:92-98; Wahlby et al., 2001 *Journal of Pharmacokinetics and Pharmacodynamics* 28:231-252; and Wahlby et al., 2002 *Journal of Pharmacokinetics and Pharmacodynamics* 29:411-412). In addition to the problems associated with the likelihood ratio test in nonlinear mixed effects models, other problems are associated with stepwise regression techniques in general, including problems with correlated or collinear predictors, multiple comparisons, artificially optimistic parameter precision, selection bias, and a lack of biologic rationale for significant predictors (Harrell 2001 *Regression modeling strategies: With applications to linear models, logistic regression, and survival analysis* (Springer-Verlag, New York; Burnham 2002 *Model selection and multimodel inference: A practical information-theoretic approach* (Springer-Verlag, New York). These performance limitations are further amplified with small datasets (Ribbing and Jonsson, 2004 *Journal of Pharmacokinetics and Pharmacodynamics* 31:109-134). Analysts using stepwise methods for covariate model building in population PK are also faced with the difficulty of reconciling statistically significant covariate effects from those effects that are clinically relevant (Burnham 2002; Gastonguay 2011 *Full Covariate Models as an Alternative to Methods Relying on Statistical Significance for Inferences about Covariate Effects: A Review of Methodology and* 42 *Case Studies*. In PAGE 20, Abstr 2299, page A16).

Given these issues and the relatively small numbers of individuals available to contribute data to the analyses, a covariate modeling approach emphasizing parameter estimation rather than stepwise hypothesis testing was implemented for these population PK and PK-PD analyses. Covariate-parameter relationships were predefined based on scientific interest, mechanistic plausibility, or prior knowledge, and a full model was constructed with care to avoid correlation or collinearity in predictors (covariates with correlation coefficients >0.35 were not simultaneously included as potential predictors) (Harrell 2001; Burnham 2002; Ette and Ludden, 1995 *Pharmaceutical Research* 12:1845-1855; and Gastonguay 2011). This full model notion is a simplification of the global model approach described by Burnham and Anderson (Burnham 2002). Population parameters, including fixed effects parameters (covariate coefficients and structural model parameters), and random effects parameters were estimated. An exploratory assessment of any remaining trends was conducted by graphical inspection of all covariate effects (plots of maximum a posteriori (MAP) Bayes estimates of individual random effects ($\eta_i$) and/or weighted residuals (WRES) from the full model versus covariates). Inferences about clinical relevance of parameters were based on the resulting parameter estimates of the full model and measures of estimation precision (asymptotic standard errors). No hypothesis testing was conducted. This approach enabled the direct assessment of clinical relevance of covariate effects and also provided some explanation for the apparent absence of a covariate effect (true lack of an effect vs. lack of information about that effect). The influence of additional covariates that were not prespecified was evaluated similarly but in an exploratory post hoc fashion.

Regulatory guidance documents on population pharmacokinetics suggest that a model evaluation step should be performed to assess the adequacy of the population PK model for the intended purposes (Guidance for Industry: Population pharmacokinetics. Technical report, Food and Drug Administration, Center for Drug Evaluation and Research, Center for Biologics Evaluation and Research (1999)). The final asfotase alfa population PK and PK-PD models were evaluated using a simulation-based predictive check method. This method is derived from the posterior predictive check methods but assumes that parameter uncertainty is negligible relative to interindividual and residual variance (Gelman et al. 2004 Bayesian data analysis (Chapman & Hall/CRC, New York; Yano et al., 2001 *Journal of Pharmacokinetics and Biopharmaceutics* 28:171-192). The basic premise is that a model and parameters derived from an observed dataset should produce simulated data that are similar to the original observed data. The predictive check is a useful adjunct to typical diagnostic plots in that the predictive check provides information about the performance of random effects parameter estimates whereas typical diagnostic plots are primarily informative about the fixed effects parameter estimates. Five hundred Monte Carlo simulation replicates of the original dataset were generated using the final population PK and PK-PD models. For the PK predictive checks observations or predicted values below the quantifiable limit were excluded. Distributions of a characteristic of the simulated data were compared with the distribution of the same characteristic in the observed asfotase alfa dataset, using exploratory graphics (quantile-quantile plots, histograms, and visual predictive checks). Any problems evident by visual inspection of exploratory graphics were investigated and further model development was conducted as necessary.

Model Parameterization and Distributional Assumptions

The approximate joint posterior distribution of estimated population parameters (e.g., covariance matrix of the estimates) follows a Multivariate Normal (MVN) distribution. PK and PD model parameters were modeled in the log-domain to maintain consistency with this distributional assumption (Eq. 3).

For any parametric nonlinear mixed effects model, it is necessary to assume parametric distributions for the random effects. As a starting point for this analysis, all interindividual error terms were described by an exponential error model or log-normal parameter distribution (Eq. 3). An attempt was made to define a full covariance matrix for the interindividual random effects (S2) when possible.

$\hat{P}$ exp($\theta$)

$$P_i = \hat{P} \cdot \exp(\eta_{Pi}) \tag{3}$$

where:

$\theta$ is the log-transformed typical population value of the parameter.

$P_i$ is the estimated parameter value for individual I.

$\hat{P}$ is the typical population value (geometric mean) of the parameter $\eta_{Pi}$ are individual-specific inter-individual random effects for individual i and parameter P and are assumed to be distributed: $\eta \sim N(0, \Omega)$.

For observations in these analyses, the residual error models were initially described by a combined additive and proportional error model for endpoints with untransformed observations (Eq. 4) or an additive error model for endpoints with transformed observations (Eq. 5), e.g., logarithm or logit transforms.

$$C_{ij} = \hat{C}_{ij}(1+\varepsilon_{pij}) + \varepsilon_{aij} \tag{4}$$

$$C_{ij} = \hat{C}_{ij} + \varepsilon_{aij} \tag{5}$$

where:

$C_{ij}$ is the jth measured observation (plasma asfotase alfa exposure) in individual i.

$\hat{C}_{ij}$ is the jth model predicted value (plasma asfotase alfa exposure) in individual i.

$\varepsilon_{pij}$ and $\varepsilon_{aij}$ are proportional and additive residual random errors, respectively, for individual i and measurement j and are each assumed to be independently and identically distributed: $\varepsilon \sim N(0, \sigma^2)$.

An attempt was made to incorporate known physiologic relationships into the covariate-parameter models. For example, the change in physiologic parameters as a function of body size is both theoretically and empirically described by an allometric model (Eq. 6).

$$TVP = \theta_{TVP} \cdot \left(\frac{WT_i}{WT_{ref}}\right)^{\theta_{allo}} \tag{6}$$

where
- the typical value of a model parameter (TVP) is described as a function of individual body weight (WTi), normalized by a reference weight (WTref).
- $\theta_{TVP}$ is an estimated parameter describing the typical PK parameter value for an individual with weight equal to the reference weight and
- $\theta_{allo}$ is a allometric power parameter, which is either estimated or assigned a value of 0.75 for physiologic processes, such as clearances, and fixed to a value of 1 for anatomical volumes.

In those cases where no physiologic relationship is known a priori, the effects of continuous covariates will be modeled using a normalized power model while the effects of categorical covariates were similarly described (Eq. 7).

$$TVP = \theta_n \cdot \prod_i^m \left(\frac{cov_{mi}}{ref_m}\right)^{\theta_{(m+n)}} \cdot \prod_i^p \theta_{(p+m+n)}^{cov_{pi}} \tag{7}$$

where the typical value of a model parameter (TVP) is described as a function of individual continuous covariates ($cov_{mi}$), and p individual categorical (0-1) covariates ($cov_{pi}$), such that $\theta_n$ is an estimated parameter describing the typical PK parameter value for an individual with covariates equal to the reference covariate values ($cov_{mi}=ref_m$, $cov_{pi}$, =0), $\theta_{(m+n)}$ and $\theta_{(p+m+n)}$, are estimated parameters describing the magnitude of the covariate-parameter relationships.

These modeling assumptions were evaluated using standard diagnostics based on model outputs.

Population PK/PD Modeling

Response endpoints of interest for population PK/PD modeling include the biomarkers serum PPi and PLP; the radiologic endpoints RSS and RGI-C; and the functional endpoints, 6MWT and BOT-2.

Previous analyses of these endpoints with a subset of the present data have demonstrated that asfotase alfa influences the responses according to an indirect PK/PD relationship. Given knowledge of the indirect relationship between PK time-course and clinical response for asfotase alfa, model development will focus on indirect PD response models. Ultimately, the complexity of the model development will depend on the information available in the data.

The indirect PD response models assume homeostasis of the response variable prior to drug treatment, governed by some zero-order production process and a first-order degradation process. The assumption of a time-constant baseline response with no placebo effect will be implemented for all endpoints. The appropriateness of this assumption will be evaluated for the imaging endpoints (RSS, RGI-C) using historical control data. No control or historical data is available for the other endpoints.

Multiple variants of the basic indirect PD response have been described, allowing drug effects to be mediated via the following general mechanisms:
- Increase response by inhibiting degradation of response or stimulating production of response.
- Decrease response by stimulating degradation of response or inhibiting production of response.

Consistent with prior analyses, the initial modeling plan is to incorporate asfotase alfa concentrations into the indirect PD response model using a Emax model to describe the total effect on response endpoints (Equation 8).

$$PD(C_{asfotasealfa}) = \frac{E_{max,asfotasealfa} \cdot C_{asfotasealfa}}{EC_{50,asfotasealfa} + C_{asfotasealfa}} \tag{8}$$

where:
- $PD(C_{asfotase\ alfa})$ is the pharmacodynamic effect based on activity of asfotase alfa.
- $E_{max,asfotase\ alfa}$ is the maximum effect of asfotase alfa.
- $EC_{50,asfotase\ alfa}$ is the activity of asfotase alfa that produces half-maximal effect.
- $C_{asfotase\ alfa}$ is the serum activity of asfotase alfa.

The proposed initial indirect effect models are expressed in Equations 9 and 10.

$$\frac{dR}{dt} = K_{in} - K_{out} \cdot (1 - PD(C_{asfotasealfa})) \cdot R \tag{9}$$

$$R_o = K_{in} / K_{out}$$

$$\frac{dR}{dt} = K_{in} - K_{out} \cdot (1 + PD(C_{asfotasealfa})) \cdot R \tag{10}$$

$$R_o = K_{in} / K_{out}$$

where:
- R is the response endpoint.
- $R_o$ is the baseline response endpoint.
- $K_{in}$ is the zero order input (synthesis) rate of the response.
- $K_{out}$ is the first order output (turnover) rate constant of the response.
- $PD(C_{asfotase\ alfa})$ is the pharmacodynamic effect based on concentration of asfotase alfa.

Models where $PD(C_{asfotasealfa})$ influenced $K_{in}$ in a manner as described for $K_{out}$ will also be considered if appropriate. For each endpoint, the parameters of a null model, i.e., a model excluding any effect of asfotase alfa on pharmacodynamic response, were estimated as a basis for further understanding the extent of impact of asfotase alfa. The responses will be transformed (or the model predictions transformed as shown in Table 2.

TABLE 2

Observation Transformations

| Endpoint | Transform Type | Transformation |
|---|---|---|
| Asfotase alfa activity | log | LDV = log(DV) |
| PPi | none | LDV = DV |
| PLP | none | LDV = DV |
| RGIC | logit | $LDV = \log\left(\frac{\frac{(DV+3]}{6}}{1 - \frac{(DV+3]}{6}}\right)$ |
| RSS-Knee | none* | LDV = DV |
| RSS-Wrist | none* | LDV = DV |
| 6MWT | none | LDV = DV |
| BOT-2 | logit | $LDV = \log\left(\frac{\frac{(DV-20]}{60}}{1 - \frac{(DV-20]}{60}}\right)$ |

DV = observation,
LDV = transformed observation
*Logit transforms were used to constrain model predictions to the interval of 0-4 for RSS-Wrist and 0-6 for RSS-Knee Simulations to Evaluate Exposure-Response and Compare Dose Regimens Simulation methods were used to more fully elaborate the exposure-response relationship for asfotase alfa and biomarkers, X-ray endpoints, and functional endpoints. Additionally, simulations were used as a basis for comparing the effect of two regimens of asfotase alfa 1 mg/kg given six times per week and 2 mg/kg given three times per week.

For the exposure-response simulations, a template dataset was created that contained subcutaneous administration of 0.02, 0.1, 0.25, 0.3, 0.5, 0.75, 1, and 2 mg/kg given seven times per week, 1 mg/kg given six times per week, and 2 mg/kg given three times per week. In the template, one dose regimen was given to one patient repeatedly until the observation time for the endpoint. Half of these regimens were studied in the clinical investigations; half were selected to interpolate or extrapolate exposure data to provide a more extensive understanding of exposure-response.

The observation times for the simulated endpoints were as follows: PPi, 7 and 24 weeks; PLP, 24 weeks; RSS, RGI-C, BOT-2, and 6MWT, 72 weeks. These timepoints were selected to demonstrate the exposure-response at a relevant timepoint for the endpoint. For example, Week 72 was chosen for radiologic endpoints as demonstrable and clinically meaningful response is expected to take more time to achieve than a biomarker such as PPi or PLP.

For each endpoint, 500 replicates were performed. Thus, each regimen was represented 500 times. Asfotase alfa product characteristics in the simulations were a sialic acid level of 2.2 (mol/−mol), a 20,000 L batch size, and a drug activity of 990 U/mg.

The population of patients comprising the simulation was constructed in the context of the simulation. The patients were assumed to not manifest anti-drug or neutralizing antibodies. To obtain a faithful representation of simulated patients' body weights over time, the frequency of ages in the analysis dataset and the correlation between patient age and body weight were leveraged to create a body weight time-course. A four-part process was used. The first three parts simulate baseline ages for the patients, with the goal of approximately representing the distribution of ages in the analysis dataset. The last part transformed patient age into a body weight.

First, the analysis dataset was used to determine the proportion of baseline ages in each of a number of pre-defined bins where the number of bins and the age cutoffs for each of the bins depended on the endpoint being simulated. Second, simulated patients were randomly assigned to an age bin with a probability matching the observed frequency of subjects in that age bin in the analysis dataset as determined in the first step. Third, once a simulated patient was assigned to an age bin, the patient's actual baseline age was sampled from a uniform distribution of ages between the age cutoffs defining that bin. Subsequently, the patient's age was incremented throughout the time-course underlying the simulation, e.g., 72 weeks in the case of radiologic endpoints. The final step was to use a modeled age-weight relationship using data in analysis dataset to convert the patient age to a body weight.

For the exposure-response simulations, the variable of interest was the median response and the 90% confidence interval for response for each regimen, where the confidence interval characterized uncertainty inherent in the pharmacodynamic parameter estimates. Therefore, the simulations did not included random interindividual variability beyond that introduced through incorporation of patient-specific covariates. The pharmacodynamic parameters were assumed to have mean values equal to the point estimates obtained in the modeling step and variance-covariance equal to the estimated variance-covariance matrix. It is important to note that this multivariate normal distribution represents the uncertainty in the population parameter estimates, not the variability in patient-level pharmacodynamic parameters. The median age and weight were calculated for each endpoint as a representative patient for the simulation. In the simulations used for comparing the 1 mg/kg given six days weekly regimen and 2 mg/kg given three days weekly regimen, the variable of interest was the distribution of patient-level responses. Therefore, variability was due to patient specific covariates and random interindividual pharmacokinetic and pharmacodynamic variability. The point estimates of the pharmacokinetic and pharmacodynamic parameters were assumed to be known without imprecision. As a component of the simulations, the time-courses of asfotase alfa activity-time profiles were constructed and reported.

Biomarker (PLP, PPi) Exposure-Response

Population nonlinear mixed effects exposure-response models for repeated measures biomarker data will be developed separately for the PLP and PPi biomarkers. Data will be pooled across studies, with phenotype to be included as a covariate effect in the exposure-response model. Although no control or placebo data are available for these endpoints, exposure-response modeling will proceed under the assumption that both biomarkers have reached a steady-state disease severity, and that the untreated response would have continued with no time-dependence (e.g. linear disease progression with slope=0). Prior exploratory modeling and graphics revealed an indirect relationship between plasma asfotase alfa exposure time course and biomarker response time course. As such, the model-based prediction of continuous asfotase alfa exposure time course will be linked to indirect pharmacodynamic response models, with drug effect implemented as a stimulation of the first-order offset for the biomarker effect kinetics. Final models and parameter estimates will be qualified using predictive checks. Standard errors, or other measures of parameter estimation precision will be obtained from the asymptotic covariance matrix of the estimates.

The resulting biomarker exposure-response model will be used to support dose selection, and will be used as a simulation tool to illustrate the impact of dosing regimen (e.g. 1 mg/kg six times per week vs. 2 mg/kg three times per week) on steady-state PLP and PPi response.

Radiologic Endpoint Exposure-Response

The RGI-C endpoint will be the mean of the three readers at each time-point. The RSS endpoint will be divided into wrist and knee subcomponents for separate exposure-response analyses.

Analysis of the radiologic endpoints in treated patients will be preceded by analysis of the historical control dataset, comprised of both Infantile and Juvenile phenotypes. This analysis will be performed to test the assumption of no underlying disease progression or improvement. Since the conclusion regarding underlying time course of disease is performed on a dataset with a specific age range, subsequent analyses of treated patients will be constrained to approximately the same age range. The historical control data will be analyzed as follows:

RGI-C Natural History:
  Natural history data are available as matched pairs of X-Ray observations over time, within each individual. In these data the baseline or reference X-Ray for each pair is different. This prohibits analysis with a single model for repeated-measures data. Instead, each pair will be used to define a rate of RGI-C change (or slope), but dividing the resulting mean RGI-C score by the time elapsed between the two X-Rays in the pair. Each individual in this cohort was studied at multiple occasions, with multiple X-Ray pairs assessed, and therefore, each individual will contribute multiple RGI-C slopes. Given the derived RGI-C slopes, a population mixed-effects model will be derived to estimate the mean (and 95% CI) slope. The resulting slope estimate will be used as the disease progression rate for the subsequent analysis of asfotase alfa-treated cohorts. If the 95% CI for the RGI-C slope includes the null value of zero, a disease progression of zero-slope will be assumed for the subsequent exposure-response modeling.

RSS Natural History:

Natural history data are available for both RSS-wrist and RSS-knee subscores. As an exploratory effort, a population mixed-effects model will be derived to estimate the rate of disease progression for both wrist and knee endpoints. Linear models will be explored, but alternative structures may be implemented given results of goodness of fit diagnostics. The resulting disease progression models will be used to anchor the disease progression rates for the subsequent exposure-response analyses of asfotase alfa-treated cohorts. If the 95% CI for either the knee or wrist disease progression includes the null value, a disease progression of zero-slope will be assumed for the subsequent exposure response modeling.

Exposure-response data from asfotase alfa active treatment arms will be analyzed conditioned on the exploratory natural history analyses described above.

RGI-C Active Treatment:

Population nonlinear mixed effects exposure-response models for continuous, repeated measures RGI-C data will be developed. Data will be pooled across studies. The disease progression component of this model will be anchored to fixed parameters from the natural history analysis described above. It is anticipated that asfotase alfa effects on RGI-C will follow an indirect relationship between plasma asfotase alfa exposure time course and efficacy response time course. As such, the model based prediction of continuous asfotase alfa exposure time course will be used to drive an indirect pharmacodynamic response model, with drug effect implemented as a stimulation of the zero-order formation rate for RGI-C response. Initially, serum asfotase alfa activity will be passed into the indirect effect model using an Emax model to describe the total effect on the response endpoints.

RSS Active Treatment:

Population nonlinear mixed effects exposure-response models for continuous, repeated measures RSS-wrist and RSS-knee data will be developed. Models for wrist and knee subscore data will be developed separately. Data will be pooled across studies. The disease progression components of these models will be anchored to fixed parameters from the natural history analysis described above. It is anticipated that asfotase alfa effects on RSS will follow an indirect relationship between plasma asfotase alfa exposure time course and efficacy response time course. The model-based prediction of continuous asfotase alfa exposure time course will be used to drive indirect pharmacodynamic response models, with drug effects implemented as inhibition of the zero order formation rate for RSS-wrist and RSS-knee responses. Initially, serum asfotase alfa activity will be passed into the indirect effect model using an Emax model to describe the total effect on the response endpoints (RSS).

Final models and parameter estimates will be qualified using predictive checks. Standard errors, or other measures of parameter estimation precision will be obtained from the asymptotic covariance matrix of the estimates. The resulting RGI-C and RSS exposure response models will be used to support dose selection and will be used via simulation to illustrate impact of dosing regimen (e.g. 1 mg/kg six times per week vs. 2 mg/kg three times per week) on steady-state RGI-C and RSS response.

Functional Endpoints (BOT-2 and 6MWT) Exposure-Response

Population nonlinear mixed effects exposure-response models for continuous, repeated measures BOT-2 strength and agility composite standard score and percent predicted 6MWT will be developed separately. Data will be pooled across studies for the Juvenile phenotype only. Although no control or natural history cohorts are available for these endpoints, the scores are internally calibrated to reflect response relative to a normal individual of similar age. No additional disease progression correction is planned. It is anticipated that asfotase alfa effects on BOT-2 strength and agility composite standard score and percent predicted 6MWT will follow indirect relationships between plasma asfotase alfa exposure time course and efficacy response time course. The model-based prediction of continuous asfotase alfa exposure time course will be used to drive indirect pharmacodynamic response models, with drug effects implemented as stimulation of the zero-order onset rate for both responses.

The resulting BOT-2 strength and agility composite standard score and percent predicted 6MWT exposure response models will be used to support dose selection, and will be used via simulation to illustrate impact of dosing regimen (e.g. 1 mg/kg six times per week vs. 2 mg/kg three times per week) on steady-state responses.

Histomorphometric Efficacy (Osteoid Thickness) Exposure-Response

Osteoid thickness data were collected at baseline and at a post-baseline assessment time. As a result, a single change-from baseline endpoint is available, per individual. No repeated measures data analyses will be implemented. In addition, no control or natural history cohort data are available for this endpoint. This results in a confounding of disease progression and drug effects, and makes quantitative interpretation of exposure-response models difficult, at best. Given this data limitation, results will be presented in descriptive tables, as exposure quartiles vs. response. Response will be defined as the mean (and 95% CI) change from baseline observation by quartile of $C_{avg,study}$ and will be presented for the juvenile phenotype only.

Safety Endpoints Exposure-Response

Safety data will be analyzed across all studies, and will include the following endpoints of interest:
 ectopic calcification
 injection or infusion associated reactions
 injection site reactions Exposure-response relationships will be explored via descriptive statistics. Study population event frequency, and individual patient event rates will be summarized by $C_{avg,\,study}$ exposure quartiles, and tabulated for the total trial population and by phenotype. Responses will be defined as 1) the percentage of total individuals with a given event incidence (event frequency), and 2) the mean (and 95% CI) of individual event rates, which are defined as total number of events within an individual divided by total study duration. Naive pooled logistic or nonlinear regression models may be developed for endpoints exhibiting exposure-response relationships in the descriptive analysis. Final models and parameter estimates will be qualified using simulation-based diagnostics or predictive checks. Standard errors, or other measures of parameter estimation precision will be obtained from the asymptotic covariance matrix of the estimates.

Results

Data from 73 total patients with HPP (38 females and 35 males, ranging in age from 1 day to 66.8 years at study entry) were included in the master population PK-PD dataset. This included patients who received both IV and SC asfotase alfa from multiple lots of drug product. Of that group, 68 individuals contributed a total of 1370 PK observation records towards the PK analysis. Five (5) of the 73 individuals had no PK observations (below the lower limit of quantification (BLQ) or otherwise), but contributed dosing records, covariate information, and PD observations to the dataset.

Multiple lots of asfotase alfa drug substance and drug product were used for the clinical trial supply. These lots were characterized by differences in asfotase alfa activity (potency), sialic acid content (TSAC), batch size, and differences in usage based on number of doses administered across the entire clinical program. Lot-specific factors were of interest with respect to possible impact on PK and were included in the analysis dataset by linking them to doses expected to have been administered with each different lot supply. Since the enzyme activity of some drug product batches were not available, the enzyme activity (and TSAC) from the drug substance batches was employed.

Longitudinal, repeated-measures PD biomarker and efficacy endpoint data were also included in the population PK-PD dataset. Data for PK-PD model-based analyses were derived from the master PK-PD dataset after a merge with MAP Bayes estimates of individual random effects for CL, $V_2$, $V_3$ and $k_a$, as described herein. The derived dataset was used in subsequent PK-PD analyses.

Biomarker endpoints included data from all HPP phenotypes, while all functional endpoint analyses were limited to the Juvenile phenotype. The majority of patients in the dataset were Infant or Juvenile phenotype, while patients with Unknown (PPi N=1 and PLP N=3) or Adult (PPi N=2 and PLP N=1) phenotypes represented only a small number of patients. The BOT-2 data were further restricted to subjects with ages from 4 years old to less than 22 years old, as this is the clinically relevant population for this measurement.

For patients with pediatric onset of HPP, the endpoints of interest for performing the pooled PK and PK/PD analyses included:

TNSALP substrates (plasma inorganic pyrophosphate [PPi] and pyridoxal-5'-phosphate [PLP]);
Radiographic measurements (Radiographic Global Impression of Change [RGI-C] and Rickets severity scale [RSS]); and
Functional endpoints (% predicted 6-minute walk test [6MWT] and Bruininks-Oseretsky Test of Motor Proficiency, Second Edition [BOT-2]).

For the X-ray endpoints, a reference natural progression historical control dataset was available. Subjects with both Infantile and Juvenile phenotypes and with ages 4 years to less than 13 years old were represented in the historical control data for both RGI-C and RSS endpoints. A subset of the treated HPP patient data was selected in order to match the population characteristics in the historical control dataset.

TABLE 3

Exploratory Exposure-Response Quartile Table: Week 24

| phenotype | endpoint (Δ baseline) | statistic | quartile 1 | quartile 2 | quartile 3 | quartile 4 |
| --- | --- | --- | --- | --- | --- | --- |
| Infantile | | exposure Cavg steady-state range (ng/mL) | [383, 1002] | (1002, 1202] | (1202, 1717] | (1717, 3975] |
| Infantile | | Subjects | 12 | 12 | 12 | 12 |
| Infantile | RSS-knee total score | n | 11 | 10 | 10 | 11 |
| Infantile | RSS-knee total score | mean (95% CI) | −1.3 (−2.3, −0.21) | −2.6 (−3.7,−1.5) | −1.4 (−2.5, −0.4) | −1.6 (.3, −0.26) |
| Infantile | RSS-knee total score | median | −0.5 | −2.5 | −1 | −2 |
| Infantile | RSS-wrist total score | n | 11 | 10 | 10 | 11 |
| Infantile | RSS-wrist total score | mean (95% CI) | −0.64 (−1.4, 0.1) | −1 (−1.9, −0.12) | −1.1 (−1.8, −0.33) | −0.82 (−2.1, 0.49) |
| Infantile | RSS-wrist total score | median | 0 | −1 | −0.75 | −0.5 |
| Infantile | RGI-C score | n | 12 | 11 | 11 | 11 |
| Infantile | RGI-C score | mean (95% CI) | 1.4 (0.89, 1.8) | 1.9 (1.4, 2.5) | 1.9 (1.4, 2.5) | 1.5 (0.96, 2.1) |
| Infantile | RGI-C score | median | 1.7 | 2 | 2 | 2 |
| Infantile | osteoid thickness (mm) | n | 1 | 0 | 4 | 0 |
| Infantile | osteoid thickness (mm) | mean (95% CI) | −5.4 | | 2.5 (−7.2, 7.7) | |
| Infantile | osteoid thickness (mm) | median | −5.4 | | −1 | |
| Infantile | Strength and agility composite standard score | n | 1 | 2 | 3 | 0 |
| Infantile | Strength and agility composite standard score | mean (95% CI) | 12 | 4 (2, 6) | 3.3 (−3.5, 10) | |
| Infantile | Strength and agility composite standard score | median | 12 | 4 | 4 | |
| Infantile | 6 min. walk test (m) | n | 1 | 2 | 4 | 0 |
| Infantile | 6 min. walk test (m) | mean (95% CI) | 29 | 4.6 (3, 6.2) | 16 (4.4, 27) | |
| Infantile | 6 min. walk test (m) | median | 29 | 4.6 | 14 | |
| Juvenile | | exposure Cavg steady-state range (ng/mL) | [508, 1084] | (1084, 1364] | (1364, 1652] | (1652, 3310] |
| Juvenile | | Subjects | 5 | 5 | 5 | 5 |
| Juvenile | RSS-knee total score | n | 1 | 4 | 3 | 2 |
| Juvenile | RSS-knee total score | mean (95% CI) | −1 | −1.2 (−1.7, −0.76) | −0.5 (−1.5, 0.48) | −0.75 (−1.2, −0.26) |

TABLE 3-continued

Exploratory Exposure-Response Quartile Table: Week 24

| phenotype | endpoint (Δ baseline) | statistic | quartile 1 | quartile 2 | quartile 3 | quartile 4 |
| --- | --- | --- | --- | --- | --- | --- |
| Juvenile | RSS-knee total score | median | −1 | −1.5 | 0 | −0.75 |
| Juvenile | RSS-wrist total score | n | 1 | 4 | 3 | 2 |
| Juvenile | RSS-wrist total score | mean (95% CI) | −1 | −1 (−1.4, −0.6) | −0.67 (−1.3, −0.013) | −0.5 (−1.5, 0.48) |
| Juvenile | RSS-wrist total score | median | −1 | −1 | −1 | −0.5 |
| Juvenile | RGI-C score | n | 2 | 4 | 3 | 2 |
| Juvenile | RGI-C score | mean (95% CI) | 1.2 (−0.47, 2.8) | 2 (1.7, 2.3) | 1.6 (0.98, 2.1) | 1.2 (0.84, 1.5) |
| Juvenile | RGI-C score | median | 1.2 | 2 | 1.7 | 1.2 |
| Juvenile | osteoid thickness (mm) | n | 3 | 4 | 4 | 2 |
| Juvenile | osteoid thickness (mm) | mean (95% CI) | −3.8 (−6.2, −1.3) | −6.4 (−8.3, −4.5) | −1.1 (−6.9, 4.7) | −3.8 (−8.1, 0.51) |
| Juvenile | osteoid thickness (mm) | median | −4.5 | −5.8 | −2.9 | −3.8 |
| Juvenile | Strength and agility composite standard score | n | 3 | 5 | 3 | 4 |
| Juvenile | Strength and agility composite standard score | mean (95% CI) | 4 (−2.9, 11) | 10 (5.7, 15) | 5.3 (−2.5, 43) | 4.8 (−2, 12) |
| Juvenile | Strength and agility composite standard score | median | 1 | 10 | 3 | 2 |
| Juvenile | 6 min. walk test (m) | n | 5 | 5 | 3 | 5 |
| Juvenile | 6 min. walk test (m) | mean (95% CI) | 8 (−5.3, 21) | 19 (13, 25) | 20 (−2.5, 43) | 11 (4.2, 19) |
| Juvenile | 6 min. walk test (m) | median | 1.1 | 18 | 23 | 8.1 |

TABLE 4

Exploratory Exposure-Response Quartile Table: Week 72

| phenotype | endpoint (Δ baseline) | statistic | quartile 1 | quartile 2 | quartile 3 | quartile 4 |
| --- | --- | --- | --- | --- | --- | --- |
| Infantile | | exposure Cavg steady-state range (ng/mL) | [383, 1002] | (1002, 1202] | (1202, 1717] | (1717, 3975] |
| Infantile | | Subjects | 12 | 12 | 12 | 12 |
| Infantile | RSS-knee total score | n | 5 | 5 | 9 | 6 |
| Infantile | RSS-knee total score | mean (95 % CI) | −2.3 (−4.7, 0.092) | −3.1 (−5, −1.2) | −1.4 (−2.5, −0.43) | −2.7 (−3.9, −1.5) |
| Infantile | RSS-knee total score | median | −1.5 | −4.5 | −1 | −2.8 |
| Infantile | RSS-wrist total score | n | 5 | 5 | 9 | 6 |
| Infantile | RSS-wrist total score | mean (95% CI) | −1 (−2.5, 0.55) | −1.5 (−2.9, −0.15) | −0.94 (−1.8, −0.14) | −1.4 (−2.8, −0.044) |
| Infantile | RSS-wrist total score | median | −0.5 | −1.5 | −0.5 | −1.8 |
| Infantile | RGI-C score | n | 5 | 6 | 10 | 6 |
| Infantile | RGI-C score | mean (95% CI) | 2.1 (1.8, 2.5) | 2.2 (1.2, 3.1) | 1.7 (1.1, 2.3) | 2.2 (1.6, 2.7) |
| Infantile | RGI-C score | median | 2 | 2.5 | 1.7 | 2.2 |
| Infantile | osteoid thickness (mm) | n | 0 | 2 | 1 | 0 |
| Infantile | osteoid thickness (mm) | mean (95% CI) | | 0.95 (−11, 12) | 1.1 | |
| Infantile | osteoid thickness (mm) | median | | 0.95 | 1.1 | |
| Infantile | Strength and agility composite standard score | n | 2 | 3 | 5 | 0 |
| Infantile | Strength and agility composite standard score | mean (95% CI) | 12 (−1.2, 24) | 6 (3, 9) | 1.6 (−3.8, 7) | |
| Infantile | Strength and agility composite standard score | median | 12 | 7 | 2 | |
| Infantile | 6 min. walk test (m) | n | 1 | 2 | 4 | 0 |
| Infantile | 6 min. walk test (m) | mean (95% CI) | 20 | 7.2 (−3.2, 18) | 13 (−6.2, 33) | |
| Infantile | 6 min. walk test (m) | median | 20 | 7.2 | 14 | |
| Juvenile | | exposure Cavg steady-state range (ng/mL) | [508, 1084] | (1084, 1364] | (1364, 1652] | (1652, 3310] |
| Juvenile | | Subjects | 5 | 5 | 5 | 5 |
| Juvenile | RSS-knee total score | n | 1 | 4 | 3 | 2 |
| Juvenile | RSS-knee total score | mean (95% CI) | −1 | −1.5 (−2.1, −0.93) | −1 (−1, −1) | −0.75 (−1.2, −0.26) |
| Juvenile | RSS-knee total score | median | −1 | −1.5 | −1 | −0.75 |
| Juvenile | RSS-wrist total score | n | 1 | 4 | 3 | 2 |
| Juvenile | RSS-wrist total score | mean (95% CI) | −1 | −1.1 (−1.4, −0.88) | −0.67 (−1.5, 0.2) | −0.5 (−1.5, 0.48) |
| Juvenile | RSS-wrist total score | median | −1 | −1 | −0.5 | −0.5 |
| Juvenile | RGI-C score | n | 2 | 4 | 3 | 2 |
| Juvenile | RGI-C score | mean (95% CI) | 1.2 (−0.47, 2.8) | 2.1 (1.9, 2.2) | 1.4 (0.36, 2.5) | 1.3 (1.3, 1.3) |
| Juvenile | RGI-C score | median | 1.2 | 2 | 2 | 1.3 |
| Juvenile | osteoid thickness (mm) | n | 1 | 1 | 1 | 3 |
| Juvenile | osteoid thickness (mm) | mean (95% CI) | 0.3 | 0.85 | −1.4 | −2 (−3.4, −0.59) |
| Juvenile | osteoid thickness (mm) | median | 0.3 | 0.85 | −1.4 | −2.7 |
| Juvenile | Strength and agility composite standard score | n | 4 | 5 | 3 | 3 |
| Juvenile | Strength and agility composite standard score | mean (95% CI) | 4.2 (−2.3, 11) | 11 (4.2, 19) | 6.3 (−2.2, 15) | 3.7 (−3.7, 11) |
| Juvenile | Strength and agility composite standard score | median | 1.5 | 15 | 2 | 4 |

TABLE 4-continued

Exploratory Exposure-Response Quartile Table: Week 72

| phenotype | endpoint (Δ baseline) | statistic | quartile 1 | quartile 2 | quartile 3 | quartile 4 |
|---|---|---|---|---|---|---|
| Juvenile | 6 min. walk test (m) | n | 5 | 5 | 4 | 5 |
| Juvenile | 6 min. walk test (m) | mean (95% CI) | 14 (2, 27) | 22 (13, 30) | 17 (11, 24) | 15 (0.98, 28) |
| Juvenile | 6 min. walk test (m) | median | 12 | 22 | 18 | 18 | osteoid thickness evaluated at 48 weeks

Data were also collected and assembled for an exploratory population exposure-response analysis of osteoid thickness data. Change from baseline to week 24 osteoid thickness data were available from 5 individuals of Infantile phenotype and 13 individuals of Juvenile phenotype. At week 48, change from baseline data were available from 3 individuals of Infantile phenotype and 6 individuals of Juvenile phenotype (Tables 3 and 4).

Adverse event data were assembled for additional exploratory exposure-response analyses. All 68 individuals in the database were included for these analyses. A total of 897 events were observed across multiple endpoints, including ectopic calcification, injection/infusion associated reactions, and injection site reactions.

The population dataset included multiple covariate effects, such as the time-dependent variables: age, height, body weight (WT), tanner stage, ALT, AST, serum creatinine (SCR), etc. (Table 5.)

Formulation-specific covariates, such as asfotase alfa substance lot TSAC (mol/mol) and batch size (SIZE) were also included as time-dependent covariates, associated with the specific characteristics of lots administered for each dose. Investigation of baseline covariate values indicated some clusters of strong correlation, such as WT, height (HT), SCR, and age, as well as ALT and AST. Some correlations were also observed between continuous and categorical covariates. The group of age, height, weight, and SCR were all correlated with tanner stage, phenotype, and supplementation with vitamin D and B6. On the other hand, minimal correlation was observed between continuous covariates and other categorical variables.

Population PK Modeling

Exposure to asfotase alfa was assessed by measurement of serum asfotase alfa enzymatic activity in an ex vivo assay. PK samples were obtained longitudinally, in a sparse sampling manner for each patient. The observed data exhibited considerable inter-patient variability, due not only to fixed and random sources of variability in individual-specific PK parameters, but also due to the variety of dosing regimens and drug lots used within and between patients. Asfotase alfa activity was sampled at various times throughout the dosing interval, with an increased density of points early in the treatment history.

TABLE 5

Summary of PK continuous covariates by study

| Study | Type | WT (kg)* | HT (cm)* | Age (yr)* | ALT (U/L)* | AST (U/L)* | EGFR (ml/min/1.73 m$^2$) | SCR (umol/L)* | TSAC (mol/mol)* |
|---|---|---|---|---|---|---|---|---|---|
| All | Baseline | 27.9 [15.7] (2.21, 90.7) | 102 [101] (39.0, 178) | 14.7 [5.54] (0.00406, 66.8) | 28.5 [19.0] (6.00, 484) | 39.0 [33.0] (14.0, 415) | 124 [126] (19.8, 384) | 42.6 [35.0] (9.00, 106) | 1.82 [1.80] (1.10, 2.80) |
| #1 | Baseline | 70.6 [77.2] (47.7, 86.5) | 159 [160] (146, 172) | 45.4 [48.2] (24.6, 58.5) | 28.1 [25.4] (15.0, 56.0) | 30.0 [29.0] (20.0, 38.9) | 126 [103] (60.6, 223) | 70.8 [66.5] (62.0, 88.0) | 1.70 [1.70] (1.70, 1.70) |
| #2/#3 | Baseline | 5.80 [4.13] (2.21, 9.19) | 59.5 [56.5] (39.0, 83.0) | 1.13 [0.566] (0.0537, 3.03) | 66.0 [21.0] (12.0, 484) | 74.7 [41.0] (30.0, 415) | 109 [103] (44.9, 160) | 22.8 [24.0] (17.0, 29.0) | 1.88 [1.90] (1.70, 1.90) |
| #4/#5 | Baseline | 26.3 [21.1] (11.4, 62.3) | 121 [117] (89.0, 144) | 8.91 [8.72] (2.04, 12.5) | 17.3 [15.0] (10.0, 24.0) | 29.9 [29.0] (20.0, 45.0) | 150 [156] (121, 188) | 39.9 [44.0] (27.0, 53.0) | 1.50 [1.50] (1.50, 1.50) |
| #6 | Baseline | 65.3 [68.4] (22.1, 90.7) | 156 [161] (109, 178) | 40.7 [53.9] (13.8, 66.8) | 18.4 [18.0] (10.0, 34.0) | 22.7 [21.0] (16.0, 40.0) | 90.6 [86.1] (55.7, 153) | 76.1 [80.0] (44.0, 106) | 2.06 [2.00] (1.10, 2.80) |
| #7 | Baseline | 8.21 [6.11] (2.52, 17.0) | 71.6 [63.5] (39.0, 108) | 2.33 [1.36] (0.00406, 6.05) | 24.4 [18.0] (6.00, 57.0) | 39.7 [35.0] (14.0, 70.0) | 135 [130] (19.8, 384) | 28.2 [27.0] (9.00, 80.0) | 1.84 [1.80] (1.10, 2.20) |
| All | EOS | 34.2 [21.4] (4.91, 91.5) | 116 [113] (53.8, 182) | 17.2 [7.47] (0.237, 69.5) | 22.5 [19.0] (11.0, 73.0) | 32.9 [30.0] (13.0, 83.0) | 138 [133] (37.8, 432) | 47.3 [37.0] (13.0, 159) | 2.06 [2.00] (1.50, 2.70) |
| #1 | EOS | 67.1 [67.1] (47.7, 86.5) | No data present | 48.5 [48.5] (38.3, 58.7) | 27.9 [27.9] (27.9, 27.9) | 38.9 [38.9] (38.9, 38.9) | 202 [202] (180, 223) | No data present | 1.70 [1.70] (1.70, 1.70) |
| #2/#3 | EOS | 14.1 [13.5] (5.70, 20.8) | 91.5 [99.6] (53.8, 108) | 4.67 [4.49] (0.634, 7.47) | 21.3 [21.0] (12.0, 31.0) | 34.4 [35.0] (21.0, 40.0) | 140 [147] (61.1, 195) | 31.6 [31.0] (27.0, 41.0) | 2.02 [1.90] (1.70, 2.70) |
| #4/#5 | EOS | 42.0 [34.4] (17.0, 79.6) | 142 [138] (105, 170) | 12.2 [12.2] (9.50, 16.0) | 18.0 [17.0] (11.0, 33.0) | 28.2 [29.0] (15.0, 45.0) | 150 [156] (105, 170) | 55.1 [53.0] (35.0, 80.0) | 1.92 [2.00] (1.50, 2.00) |
| #6 | EOS | 69.4 [72.8] (23.0, 91.5) | 158 [162] (126, 182) | 44.3 [56.7] (16.2, 69.5) | 21.2 [16.0] (11.0, 73.0) | 22.4 [22.0] (13.0, 40.0) | 97.4 [80.3] (37.8, 432) | 77.9 [71.0] (18.0, 159) | 1.95 [2.00] (1.70, 2.10) |
| #7 | EOS | 12.3 [9.96] (4.91, 27.9) | 85.1 [77.8] (56.0, 125) | 3.74 [3.12] (0.237, 8.57) | 25.6 [21.0] (11.0, 55.0) | 41.0 [35.0] (24.0, 83.0) | 159 [148] (48.0, 324) | 28.1 [26.0] (13.0, 72.0) | 2.24 [2.10] (1.70, 2.70) |

*mean [median] (min, max)
ALT = alanine aminotransferase;
AST = asparate aminotransferase;
EGFR= estimated glomerular filtration rate (MDRD for adults, Schwartz for children);
EOS = end of study;
HT = height;
SCR = serum creatinine;
TSAC = lot sialic acid content;
WT = body weight With the inclusion of the IV data, it was clear that a multi-compartmental disposition model would be required to describe the data. Comparison of profiles following IV administration and subcutaneous administration also suggested the presence of pharmacokinetic "flip-flop," i.e., when absorption from an extravascular compartment becomes the rate limiting step in the disposition of a drug. For the purpose of comparison, structural PK models with one-, two-, or three-compartment disposition were evaluated. All models allowed for dosing into a depot and central compartment, to accommodate the SC and IV routes of administration, respectively. Models were implemented using the PREDPP library, which accounts for multiple dosing conditions using recursive superposition. PK parameters were estimated in the log transformed domain to ensure consistency with the MVN distribution of the parameter uncertainty (e.g., MVN covariance matrix of the estimates). Various compartmental and random effect model structures were evaluated, as guided by standard diagnostics. The one-compartment model was not adequate to capture the full IV PK profile. On the other hand, a three-compartment model appeared to result in a good fit to the data, but was characterized by instability and strong correlation in the parameter estimates, as seen in the correlation matrix of the estimates, indicating possible over-parameterization. A two-compartment structural model, parameterized in terms of CL, $V_2$, $V_3$, Q, F, $k_a$, and ALAG, provided a good description of the asfotase alfa PK data. This model was implemented using the PREDPP subroutine ADVAN4 TRANS4. Asfotase alfa lot potency (U/mg) was directly multiplied by administered dose (mg) to convert dose to units. The dependent variable was log-transformed to allow for a true exponential residual variance structure. Interindividual random effect distributions were modeled using exponential variance models, with independent random effects for CL, $V_2$, $V_3$, and $k_a$.

The covariate modeling step included two components; a prespecified covariate model for inferential purposes, and an exploratory, hypothesis-generating, covariate model evaluated post hoc. The full covariate model included the prespecified effects of allometrically-scaled WT, TSAC, anti-drug antibody, and neutralizing antibody on CL; allometrically-scaled WT on $V_2$, $V_3$, and Q; and batch size on relative bioavailability and $k_a$. Of course, observed drug substance activity for each lot was also included in the model as a direct factor of dose, but this was not an estimated covariate effect. In a previous analysis of a subset of the present data, subject age was also a prespecified covariate for CL. Given the strong correlation between age and weight in this dataset and substantial imprecision in the age-CL parameter estimate, an alternative full model, which eliminated the age effect but allowed for an estimated allometric exponent on CL, was implemented. The prespecified covariate model was essentially an update to the previously reported model accounting for the expanded dataset available for the present analysis (Model 522008). The exploratory covariate model was conducted in the context of Model 522008 to examine potential relationships, after accounting for the prespecified covariates. Relationships between asfotase alfa CL and renal function as measured by eGFR, liver function as measured by ALT and AST, and race, were evaluated. After the covariate evaluations, the previously used interindividual variance matrix was updated from diagonal (variance) terms only to a full variance-covariance structure (including all off-diagonal terms). The expanded dataset used in the present analysis supported the estimation of the more comprehensive variance-covariance model. Therefore, the final model, contained in Model 52200820, includes the prespecified covariate model was well as the full variance-covariance model.

Figure 7:
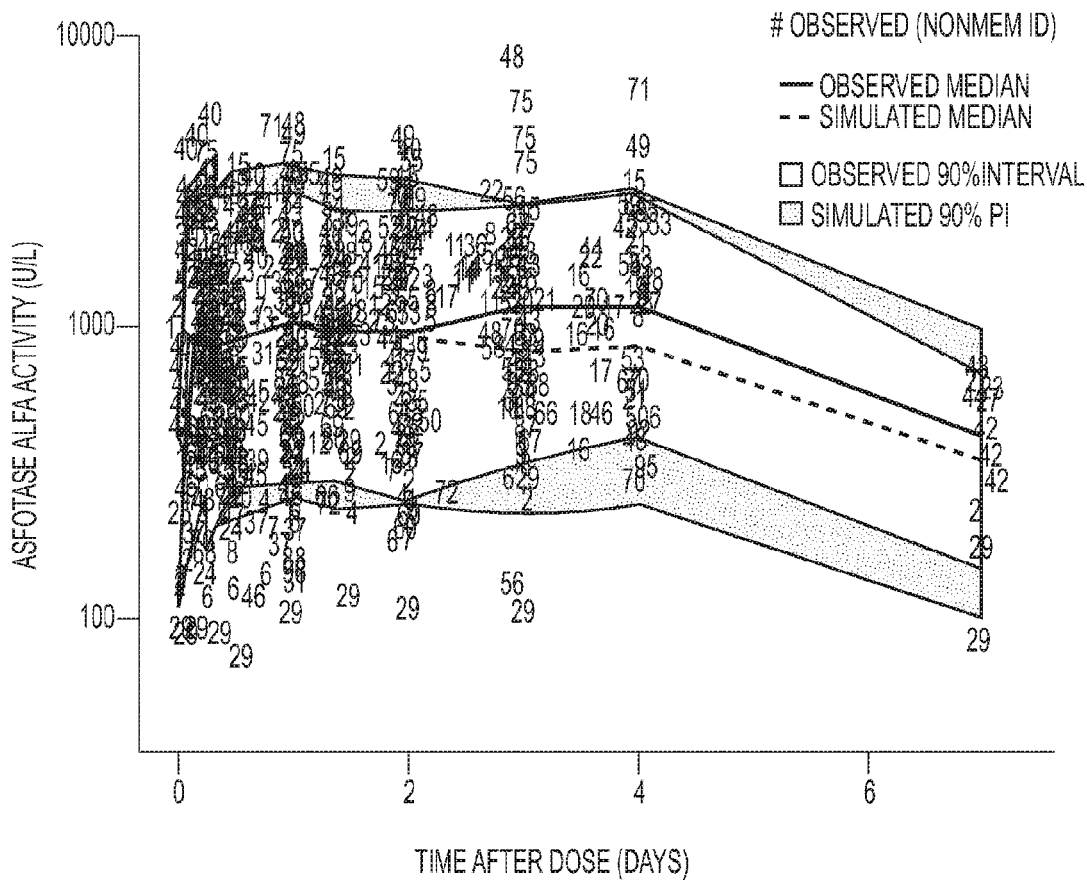
FIG. 7 depicts the model performance for PK observations (SC), showing the agreement between the observed (open) and model-predicted (shaded) asfotase alfa levels.

Inferences about covariate effects were made from parameter estimates from the final prespecified full covariate model and from simulations using that model. This model excluded the exploratory, hypothesis-generating covariates. Effects on CL were of primary interest, due to the intended application of the model to predict steady-state exposure. Parameter estimates indicated that CL increased with increasing weight, anti-drug antibody presence, and neutralizing antibody presence, but decreased with increasing TSAC. Bodyweight was a determinant of variability in CL, with an estimated allometric exponent (95% CI) of 0.776 (0.702, 0.851). This estimate is quite close to, and statistically indistinguishable from, the usually anticipated value of 0.75. Further evaluation of covariate effects was conducted via simulation of expected asfotase alfa average concentration during the dosing interval at steady-state ($C_{avg,ss}$) given the approximate posterior distribution (or uncertainty) in the model parameters, and a regimen of 2 mg/kg SC, 3 times per week. The relationship between WT and simulated $C_{avg,ss}$ illustrated the impact of WT on CL in a clinically relevant manner. This relationship clearly indicated that $C_{avg,ss}$ was lower in younger, smaller individuals relative to fully grown adults at the same mg/kg dose, a finding that is entirely consistent with an allometrically-scaled CL. Although confounded with age-related effects, the estimated WT effect on CL is most likely reflecting body size-related changes. Variability in TSAC content was also highly related with changes in CL and $C_{avg,ss}$, with CL decreasing as TSAC increased, and $C_{avg,ss}$ conversely increasing. The impact of antidrug antibodies on CL was small and precisely estimated, with a 95% CI indicating an increase in CL by a factor of 1.06 to 1.17. The addition of neutralizing antibody presence resulted in a slightly larger CL increase (95% CI of 1.08 to 1.37). Both of these effects were illustrated on simulated $C_{avg,ss}$, and the temporal, transient, nature of these immunogenicity effects in the context of individual CL estimates over time was also evaluated. Note that these temporal depictions of individual CL estimates included all covariate effects and random interindividual variability. FIGS. 1 and 7 show that for the present data, the relationship between asfotase alfa clearance and antibody level has been sufficiently characterized.

The relationship between $C_{avg,ss}$ and key levels of eGFR was found that under the present model and available data, calculated eGFR has minimal impact on asfotase alfa CL. Likewise, ALT and AST shown influence on asfotase alfa CL. It is important to note however that both ALT and AST values were mostly in expected normal ranges. Patients of Asian race (comprised of five Japanese Asians and one non-Japanese Asian) appeared to have higher $C_{avg,ss}$ than non-Asians, but the prediction of typical $C_{avg,ss}$ was imprecise. In addition, the full model (not including a race covariate) predictive performance was not consistent across individuals in the Asian group. Based on patient-level visual predictive checks, half of the Asian patients were well described by this model, while model predictions for other half of Asian patients were characterized by runs of well described observations, and runs of systematically biased predictions, within the same subject. No obvious predictors of this bias were evident from the source data.

Covariate effects on other PK parameters were also observed. V2, V3, and Q all increased with weight according to the fixed allometric relationships. Lot batch size had a poorly defined effect on $k_a$, with a rate constant (90% CI) for the 20,000 L batch of approximately 93.0% (72.5%, 119%) of the 2000 L size. Note that this interval was not distinguishable from a null effect. The effect of batch size on bioavailability of 20,000 L relative to 2000 L revealed a small effect, with a 90% CI of 85.6%-96.8%, and a clinically unimportant impact on expected $C_{avg,ss}$.

The effects of all covariates on $C_{avg,ss}$ were also illustrated in a single plot (FIG. 1). In addition to the effects already described, this simulation included combinations of covariate effects that were likely to result in extremes of asfotase alfa exposure. These are shown in the first two entries in FIG. 1. The combination of covariates selected for these two scenarios (Scenario 1: WT, 4.5 kg; TSAC, 1.0 mol/mol; ADA+/NAb+; and 20K L batch size and Scenario 2: WT, 75 kg; TSAC, 3.0 mol/mol, ADA−, and 20K L batch size) were chosen to depict a series of conditions that would be expected to result in low extreme (Scenario 1) and high extreme (Scenario 2) $C_{avg,ss}$. Nearly all scenarios resulted in $C_{avg,ss}$ that exceeded the targeted exposure range for clinical effect as ascertained from non-clinical experiments (dashed vertical reference lines).

An additional exploratory analysis was implemented to evaluate the impact of analytical assay (CBRG vs. WIL Research) on asfotase alfa PK. Results obtained from an assay of spiked samples and re-assayed clinical samples in an assay cross validation study were compared graphically and analyzed using linear regression to inform the exploratory analysis. Results show a high degree of correlation between the two assay methods. Linear regression analysis estimated the slope and intercept of log-transformed CBRG data and log-transformed WIL Research data.

In the context of the final population PK model, the following residual error model was evaluated in Eq. 11.

$$\ln(C_{ij}) = (1-\text{ASSAYIND}) \cdot \ln(\hat{C}_{ij}) + \text{ASSAYIND} \cdot (\theta_{14} + \theta_{15} \cdot \ln(\hat{C}_{ij})) + \varepsilon_{aij} \cdot (1+\text{ASSAYIND} \cdot \theta_{16}) \quad (11)$$

where:
ASSAYIND assumes the value of 0 for the WIL Research Assay and 1 for the CBRG Assay; ln(Cij) is the observed asfotase alfa activity in U/L; ln(C^ij) is the model predicted asfotase alfa activity; $\theta_{14}$ and $\theta_{15}$ are the intercept and slope that scale predicted concentrations from a WIL Research result to a CBRG result. These parameters are called "bias" parameters as they would describe persistent difference between data collected using the two different assay methods. $\varepsilon_{aij}$ is an additive residual error term on the log scale that is assumed symmetrically distributed with mean 0 and variance $\sigma^2$; and $\theta_{16}$ scales the error from WIL method to CBRG. This scaling parameter is designated the "precision" parameter.

It is important to note that while the residual error model is seemingly splitting the results into WIL Research Assay and CBRG Assay methods, many other variance sources comprise σ2, not just variability due to assay. After fitting population PK models with the residual error models shown in Eq. 8, the point estimate of each fixed effect and associated 95% confidence interval was plotted. The resulting population PK parameter estimates revealed little to no impact of assay in all cases. Therefore, the final model (Model No. 522008, with $\theta_{14}$ and $\theta_{16}$ both fixed at 0 and $\theta_{15}$ fixed at 1, and no accommodation for assay differences), was selected for further model-based applications.

The full model (Run 52200820) provided a good description of the data, as indicated by individual fits and population model diagnostic plots. Population and individual model parameters were estimated using the FOCEI method. Parameter estimate 95% confidence intervals were derived from the covariance matrix of the estimates (NONMEM $COVstep); stratified non-parametric bootstrapping was not feasible with a dataset of this small size and the multiple weight related strata that would have been required. Overall, fixed effects parameters were precisely estimated. Estimated shrinkage of individual random effects to the mean of zero was minimal, CL at 5.19%, indicating that individual estimates of steady-state exposure were likely to be unbiased by the population priors. Estimated shrinkage for $k_a$ random effects was moderate at 15.3%, while much higher for V2 and V3 random effects (33.8% and 38.1%). A simulation-based model diagnostic (visual predictive check) was also implemented. This check revealed consistency between observed data and the model-simulated median and variability, indicating acceptable performance of the model for general Monte Carlo simulation purposes.

As drug product arising from 20,000 L batch sizes was intended to represent a commercial formulation, a visual predictive check was performed just for observations associated with dosing with 20,000 L batches. Additionally, the observed and predicted asfotase alfa activity for observations associate with the 20,000 L batches were compared with a result indicating reasonable characterization of pharmacokinetics associated with 20,000 L batches. A total of 185 observations, of the 1370 available for analysis, were derived from 20,000 L batch size lots. Thirty-two patients received asfotase alfa from both 2000 L and 20,000 L batch size lots. Thirty-six patients received asfotase alfa from just one batch size; seven from 20,000 L batches, and twenty-nine from 2,000 L batches.

The final PK model provided individual MAP Bayes estimates of patient PK parameters and these values were also used to derive secondary PK parameters for each individual patient. Summary statistics of predicted patient-specific average concentration since first dose, calculated as ($\text{AUC}_{cumulative}/\text{TAFD}$ (i.e., $C_{avg,study}$)) values were calculated. Table 6 provides typical values of $C_{avg,ss}$, apparent clearance after extravascular dosing (CL/F), and apparent steady-state volume of distribution after extravascular dosing ($V_{ss}/F$) (sum of apparent central volume of distribution after extravascular dosing ($V_2/F$) and apparent peripheral volume of distribution after extravascular dosing ($V_3/F$)) for key categories of age and associated body weights.

Table 7 shows the calculated area under the concentration-time curve for a dosing interval at steady-state ($\text{AUC}_{ss}$) and $C_{avg,ss}$ in units based on drug mass, in contrast to units based on the activity assay Units. The calculations assume a dose regimen of 2 mg/kg given three times per week and are derived using the clearance model with assumptions of no anti-drug or neutralizing antibodies and a sialyl level of 2.2 mol/mol protein. The $\text{AUC}_{ss}$ is the AUC for a 7 day period at steady state. The cumulative AUC and $C_{avg,study}$ in activity units were obtained using the population PK model during the model estimation. These were converted to mass units by dividing the result by the within-patient median asfotase alfa activity (in U/mg) across all doses given to the patient. The weekly $\text{AUC}_{ss}$ in mass units was calculated as the $C_{avg,ss}$ in mass units multiplied by seven.

Table 8 summarizes the steady-state exposure metrics, maximum concentration in the dosing interval at steady-state ($C_{max,ss}$), $C_{avg,ss}$, and $\text{AUC}_{ss}$, simulated using the population PK model and a dose of 2 mg/kg administered thrice weekly to steady state, under the assumptions of TSAC 2.2 mol/mol, no anti-drug or neutralizing antibodies, a batch size of 20,000 L, drug product activity of 990 U/mg, and body weights as shown in the table.

TABLE 6

Summary statistics of typical PK parameter estimates by age group

| Age Category | Weight (kg) | | | Cavg$_{ss}$ (U/L) | | | CL/F (L/day) | | | V$_{ss}$/F (L) | | |
| --- | --- | --- | --- | --- | --- | --- | --- | --- | --- | --- | --- | --- |
| | Min | Mean | Max | Min | Mean | Max | Min | Mean | Max | Min | Mean | Max |
| 0-1 month | 2.10 | 2.90 | 3.70 | 1330 | 1430 | 1510 | 1.34 | 1.72 | 2.08 | 2.88 | 3.98 | 5.08 |
| 1 month-2 years | 2.54 | 6.79 | 11.0 | 1390 | 1730 | 1930 | 1.55 | 3.33 | 4.84 | 3.49 | 9.32 | 15.1 |
| 2-12 years | 4.48 | 19.4 | 65.8 | 1580 | 2190 | 2870 | 2.41 | 7.53 | 19.4 | 6.15 | 26.6 | 90.3 |
| 12-16 years | 19.0 | 48.2 | 79.6 | 2180 | 2680 | 3000 | 7.40 | 15.3 | 22.5 | 26.1 | 66.2 | 109 |
| ≥16 years | 22.4 | 72.0 | 96.7 | 2260 | 2930 | 3130 | 8.41 | 20.8 | 26.2 | 30.8 | 98.9 | 133 |

Apparent volume of distribution at steady state (VSS/F) = V2/F + V3/F.
Parameters shown are typical values calculated using the population PK model equations for CL, V2, and V3 and F1.
Min, mean, and max values of each PK parameter are calculated using the observed min, mean, and max values of weight in the HPP analysis datasets for the age range shown.
PK parameter calculations assume a sialic acid level of 2.2 mol/mol, a batch size of 20,000 L, and absence of anti-drug antibodies.
C$_{avg, ss}$ was calculated assuming a regimen of 2 mg/kg administered thrice weekly with a drug product activity of 990 U/mg.

TABLE 7

Calculated Steady State Exposure Metrics, in Mass Units, Following Administration of a 2 mg/kg Dose Thrice Weekly

| Weight kg | Weekly Dose mg | AUCss ng - week/mL | Cavg, ss ng/mL |
| --- | --- | --- | --- |
| 3 | 18 | 1460 | 208 |
| 6 | 36 | 1700 | 243 |
| 12 | 72 | 1980 | 284 |
| 25 | 150 | 2340 | 334 |
| 50 | 300 | 2730 | 390 |
| 75 | 450 | 2990 | 427 |
| 95 | 570 | 3150 | 450 |

The body weights chosen include the approximate minimum (3 kg), median (50 kg), and maximum (95 kg) observed bodyweights of patients administered asfotase alfa from 20,000 L batch size. Other body weights shown were chosen at convenient intermediate intervals.
Dose is the total weekly dose for a regimen of 2 mg/kg given three times per week.
AUC$_{ss}$ is the steady-state AUC over one week.
The calculations assume a sialyl content of 2.2 mol/mol protein and absence of anti-drug or neutralizing antibodies.

TABLE 8

Simulated Steady-State Exposure Metrics for a Asfotase Alfa Regimen of 2 mg/kg Administered Thrice Weekly

| Regimen | Period | Body Weight(kg) | Cmax$_{ss}$ (U/L) | Cavg$_{ss}$ (U/L) | AUC$_{ss}$ (U*day/L) | AUC$_{ss}$ (U*h/L) |
| --- | --- | --- | --- | --- | --- | --- |
| 2 mg/kg 3×/week | Steady State | 6.5 | 1944 | 1713 | 11993 | 287828 |
| 2 mg/kg 3×/week | Steady State | 12.5 | 2241 | 1983 | 13880 | 333132 |
| 2 mg/kg 3×/week | Steady State | 25.0 | 2611 | 2315 | 16207 | 388962 |
| 2 mg/kg 3×/week | Steady State | 50.0 | 3043 | 2703 | 18023 | 454148 |
| 2 mg/kg 3×/week | Steady State | 75.0 | 3329 | 2960 | 20718 | 497233 |

The asfotase alfa population PK model was used to simulated steady-state exposure metrics, C$_{max, ss}$, C$_{avg, ss}$, and AUC$_{ss}$. AUC$_{ss}$ is calculated for a week interval and thus represents the exposure arising from the administration of three 2 mg/kg doses. The exposures are simulated for hypothetical subjects with the body weight shown in the table and assuming a drug product activity of 990 U/L, sialic acid level of 2.2, a 20K L batch size, and no anti-drug and neutralizing antibodies.

Population Exposure-Response

An initial exploratory evaluation of population exposure-response relationships for all analysis endpoints was implemented. Given the subject-specific C$_{avg,study}$ estimates, tables of response summaries vs. quartiles of exposure were constructed for the observed change from baseline responses at weeks 24 and 72 (Tables 3 and 4). Change from baseline osteoid thickness data were only available at weeks 24 and 48, with no additional longitudinal repeated measures. When viewed as a function of exposure, these population response summaries (means or medians) revealed no exposure-response relationships across any of the endpoints. This finding was not entirely surprising in that this display reduces the data to a single point per individual, and is essentially a naïve pooled data analysis. Given the limited dose-ranging designs in the asfotase alfa clinical trial experience, this sort of population exposure-response perspective can be misleading (Nedelman et al., 2007 StatMed 26:290-308). The population-level summary also ignores information contained in the repeated-measures, longitudinal data about within-individual exposure-response relationships caused by individual dose adjustments, lot changes, changes in neutralizing antibody, and changes in weight over time. Nevertheless, for endpoints where repeated-measures were not available, such as osteoid thickness and all of the adverse event (AE) summary endpoints, this type of population-level exposure-response was still useful as an exploratory tool. The following model-based analyses do appropriately account for the within-subject exposure-response information via repeated measures mixed effects modeling analyses.

PPi Modeling

The PPi biomarker revealed a robust response to initiation of asfotase alfa therapy, with a sharp drop in concentrations from baseline. The response-time profile was characterized by a rapid onset, with the nadir occurring following approximately 6 to 8 weeks of treatment. Continued therapy was also associated with a rebound of PPi concentrations, in some cases returning to near baseline. Considerable inter-individual variability existed in the magnitude and timing of this rebound effect. Given this observation, the simple indirect PD response model could not provide an adequate description of the observed data. Alternative models, including precursor-pool and PD feedback models were explored using a prior dataset, guided by goodness of fit. Ultimately, a model with a hypothetical indirect feedback response (zero-order production of feedback and second-order degradation, depending on both the current feedback response and the ratio of PPi response to PPi baseline) was selected. This feedback effect modulated the zero-order production of PPi, while the asfotase alfa effect was mediated as a stimulation of PPi degradation.

The final model included interindividual random effects on K$_{out}$ and E$_{max}$, and a proportional residual error model. The predefined covariate effect of phenotype entered the model as a modulator of K$_{out}$, with Unknown, Infantile and Adult phenotypes K$_{out}$ estimated to be 91.9%, 78.3% and 123% of the reference Juvenile phenotype, respectively. The final model showed an improvement in model fit over the base model (Run 7) and the model which assumed no drug effect (Run 6). The final model (Run 5) provided a good fit to the individual data, and was unbiased with respect to typical diagnostics. Estimated shrinkage of individual random effects to the mean of zero was moderate, but no inferences or decisions in the analysis were based on these PPi random effects. A simulation-based model diagnostic (visual predictive check) was also implemented. This check revealed consistency between observed data and the model-simulated median and variability, indicating acceptable performance of the model for general Monte Carlo simulation purposes.

PLP Modeling

Plasma PLP concentrations, following asfotase alfa treatment, were confounded by the co-administration of B6. Patients who received B6 at any time during the study were reviewed separately and flagged in the dataset for consideration as a covariate in the model. Repeated-measures data for the PLP biomarker revealed a robust response to initiation of asfotase alfa therapy, with a rapid drop in concentrations from baseline in most B6 treated and untreated patients. Baseline PLP levels varied considerably across patients. In general, higher PLP concentrations were observed in B6-treated patients. The response-time profile was characterized by a rapid onset, with PLP concentrations generally dropping to their lowest values after 6 to 8 weeks of treatment and stayed low throughout the study duration. The simple indirect PD response model described herein provided an adequate description of the observed data. Attempts were made during model development to include patients who received B6. Inclusion of these patients led to instability in the model and inconsistencies in the typical value model parameter estimates. Therefore, patients who received B6 were excluded from the final model Run #5. Ultimately, an indirect-response model with a zero-order production of PLP with a stimulatory effect of asfotase alfa on the first-order degradation of PLP was chosen as the final model.

The final model included a random, interindividual variance on Ro (the baseline response), a proportional residual error model for data analyzed by the Biotrial laboratory (LC/MS/MS), and a separate proportional residual error model for data analyzed by the ARUP laboratory (REA) and converted to Biotrial equivalents. The pre-defined covariate effect of phenotype entered the model as a modulator of Ro, with Unknown, Infantile and Adult phenotype Ro estimated to be 41.4%, 177% and 14.7% of the reference Juvenile phenotype, respectively. This model provided a good fit to the individual data, and was unbiased with respect to typical diagnostics. The final model showed an improvement in model fit over the base model (Run 1) and the model which assumed no drug effect (Run 3). Estimated shrinkage of the individual random effect to the mean of zero was minor in the final model, but no inferences or decisions in the analysis were based on this PLP random effect. A simulation-based model diagnostic (visual predictive check) was also implemented. This check revealed consistency between observed data and the model-simulated median and variability, indicating acceptable performance of the model for general Monte Carlo simulation purposes.

RGI-C Modeling

PK-PD analysis of the radiographic endpoint RGI-C was carried out according to the methods described with one exception. Patients of both Infantile and Juvenile phenotypes were included in the analysis, rather than a singular focus on Juvenile phenotype. Initially, it was not known that the historical control dataset included both phenotypes.

Availability of RGI-C data from a historical control group allowed for the evaluation of the natural disease progression in select HPP age ranges and phenotypes. Repeated-measures data for the historical control group were paired within an individual to match a baseline value to a post-baseline value. Values could be reused resulting in multiple pairs within an individual. A slope representing the change from baseline RGI-C value divided by the duration of time between the scored X-ray and the baseline X-ray was calculated for each pair. Graphical and mixed-effects modeling of these slopes suggested no changes in RGI-C values over time for the historical control group. As a result, the natural disease progression of changes in RGI-C was not included as part of the RGI-C PK-PD model for both the Infantile and Juvenile phenotype patients.

With the exception of two patients, repeated-measures data for the efficacy endpoint revealed an initial time-dependent improvement over baseline followed by a plateau over the course of asfotase alfa therapy. Two subjects immediately or almost immediately displayed a maximum response over the entire course of therapy (NONMEM IDs 51 and 52).

The simple indirect PD response model described herein provided an adequate description of the observed data. Attempts were made during model development to include the two patients who achieved maximal response almost immediately after starting treatment. Inclusion of these patients led to instability in the model and inconsistencies in the typical value model parameter estimates. Therefore, these patients were excluded from the final model run #4. Ultimately, an indirect-response model with a zero-order increase in RGI-C with a stimulatory effect of asfotase alfa on Kin was fit to the data. Model predictions were constrained within the observed scale ranges, using a logit transformation.

The final model included interindividual random effects on $K_{in}$ and $E_{max}$, and an additive residual error model. $K_{out}$ was inversely proportional to baseline response. The final model showed an improvement in model fit over the base model (Run 5) and the model which assumed no drug effect (Run 6). The predefined covariate effect of phenotype entered the model as a modulator of $K_{in}$, with Infantile phenotype $K_{in}$ estimated to be 59.7% of the reference Juvenile phenotype. This model provided a good fit to the individual data, and was unbiased with respect to typical diagnostics. Estimated shrinkage of individual random effects to the mean of zero was moderate for IIV $K_{in}$ (19.5%) and negligible for IIV $E_{max}$ (7.77%), but no inferences or decisions in the analysis were based on these random effects. A simulation-based model diagnostic (visual predictive check) was also implemented. This check revealed consistency between observed data and the model-simulated median and variability, indicating acceptable performance of the model for general Monte Carlo simulation purposes.

RSS Modeling

The analysis of repeated-measures RSS data was based on the individual RSS components, $RSS_{wrist}$ and $RSS_{knee}$. This analysis strategy allowed for differences in the time-course and intensity of drug response between these two sites. Both Infantile and Juvenile phenotypes were included, rather than a singular focus on Juvenile phenotype.

The initial effort was focused on estimating any time-dependent disease progression, over the period of time studied, using the historical control dataset. The observed data revealed the variability in the trajectory of responses over time, but no systematic trends were evident. Linear mixed effects models were applied to the repeated-measures wrist and knee RSS historical control datasets. Results revealed that the time-dependent disease progression slopes for wrist and knee were not significantly different from zero. Given this finding, no time-dependent disease progression was required for the analysis of the active asfotase alfa treatment data.

For the active treatment data, the observed RSS wrist and knee endpoints exhibited a systematic decrease in scores over time. Indirect PD response models were implemented for both endpoints, with asfotase alfa concentration inhibiting production of response (e.g., inhibitory Emax model on Kin). Model predictions were constrained within the observed scale ranges (0-4 for wrist scores and 0-6 for knee scores), using a logit transformation of the prediction. The indirect model results were compared with a null model excluding any effect of asfotase alfa. For both endpoints, the maximum inhibitory effect was estimated near 100%, and Emax was subsequently fixed to a value of 1. Final models included individual random effects on baseline (R0) and EC50, as well as a combined additive and proportional residual error model. Parameter estimates for Kin and concentration resulting in 50 percent of maximum effect (EC50) were generally greater for the wrist model as compared with the knee models. The additive effects of Infantile phenotype on R0, relative to Juvenile, were small and the 95% CI included zero, indicating minimal differences between phenotypes in the RSS datasets. Interindividual random effects were relatively high for both knee and wrist models. Shrinkage of individual random effects to the mean of zero was minimal for most parameters, with moderate shrinkage noted in the IIV EC50 for RSS-Knee. No inferences or decisions in the analysis were based on these random effects.

Diagnostics for both models were indicative of an accurate description of the observed data. Visual predictive checks demonstrated consistency between observed data and the model-simulated median and variability, indicating acceptable performance of the models for general Monte Carlo simulation purposes.

6MWT Modeling

Repeated-measures data for the functional efficacy endpoint, 6MWT, revealed a time-dependent increase in the percent of normal response throughout the duration of asfotase alfa therapy. The rate of improvement in 6MWT was relatively consistent across individuals, but the baseline response was clustered into two groups. The majority of the treatment population exhibited a baseline6MWT of approximately 60% of predicted normal, while two individuals (IDs 29 and 34), had baseline values near zero. This was explained by differences in baseline inclusion criteria across studies. Variations on the indirect PD response model were evaluated. Models were implemented with asfotase alfa stimulating Kin for 6MWT, consistent with the conceptual mechanism of improved bone formation leading to functional improvement. In order to adjust for the clear clustering of baseline response values, a separate fixed effect parameter was allowed for the two individuals with near zero function at baseline.

The final model included an interindividual covariance matrix for random effects on baseline (R0) and Emax, and an additive residual error model. Emax was inversely proportional to baseline response. No covariate effects were estimated as the analysis data were restricted to the Juvenile phenotype only. This model provided a good fit to the individual data, and was unbiased with respect to typical diagnostics. Estimated shrinkage of individual random effects to the mean of zero was less than 13%. A simulation-based model diagnostic (visual predictive check) was also implemented. This check revealed consistency between observed data and the model simulated median and variability, indicating acceptable performance of the model for general Monte Carlo simulation purposes.

BOT-2 Modeling

Repeated-measures data for the functional efficacy endpoint, BOT-2, revealed a time-dependent increase in the strength and agility composite standard score throughout the duration of asfotase alfa therapy. The rate of improvement in BOT-2 was relatively consistent across individuals, with the exception of two individuals (IDs 33 and 38). Subject 33 exhibited a score of approximately 60 units from baseline through end of study. A score of 60 was consistent with the normal range for this test, indicating a lack of disease-related BOT-2 impairment for this particular individual at the start of the study. Subject 38 had an atypical profile (3 observations total) showing improvement from baseline followed by a significant abrupt decline in response. For these reasons, individuals 33 and 38 were excluded from the PK-PD analysis. Individual 34 had only one observed BOT-2 score which occurred at approximately 650 days after the first dose. Without a baseline observation the time-dependent change in BOT-2 could not be adequately described in this individual. For that reason, individual 34 was excluded from the PK-PD analysis. Compared to prior preliminary datasets, the current expanded dataset included the addition of ID 34 and the two post-first dose observations from ID 38. Inclusion of IDs 34 and 38 resulted in parameter estimates that were inconsistent with prior BOT-2 models developed from preliminary datasets; this inconsistency was not observed when both individuals were excluded from the analysis. Furthermore, typical diagnostics plots showed that the model with IDs 34 and 38 included did not provide an adequate description of the data and systematic bias was evident.

The indirect PD response model was similar to the one used for the analysis of 6MWT data, where asfotase alfa effect was implemented as a stimulation of Kin. Baseline score was constrained within the plausible range of scale values, using a logistic transformation. The final model included interindividual random effects on baseline (R0) and Emax, and an additive residual error model. The phenotype covariate was not evaluated as the analysis dataset was limited to the Juvenile phenotype, only. This model provided a good fit to the individual data, and was unbiased with respect to typical diagnostics. Estimated shrinkage of individual random effects approached 35%, but no inferences or decisions in the analysis were based on these BOT-2 random effects. A simulation-based model diagnostic (visual predictive check) was also implemented. This check revealed consistency between observed data and the model-simulated median and variability, indicating acceptable performance of the model for general Monte Carlo simulation purposes.

Adverse Events: Exploratory Exposure-Response

An exploratory evaluation of population exposure-response relationships for specific AEs was implemented. These included ectopic calcification, injection/infusion associated reactions, and injection site reaction events during the entire treatment duration for all studies in the PK-PD analysis dataset. A total of 897 events occurred across the 3 endpoints. Given the subject-specific $C_{avg,study}$ estimates, tables of AE incidence and rate (number of events/time) vs. quartiles of exposure were constructed. When viewed as a function of exposure quartiles, AE summaries revealed no dependence on exposure.

Exposure-Response Simulations

Final PK-PD models for all response endpoints were used to simulate the expected (median) exposure response relationships across several asfotase alfa dosing regimens, as described herein. The result is a simulation-based extrapolation of the model-derived exposure response relationship for typical HPP patients. Simulations of all endpoints resulted in responses which improved with rising exposures and established a plateau in the exposure-response relationship.

Biomarker Endpoints: Exposure-Response

Figure 2A:
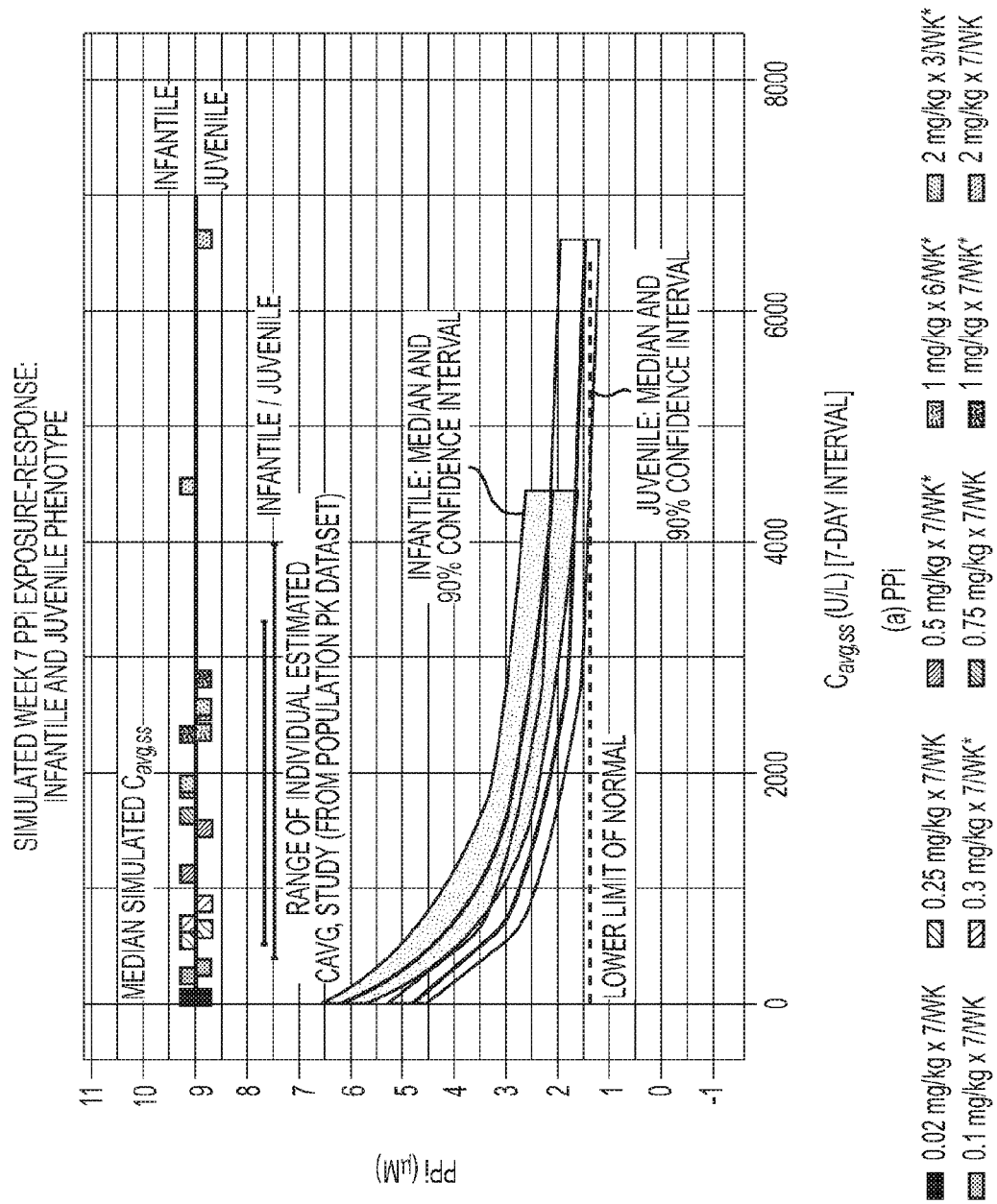
FIGS. 2A-2B illustrate the median (solid line) and 90% confidence intervals (shaded) for typical exposure-response. Median simulated ages and weights, by phenotype and endpoint were PPi (FIG. 2A)(Infantile baseline 3.11 yr and 10.8 kg; Infantile Week 7 3.25 yr and 11.1 kg; Juvenile Baseline 11.8 yr and 34.0 kg; JuvenileWeek 7 11.0 yr and 34.5 kg; Adult Baseline 40.2 yr and 76.1 kg; Adult Week 7 40.3 yr and 76.1 kg), and PLP (FIG. 2B)(Infantile Baseline 3.11 yr and 10.8 kg; Infantile Week 24 3.57 yr and 11.8 kg; Juvenile Baseline 11.8 yr and 34.0 kg; Juvenile Week 24 12.3 yr and 35.6 kg). Also shown are the median simulated $C_{avg,ss}$ values for each regimen and the range of subject-specific estimates of $C_{avg,study}$ values based on modeling of observed data. Asterisks (*) indicate dose regimens studied in the clinical development program.
Figure 2B:
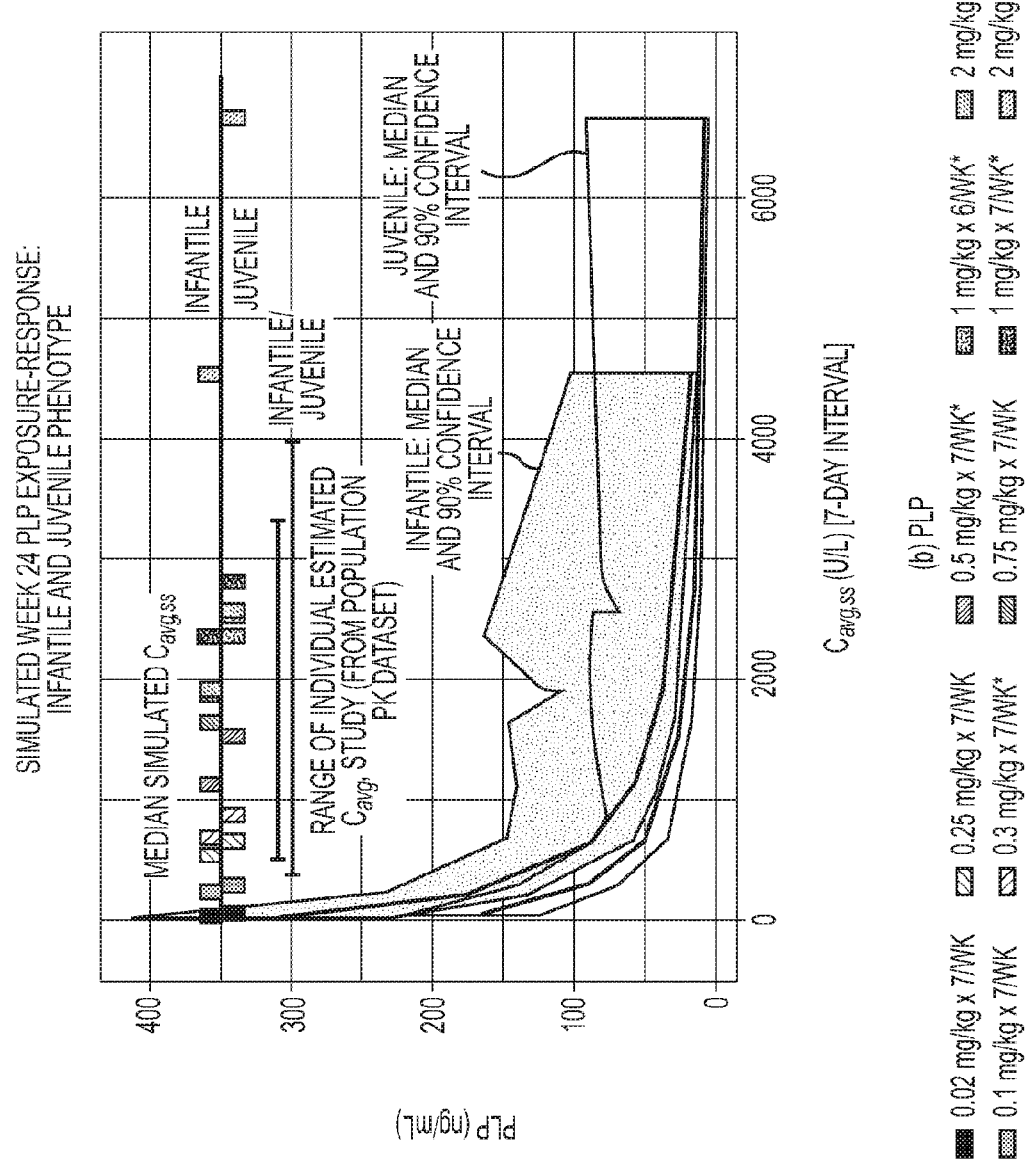

The exposure-response relationship for the plasma biomarker endpoints were simulated in Infantile and Juvenile (PPi and PLP) and Adult (PPi) phenotype HPP patients ages from 0 to <80 years at weeks 7 and 24 for PPi and at week 24 for PLP. The Adult phenotype PLP exposure-response relationship was not simulated since the model parameter estimate was based on an n=1 in the PKPD dataset. A summary of both PPi and PLP exposure response simulations for Infantile and Juvenile phenotypes was carried out. Simulations for PPi were performed at weeks 7 and 24 in order to better describe the time-course of the exposure response relationship due to the rebound relationship observed in plasma PPi with asfotase alfa treatment (FIGS. 2A-2B). Plots of response versus $C_{avg,ss}$ for both biomarker endpoints show decreasing plasma concentrations with increasing dose and a plateauing of the relationship in all phenotypes at the higher dose regimens. The wide 90% confidence interval (CI) reflects relatively poor precision in some of the population estimates, particularly in $EC_{50}$ and $E_{max}$.

Simulated plasma PPi concentrations were generally lower at week 7 than at week 24. This is reflected in the probabilities of the simulated plasma PPi values falling below the reference lower limit of normal plasma PPi (1.33 μM).

X-Ray Efficacy Endpoints: Exposure-Response

Figure 3A:
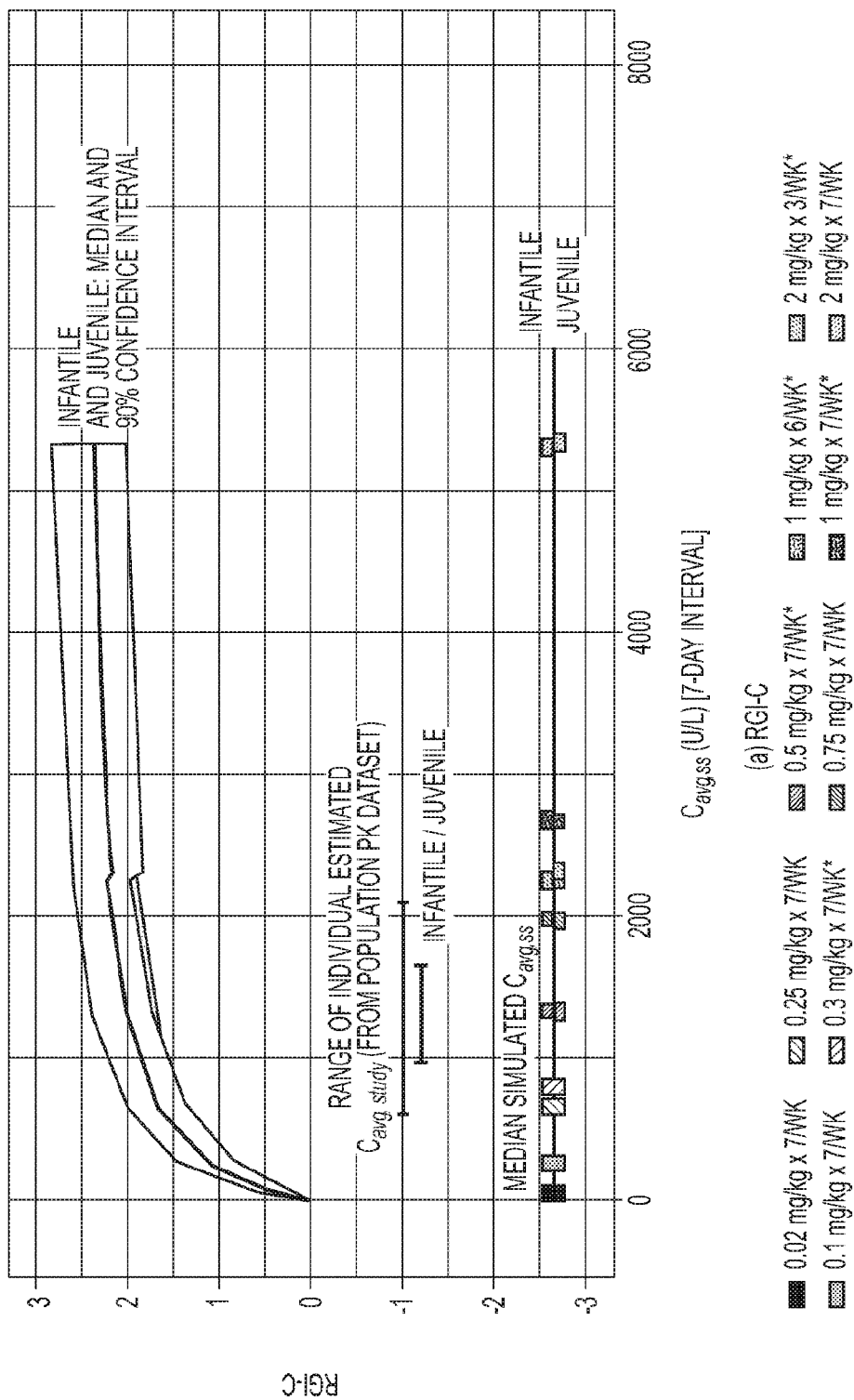
FIGS. 3A-3C depicts X-Ray Efficacy Endpoints: Simulated Week 72 Response Plots, representing the median (solid line) and 90% confidence intervals (shaded) for typical exposure-response. Median simulated ages and weights, by phenotype and endpoint were RGI-C (Infantile Baseline 6.82 yr and 19.3 kg; Infantile Week 72 8.20 yr and 23.0 kg; Juvenile Baseline 6.78 yr and 19.2 kg; JuvenileWeek 72 8.16 yr and 22.9 kg), and RSS (Infantile Baseline 6.84 yr and 19.4 kg; Infantile Week 72 8.21 yr and 23.0 kg; Juvenile Baseline 6.75 yr and 19.1 kg; Juvenile Week 72 8.17 yr and 22.9 kg). Also shown are the median simulated Cavg,ss values for each regimen and the range of subject-specific estimates of $C_{avg,study}$ values based on modeling of observed data. Asterisks (*) indicate dose regimens studied in the clinical development program.
Figure 3B:
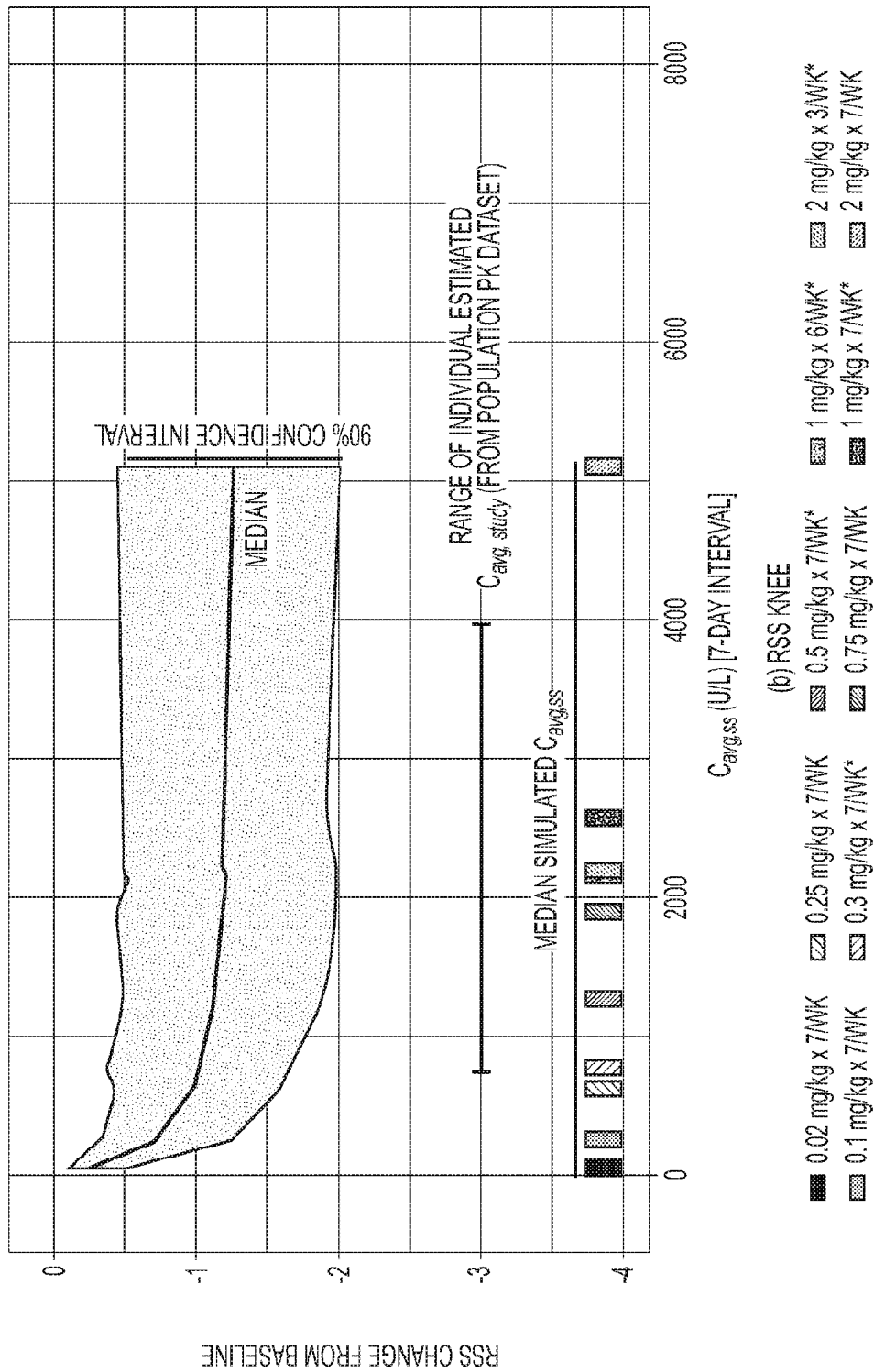
Figure 3C:
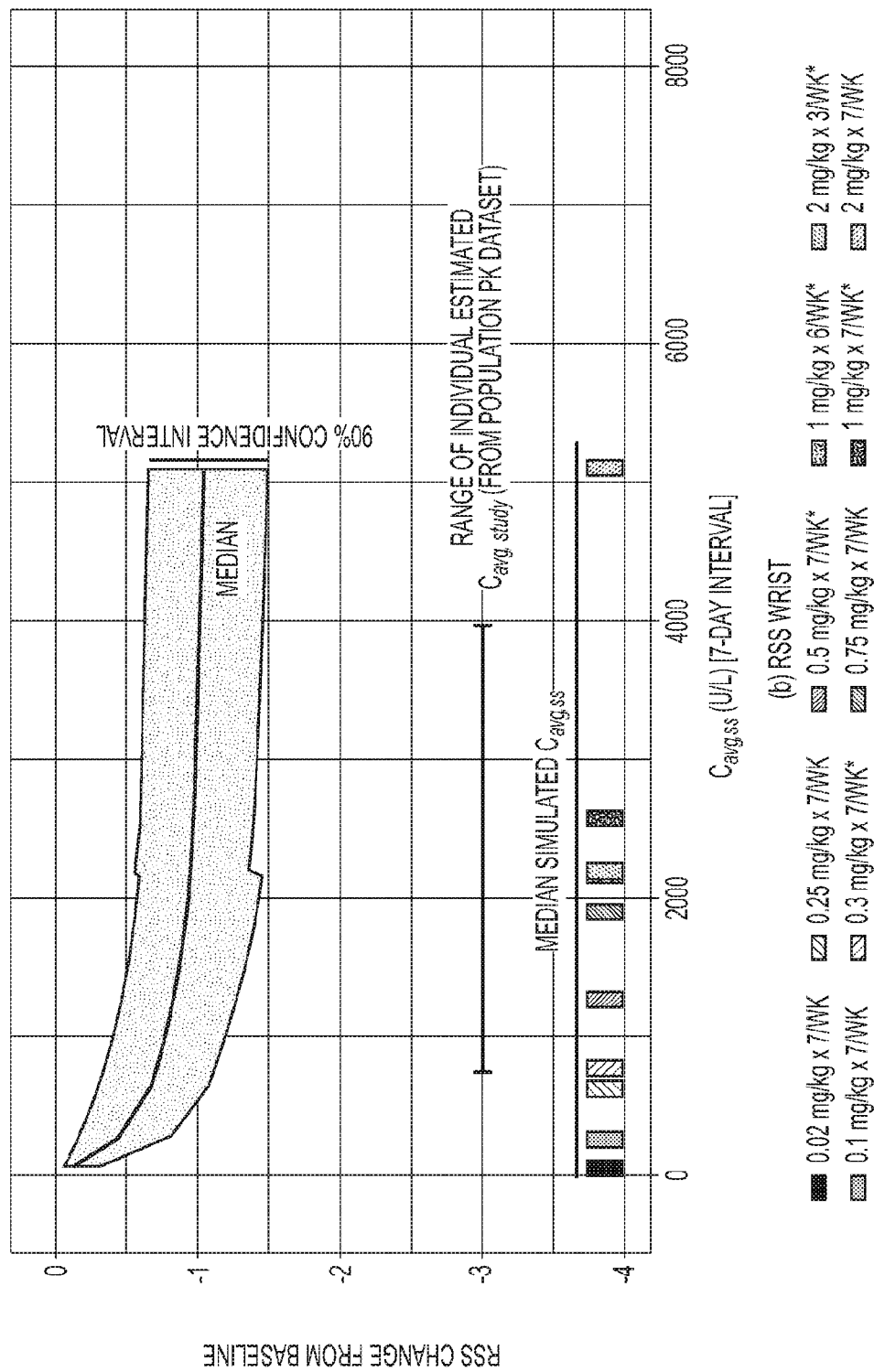

The exposure-response relationship for the X-ray efficacy endpoints RGI-C, $RSS_{Wrist}$, and $RSS_{Knee}$, were simulated in Infantile and Juvenile phenotype HPP patients' ages from 4 to <13 years at Week 72. A summary of all X-ray exposure-response simulations for Infantile and Juvenile phenotypes is shown in FIG. 3. The phenotype covariates effects estimated in the models for RSS were negligible. Because of this, and since the simulation results are shown as change from baseline, no distinctions are made in the RSS plots for Infantile versus Juvenile phenotypes.

Plots of change from baseline responses versus $C_{avg,ss}$ for all efficacy endpoints showed improving efficacy with increasing dose which approached a plateau at the higher dosing regimens. Median (90% CI) change from baseline RGI-C scores in Infantile patients across the simulated dose range ranged from 0.348 (0.201, 0.547) to 2.38 (2.03, 2.76) (Table 9). Similar scores for Juvenile patients for RGI-C ranged from 0.36 (0.226, 0.526) to 2.37 (2.04, 2.84) across the dose range (Table 10). Median (90% CI) change from baseline RSS-Wrist and RSS-Knee scores ranged from −0.116 (−0.323, −0.0367) to −1.03 (−1.48, −0.640) and −0.254 (−0.521, −0.0885) to −1.27 (−2.02, −0.446), respectively (Table 10). The range in predicted $C_{avg,study}$ for HPP clinical trial patients included in the estimation datasets represented the mid-range of the simulated $C_{avg,ss}$ values in the exposure-response relationships for RGI-C, RSS-Wrist, and RSS-Knee.

Functional Efficacy Endpoints: Exposure-Response

Figure 4A:
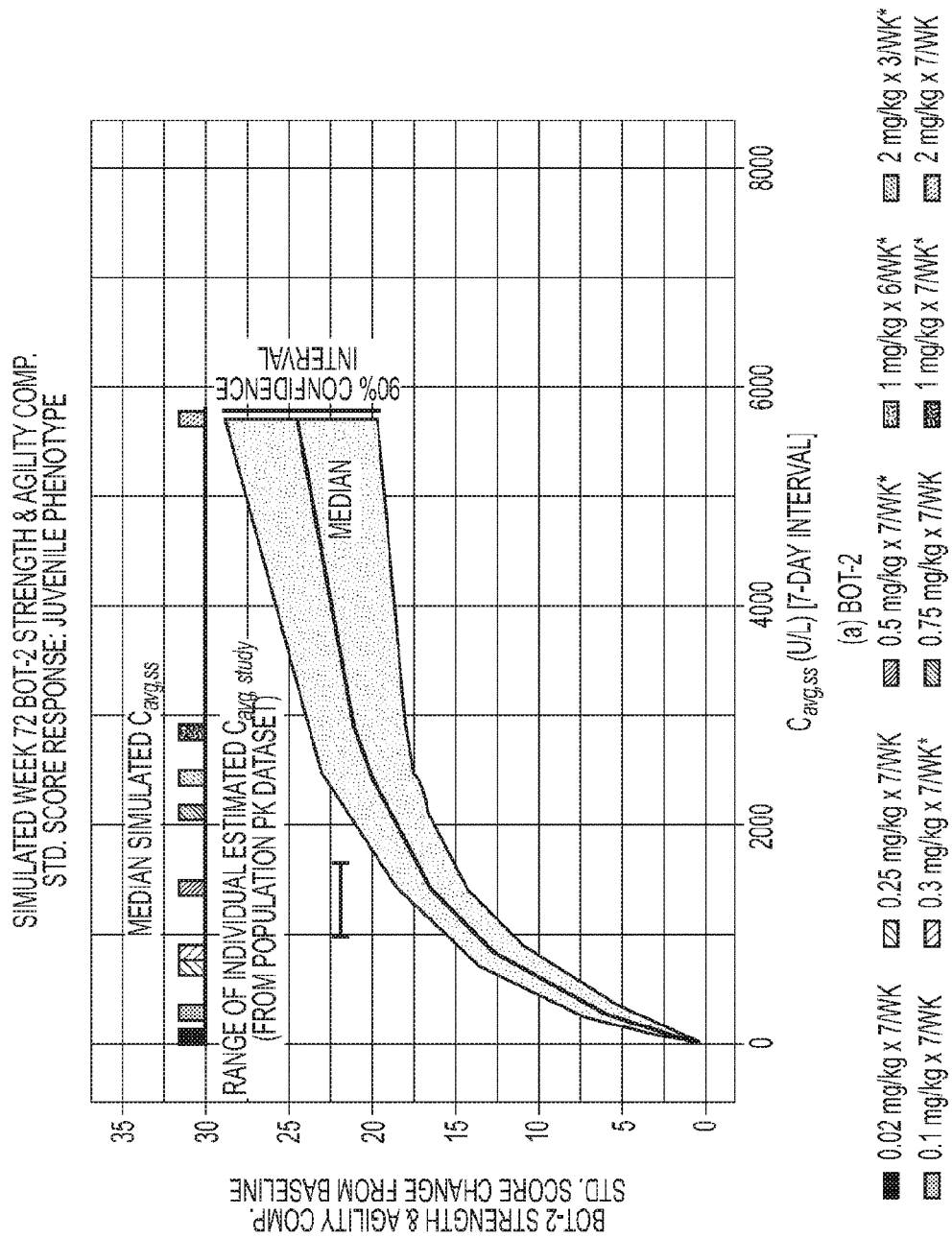
FIGS. 4A-4B depicts Functional Endpoints: Simulated Week 72 Response, representing the median (solid line) and 90% confidence intervals (shaded) for typical exposure-response. Median simulated ages and weights, by endpoint were BOT-2 (Baseline 9.67 yr and 27.2 kg; Week 72 11.0 yr and 31.5 kg), and 6MWT (Baseline 18.2 yr and 60.0 kg; Week 72 19.5 yr and 66.9 kg). Also shown are the median simulated $C_{avg,ss}$ values for each regimen and the range of subject-specific estimates of $C_{avg,study}$ values based on modeling of observed data. Asterisks (*) indicate dose regimens studied in the clinical development program.
Figure 4B:
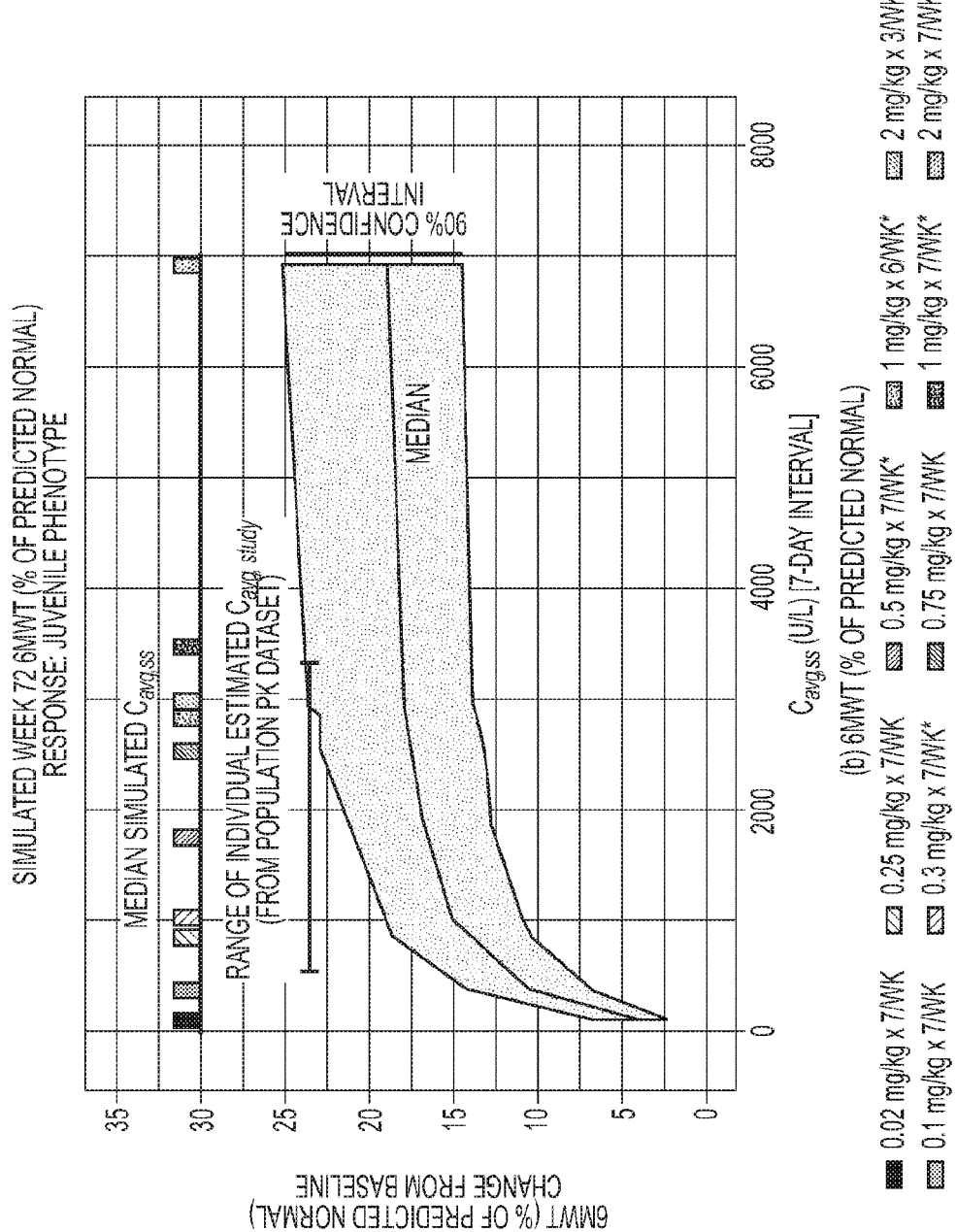

The exposure-response relationship for the functional endpoints of BOT-2 strength and agility composite standard score and percent predicted 6MWT were simulated in Juvenile phenotype HPP patients (FIG. 4) at Week 72. A summary of both BOT-2 and 6MWT exposure-response simulations is provided in FIG. 4A and FIG. 4B. Plots of change from baseline response versus $C_{avg,ss}$ for both functional endpoints show increasing functional responses with increasing dose, though 6MWT approaches a plateau after the 1 mg/kg 7 times/week regimen while the BOT-2 scores continue to rise (FIG. 4B). As summarized in Table 10, median (90% CI) change from baseline BOT-2 scores ranged from 1.53 (1.01, 2.23) to 24.5 (19.7, 28.9) across the simulated dose range. Median (90% CI) change from baseline percent predicted 6MWT ranged from 3.62 (1.84, 6.21) to 19 (14.6, 25.1). The range in predicted $C_{avg,study}$ for HPP clinical trial patients included in the estimation datasets represented the mid-to-lower range of the simulated $C_{avg,ss}$ values in the exposure-response relationships for BOT-2 and 6MWT. For the functional efficacy endpoints, simulations were also performed to visualize the impact of estimated interindividual pharmacodynamic variability on the range of responses, as depicted by a 90% population variability interval. Patients were simulated as previously described, assuming no unexplained variability in PK, but incorporating unexplained variability in PD parameters using the estimated interindividual variance-covariance matrix. Model parameters were assumed to be estimated with no uncertainty.

TABLE 9

Predicted Dose-Response Summary Table for All Endpoints: Infantile Phenotype

| Dose (mg/kg) | Regimen | Wk 7 Prob (PPi < LLN) | Wk 24 Prob (PPi < LLN) | Wk 72 CFB RGI-C Median (90% CI) | *Wk 72 CFB RSS-knee Median (90% CI) | *Wk 72 CFB RSS-wrist Median (90% CI) |
|---|---|---|---|---|---|---|
| 0.02 | 7 days/wk | 0% | 0% | 0.348 (0.201, 0.547) | −0.254 (−0.521, −0.0885) | −0.116 (−0.323, −0.0367) |
| 0.1 | 7 days/wk | 0% | 0% | 1.13 (0.810, 1.42) | −0.72 (−1.26, −0.332) | −0.405 (−0.789, −0.162) |
| 0.25 | 7 days/wk | 0% | 0% | 1.65 (1.35, 1.98) | −0.987 (−1.58, −0.437) | −0.641 (−1.06, −0.294) |
| 0.3 | 7 days/wk | 0% | 0% | 1.76 (1.46, 2.02) | −1.01 (−1.64, −0.376) | −0.697 (−1.09, −0.346) |
| 0.5 | 7 days/wk | 0% | 0% | 2.01 (1.71, 2.34) | −1.13 (−1.89, −0.487) | −0.825 (−1.28, −0.457) |
| 0.75 | 7 days/wk | 0% | 0% | 2.14 (1.82, 2.50) | −1.18 (−1.99, −0.437) | −0.915 (−1.42, −0.545) |
| 1 | 7 days/wk | 0% | 0% | 2.2 (1.88, 2.53) | −1.22 (−1.99, −0.535) | −0.92 (−1.45, −0.579) |

TABLE 9-continued

Predicted Dose-Response Summary Table for All Endpoints: Infantile Phenotype

| Dose (mg/kg) | Regimen | Wk 7 Prob (PPi < LLN) | Wk 24 Prob (PPi < LLN) | Wk 72 CFB RGI-C Median (90% CI) | *Wk 72 CFB RSS-knee Median (90% CI) | *Wk 72 CFB RSS-wrist Median (90% CI) |
|---|---|---|---|---|---|---|
| 2 | 7 days/wk | 0% | 0% | 2.22 (1.90, 2.56) | −1.19 (−1.97, −0.495) | −0.914 (−1.37, −0.535) |
| 1 | 7 days/wk | 0% | 0% | 2.25 (1.93, 2.61) | −1.21 (−1.91, −0.495) | −0.956 (−1.40, −0.588) |
| 2 | 7 days/wk | 0% | 0% | 2.38 (2.03, 2.76) | −1.27 (−2.02, −0.446) | −1.03 (−1.48, −0.640) |

*Covariate effect of phenotype on the exposure-response relationship for RSS wrist and knee was negligble; therefore, the simulated data for both Infantile and Juvenile phenotypes was pooled together to calculate the summary statistics.
CFB = change from baseline;
CI = confidence interval;
LLN = lower limit of normal for PPi (1.33);
PPi = inorganic pyrophosphate;
Prob = probability;
RGI-C = Radiographic Global Impression of Change;
RSS = Rickets Severity Scale

TABLE 10

Predicted Dose-Response Summary Table for All Endpoints: Juvenile Phenotype

| Dose (mg/kg) | Regimen | Wk 7 Prob (PPi < LLN) | Wk 24 Prob (PPi < LLN) | Wk 72 CFB RGI-C Median (90% CI) | *Wk 72 CFB RSS-knee Median (90% CI) | *Wk 72 CFB RSS-wrist Median (90% CI) | Wk 72 CFB BOT-2 SACSS Median (90% CI) | Wk 72 CFB % Pred6MWT Median (90% CI) |
|---|---|---|---|---|---|---|---|---|
| 0.02 | 7 days/wk | 0% | 0% | 0.36 (0.226, 0.526) | −0.254 (−0.521, −0.0885) | −0.116 (−0.323, −0.0367) | 1.53 (1.01, 2.23) | 3.62 (1.84, 6.21) |
| 0.1 | 7 days/wk | 0% | 0% | 1.1 (0.815, 1.46) | −0.72 (−1.26, −0.332) | −0.405 (−0.789, −0.162) | 6.27 (4.51, 7.95) | 10.4 (6.68, 14.1) |
| 0.25 | 7 days/wk | 0% | 0% | 1.69 (1.36, 2.00) | −0.987 (−1.58, −0.437) | −0.641 (−1.06, −0.294) | 11.5 (9.13, 13.6) | 14 (10.1, 18.5) |
| 0.3 | 7 days/wk | 0% | 0% | 1.77 (1.45, 2.11) | −1.01 (−1.64, −0.376) | −0.697 (−1.09, −0.346) | 12.9 (10.5, 14.8) | 15.1 (10.9, 19.2) |
| 0.5 | 7 days/wk | 0% | 0% | 2.01 (1.73, 2.40) | −1.13 (−1.89, −0.487) | −0.825 (−1.28, −0.457) | 16.4 (14.3, 18.6) | 16.6 (12.5, 21.0) |
| 0.75 | 7 days/wk | 0% | 0% | 2.17 (1.89, 2.51) | −1.18 (−1.99, −0.437) | −0.915 (−1.42, −0.545) | 19.1 (16.7, 21.6) | 17.5 (13.1, 22.8) |
| 1 | 6 days/wk | 0% | 0% | 2.22 (1.97, 2.58) | −1.22 (−1.99, −0.535) | −0.92 (−1.45, −0.579) | 20.1 (17.2, 22.8) | 17.8 (13.5, 23.0) |
| 2 | 3 days/wk | 0% | 0% | 2.17 (1.85, 2.56) | −1.19 (−1.97, −0.495) | −0.914 (−1.37, −0.535) | 19.9 (17.4, 22.6) | 17.9 (13.7, 23.7) |
| 1 | 7 days/wk | 0% | 0% | 2.22 (1.89, 2.57) | −1.21 (−1.91, −0.495) | −0.956 (−1.40, −0.588) | 21 (18.0, 23.8) | 18 (13.7, 23.7) |
| 2 | 7 days/wk | 29.5% | 0% | 2.37 (2.04, 2.84) | −1.27 (−2.02, −0.446) | −1.03 (−1.48, −0.640) | 24.5 (19.7, 28.9) | 19 (14.6, 25.1) |

*Covariate effect of phenotype on the exposure-response relationship for RSS wrist and knee was negligble; therefore, the simulated data for both Infantile and Juvenile phenotypes was pooled together to calculate the summary statistics.
6MWT = six-minute walk test (% of predicted normal);
BOT-2 = Bruininks-Oseresky Test of Motor Proficiency, Second Edition;
BOT-2 SACSS = BOT-2 strength and agility composite standard score;
CFB = change from baseline;
CI = confidence interval;
LLN = lower limit of normal for PPi (1.33);
PPi = inorganic pyrophosphate;
Prob = probability;
RGI-C = Radiographic Global Impression of Change;
RSS = Rickets Severity Scale

TABLE 11

Predicted Dose-Response Summary Table for All Endpoints: Adult Phenotype

| Dose (mg/kg) | Regimen | Wk 7 Prob (PPi < LLN) | Wk 24 Prob (PPi < LLN) |
|---|---|---|---|
| 0.02 | 7 days/wk | 0% | 0% |
| 0.1 | 7 days/wk | 0% | 0% |
| 0.25 | 7 days/wk | 0% | 0% |
| 0.3 | 7 days/wk | 0% | 0% |

TABLE 11-continued

Predicted Dose-Response Summary Table
for All Endpoints: Adult Phenotype

| Dose (mg/kg) | Regimen | Wk 7 Prob (PPi < LLN) | Wk 24 Prob (PPi < LLN) |
|---|---|---|---|
| 0.5 | 7 days/wk | 0% | 0% |
| 0.75 | 7 days/wk | 16.7% | 0% |
| 1 | 6 days/wk | 42.1% | 0% |
| 2 | 3 days/wk | 17.6% | 0% |
| 1 | 7 days/wk | 31.6% | 0% |
| 2 | 7 days/wk | 78.9% | 10.5% |

LLN = lower limit of normal for PPi (1.33);
PPi = inorganic pyrophosphate;
Prob = probability Integrated Exposure-Response Across Doses Simulation results for all endpoints were summarized across asfotase alfa doses and regimens in Table 9 (Infantile phenotype), Table 10 (Juvenile phenotype), and Table 11 (Adult phenotype). This integrated view of dose-regimen exposure-response revealed some consistent trends. All efficacy responses approached a plateau around a weekly dose of 6 mg/kg, with minimal gain in response at higher dosing regimens. The probability of PPi dropping below the lower limit of normal (1.33 µM; a conservative reference point for possible safety concerns) was negligible for most regimens and phenotypes. There was a trend toward increased probability of PPi below the lower limit of normal in the Adult phenotype, but when Weeks 7 and 24 results were compared, the effect was clearly transient, rebounding back to normal values over time.

Dosing Regimen Simulations

The PK and PD effects of an asfotase alfa dosing regimen (1 mg/kg×6 times/week and 2 mg/kg×3 times/week) were simulated using final model typical parameter estimates and estimates of interindividual variability as described herein. Aside from the expected fluctuations in asfotase alfa activity over time and across ages, no notable differences in simulated PK or PD responses for any endpoints were noted between the two regimens.

Regimen Effects on PK

Figure 5:
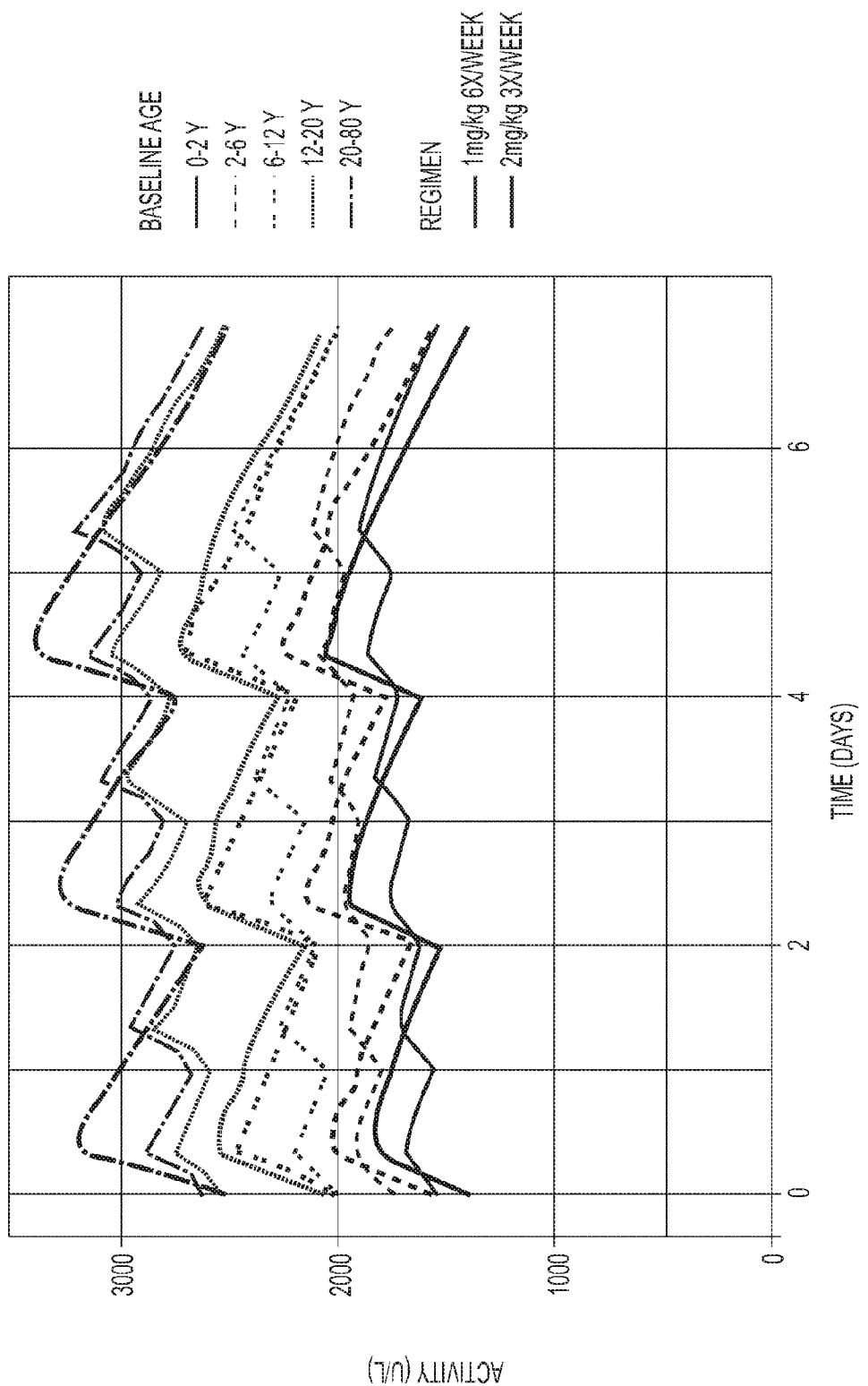
FIG. 5 depicts pharmacokinetic (PK) analysis on Simulated Median Steady-State Activity-Time Profiles for Two Asfotase Alfa Regimens. The final PK model was used to simulate the expected (median) exposure vs. time at steady-state for asfotase alfa regimens of 1 mg/kg given 6 times/week and 2 mg/kg given 3 times/week for each baseline age.

PK simulations used final model parameter estimates from run #52200820. Plots of the resulting simulated median asfotase alfa activity vs. time at steady-state are shown for ages 0 to 2 years, 2 to 6 years, 6 to 12 years, 12 to 20 years, and greater than 20 years (FIG. 5). Expected fluctuations in asfotase alfa activity over time were observed across regimens, with considerable overlap in simulated population weekly exposure for the two regimens for all age ranges. Differences in the relative shapes of the asfotase alfa activity vs. time relationships across age groups can be attributed to the effects of using fixed mg/kg dosing when an allometric relationship better describes PK disposition parameters.

Regimen Effects on PD Endpoints

No discernible differences were noted in simulated PD responses between dosing regimens (1 mg/kg given 6 times/week and 2 mg/kg given 3 times/week) for PPi, PLP, RGI-C, RSS-Wrist, RSS-Knee, percent predicted 6MWT, and BOT-2. Simulations to Evaluate the Influence of Body Weight-Dependent Pharmacokinetics on Pharmacodynamic Response As stated herein, the final PK population model predicts a range in exposure across different age groups, given a fixed mg/kg asfotase alfa dose. Simulations were conducted to translate the impact of weight-related differences in PK to the expected differences in PD. Due to the correlation of patient age and bodyweight, weight-related differences in PK and subsequently PD may also have an age-dependent component that was difficult to resolve independently in the PK modeling. PPi and PLP were used as the endpoints of interest in this assessment, since these were the only endpoints where data used in model development were available over the entire age range of 0 to ~70 years.

Simulations were performed as described herein for the exposure-response analysis and included measures of population parameter uncertainty from the final PPi, and PLP models. The 90% CIs for $C_{avg,ss}$ for defined age groups were overlayed on exposure-response plots for each endpoint. Separate plots were shown for each HPP phenotype, and age groups were matched accordingly. Expected responses overlapped considerably across the ranges in exposure for the different age groups. Poor precision in some of the PLP parameter estimates are reflected in the relatively wide 90% CIs in this exposure-response relationship. Plots of the Infantile phenotype for PLP and PPi exposure-response showed the greatest range in expected serum asfotase alfa exposure across the ages. For HPP Infantile phenotypes, plasma concentrations of PPi and PLP were not quite at maximal inhibition over the range in serum asfotase alfa Cavg,ss, though the exposure-response relationships were relatively shallow in this range and considerable overlap was noted in expected responses between the youngest (newborn) and oldest age groups (~60 years). For HPP Juvenile phenotypes, the expected PPi and PLP concentrations were near maximum inhibition over the range in serum asfotase alfa $C_{avg,ss}$, and overlap was noted in the expected responses across the age range. For HPP Adult phenotype patients ~60 years of age, the expected range in PPi concentrations covered a relatively flat portion of the exposure-response relationship.

Simulations of Typical PK-PD Time-Courses at Select Age/Weight Combinations

Final model typical parameter estimates were used to simulate the time-course of asfotase alfa activity, and all biomarker, functional, and efficacy endpoints in typical patients. Simulations assumed patients received a 2 mg/kg, 3 times/week, SC dose of an asfotase alfa 20,000 L batch lot with sialic acid content of 2.2 mol/mol and 990 U/mg potency. No presence of anti-drug or neutralizing antibodies was assumed in the simulations. Although body weight is an important determinant of asfotase alfa disposition, simulations were conducted by first selecting meaningful baseline ages, and then calculating body weight from age using an algorithm developed from the age-weight relationship of patients in the analysis dataset. Selected baseline ages for the typical patients were 0.042, 0.5, 2, 6, and 18 years and included Infantile and Juvenile phenotypes, where appropriate. The representative ages and phenotypes of patients in each simulation were based on their range and inclusion in the associated estimation dataset. PK-PD values were simulated weekly from 0 (pre-dose) to 72 weeks.

Figure 6:
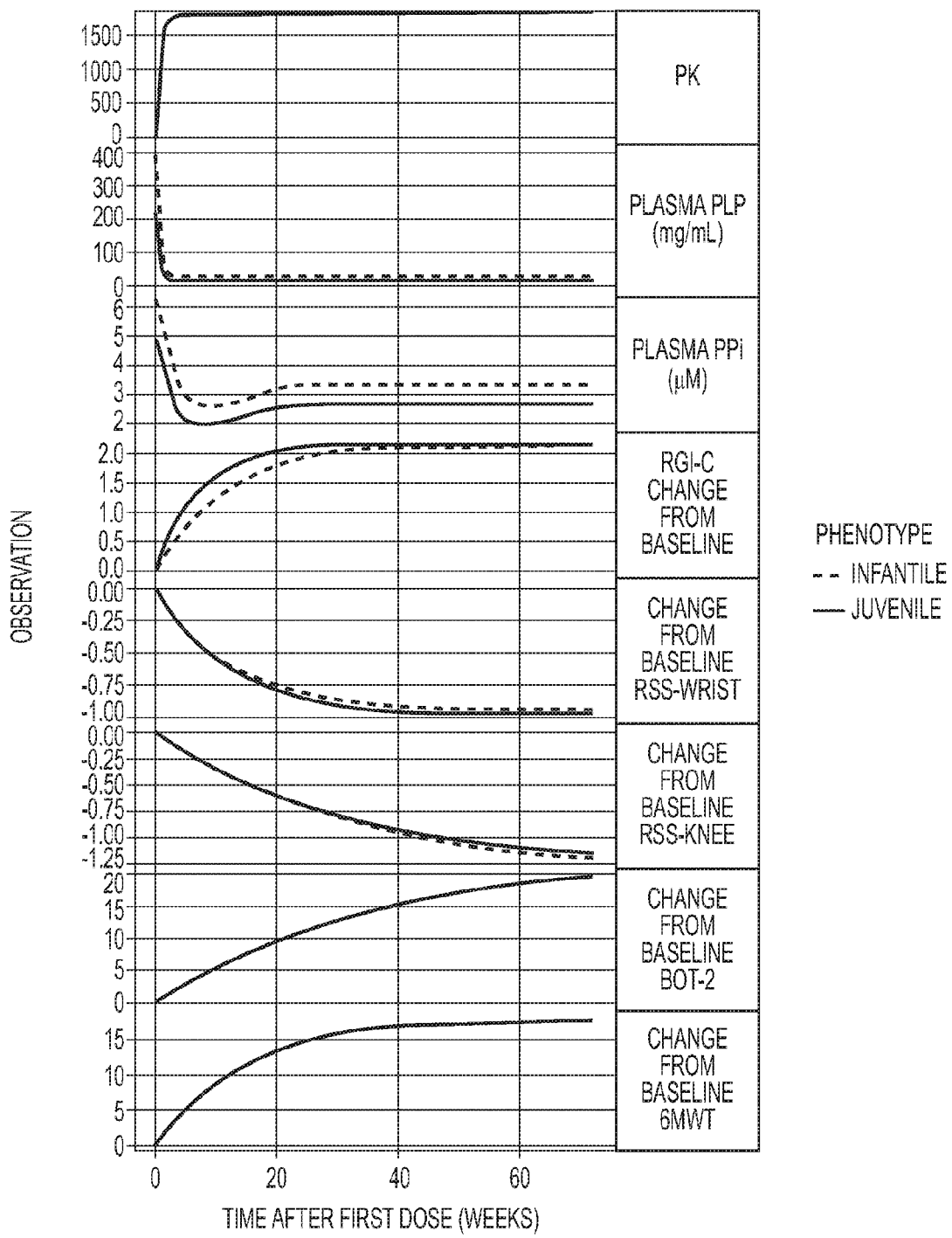
FIG. 6 depicts a simulated pharmacokinetic/pharmacodynamic (PK-PD) time course of a typical patient from time 0 to 72 weeks with a weight=17.29 kg. The final PK-PD models for PK, PPi, PLP, RGI-C, RSS-Knee, RSS-Wrist, BOT-2, and 6MWT were used to simulate the time course of each observation for a typical patient from time 0 to 72 weeks following a 2 mg/kg SC dose given 3 times/week. Here, a typical patient was defined with a baseline weight=17.29 kg, baseline age=6 yr, Infantile and Juvenile phenotypes, assumed no neutralizing antibody formation, and assumed an asfotase alfa drug lot with activity=990 U/mg and sialic acid content=2.2 mol/mol protein. The final PK model did not include an estimate of any phenotype effect, so the time course of typical Infantile and Juvenile phenotypes were identical in this simulation. The final models for BOT-2 and 6MWT were developed in Juvenile patients only. Weight and age at 72 weeks were 20.77 kg and 7.38 yr, respectively.

Simulations of Typical PK-PD Time-Courses at Select Age/Weight Combinations: Results In typical 6-year old HPP patients weighing 17.29 kg, the time to maximal effects of asfotase alfa administration is expected to vary across endpoints (FIG. 6). Asfotase alfa activity is expected to increase rapidly during the first few weeks of treatment, then plateau after approximately 3 weeks. Likewise, plasma PLP concentrations are expected to decrease and achieved a plateau within the first few weeks of treatment. Plasma PPi concentrations are expected to decrease within the first few weeks of treatment, then rebound slightly to a achieve a plateau after approximately 20 weeks. Maximum RGI-C changes are also expected to occur after ~30 weeks, while changes in RSS-Wrist and Knee scores are expected to occur later. The expected percent predicted change from baseline 6MWT values appear to plateau after about 50 weeks of treatment, while the maximum change from baseline BOT-2 values are expected to take longer than 72 weeks. In general, the changes in these endpoints over time are expected to be similar across Infantile and Juvenile HPP patients and across a wide range of typical age/weight combinations.

DISCUSSION

The final PK model which best described the data was a linear two-compartment structural model incorporating covariates of interest such as body weight, anti-drug and neutralizing antibody status, and asfotase alfa drug lot characteristics. PK and all PK-PD models included measures of random interindividual and residual variability. The adequacy of the PK model was assessed using a visual predictive check (FIG. 7), which showed agreement between the observed (open) and model-predicted (shaded) asfotase alfa levels. In addition, the majority of the observed data fell within the region representing the 90% prediction interval (PI).

Figure 8B:
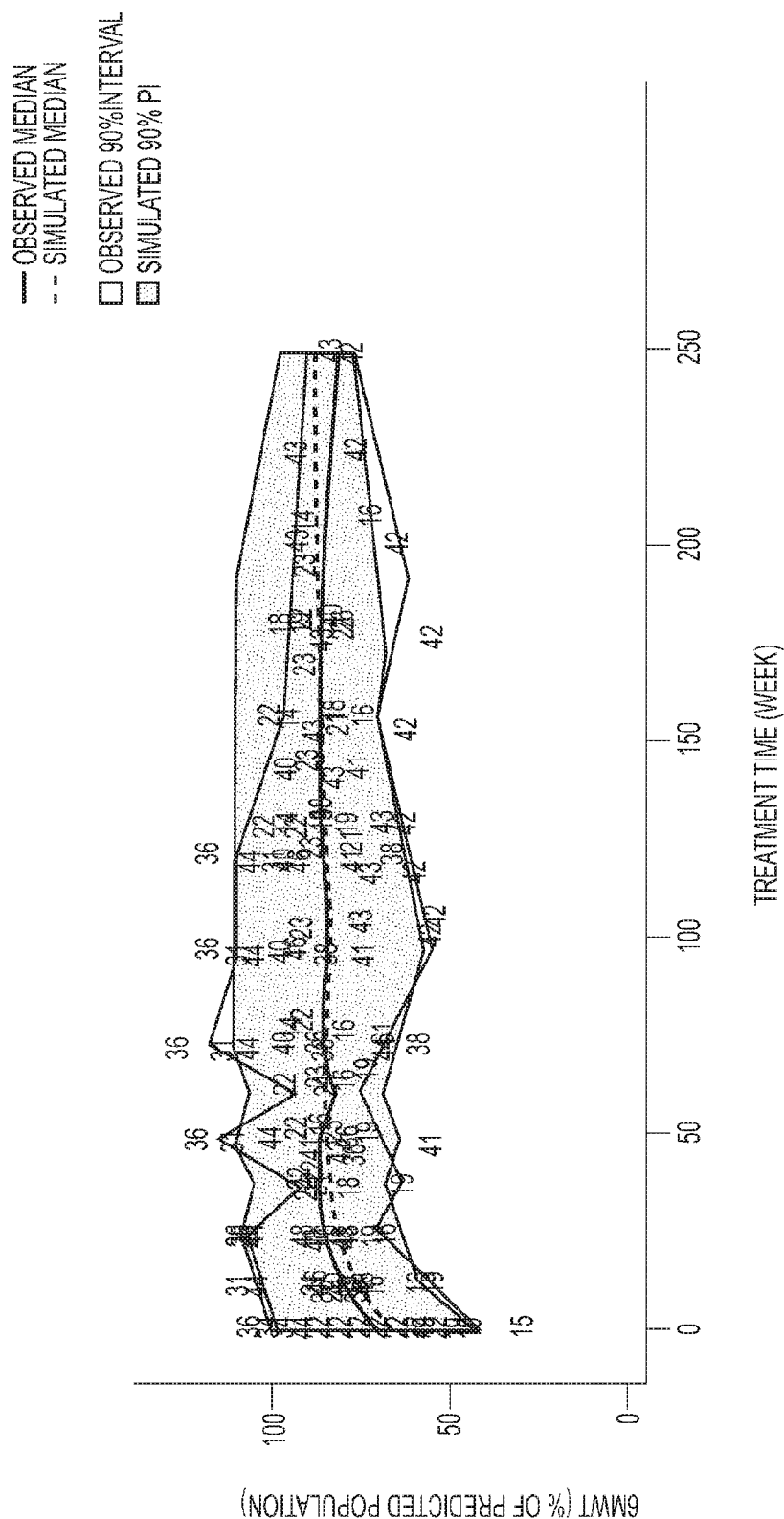

The adequacy of the PK-PD model was also assessed using a visual predictive check. FIG. 8 showed agreement between the observed (open) and model-predicted (shaded) for two of the PD endpoints (RGI-C, 6MWT), highlighting the ability of the PK-PD models to predict the central tendency of the observed data (FIG. 8A-8B). In addition, the majority of the observed data fell within the region representing the 90% prediction interval (PI).

Biomarker endpoints PPi and PLP revealed a rapid drop in concentrations following initiation of asfotase alfa therapy across Infantile, Juvenile, and Adult phenotype HPP patients. Efficacy endpoints RGI-C (i.e., radiographic global impression of change), RSS-knee ("RSS" stands for Rickets Severity Scale), and RSS-wrist were modeled in a subset of Infantile and Juvenile phenotype HPP patients with baseline ages ≥4 to <13 years. Historical control X-ray data from an age and phenotype-matched HPP dataset suggested no disease progression in these endpoints. All efficacy endpoints showed improved X-ray scores following initiation of asfotase alfa therapy. Functional endpoints BOT-2 (i.e., Bruininks-Qserestsky test of motor proficiency, $2^{nd}$ Ed.) strength and agility composite standard score and six-minute walk test (6MWT; % of predicted normal) were modeled in a subset of Juvenile phenotype HPP patients. Both functional endpoints showed a time-dependent increase in response throughout the duration of asfotase alfa therapy. The effects of asfotase alfa therapy on these biomarker, efficacy, and functional endpoints were best described by indirect-response models. Models for biomarker and X-ray endpoints included HPP phenotype as a covariate in the model.

When viewed as a function of exposure quartiles, exploratory analysis of osteoid thickness measurements at weeks 24 and 48 and specific adverse event (AE) summaries revealed no dependence on exposure.

Simulations of all endpoints across weekly SC dosing regimens ranging from 0.02 mg/kg, 7 times/week (i.e., 0.14 mg/kg/week) to 2 mg/kg, 7 times/week (i.e., 14 mg/kg/week) using the respective final PK-PD models showed that drug response increased with increasing dose/drug exposure and established a plateau in the exposure-response relationship. An integrated view of dose-regimen-response revealed the efficacy responses approached a plateau around a weekly dose of 6 mg/kg. Given the relationship between body weight and asfotase alfa exposure, a simulation approach was used to compare expected biomarker responses across a wide range in patient weights. Responses across the weights overlapped considerably and lower exposures were still associated with near maximal biomarker response.

Simulations of 1 mg/kg×6 times/week and 2 mg/kg×3 times/week dosing regimens revealed no notable differences in responses for any endpoint.

It was also found that disease onset subtypes (e.g., infantile [onset <6 months of age] vs. juvenile [onset 6 months-17 years, inclusive]) did not affect the dose vs. response relationships for the endpoints of interest.

Figure 9:
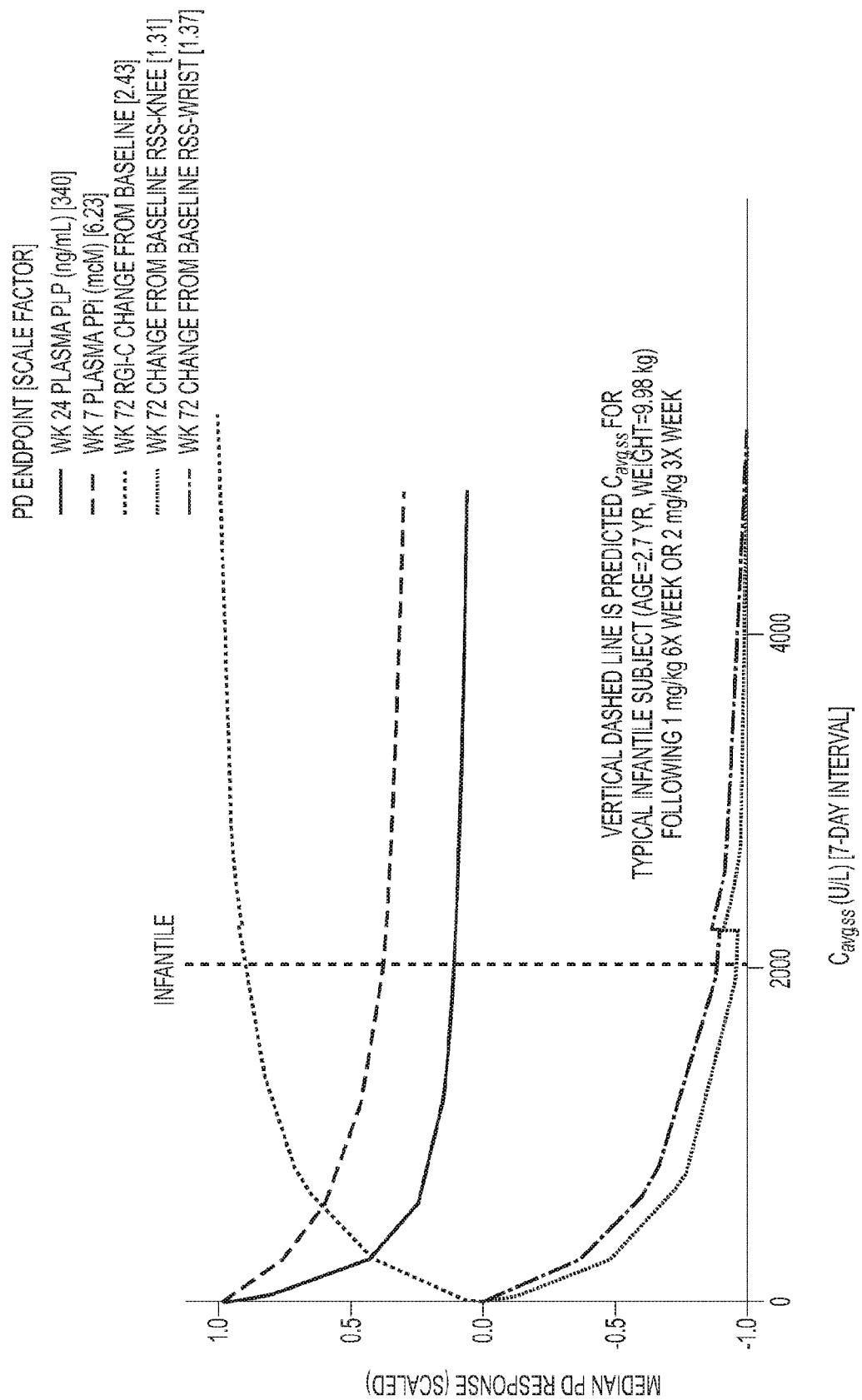
FIG. 9 depicts the exposure vs. response relationships (scaled) for HPP infantile disease onset.
Figure 10:
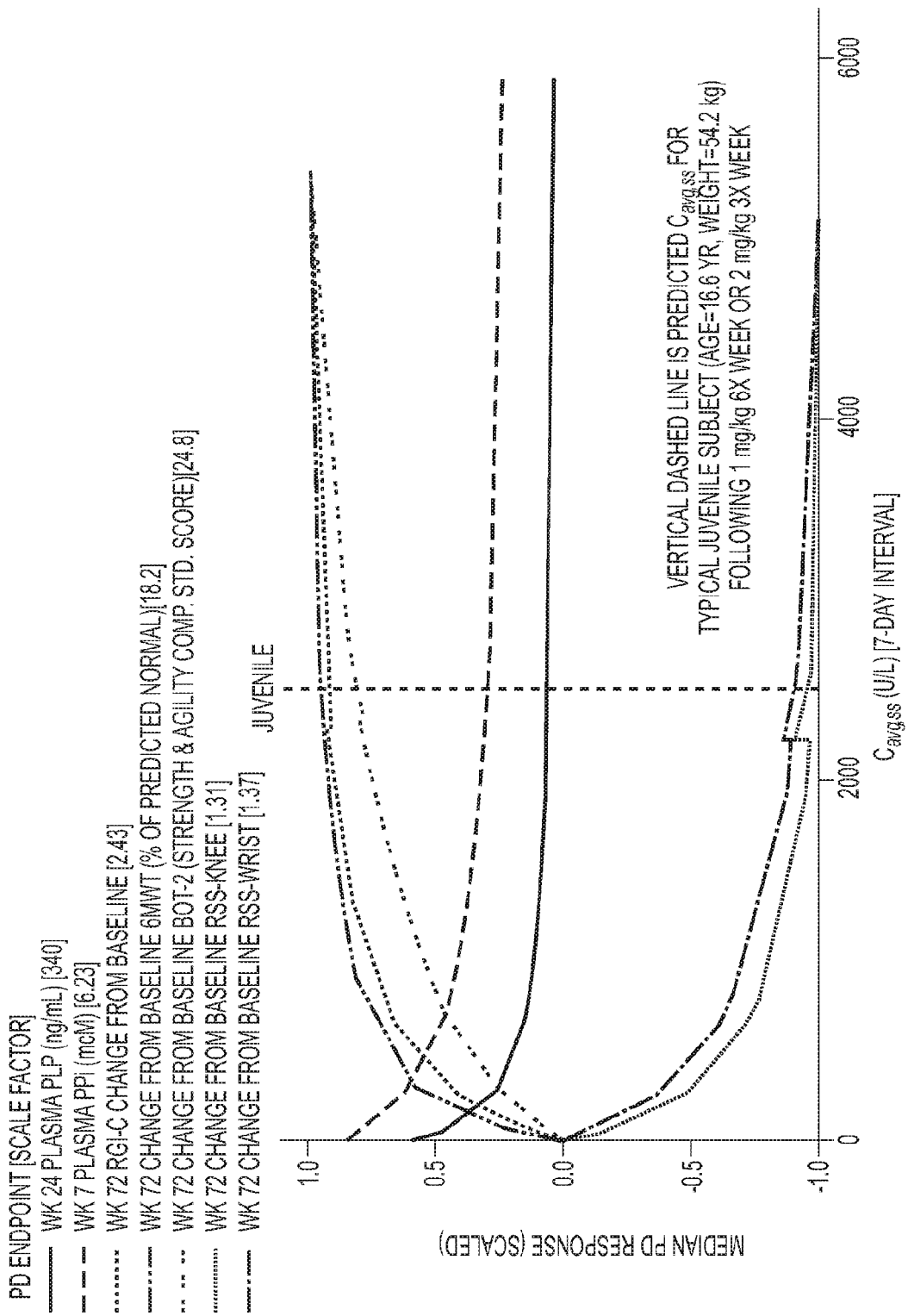
FIG. 10 depicts the exposure vs. response relationships (scaled) for HPP juvenile disease onset.

The simulated PD responses of interest consistently reached plateau around PK exposures achieved by the proposed dose of 6 mg/kg/wk of asfotase alfa for infantile (FIG. 9) and juvenile (FIG. 10) disease onset. A vertical dashed line represents the predicted $C_{avg,ss}$ for a typical infantile disease onset subject (age=2.7 years, weight=9.98 kg) (FIG. 9) or for a typical juvenile disease onset subject (age=16.6 years, weight=54.2 kg) (FIG. 10), following 1 mg/kg 6× week or 2 mg/kg 3× week dosing. The original PD endpoint values are scaled with scale factor so that all endpoints are on the same plot for comparison.

Figure 11:
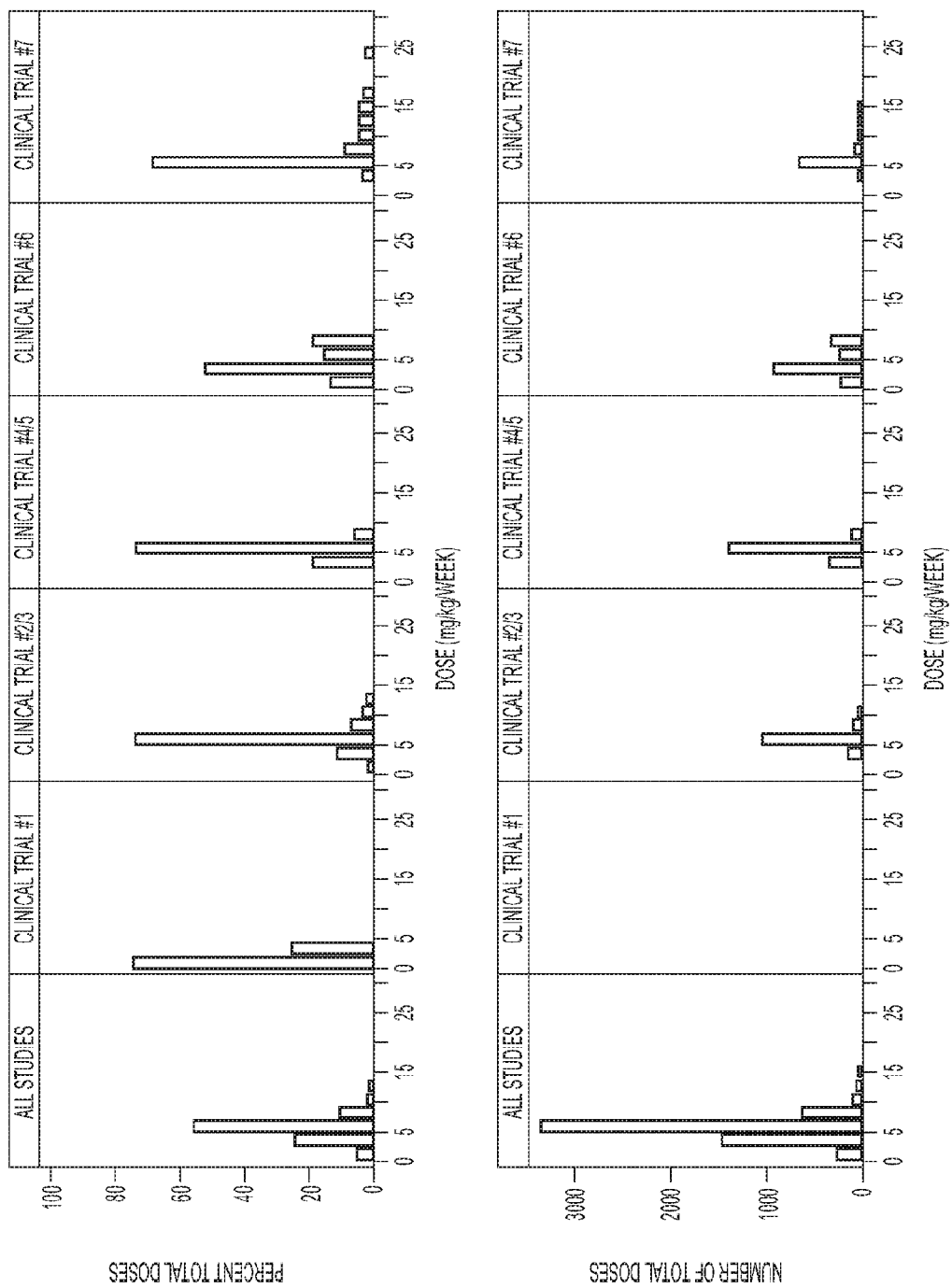
FIG. 11 depicts the distribution of weekly doses in HPP patients in seven clinical trials.

FIG. 11 shows the distribution of the percentage of total doses (upper panel) and the number of total weekly doses (lower panel) for all the studies together and each study separately (5 studies). The administered doses ranged from 1 to 28 mg/kg/week with the median dose close to 6 mg/kg/week. The 6 mg/kg/week dose, which was the median of the doses administered in the trials, agreed with the dose-exposure-response simulations findings.

Figure 12:
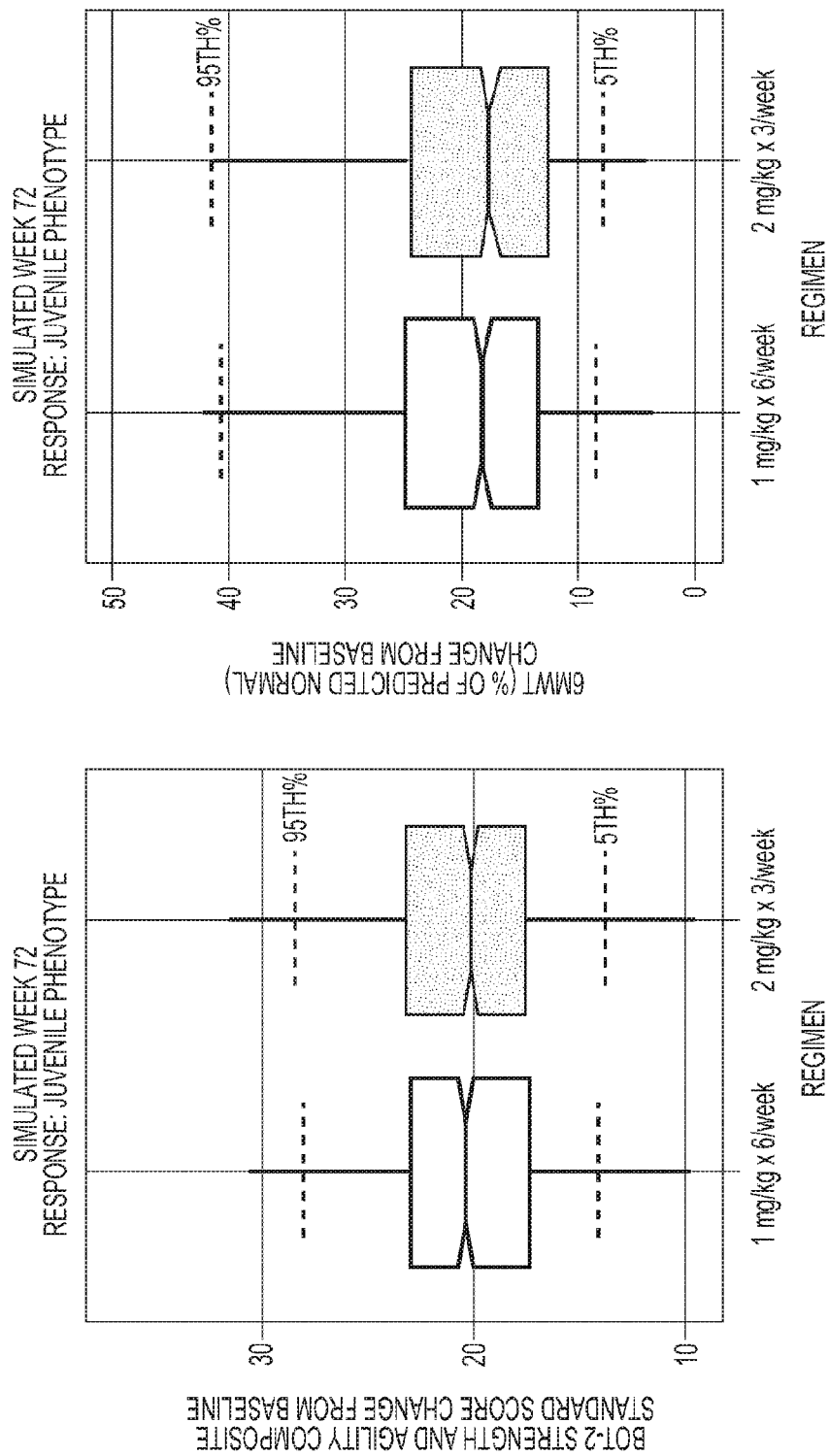
FIG. 12 depicts the simulated PD responses across dosing regimens (6 mg/kg/week, administered as 2 mg/kg three-times-a-week vs. 1 mg/kg six-times-a-week) for 6MWT and BOT-2 responses.

FIG. 12 shows no discernible differences in simulated PD responses across dosing regimens (6 mg/kg/week administered as 2 mg/kg three-times-a-week vs. 1 mg/kg six-times-a-week) for percent predicted 6MWT and BOT-2 endpoints. The top and bottom of vertical lines cross the middle of boxes show the maximum and minimum values. The upper horizontal side of box is the third quartile, and the lower horizontal side of box is the first quartile. The middle horizontal line dividing the box into two is the 50th percentile. The horizontal dashed lines are the 90% prediction intervals for the population responses. Disease onset subgroup is sometimes referred to as phenotype.

Relationships between quartiles of average concentration over the study treatment, calculated as $AUC_{cumulative}/TAFD$ ($C_{avg,study}$), and the incidence rate of adverse events was examined for ectopic calcification, injection/infusion associated reactions, and injection site reactions. When viewed as a function of exposure quartiles, adverse event summaries showed no dependence on exposure. Table 12 compares exposure quartiles and safety analysis.

TABLE 12

Exposure Quartiles vs. Safety Analysis

| Adverse Event | | Quartile 1 | Quartile 2 | Quartile 3 | Quartile 4 |
|---|---|---|---|---|---|
| | $C_{avg, study}$ (ng/mL) | 383-1002 | 1002-1240 | 1240-1666 | 1666-3975 |
| | Total subjects in quartile | 17 | 17 | 17 | 17 |
| Ectopic calcification | Mean rate (95% CI) | 0.14 (0.093-0.24) | 0.017 (0.011-0.029) | 0.15 (0.1-0.26) | 0.16 (0.1-0.27) |
| Injection/Infusion associated reactions | Mean rate (95% CI) | 0.72 (0.47-1.2) | 0.18 (0.12-0.32) | 0.12 (0.078-0.2) | 0.76 (0.5-1.3) |
| Injection site reactions | Mean rate (95% CI) | 8.6 (5.6-15) | 3.2 (2.1-5.4) | 7.2 (4.7-12) | 3.2 (2.1-5.4) |

The results of these analyses illustrate the impact of intrinsic and extrinsic factors on asfotase alfa exposure, and the consistent exposure-response relationship for asfotase alfa across relevant biomarker, functional, and imaging endpoints. The model-based analyses provide useful guidance with respect to dose and regimen assessment, and provide supportive evidence of efficacy with respect to the clinical endpoints analyzed. Nevertheless, limitations of the analyses and underlying data should be considered.

The population pharmacokinetic analysis provided reasonably precise estimates of disposition parameters as well as the degree of impact of both drug characteristics and potential covariates of clinical interest. The magnitude of influence of these variables on expected steady-state exposure was shown in FIG. 1 and will be discussed in the context of exposure-response below. While not studied specifically as a covariate, the potency of drug substance/drug product also has a direct correlation with expected exposure levels. In this analysis the activity of drug substance was used to scale the dose in mg to the dose in activity units (U).

Based on analysis of prespecified covariates, $C_{avg,ss}$ is influenced by bodyweight, sialic acid content, and the presence of anti-drug antibodies and specifically, neutralizing antibodies. These findings are consistent with expectations and prior analyses. As a hypothesis-generating exercise, the exploratory covariates, eGFR as a measure of renal function, ALT, AST, and race were evaluated post hoc. Neither eGFR nor the liver enzymes showed any material influence on asfotase alfa CL. Race was partitioned into two groups, Asians (which were primarily Japanese), and non-Asians (which were primarily whites). Expected $C_{avg,ss}$ did appear to show a difference between the two groups. It was estimated that Asians had a clearance 68.8% of the estimate in non-Asians. However, the 95% confidence interval was rather wide (52.6% to 90.0%) indicating imprecision of this estimate. This is not surprising given that there are only six Asian subjects in the dataset. While subject-level VPCs generally show good model performance on an individual basis across the analysis dataset, the VPCs for the Asian subjects reveal inconsistent performance across, and within, subjects. In the exploratory covariate analysis, the race effect was estimated as a categorical effect for the entire Asian group of six subjects, but individual VPCs from the full model reveal that the bias is not evident in the Asian group as a whole. The discrepancies appear in a subset of Asian subjects, and also appear to occur systemically as runs within subjects over time. As no obvious predictor of this bias was observed in the source data, this further reduces confidence in the interpretability of the findings of race-based differences in asfotase alfa disposition for such a small sample size.

Since two different assays were employed in the quantitation of asfotase alfa activity, the impact of bioanalytical assay (CBRG vs. WIL) on PK parameter estimates was evaluated and shown to be negligible. This finding was consistent whether assay bias was estimated in the context of the population PK model or fixed in the model based on analysis of assay cross validation study results. Due to the confounding of assay with route of administration, i.e., essentially all samples resulting from IV administration were analyzed with the CBRG method, a separate analysis of the data with and without CBRG data could not be conducted with the expectation of valid findings. Thus, the assay cross-validation results provide an unconfounded comparison of bioanalytical methods, with the population PK model affirming the findings of the cross validation study.

The influence of asfotase alfa exposure on a range of clinically meaningful endpoints has been comprehensively characterized and quantified. A model-based approach to this characterization was warranted due to a lack of formal dose-ranging studies with a prospective control arm in the asfotase alfa development program. However, an assumption about the underlying disease trajectory in the absence of treatment was necessary. Analysis of available historical control data for the imaging endpoints RSS and RGI-C did support the assumption of no disease progression, as evidenced by a zero-magnitude slope over the period of time of asfotase alfa trial duration. This finding, along with expert clinical opinion, served as the basis for extrapolation to other endpoints.

When longitudinal repeated-measures response data were anchored with baseline data, and a zero-slope disease progression, a clear exposure response relationship was evident for all endpoints. It was also shown that the exposure-response relationship approached a plateau at higher asfotase alfa exposures, consistent with the $E_{max}$ models for drug effect implemented within the indirect pharmacodynamic response structure. The limited dose-ranging data did adversely impact the precision of $EC_{50}$ estimation, particularly for the biomarker endpoints, and inferences should not be made directly based on this parameter alone. Despite the less-than-optimal precision for $EC_{50}$, there was reasonable precision in prediction of responses, based on the exposure-response model. This was due to some modest correlation in the estimation error between $EC_{50}$ and the more precisely estimated $E_{max}$. Given these results, inferences based on the predicted exposure-response relationship were well supported by the analyses.

Inferences about appropriateness of dose and regimen selection were supported by trial outcomes and the model-based exposure response relationship. Although no specific clinical target exposure range had been defined for asfotase alfa it was evident that a SC dosing regimen of 2 mg/kg, administered three times per week, achieved average steady-state concentrations that were above concentrations associated with efficacy in non-clinical studies. Furthermore, when viewed in the context of the exposure-response relationship, this dosing regimen achieved responses that were consistent with near maximal efficacy.

In younger children, where the mg/kg dosing regimen leads to slightly lower steady-state exposure than in adolescents and adults, predicted response is still near maximal efficacy, and consistent with findings based on trial outcomes. No further dose-adjustment, beyond mg/kg dosing, is likely necessary in these younger individuals. Due to the small sample size necessitated by this ultra-rare disorder, further evaluation of very young patients may be warranted.

When analyzed as a time-varying covariate, the effect of immunogenicity on asfotase alfa clearance was precisely estimated, and revealed an increase in CL by a factor of approximately 1.11 and 1.21 for ADA+/Nab− and ADA+/NAb+ categories, respectively, relative to the ADA− state. When viewed in context of the exposure-response relationship, the resulting decrease in steady-state exposure would not translate to a meaningful change in response. As such, no dose-adjustment is recommended based on immunogenicity status. It should be noted that the range of reported titers for ADA is somewhat narrow (up to 2048). Thus, these findings are applicable to the level of titers observed in the present dataset.

In the clinical trials, dose was not adjusted for drug TSAC or potency. In the population PK model context, the effect of TSAC definitively influenced steady-state exposure. While not evaluated as a model parameter specifically, drug substance potency also directly impacts exposure and pharmacodynamics response since dose is expressed as a function of potency. Simulation-based inferences indicated that low TSAC would lead to decreased exposures and approach the therapeutic exposures target range established in non-clinical studies. The result would shift response downward from the maximal efficacy plateau. Likewise, high TSAC content, coupled with high potency drug substance could have implications for asfotase alfa safety and tolerability. Thus, good formulation control is an important factor for successful clinical use of asfotase alfa.

CONCLUSIONS

The PK of asfotase alfa following IV and SC administration were adequately described using a two-compartment model with first-order absorption and elimination as assessed by model diagnostics and parameter estimates. Although there was evidence of pharmacokinetic flip-flop based on graphical assessment of activity-time profiles, simultaneous modeling of both IV and SC data permitted proper characterization of asfotase alfa disposition. In addition, model diagnostics supported the model assumptions of linearity and superposition.

Based on population PK modeling results, typical values of apparent clearance for mean body weight in different age categories were 1.72 L/day (0-1 month); 3.33 L/day (1 month-2 years); 7.53 L/day (2-12 years); 15.3 L/day (12-16 years); and 20.8 L/day (≥16 years). Likewise, typical values of apparent volume of distribution at steady state were 3.98 L (0-1 month); 9.32 L (1 month-2 years); 26.6 L (2-12 years); 66.2 L (12-16 years); and 98.9 L (≥16 years). Estimated absolute bioavailability was 0.571 for drug product arising from 2000 L batch size and 0.520 for drug product arising from 20,000 L batch size.

The mean (SD) of individual estimates of distributive and elimination half-lives were 0.0318 (0.0265) days and 2.51 (1.23) days, respectively.

The effects of body weight, sialic acid content, and immunogenicity on asfotase alfa clearance were well characterized and estimated with precision. Based on examination of simulated average concentration during the dosing interval at steady-state ($C_{avg,ss}$) following a regimen of 2 mg/kg thrice weekly, sialic acid content was the most influential of these three time-varying covariates. Over a range of TSAC of 1.0 to 3.0 mol/mol, $C_{avg,ss}$ is expected to range from 971 U/L to 3166 U/L, within fixed assumptions about other covariates such as weight. The presence of anti-drug antibodies increased asfotase alfa clearance by a factor of 1.11 (95% confidence interval (CI): 1.06-1.17). The presence of neutralizing antibodies increased clearance by a factor of 1.21 (95% CI: 1.08-1.37) relative to the negative anti-drug antibody state. This magnitude of clearance change is unlikely to have clinically meaningful impact on asfotase alfa clinical activity.

The effect of lot drug substance activity (potency), accounted for as a direct unit conversion of the administered dose, scales asfotase alfa exposure as a direct factor of dose, and therefore, is a direct factor of $C_{avg,ss}$.

Evaluation of exploratory covariates for purposes of hypothesis generation suggests that renal function (as measured by estimated glomerular filtration rate (eGFR)) and liver enzymes index, i.e., serum alanine transaminase in U/L (ALT) and serum aspartate transaminase in U/L (AST), are not associated with asfotase alfa clearance (CL). The results point to a possible association of Asian race in asfotase alfa disposition. However, the availability of limited data from subjects of Asian race amongst other issues suggests caution in interpreting the effect of Asian race.

Clinically relevant exposure-response relationships were identified and quantified using nonlinear mixed effects models for repeated-measures data for the biomarker and efficacy endpoints (PPi, PLP, RSS-wrist, RSS-knee, RGI-C, BOT-2, and 6MWT).

These exposure-response relationships were used to quantify clinically meaningful changes in response as function of a range of unstudied dosing regimens. The dose regimens showed normalization of TNSALP substrates from elevated levels prior to treatment, clinically meaningful improvement in bone mineralization, and substantial improvement in skeletal morphology and musculoskeletal function.

Given 3 adverse event (AE) endpoints (ectopic calcification, injection/infusion associated reactions, and injection site reactions) and 897 total events, no exposure-response relationships were identified for AE endpoints. Thus, the fact that there is no apparent relationship between PK and any safety variables of interest suggests that a dose of about 6 mg/kg/week or greater will provide the maximal benefit with minimal risk in HPP patients.

No population exposure-response trend was observed for osteoid thickness, possibly due to the paucity of data for this endpoint.

The dose/regimen/response relationship supported the selection of 6 mg/kg per week, which was the predominant dose used in initial clinical trials.

Given a dose of 6 mg/kg per week, the impact of dosing regimen (six times of dosing (1 mg/kg) per week vs. three times of dosing (2 mg/kg) per week) was shown to have no clinically meaningful impact when explored by model-based simulation:

Some expected differences in PK peak to trough fluctuation were observed, but average PK exposure was unaffected by regimen;

PD and efficacy responses at steady state were comparable between regimens.

Differences in exposure as a function of weight were identified, with exposures generally decreasing with decreased body size at the same mg/kg dose. Those lower exposures were still associated with strong clinical efficacy (survival data) and near maximal biomarker response.

Figure 13:
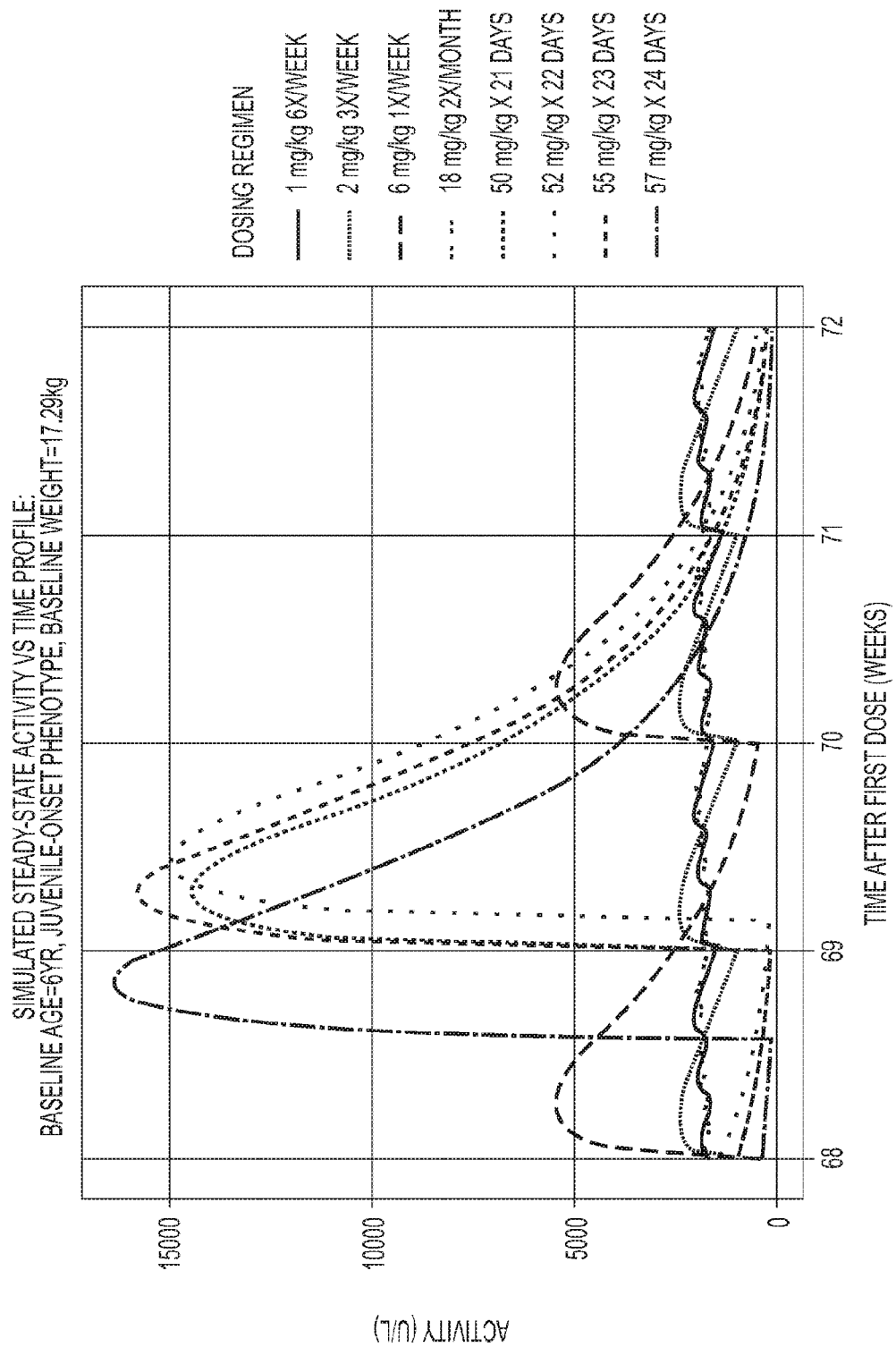
FIG. 13 depicts simulated steady-state activity vs. Time profile.
Figure 14:
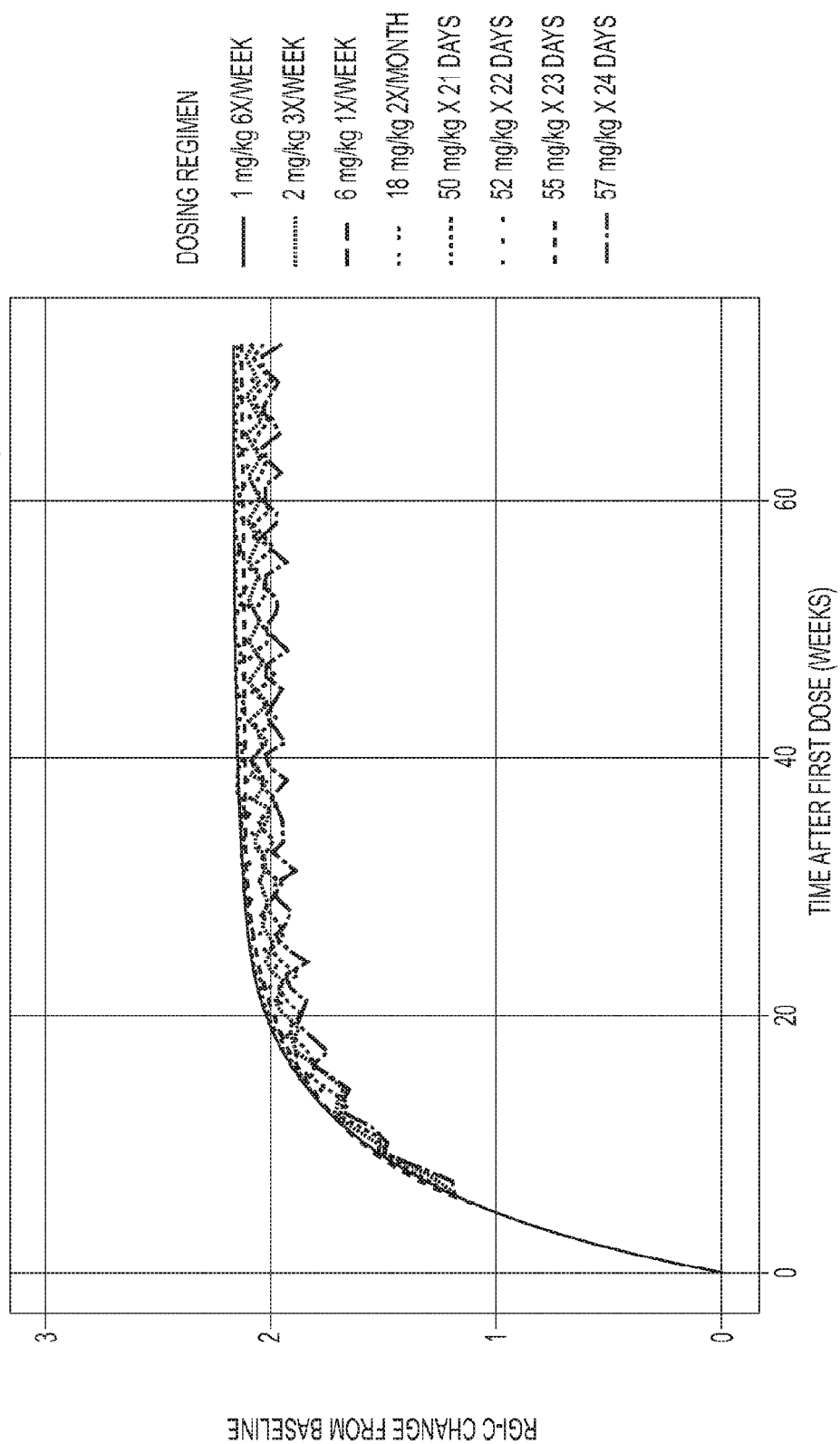
FIG. 14 depicts simulated change from baseline RGI-C vs. Time profile.
Figure 15:
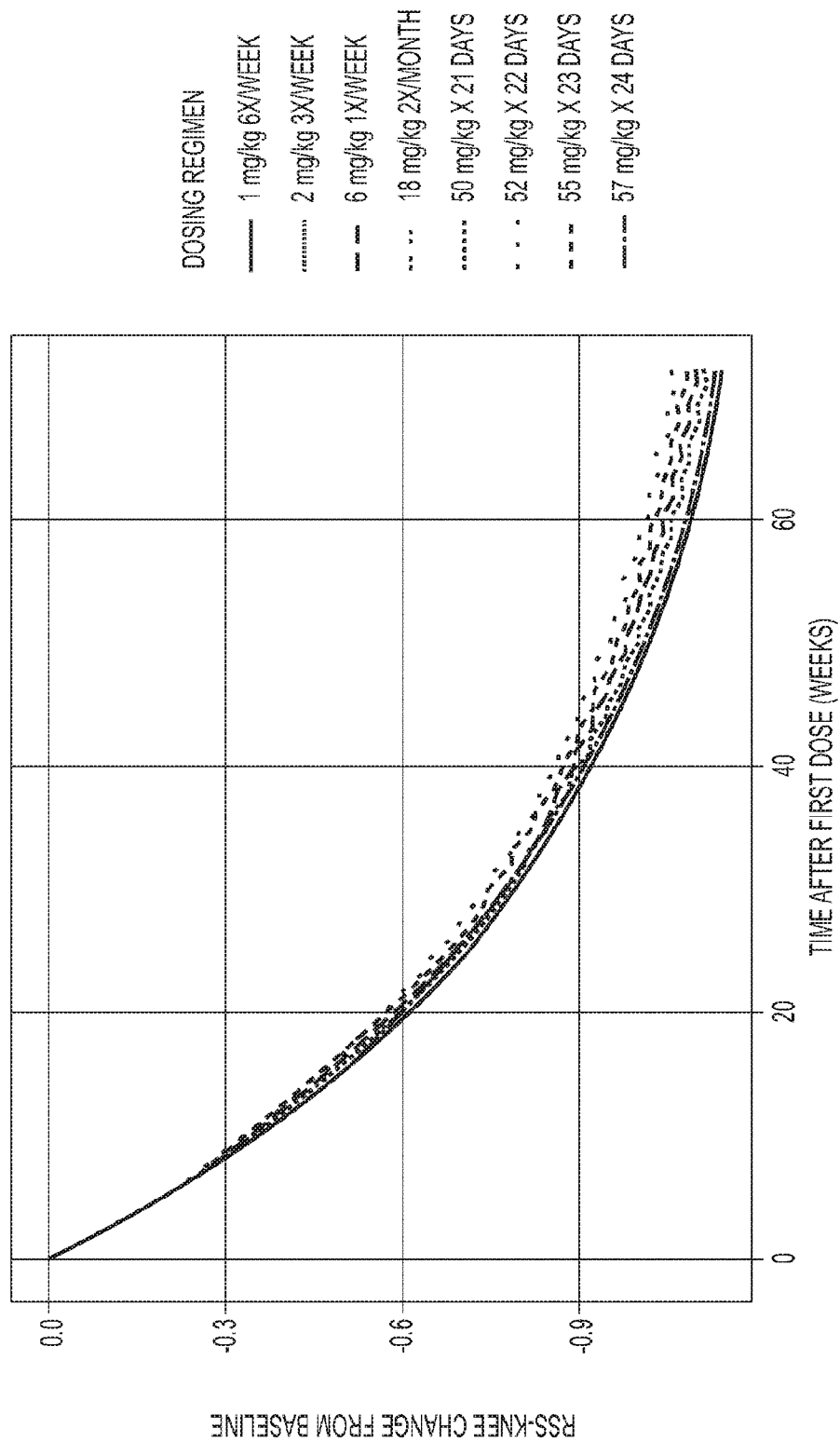
FIG. 15 depicts simulated RSS-knee change from baseline vs. Time profile.
Figure 16:
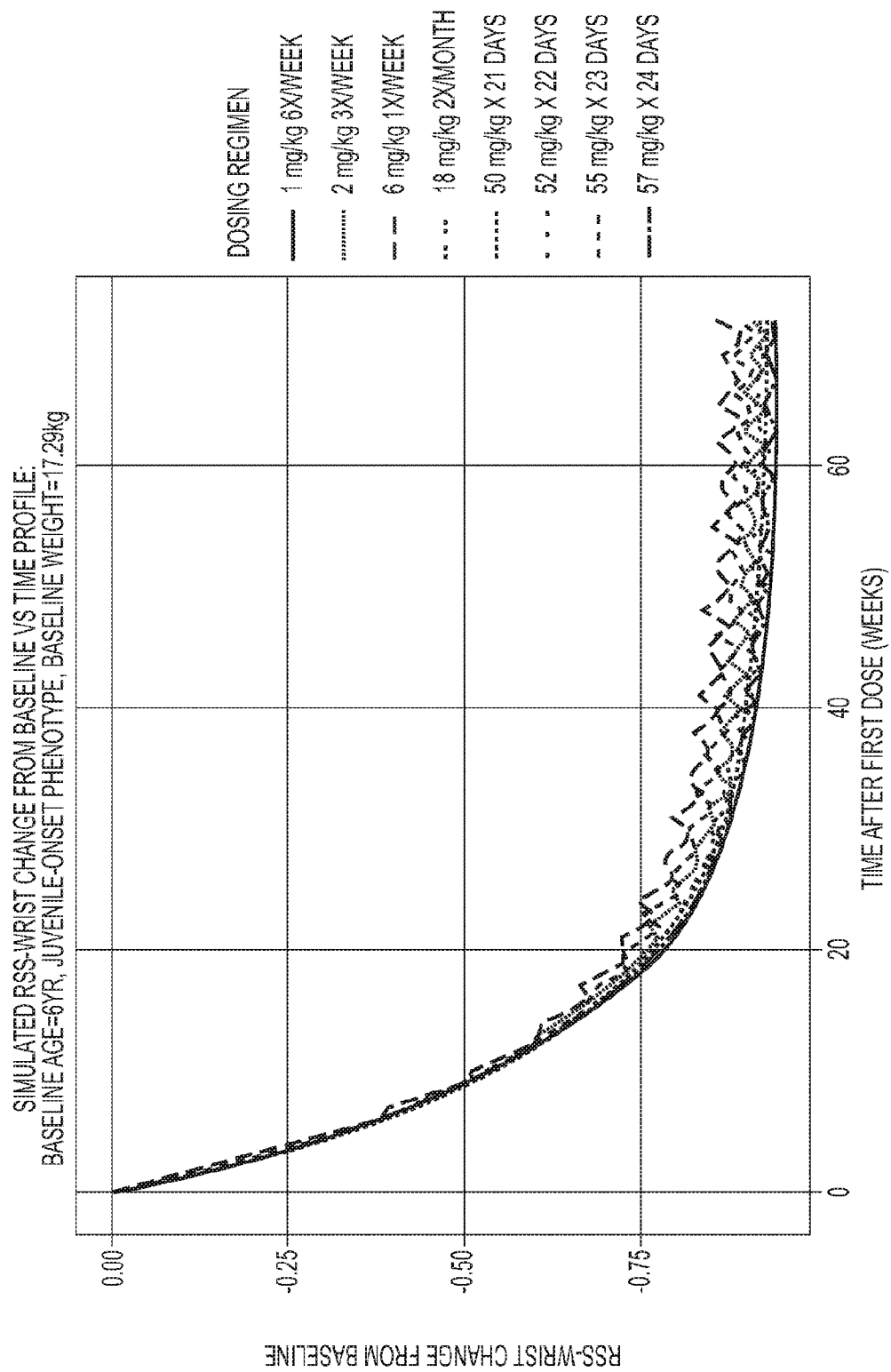
FIG. 16 depicts simulated RSS-wrist change from baseline vs. Time profile.
Figure 17:
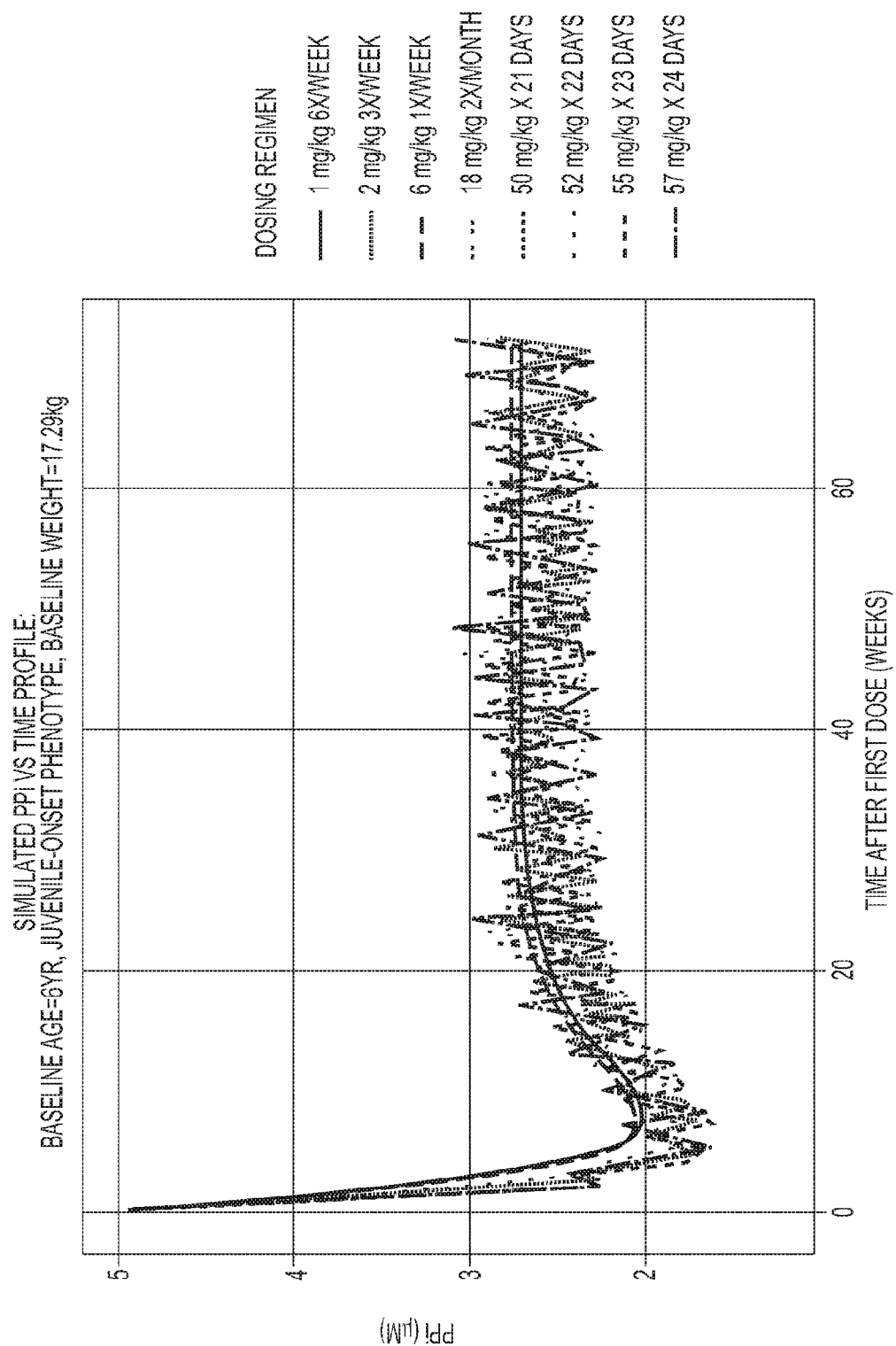
FIG. 17 depicts simulated PPi concentration vs. Time profile.
Figure 18:
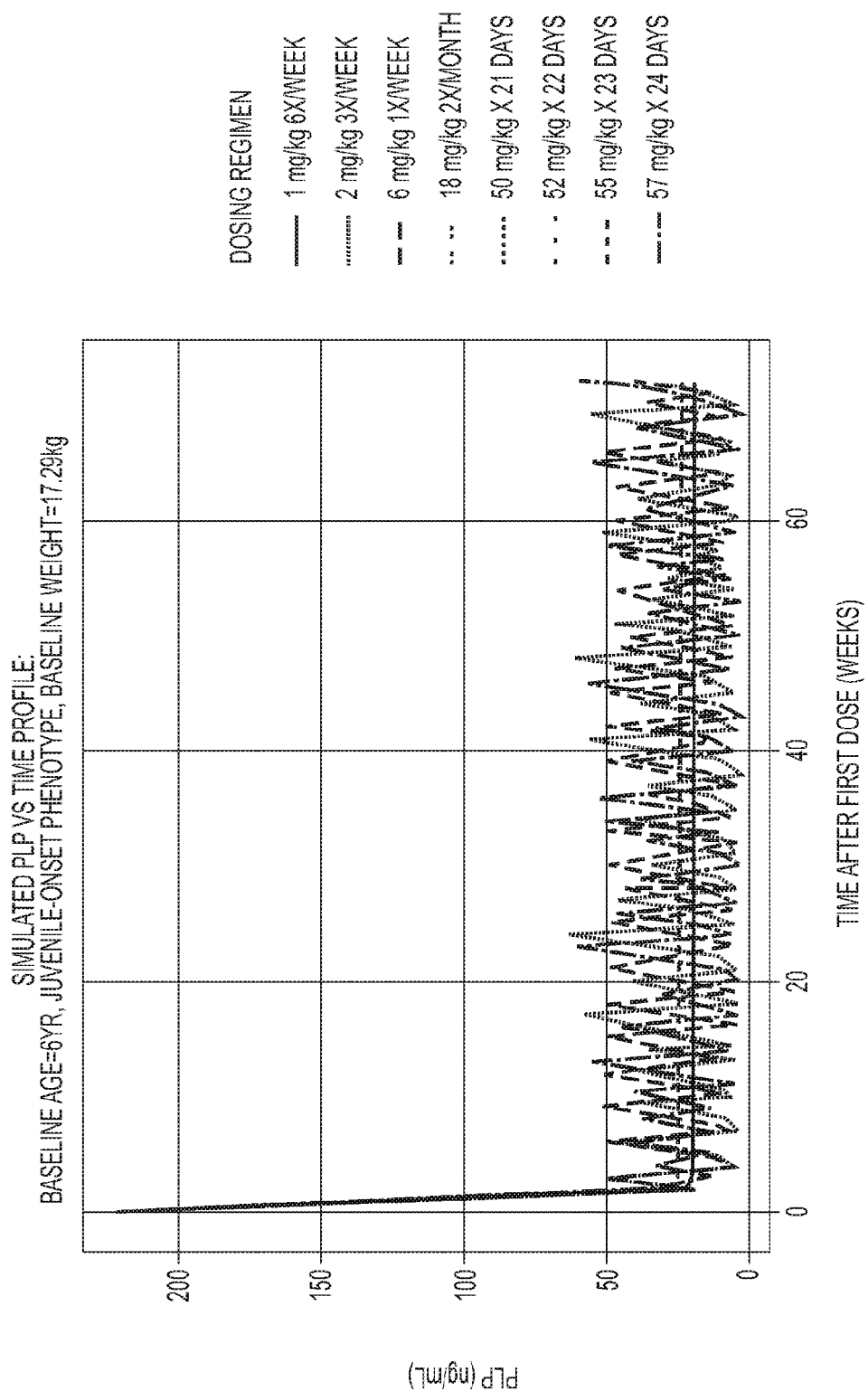
FIG. 18 depicts simulated PLP concentration vs. Time profile.
Figure 19:
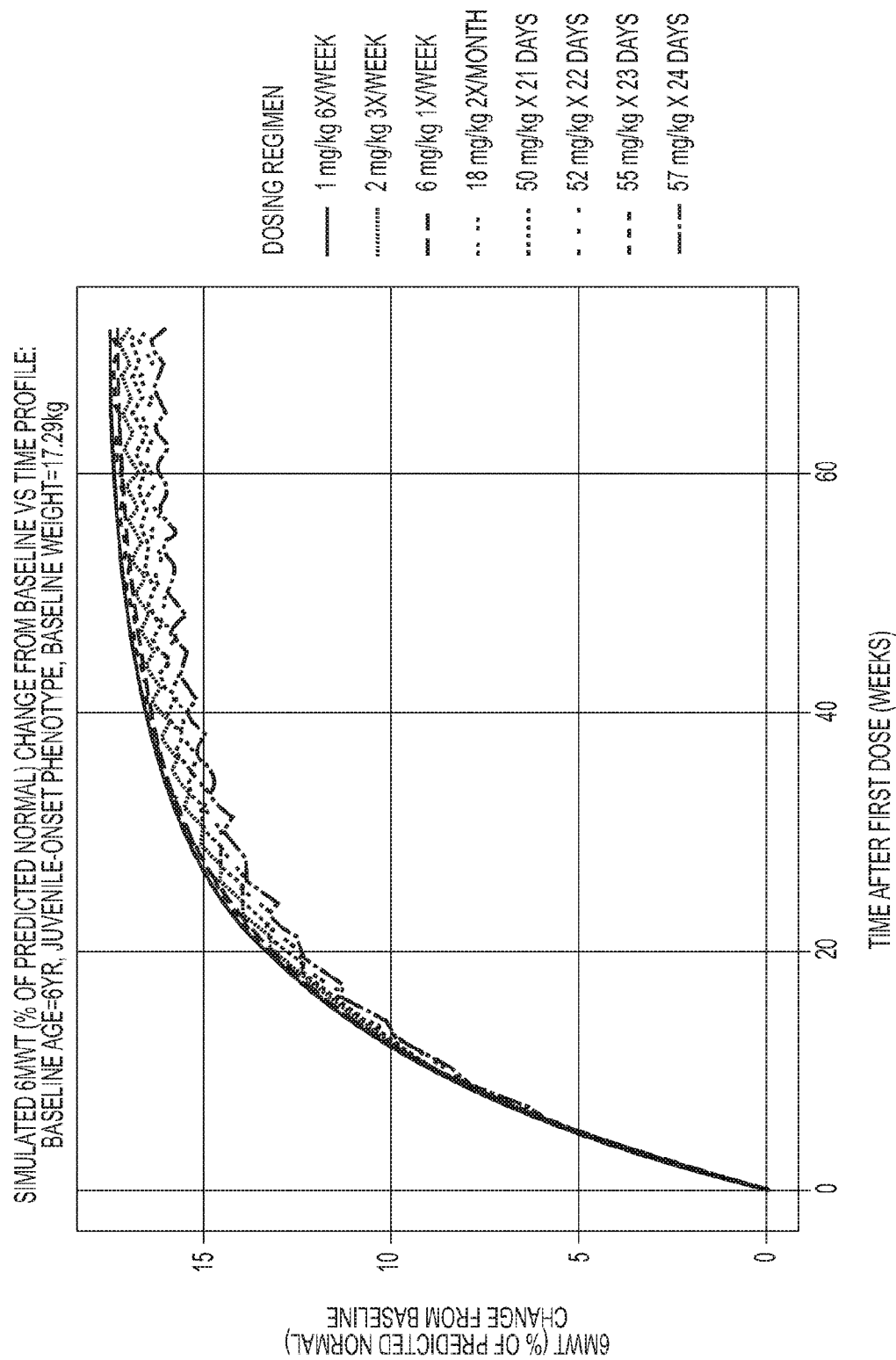
FIG. 19 depicts simulated 6MWT (% of predicted normal) change from baseline vs. Time profile.
Figure 20:
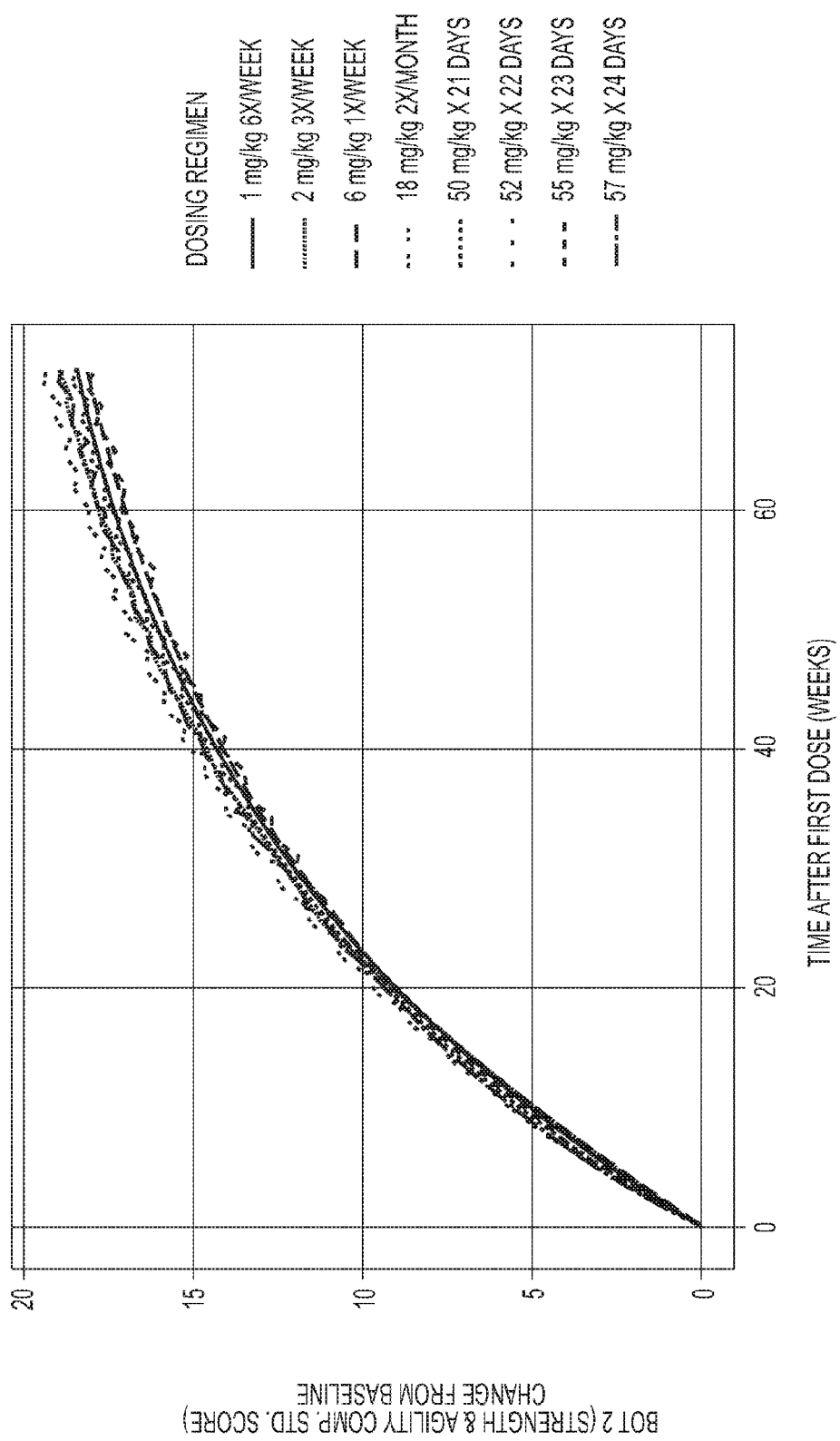
FIG. 20 depicts simulated BOT2 (strength & agility comp. std. score) change from baseline vs. Time profile.
Figure 21:
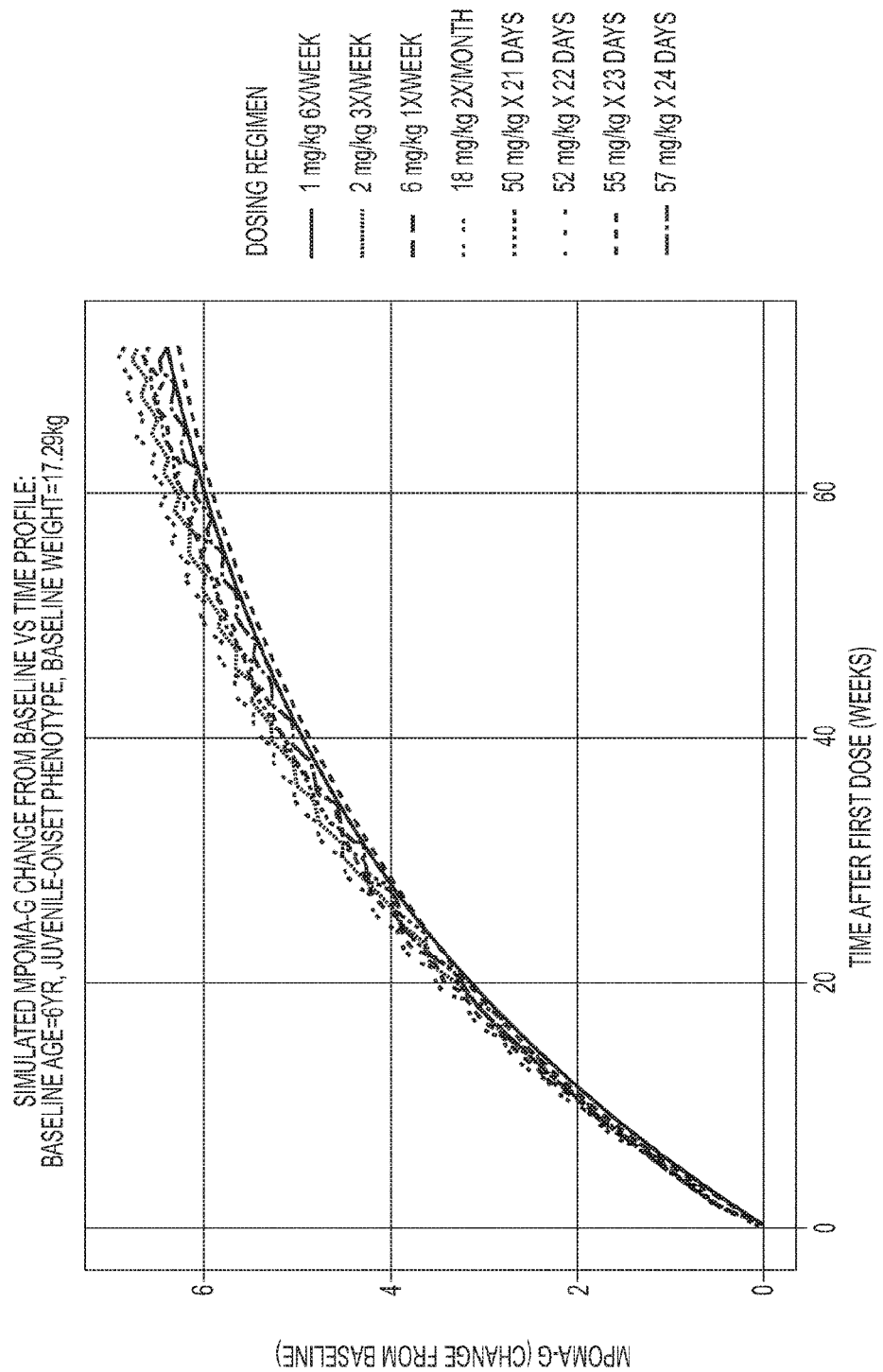
FIG. 21 depicts simulated MPOMA-G change from baseline vs. Time profile.

FIG. 13 depicts asfotase alfa activity and responses over time for different dose regimens in HPP patients. This evidence shows that dosing up to once every 24 days will provide efficacious benefit. Dosing less frequently than once-every 24 days requires increasing doses to a level beyond the no-observed-adverse-event-level (NOAEL). These results support the claim that asfotase alfa is safe and efficacious for enzyme supplement therapy in HPP patients regardless of patient genotype or phenotype over a range of dosing regimens from once a day to once every 24 days. It was discovered that TNSALP-ERT is safe and efficacious in HPP patients regardless of genotype or phenotype over a range of dosing regimens from once a day to once every-other-week. The following asfotase alfa dosing regimens are suggested: drug administered as once a week, as once a day, as twice a week, as three times a week, as four times a week, as five times a week, as six times a week, as once every other week, as once every eight days, as once every nine days, as once every ten days, as once every eleven days, as once every twelve days, as once every thirteen days, as once every three weeks, as once every fifteen days, as once every sixteen days, as once every seventeen days, as once every eighteen days, as once every nineteen days, as once every twenty days, as once every twenty two days, as once every twenty three days, and as once every twenty four days.

FIGS. 14-21 further depict the similar therapeutic effect for different dosing regimens, in view of multiple biomarkers and endpoints as discussed herein.

Example 2. Use of Asfotase Alfa in Patients with Hypophosphatasia

Asfotase alfa is a human recombinant tissue-nonspecific alkaline phosphatase-Fc-deca-aspartate fusion protein. It is a soluble glycoprotein of 1452 amino acids made from the catalytic domain of human tissue-nonspecific alkaline phosphatase, the human immunoglobulin G1 Fc domain and a deca-aspartate peptide domain.

Asfotase alfa is administered to patients with hypophosphatasia to cleave inorganic pyrophosphate, to release inorganic phosphate to form hydroxyapatite crystals that mineralize bone and so restore skeletal integrity. Enzyme activity also permits pyridoxal to enter cells to act as a cofactor for many enzymatic reactions.

The product is presented as a sterile aqueous solution for injection, at two strengths: 100 mg/mL in a single presentation (80 mg in 0.8 mL) and 40 mg/mL in four presentations (12 mg in 0.3 mL, 18 mg in 0.45 mL, 28 mg in 0.7 mL and 40 mg in 1 mL) in single use Type I glass vials, for subcutaneous administration. The vials are stoppered with siliconized rubber stoppers and sealed with aluminum seals with polypropylene flip-off caps.

Example 3. Non-Clinical Aspects

Pharmacology
Primary Pharmacodynamic Studies

In vitro, asfotase alfa was shown to have a 32-fold greater affinity to purified hydroxyapatite than kidney TNSALP lacking the deca-aspartate peptide.

Following 5 days of ascorbic acid and β-GP-induced extracellular matrix deposition and mineralization, MC3T3-E1 cell cultures were exposed to various treatments of PPi (±5 µM) in the presence or absence of asfotase alfa (132 U/L) for one week. In MC3T3-E1 cell cultures, asfotase alfa abolished the PPi-induced reduction of calcium concentrations. None of the treatments affected collagen matrix deposition.

In vivo, preclinical efficacy studies with asfotase alfa were conducted in a murine knockout model (designated Akp2$^{-/-}$) of human HPP. The Akp2$^{-/-}$ mice were characterized by a number of features including endogenous accumulation of the alkaline phosphatase (ALP) substrates PPi and pyridoxal-5' phosphate (PLP) in the plasma, excess of unmineralized bone matrix and impaired growth. They also exhibit a mineralization deficit at the Achilles tendon enthesis, and abnormalities in skull development and morphology. Episodes of apnoea and epileptic seizures were also evident and reportedly contributed to early death. The clinical features of the Akp2$^{-/-}$ mouse were similar to those of the infantile form of human HPP. The Akp2$^{-/-}$ mouse was therefore reported to be a relevant model to evaluate asfotase alfa for the treatment of HPP. It was indeed demonstrated that TNSALP enzyme replacement starting in neonates rescues all craniofacial skeletal abnormalities seen in Alpl$^{-/-}$ mice. Micro-CT, histologic and digital caliper based analyses show that the skulls of treated P15 Alpl−/− mice (n=44) are significantly different than those of untreated Alpl$^{-/-}$ mice (n=44), but not significantly different than those of wild type mice (n=45). These findings suggest that post-natal TNSALP enzyme replacement therapy is efficacious for preventing HPP-associated craniofacial skeletal abnormalities when initiated shortly after birth in mice.

In Akp2$^{-/-}$ mice, subcutaneous (SC) prophylactic treatment with asfotase alfa at doses of 0.5 to 8.2 mg/kg/day (corresponding to 303 to 8241 Units of alkaline phosphatase activity/kg/day) prevents hindpaw bone mineralization-associated defects in a dose-dependent manner. In vehicle-treated Akp2$^{-/-}$ mice, the median survival time was reported to be 19.5 days. Prophylactic treatment of Akp2$^{-/-}$ mice with asfotase alfa significantly increased survival at all doses tested. A dose-response relationship was observed between the normalized daily dose of asfotase alfa (0.5 to 8.2 mg/kg/day) and survival.

Prophylactic treatment of Akp2$^{-/-}$ mice also demonstrated that asfotase alfa prevented accumulation of PPi and PLP in plasma, reduced enthesis mineralization defects and reversed suppression of weight gain and bone growth. The lengths of the left tibiae and femurs from Akp2$^{-/-}$ mice treated with 8.2 mg/kg/day asfotase alfa for 43 days were similar to WT in one study but shorter than WT (by up to 6%) in another study. The differences in bone length observed between the two studies may represent a more sensitive parameter for efficacy evaluation at higher doses. Cessation of dosing reversed the effects of asfotase alfa prophylactic treatment on weight gain and survival, suggesting that continuous therapy with asfotase alfa was required for sustained benefit. Concerning the effects of asfotase alfa on PLP levels, a study was conducted using a certified commercial laboratory rodent diet with no vitamin B6 supplementation. By this way PLP (the primary vitamin B6 coenzymic form) measurements would not be affected by dietary intake. The evaluation was carried out as a pilot to a planned study ALP-PT-26, which confirmed the previously results. It has been shown that continuous treatment of Akp2$^{-/-}$ mice with asfotase alfa for the full duration of the study (47 days) partially improved the reduced grip strength in the forelimbs, completely prevented the increase in both plasma PLP and liver glycogen levels, partially reversed the decreased bone length, and completely reversed the suppression of weight gain, in comparison to the 35-day asfotase alfa administration followed by 12 days vehicle injection.

In therapeutic preclinical studies, treatment with asfotase alfa was initiated 12 or 15 days after birth, a time point at which significant mineralization-associated defects are observed in Akp2$^{-/-}$ mice. Treatment of Akp2$^{-/-}$ mice with asfotase alfa reduced mineralization defects of bones and reversed suppression of body weight gain. Therapeutic treatment with asfotase alfa significantly increased survival in the Akp2$^{-/-}$ mouse using various doses and SC dosing regimen. The daily dosing regimen was generally the most efficacious. These therapeutic effects were similar to those observed following prophylactic treatment.

Safety Pharmacology Program

In a study in Akp2$^{-/-}$ mice administered either 1 or 4 SC doses of asfotase alfa at 8.2 mg/kg/day beginning on day 12, there was no induction of hypocalcaemia or hypophosphatemia.

The bolus intravenous (IV) administration of 180 mg/kg asfotase alfa produced acute reactions in rats. The administration of asfotase alfa by slow IV infusion or pre-treatments of diphenhydramine or dexamethasone SC reduced the reactions but did not completely alleviate the acute response. There was no evidence detected of a complement-based etiology.

A single IV injection of asfotase alfa at dose levels of 30 and 88 mg/kg produced immediate but transient and reversible effects (abnormal gait and reduced mobility, reduced extensor thrust reflex, altered landing foot splay and lower grip strength) on the general behavior of male rats. Paw swelling and redness, decreased body temperature, and irregular/labored breathing were also seen in the 30 and 88 mg/kg dose groups. An IV dose of asfotase alfa at 3 mg/kg did not result in any measurable behavioral effects.

In a respiratory study in rats, asfotase alfa induced dose-dependent depressive effects on respiratory function. These effects were most notable during the first 2 hours after dosing. These effects coincided with the transient, acute infusion reactions observed in other rat IV toxicity studies and were not observed in rats administered asfotase alfa by SC administration.

No significant effects on ECG were seen in juvenile monkeys administered SC doses of up to 10 mg/kg/day asfotase alfa for 6 months.

Pharmacokinetics

The pharmacokinetic parameters of asfotase alfa have been studied in mice, rats, rabbits, and monkeys.

Absorption:

Following a single IV administration, clearance (CL) of asfotase alfa ranged from 0.00504-0.0540 L/h/kg in mice, rats, rabbits and monkeys with apparent terminal t½ raging from ~30-40 hours. Vdss observed in these species suggest distribution of asfotase alfa into peripheral tissues. Linear kinetics, with an approximately constant CL over a dose range of 5-180 mg/kg, was observed in adult monkeys, while kinetic linearity was not assessed in mice, rats and rabbits because only one dose level was evaluated in the single dose PK studies.

Following repeated IV or SC administration of asfotase alfa for either 4 weeks or 26 weeks, AUC and/or $C_{max}$ values increased either proportionately (suggesting linear kinetics) or disproportionately (higher or lower, suggesting nonlinear kinetics) with increasing dose across the studies. Multiple factors, such as study design, drug lot, immunogenicity profile and/or age of animal may have affected the dose proportionality assessment, particularly between studies. Based on the estimated half-life values, the extent of drug accumulation in juvenile rats and monkeys were dependent on dosing frequency. At a weekly dosing schedule, no drug accumulation was observed. With a daily dosing regimen, drug accumulation was apparent. Sex differences in TK parameters were not observed in juvenile rats or juvenile monkeys.

A study was conducted where pregnant (CD-1) and non-pregnant (C57BL/6) mice were administered daily SC doses of 0 (vehicle), 0.5, 2 or 8.2 mg/kg/day asfotase alfa for 5 days on gestation days 13-17 (ALP-PT-15). Asfotase alfa concentrations were reported to be higher in non-pregnant mice. However, this could be due to strain differences. After repeated SC administration to pregnant mice at a dose range of 0.5-8.2 mg/kg, asfotase alfa levels were quantifiable in fetuses at all doses tested, suggesting cross-placental transport of asfotase alfa.

As asfotase alfa contains human immunoglobulin G1 (IgG1) Fc domain, an immunogenic response in non-human animals was expected. Development of anti-drug antibody (ADA) was observed in 4 out of the 5 repeated dose studies. The incidence rate of ADA per time point per group was 0-100% in both rats and monkeys. The impact of ADA on systemic exposures in rats and monkeys varied from negligible to ~85% reduction in AUCs (relative to the corresponding group mean AUC values).

A toxicokinetic study of asfotase alfa was conducted in juvenile rats administered IV doses of 1, 3 or 13 mg/kg/day asfotase alfa for 26 weeks. Systemic exposures in Week 26 increased in a greater than dose proportional manner, suggesting non-linear kinetics. It was noted that drug lots of asfotase alfa with different TSAC levels (1.9 and 1.0) were used at weeks 1 to 19 and 20 to 26. Although some drug lots were expected to show a higher drug exposure, the reported exposure for week-26 was expected to be conservative compared to the exposures attained in the earlier phase of the study, i.e. week 1 through week 19.

In a local tolerance study using male juvenile rats administered SC doses of 0, 0.84, 8.4 or 25.2 mg/kg/day asfotase alpha, ADA was detected in the blood samples from all dose groups including control animals.

In an embryo-fetal development study in pregnant rats administered daily IV doses of asfotase alfa at 13, 25 or 50 mg/kg on gestation days 6-19, Cmax increased in a greater than dose proportional manner, suggesting non-linear kinetics. In contrast to other studies, drug accumulation was not observed. The reason for this remained unclear.

In a pre- and post-natal toxicology study of asfotase alfa in which pregnant rats were administered daily IV doses of asfotase alfa at 10, 25 or 50 mg/kg/day from gestation Days 6-19, the increase in systemic exposure was greater than dose proportional. The AUC values in this study were higher than those detected in pregnant rats of another study.

In an embryo-fetal development study in which pregnant rabbits were administered IV doses of asfotase alfa (with a TSAC of 2.7) at 10, 25 or 50 mg/kg/day from postcoitum days 7-19, systemic exposure increased in an equal to or greater than dose proportional manner. The AUC values in this study were higher than those detected in pregnant rabbits of a dose-range study. There was high inter-animal variability in serum concentrations of asfotase alfa and this was attributed to the possible development of ADAs. In pregnant rabbits administered IV doses of asfotase alfa at 10, 25 or 50 mg/kg/day, ADAs were detected in 70, 65 and 75% of animals, respectively.

In juvenile cynomolgus monkeys administered once weekly IV doses of 0, 5, 15 or 45 mg/kg/dose for 4 weeks, the increase in systemic exposure was equal to or greater than dose proportional. ADA was observed in all dose groups. However, the incidence was higher in the 45 mg/kg dose group.

In juvenile cynomolgus monkeys administered SC doses of 0.43, 2.14 or 10 mg/kg/day for 6 months, the increase in systemic exposure was equal to or slightly greater than dose proportional. Exposures were low in the 2.14 mg/kg/day dose group at Weeks 4 and 26 and the reason for this was unclear. Drug accumulation was seen at all doses. At Week 30, ADAs were detected in the 0.43 and 2.14 mg/kg/day dose groups (in 25 and 75% of animals tested, respectively) but not in the 10 mg/kg/day dose group.

Distribution:

Tissue distribution of asfotase alfa was characterized in juvenile mice administered a single IV dose of 5 mg/kg $^{125}$I-asfotase alfa and newborn mice that received repeated SC doses of 4.3 mg/kg $^{125}$I asfotase alfa for 14 days.

The distribution of $^{125}$I-asfotase alfa to long bones was observed. AUC and Cmc were higher in bone tissue, femur, than that in soft tissue, such as kidney, liver, lung and muscle. Radioactivity remained in the long bones for at least 64 hours without a noticeable decline over the 96-168 hours of study period, suggesting bone retention. The radioactivity in blood/serum was eliminated more rapidly than that in bone tissues.

In the distribution study the protracted presence of $^{125}$I-asfotase alfa in calvaria, tibia and femur might indicate accumulation, retention or slow clearance of the component from these tissues.

Other Pharmacokinetic Studies:

Neonatal Fc receptor (FcRn) binding affinity of asfotase alfa was reported to be similar to two other positive controls, abatacept and etanercept (Fc domain-containing fusion proteins). The correlation analysis between FcRn binding affinity and clinical half-life showed that clinical half-life of asfotase alfa was comparable to abatacept and etanercept, suggesting that the contribution of FcRn-mediated recycling to asfotase alfa clearance is similar to other Fc-fusion proteins.

Toxicology

A range of nonclinical studies was performed in support of the asfotase alfa development program. These studies include single- and repeated-dose toxicology studies, reproductive and developmental toxicity studies. Toxicokinetic evaluations were performed in most of the repeated-dose studies. Anti-drug antibody (ADA) assessments were also conducted. In addition, local tolerance was also evaluated as part of the repeated dose studies.

The juvenile Sprague Dawley rat and juvenile cynomolgus monkey were selected as the appropriate rodent and non-rodent species, respectively, to evaluate the nonclinical safety of asfotase alfa.

Single Dose Toxicity:

In a single dose study in juvenile cynomolgus monkeys, the IV administration of up to 180 mg/kg was considered to be well-tolerated. A marked dose-proportional increase in ALP activity was observed in all animals throughout the study due to the presence of circulating test article. Transient increases in serum ALT and AST activities were observed in three animals.

Repeated Dose Toxicity:

Weekly administration of asfotase alfa by the IV route to juvenile rats for 4 weeks at nominal doses of 0, 2.6, 26, 77 mg/kg was associated with a limited number of effects. The most consistent effect noted was a transient injection reaction (partially closed eyes, decreased muscle tone, lying on the side, hunched posture, cool to touch, uncoordinated movements, decreased activity, abnormal gait and/or blue, red and/or firm swollen hindpaws and/or forepaws) observed up to 60 minutes post dose. A reduction in the appendicular skeleton (femur and tibia) was also detected. However, no consistent effect on the axial skeleton and no effect in the crown to rump length was noted.

Increased levels of serum phosphorus and total serum calcium, and decreased C-telopeptide values were observed in juvenile rats administered 77 mg/kg/week for 4 weeks. There were no effects observed on bone architecture.

The daily IV injection of 1, 3 or 13 mg/kg/day of asfotase alfa to juvenile rat for 26 weeks was associated with transient clinical signs including red and sometimes swollen muzzles, fore- and hind-paws for up to 1 hour post-dose throughout the dosing period and most consistently in the 13 mg/kg/day group. No toxicologically meaningful changes were seen in most of the parameters assessed during the study.

The increased serum ALP activities observed were attributed to circulating levels of asfotase alfa. Based on observations of transient clinical signs during the treatment period, which were completely reversible and did not result in any effect on the parameters used to assess toxicity at dose levels of 1, 3 or 13 mg/kg/day, the no-observed-adverse-effect level (NOAEL) was considered to be 13 mg/kg/day.

A study was conducted to investigate the effects of asfotase alfa administered once weekly by slow IV injection to juvenile cynomolgus monkeys for 4 weeks followed by a 28-day recovery period. The only affect seen was a dose-related increase in ALP activity. This is believed to be caused by the presence of circulating recombinant ALP test article in the animals after each dose administration. The levels of ALP were generally similar to control values by the end of the recovery period. No effect on bone development was observed. No other toxicologically significant effects were reported.

Based on the results of this study, weekly IV injection of asfotase alfa to male and female cynomolgus monkeys for 4 weeks, at dose levels of 0, 5, 15 and 45 mg/kg, and followed by a 4-week recovery period, did not lead to toxicity at any dose level. Therefore, the high dose level tested, 45 mg/kg/week, was considered to be the NOAEL.

Increased serum alkaline phosphatase activity levels were attributed to circulating levels of asfotase alfa. There were trends for increased bone mass (at the tibia metaphysis and/or lumbar spine) and cortical thickness (at the tibia diaphysis) but no clear treatment-related effects. There was no indication that bone growth was slowed or in any way adversely affected by treatment, or any evidence of ectopic calcification in any tissue. The calvarium was examined from two sites containing the coronal and lambdoidal sutures. There were no abnormalities (e.g. premature suture closure) noted for the age of juvenile monkey used. Focal granulomatous inflammation with mineralization (ectopic calcification) and mononuclear cell infiltration of the injection site was observed in animals from all treated groups and was partially to completely reversed, following 4-weeks of recovery. Focal minimal persistent inflammation remained in some injection sites from the high dose group. The clinical signs at the injection sites (characterized as ectopic calcification or mineralization) during the treatment period were from partially to completely reversible and the injection was well tolerated. Thus, the NOAEL level was considered to be 10 mg/kg/day.

Although the rats (21 days) and monkeys (1 year) used in studies 670314 (rats) and 670388 (monkeys) cover the pediatric population aged >0.1 month to approximately 24 months, the animals used of both species had not reached the age at which the fusion of 2° ossification centers was complete (15-162 weeks in the rat and 3-6 years in the monkeys) (Zoetis 2003 *Birth Defects Res B Dev Reprod Toxicol.* 68:86-110).

The relevance of ossification center fusion in those animals to pediatric patients aged 2-18 was taken into consideration in the 26 week study in rats (670315), although the ossification was not examined in the two repeat dose monkey studies.

Toxicokinetics:

The toxicokinetics of asfotase alfa have been investigated in a series of repeated dose IV and SC toxicity studies of up to 26 weeks duration in the rat, rabbit, and monkey. Following repeated IV or SC administration of asfotase alfa for either 4 weeks or 26 weeks, AUC and/or Cmax values increased either proportionately (suggesting linear kinetics) or disproportionately (higher or lower, suggesting nonlinear kinetics) with increasing dose across the studies. Multiple factors, such as study design, drug lot, immunogenicity profile and/or age of animal may have affected the dose proportionality assessment, particularly between studies. Based on the estimated half-life values, the extent of drug accumulation in juvenile rats and monkeys were dependent on dosing frequency. At a weekly dosing schedule, no drug accumulation was observed. With a daily dosing regimen, drug accumulation was apparent. Sex differences in TK parameters were not observed in juvenile rats or juvenile monkeys.

For safety margin estimations, no extrapolation was used during AUC calculations since observed data were employed. Also, it was specified that safety margin calculations were appropriately conducted on the basis of both exposure and enzymatic activity data at 26 weeks. The impact of ADA on the non-clinical asfotase alfa PK may not be made. However, ADA impact on asfotase alfa clearance at the D150 step of the procedure was tested, using the accumulation factor (AF) as an appropriate monitoring approach in relation to the drug half-life, where the AF is calculated as a ratio of AUC at the end of treatment (where ADA has been developed) to the AUC at the beginning of treatment (where the ADA is presumably close to zero).

Reproductive and Developmental Toxicity:

In a fertility and early embryonic development study in rats, the administration of asfotase alfa at 10, 25 or 50 mg/kg/day by once daily IV injection was associated with acute injection reactions typical of those observed after previous studies utilizing IV administration of asfotase alfa in rats. Males administered 50 mg/kg/day had slightly decreased body weights. Fertility and early embryofoetal development at doses ≤50 mg/kg/day were not different compared to vehicle-treated rats. Based on these results, the NOAEL was considered to be 25 mg/kg/day for males and 50 mg/kg/day for females. The NOAEL for the fertility and early embryofoetal development was considered to be 50 mg/kg/day.

In an embryofoetal development study in rats, the administration of asfotase alfa once daily by IV injection at dose levels of 13, 25 or 50 mg/kg/day from gestation Day 6 to 19 was associated with transient clinical signs. These clinical signs were typical of those seen in rats after IV administration of asfotase alfa.

There was no evidence of ectopic calcification in any fetal samples examined. Based on these results, the maternal NOAEL was considered to be 13 mg/kg/day (AUC=167 and 104 at gestation days 6 and 19, respectively mg·h/L). There was no evidence of foetotoxicity, embryolethality or teratogenicity associated with asfotase alfa in this study, therefore the NOAEL for embryofoetal development was considered to be 50 mg/kg/day (AUC=1096 and 1146 mg·h/L at gestation days 6 and 19, respectively).

In an embryofoetal development study in pregnant New Zealand white female rabbits administered IV doses of 10, 25, or 50 mg/kg/day asfotase alfa from gestation Days 7 to 19, inclusive, there was no evidence of fetal toxicity, teratogenicity or embryolethality. Therefore, the NOAEL for embryofoetal development was considered to be 50 mg/kg/day. Renal tubular mineralization was detected in 2 pregnant animals administered 50 mg/kg/day. The maternal NOAEL was considered to be 25 mg/kg/day. As there was no evidence of fetal toxicity, teratogenicity, or embryolethality, the NOAEL for embryofoetal development was considered to be 50 mg/kg/day. Renal tubular mineralization was detected in 2 pregnant animals administered 50 mg/kg/day. The maternal NOAEL was considered to be 25 mg/kg/day (AUC=1978 and 1573 at gestation days 7 and 19 mg·h/L, respectively). In pregnant rabbits administered IV doses of asfotase alfa at 10, 25, or 50 mg/kg/day from gestation Days 7 to 19, anti-drug antibodies were detected in 70, 65 and 75% of animals, respectively. This could affect the detection of any embryofoetal toxicity.

A pre- and post-natal development study was conducted in female rats administered 10, 25, or 50 mg/kg/day asfotase alfa by IV injection from Day 6 of gestation to Day 21 postpartum. For the F0 generation dams, transient clinical signs typically observed following IV injections of asfotase alfa were noted in all treated groups within 4 hours of dosing. A low incidence of pup cannibalism was noted for F0 dams in the mid and high dose groups. It is uncertain whether the cannibalism was treatment-related and its clinical relevance unclear. For the F1 generation adult males at 50 mg/kg/day, there were slightly lower body weight and food consumption values noted during the post weaning period. For offspring (F1 and F2 generation) there were no effects on survival, physical development, behavior, or reproductive performance. There was no evidence of treatment-related ectopic calcification. Based on these results, the NOAEL for the F0, F1, and F2 generations was considered to be 50 mg/kg/day (AUC 1339 mg·h/L).

Local Tolerance:

In most studies, mild local irritation was noted after SC injection. However these findings were generally reversible. In a local tolerance study, the IV injection of asfotase alfa to juvenile rats once weekly for 28 days caused transient adverse clinical signs at ≥30 mg/kg that reversed within 24 hours. The SC injection of asfotase alfa in juvenile rats once daily for 4 weeks was generally well-tolerated. Treatment-related findings included focal minimal to mild perivascular/subcutaneous mononuclear cell infiltrate at the injection sites at doses of ≥0.84 mg/kg/day, and axillary lymph node enlargement, which correlated with axillary lymph node minimal lymphoid hyperplasia in animals administered ≥8.4 mg/kg/day.

Discussion on Non-Clinical Aspects

The non-clinical development program for asfotase alfa consisted of a range of pharmacodynamic, pharmacokinetic and toxicology studies, in which the activity of asfotase alfa was investigated in vitro and in vivo. Pharmacokinetic studies examined the absorption and distribution profile of asfotase alfa. In the single and repeated dose toxicity studies, asfotase alfa was given intravenously and subcutaneously (which is the same route of administration used clinically). A local tolerance study was also conducted with asfotase alfa.

Asfotase alfa demonstrated preclinical efficacy in both prophylactic and therapeutic paradigms in a murine gene knockout model of hypophosphatasia, the Akp2$^{-/-}$ mouse model. In the prophylactic studies, asfotase alfa prevented the accumulation of circulating inorganic pyrophosphate and pyridoxal-5' phosphate, reduced mineralization defects of bones, and had a beneficial effect on bone length and weight gain suppression. Survival time was also increased.

The positive effects of asfotase alfa on growth and survival were lost after dosing was discontinued, suggesting that continuous therapy with asfotase alfa is required for sustained benefit. Therapeutic treatment with asfotase alfa promoted bone mineralization, improved survival and reversed the weight gain suppression observed in Akp2$^{-/-}$ mice.

Safety pharmacology and toxicity studies were conducted in rats, rabbits and cynomolgus monkeys. Toxicokinetic and supportive ADA evaluations were conducted in several studies by measuring dose-proportional and transient IV infusion-associated reaction in rats. These reactions included depressed respiration, decreased motor activity, and swelling in the extremities. The injection response was not observed in monkeys (dosed either IV or SC), rabbits (dosed IV or SC). or in rats treated with equivalent SC doses. Injection site irritation was observed in the monkeys dosed by SC injection. These changes were mild and largely reversible. As these injection-related reactions were considered to be non-adverse and the NOAEL for each of the longer-term studies was generally considered to be the highest dose tested in each of the studies, the combined results from the toxicology studies provide some support to the clinical use of asfotase alfa.

Clinical Aspects
Pharmacokinetics
Absorption

Asfotase alfa bioavailability after SC dosing ranged from 62.9% to 98.4% after the first dose of 1 mg/kg and 54.2% to 71.3% after the first dose of 2 mg/kg. Dose proportionality and time dependencies After SC dosing, median $T_{max}$ was 24 to 48 hours with dose-proportional increases in mean $C_{max}$ and $AUC_{0-168\ h}$ between cohorts.

Within the limits of variability and the small patient number, $C_{max}$ was comparable after first and third SC doses for both cohorts, as was $AUC_{0-168\ h}$ for Cohort 2. $AUC_{0-168\ h}$ could be estimated at Week 4 only for 1 patient in Cohort 1.

Mean half-life (t½) after SC dosing was relatively consistent between cohorts and between Weeks 2 and 4. Individual patient values ranged from 111 to 166 hours. The longer t½ after SC dosing is most likely a consequence of slower absorption from the SC injection site.

Pharmacokinetic Studies

Pharmacokinetics of asfotase alfa were evaluated in a 1-month, multi-center, open-label, dose-escalating study in adults with hypophosphatasia.

Cohort 1 (n=3) of the study received asfotase alfa 3 mg/kg intravenously (IV) the first week followed by 3 doses at 1 mg/kg subcutaneous (SC) at weekly intervals from weeks 2 to 4.

Cohort 2 (n=3) received asfotase alfa 3 mg/kg IV the first week followed by 3 doses at 2 mg/kg subcutaneous at weekly intervals from weeks 2 to 4.

After the 3 mg/kg for 1.08 hours intravenous infusion, the median time (Tmax) ranged between 1.25 to 1.50 hours, and the mean Cmax (with SD) ranged between 42694 (8443) and 46890 (6635) U/L over the studied cohorts.

The absolute bioavailability after the first and third subcutaneous administration ranged from 45.8 to 98.4%, with median Tmax ranging between 24.2 to 48.1 hours.

After the 1 mg/kg weekly subcutaneous administration in Cohort 1 the mean AUC (with SD) over the dosing interval (AUC') was 66034 (19241) and 40444 (N=1) U*h/L following the first and the third dose, respectively.

After the 2 mg/kg weekly subcutaneous administration in Cohort 2 the mean AUCτ (with SD) was 138595 (6958) and 136109 (41875) following the first and the third dose, respectively.

Population Pharmacokinetics

Pharmacokinetic data from all asfotase alfa clinical trials were analyzed using population PK methods. The pharmacokinetic variables characterized by population PK analysis represent the overall hypophosphatasia patient population with age range from 1 day to 66 years and subcutaneous doses of up to 28 mg/kg/week.

Based on the results of population pharmacokinetic analysis it was concluded that asfotase alfa exhibits linear pharmacokinetics up to subcutaneous doses of 28 mg/kg/week.

The model identified body weight to affect asfotase alfa clearance and volume of distribution parameters. It is expected that PK exposures will increase with body weight.

The impact of immunogenicity on asfotase alfa PK overall was estimated to decrease PK exposures by less than 20%.

Pharmacodynamics
Primary and Secondary Pharmacology
Pharmacodynamics were evaluated in the following clinical studies:
Study #4/#5

Study #4/#5 was an open-label, non-randomized study. Thirteen patients were enrolled and 12 patients are on-going in the study. Five patients presented with hypophosphatasia at under 6 months age and 8 patients presented between 6 months and 18 yrs of age. Age at inclusion in the study was between 5 and 12 years old. The study employed historical controls from the same center as patients who received asfotase alfa and who had been subject to a similar protocol of clinical management.

The effects of asfotase alfa on x-ray appearance

Trained radiologists evaluated pre- and post-baseline x-rays of wrists and knees of patients for the following signs: apparent physeal widening, metaphyseal flaring, irregularity of provisional zone of calcification, metaphyseal radiolucencies, metadiaphyseal sclerosis, osteopenia, "popcorn" calcification in metadiaphysis, demineralization of distal metaphysis, transverse subphyseal band of lucency and tongues of radiolucency. X-ray changes from baseline were then rated using the Radiographic Global Impression of Change rating scale as follows: −3=severe worsening, −2=moderate worsening, −1=minimal worsening, 0=no change, +1=minimal healing, +2=substantial healing, +3=near-complete or complete healing. Patients who received asfotase alfa moved to scores of +2 and +3 over the first 6 months of exposure and this was sustained with on-going treatment. Historical controls did not show change over time.

Bone Biopsy

Tetracycline for bone-labelling was administered in two 3-day courses (separated by a 14-day interval) prior to acquisition of the bone biopsy. Trans-iliac crest bone biopsies were obtained by standard procedure. Histological analysis of biopsies used Osteomeasure software (Osteometrics, USA). Nomenclature, symbols, and units followed recommendations of the American Society for Bone and Mineral Research. For 10 patients in the per-protocol set (excludes those patients who received oral vitamin D between baseline and week 24) who underwent biopsy of the trans-iliac bone crest before and after receiving asfotase alfa:

Mean (SD) osteoid thickness was 12.8(3.5)μm at baseline and 9.5(5.1) μm at week 24

Mean (SD) osteoid volume/bone volume was 11.8(5.9)% at baseline and 8.6(7.2)% at week 24

Mean (SD) mineralization lag-time was 93 (70) days at baseline and 119 (225) days at week 24.

The effects of asfotase alfa on x-ray appearance

7/11 patients in the full analysis set achieved Radiographic Global Impression of Change scores of +2 at Week 24 compared to baseline radiographs.

Growth

5/11 subjects displayed apparent catch-up height-gain. Fluctuation in height-gain was apparent and may reflect the more severe disease and higher rate of morbidity in these younger patients.

Study #6

Study #6 was an open-label, randomized study. 19 patients were enrolled and 18 patients are on-going in the study. Onset of hypophosphatasia was under 6 months in 16 patients, between 6 months and 18 yrs in 4 patients and over 18 yrs in 2 patients. Age of onset was not known for 1 patient. Age at inclusion was from 13 to 66 yrs.

Growth

The adolescent (and adult) patients in this study did not display apparent height-gain.

Bone Biopsy

Patients underwent biopsy of the trans-iliac bone crest either as part of a control group or before and after exposure to asfotase alfa:

|  | Control group 5 evaluable patients | | 0.3 mg/kg/day asfotase alfa group 4 evaluable patients | | 0.5 mg/kg/day asfotase alfa group 5 evaluable patients | |
| --- | --- | --- | --- | --- | --- | --- |
|  | baseline | Week 24 | baseline | Week 48 | baseline | Week 48 |
| Osteoid thickness mean (SD) | 13 μm (1.6) | 11.9 μm (7.6) | 7.6 μm (2.2) | 8.5 μm (4.1) | 7.1 μm (2.5) | 6.3 μm (2.0) |
| Osteoid volume per bone volume mean (SD) | 11.1% (5.0) | 11.6% (8.7) | 6.6% (3.7) | 8.9% (3.3) | 5.3% (2.0) | 3.2% (1.9) |
| Mineralization lag-time mean (SD) | 226 (248) days | 304 (211) days | 1236 (1468) days | 328 (200) days | 257 (146) days | 130 (142) days8 |

Growth

Height, weight and head circumference were plotted on growth charts (series of percentile curves that illustrate distribution) available from the Centers for Disease Control and Prevention, USA. These reference data were drawn from a representative sample of healthy children and are not specific for children with special health care needs: they have been used in the absence of growth charts for children with hypophosphatasia.

For those patients who received asfotase alfa: 9/13 patients displayed persistent apparent catch-up height-gain as shown by movement over time to a higher percentile on CDC growth charts. 3/13 patients did not display apparent catch-up height-gain and 1 patient did not have enough data to permit judgement. Progress through Tanner stages appeared appropriate.

For the time period of observation of historical controls: 1/16 patients displayed apparent catch-up height-gain, 12/16 patients did not display apparent catch-up height-gain and data were inconclusive in 3/16 patients.

Study #2/#3

Study #2/#3 was an open-label, non-randomized, non-controlled study. Eleven patients were enrolled and 9 patients are on-going in the study. Onset of hypophosphatasia was under 6 months in all patients. Age at inclusion in the study was between 0.5 to 35 months.

For the 9 evaluable patients who received asfotase alfa, mean (SD) mineralization lag-time was 692 (1041) days at baseline and 218 (189) days at week 48.

Modelling Exercise

Clinical pharmacology data (pharmacokinetic, pharmacodynamic and immunogenicity data) collected up to a time line were analyzed.

The final Pop-PK model analyzed the IV and SC data simultaneously producing a final pharmacokinetic model with first-order absorption following SC administration and a two-compartment disposition with elimination from the central compartment.

Dose proportionality was inferred up to the studied SC dose of 28.0 mg/kg/wk based on the Pop-PK model analysis.

Covariate Effects

The model was used to investigate effects of (i) formulation factors on bioavailability, (ii) demographics on clearance and volume of distribution and (iii) immunogenicity effects on clearance.

A model-based assessment of the impact of assay on estimated Pop-PK model parameters was made. The model shows minimum impact of assay in all cases.

Monte Carlo simulations using final Pop-PK model and variable estimates were conducted to evaluate the covariate effects on asfotase alfa PK. Simulations by varying parameters such as batch size, immunogenicity and body weight content were carried out. Covariates such as age, sex, renal function and liver function tests (AST and ALT) along with bioanalytical method for measuring PK of asfotase alfa as activity were not found to be significant.

Population-pharmacokinetic and pooled pharmacokinetic-pharmacodynamic analyses were conducted to characterize independent exposure vs. response relationships for change in biomarkers such as plasma pyridoxal phosphate and inorganic pyrophosphate, radiologic pharmacodynamic endpoints such as the Radiographic Global Impression of Change, Rickets Severity Scale and functional efficacy endpoints such as the Bruininks-Oserestsky Test of Motor Proficiency and the 6-minute walk test.

An evaluation of population exposure-response relationships for the adverse events of ectopic calcification, injection/infusion associated reactions and injection site reaction events during the entire treatment duration for all studies in the PK-PD analysis data set. 552 events occurred across the 3 endpoints.

Given the subject specific $C_{avg}$ over the entire study, rate of adverse event incidence (number of events/time) vs. quartiles of exposure were constructed. When viewed as a function of exposure quartiles, adverse event summaries revealed no dependence on exposure.

Justification of Product Specifications

One of the product specifications for the manufacture of asfotase alfa that impact the exposure-response relationship are specific activity (U/mg, drug potency).

Based on a covariate sensitivity analysis performed using the developed Pop-PK one parameter was identified as having an impact on exposure in hypophosphatasia patients. Since this parameter and specific activity differs from lot to lot within the set formulation specifications, a model based simulation analysis was conducted to assess the magnitude of pharmacokinetic exposure changes and its subsequent impact on efficacy as a result of formulation factors.

From the modelling exercise:
  The CMC specification for asfotase alfa should provide sufficient exposure at 6 mg/kg/week dose to see efficacy.
  The maximum exposure of ~4000 U/L predicted using the maximum specific activity values specified for asfotase alfa's CMC specification is well below the >5000 U/L exposure resulting from the NOAEL dose from the 26 week GLP toxicology study in monkeys.

Discussion on Clinical Pharmacology

The pharmacodynamic results suggest that exposure to asfotase alfa results in improvement of x-ray appearances of wrists and knees associated with a reduced mineralization time-lag on bone biopsy. Many patients display apparent catch-up height-gain.

Patients with long-standing hypophosphatasia have osteoarthritis superimposed on the underlying osteomalacia condition. The physes are "closed" and metaphyseal changes are absent or minimal. For these reasons, potentially the RGI-C score will be confounded in adults with hypophosphatasia, i.e., the RGI-C score may not be fully informative in the adult population. Interpretation of bone biopsy in an adult population with hypophosphatasia may be hampered by previous exposure to medications such as bisphosphonates and by co-existing morbidities that have been acquired during life and that affect bone histology. There may be large variability from one biopsy to the next in the same person. Change in bone architecture may take years to achieve, not weeks. Further, the natural history of bone histology in patients with hypophosphatasia has not been established (and may be different to those with vitamin D sensitive osteomalacia). Potentially, the more informative measurement in the adult population would be mineralization lag time, because the measurement is a dynamic measure of cellular activity and does not require conversion to a 3-dimensional unit (i.e. it is not needed to assume isotropy of the iliac bone crest).

Clinical Efficacy

The overall analysis set included a total of 71 patients who were treated with asfotase alfa (68 with pediatric-onset hypophosphatasia [48 with perinatal/infantile-onset hypophosphatasia, 20 with juvenile-onset hypophosphatasia], 2 with adult-onset, and 1 patient with an unknown form of hypophosphatasia).

Patients ranged from 1 day to 66 years of age at initiation of treatment. For integrated efficacy analyses by age of hypophosphatasia onset, the population included 44 patients with perinatal/infantile-onset hypophosphatasia and 8 patients with juvenile-onset hypophosphatasia.

Discussion on Clinical Efficacy

Design and Conduct of Clinical Studies

The rationale put forward for "phase 2" study design is that hypophosphatasia:
  is rare
  has high unmet medical need
  is associated with serious morbidity and mortality risk
  bears potential for irrevocable harm
  does not have any alternative treatments The prevalence of the less severe or moderate forms of hypophosphatasia is not established but has been estimated to be (about) 1/5000 in the European population (Mornet et al. 2011 *Ann Hum Genet.* 75:439-45). The prevalence is likely to be higher in the Mennonite community where all forms are known to be over-represented.

Efficacy Data and Additional Analyses

The studied patient population is representative of subjects with hypophosphatasia. The main clinical efficacy outcomes are (i) the Radiographic Clinical Impression of Change, a technique to assess change in x-ray appearance over time, (ii) growth as assessed by serial measurements of height, weight and head circumference and (iii) change over time in bone histology.

The Radiographic Clinical Impression of Change Tool

Trained radiologists evaluated pre- and post-baseline x-rays of wrists and knees of patients for the following signs: apparent physeal widening, metaphyseal flaring, irregularity of provisional zone of calcification, metaphyseal radiolucencies, metadiaphyseal sclerosis, osteopenia, "popcorn" calcification in metadiaphysis, demineralization of distal metaphysis, transverse subphyseal band of lucency and tongues of radiolucency. X-ray changes from baseline were then rated using the Radiographic Global Impression of Change (RGI-C) rating scale as follows: −3=severe worsening, −2=moderate worsening, −1=minimal worsening, 0=no change, +1=minimal healing, +2=substantial healing, +3=near-complete or complete healing.

Study #4/#5

Study #4/#5 was an open-label study of 24 weeks duration with an on-going extension. 13 patients aged 5 to 12 yrs were enrolled and, on the basis of emerging data, were exposed to 6 mg/kg/week study drug. This study also enrolled 16 historical controls. X-ray appearances of wrists and knees assessed by the RGI-C tool Data for study #4 suggest that subjects display improvement in the x-ray appearances of wrists and knees (as assessed by the Radiographic Impression of Change tool). Patients who received asfotase alfa moved to scores of +2 and +3 over the first 6 months of exposure and this was sustained with on-going treatment. By contrast, a change in the RGI-C score over a comparable time period was not apparent in historical controls.

Bone Biopsies

The following results were obtained for 10 patients in the per-protocol set (excludes those patients who received oral vitamin D between baseline and week 24) who underwent biopsy of the trans-iliac bone crest before and after receiving asfotase alfa:

Mean (SD) osteoid thickness was 12.8 (3.5) µm at baseline and 9.5 (5.1) µm at week Mean (SD) osteoid volume/bone volume was 11.8 (5.9)% at baseline and 8.6(7.2)% at week 24

Mean (SD) mineralization lag-time was 93 (70) days at baseline and 119 (225) days at week 24

Apparent "Catch-Up Growth" in Response to Exposure to Study Drug

For those patients who received asfotase alfa: 9/13 patients displayed persistent apparent catch-up height-gain as shown by movement over time to a higher percentile on CDC growth charts. 3/13 patients did not display apparent catch-up height-gain and 1 patient did not have enough data to permit judgement.

By contrast, for the time period of observation of historical controls: 1/16 patients displayed apparent catch-up height-gain, 12/16 patients did not display apparent catch-up height-gain and data were inconclusive in 3/16 patients.

Studies #2/#3 and #7

The need for ventilation support in studies 02-08/03-08 and 10/10 (patients aged 0.1 to 270 weeks at baseline) include:

21 patients required ventilation support:
14 patients required invasive ventilation support (intubation or tracheostomy) at baseline (one had a brief period of non-invasive ventilation at baseline before transfer).
7 patients were weaned off ventilation (time on ventilation from 24 to 168 weeks), all had achieved an RGI-C score ≥2
3 patients continued with ventilation support, RGI-C score ≤2
3 patients died whilst on ventilation support
1 patient withdrew consent
7 patients started non-invasive ventilation (BiPAP or CPAP) after baseline (2 patients required brief support with invasive ventilation).
5 patients were weaned off ventilation (time on ventilation from 4 weeks to 48 weeks)
2 patients died The natural history of untreated infant hypophosphatasia patients described in study 11-10 suggests a high mortality if ventilation is required.

Study #6

Results of clinical efficacy from study #6 are limited in adult subjects. Further data on adult subjects will be generated as a post-authorization commitment.

CONCLUSIONS ON THE CLINICAL EFFICACY

Hypophosphatasia is characterized by failure to mineralize bone. The Radiographic Global Impression of Change tool was developed to assess changes over time in skeletal mineralization in patients with hypophosphatasia in response to asfotase alfa treatment and was chosen as the primary endpoint for the main clinical studies of asfotase alfa in pediatric-onset hypophosphatasia. The ability of the tool to assess mineralization of bone would make it clinically relevant in the assessment of response of patients with hypophosphatasia to exposure to asfotase alfa.

Validation of the Radiographic Global Impression of Change tool includes:

Results obtained using the RGI-C tool have demonstrated an acceptable level of agreement in inter-rater and intra-rater scores.

Sensitivity to change of the Radiographic Global Impression of Change tool may be inferred (internal to the tool) from the pattern of response of subjects to asfotase alfa who move from a score of "0" to between "+2" and "+3" over the first 6 months of exposure and then fluctuate between "+2" and "+3" thereafter upon continued exposure.

Sensitivity to change of the Radiographic Global Impression of Change tool may be inferred (external to the tool) by the concomitant display of (i) apparent catch-up height gain and (ii) the apparent improvement in histological appearance of bone biopsies over the first 6 months of exposure.

With regard to 1) the improvement in x-ray appearance as assessed by the Radiographic Clinical Impression of Change tool, 2) the histological appearance of bone biopsy material and 3) the apparent catch-up height-gain demonstrated by patients, these clinical effects showed:

Biological plausibility: supplementing a deficient enzyme that is involved in bone mineralization is likely to lead to improved appearance of bone histology and improved x-ray appearances of bones and joints. It was therefore found to be plausible that there would be consequent gain in height and may have improved respiratory ability.

Biological coherence: pre-clinical studies further supported the claims for clinical efficacy.

Temporal relationship: the effects became evident subsequent to exposure and persisted with continuing exposure.

Direction of effect: the changes in x-ray appearance and bone histology were in the direction anticipated.

Consistency: the effects did occur in most (though not all) patients and were found in more than one study under similar circumstances.

Specificity of outcome: it was not apparent that organs other than bone were affected. There may be an indirect effect on muscle strength but the studies (such as the 6-minute walk test) were not able to show this conclusively.

The bulk of evidence in support of clinical efficacy is in subjects under 13 yrs of age (between 0.5 months and 12 yrs of age at time of inclusion in the studies). Extension of studies #5 and #6 is expected to provide more data (such as, but not limited to, RGI-C scores, height and weight change, biomarkers measurement, etc.) in patients 13 to 18 year-old of age. Multicenter, randomized, open-label, Phase 2a study of asfotase alfa in adult patients with hypophosphatasia (HPP) was designed to:

(i) evaluate pharmacokinetics (PK) of asfotase alfa in adults following administration of the dose advised in children; and (ii) provide dose response data on plasma inorganic pyrophosphate (PPi) and pyridoxal-5'-phosphate (PLP) and to explore evidence of clinical benefit.

The invention claimed is:

1. A method of treating a human with hypophosphatasia comprising administering to the human by subcutaneous injection two or more doses of a polypeptide comprising the amino acid sequence of SEQ ID NO: 1 wherein the doses are administered no more than once every three weeks and each dose comprises at least 50 mg/kg of the polypeptide.

2. The method of claim 1, wherein the human has a lack of or an insufficient amount of functional alkaline phosphatase.

3. The method of claim 2, wherein the alkaline phosphatase is tissue-non-specific alkaline phosphatase (TNALP).

4. The method of claim 1, wherein the polypeptide catalyzes the cleavage of at least one of inorganic pyrophosphate (PPi), pyridoxal 5'-phosphate (PLP), and phosphoethanolamine (PEA).

5. The method of claim 1, wherein each said dose is administered once every 22 days, once every 23 days, or once every 24 days.

6. The method of claim 1, wherein administering the polypeptide reduces plasma levels of at least one of pyridoxal-5'-phosphate (PLP) and inorganic pyrophosphate (PPi) in the human.

7. The method of claim 1, comprising improving in the human at least one of a Radiographic Global Impression of Change (RGI-C) score, Rickets Severity Scale (RSS) score, and osteoid thickness.

8. The method of claim 1, comprising improving in the human at least one of the functional efficacy endpoints selected from the group consisting of Bruininks-Oseretsky Test of Motor Proficiency, Second Edition (BOT-2), percent predicted distance walked on a 6-minute walk test (6MWT), and modified performance-oriented mobility assessment-gait (MPOMA-G).

9. The method of claim 1, wherein administering the polypeptide results in a therapeutic effect comparable to administering the polypeptide at the same time-averaged dosage but in a higher frequency.

10. The method of claim 9, wherein the comparable therapeutic effect comprises at least one endpoint measurement selected from the group consisting of plasma levels of pyridoxal-5'-phosphate (PLP), plasma levels of inorganic pyrophosphate (PPi), RGI-C score, RSS score, osteoid thickness, BOT-2 score, 6MWT score, and MPOMA-G score.

11. The method of claim 1, wherein the human has juvenile-onset or adult-onset HPP.

12. The method of claim 1, wherein the human is an adult or adolescent.

13. The method of claim 1, wherein each said dose is administered at a dosage and frequency per dose of about 52 mg/kg once every 22 days.

14. The method of claim 1, wherein each said dose is administered at a dosage and frequency per dose of about 55 mg/kg once every 23 days.

15. The method of claim 1, wherein each said dose is administered at a dosage and frequency per dose of about 57 mg/kg once every 24 days.

16. The method of claim 1, wherein the method promotes bone mineralization.

* * * * *